(12) United States Patent
Serber et al.

(10) Patent No.: US 8,110,360 B2
(45) Date of Patent: *Feb. 7, 2012

(54) COMPOSITIONS AND METHODS FOR THE ASSEMBLY OF POLYNUCLEOTIDES

(75) Inventors: Zach Serber, Emeryville, CA (US); Raymond Lowe, Emeryville, CA (US); Jeffrey A. Ubersax, Emeryville, CA (US); Sunil S. Chandran, Emeryville, CA (US)

(73) Assignee: Amyris, Inc., Emeryville, CA (US)

( * ) Notice: Subject to any disclaimer, the term of this patent is extended or adjusted under 35 U.S.C. 154(b) by 218 days.

This patent is subject to a terminal disclaimer.

(21) Appl. No.: 12/684,874

(22) Filed: Jan. 8, 2010

(65) Prior Publication Data

US 2010/0124768 A1    May 20, 2010

Related U.S. Application Data

(63) Continuation of application No. 12/622,401, filed on Nov. 19, 2009.

(60) Provisional application No. 61/116,109, filed on Nov. 19, 2008, provisional application No. 61/162,230, filed on Mar. 20, 2009.

(51) Int. Cl.
   *C12Q 1/68* (2006.01)
(52) U.S. Cl. ...... 435/6.12; 435/91.2; 435/483; 536/23.1
(58) Field of Classification Search .................. None
   See application file for complete search history.

(56) References Cited

U.S. PATENT DOCUMENTS

| | | |
|---|---|---|
| 6,204,025 B1 | 3/2001 | Liu |
| 6,936,470 B2 | 8/2005 | Liang et al. |
| 2003/0022179 A1 | 1/2003 | Chesnut et al. |

FOREIGN PATENT DOCUMENTS

| | | |
|---|---|---|
| GB | 2393441 | 3/2004 |
| WO | WO 2007/038276 A2 | 4/2007 |
| WO | WO 2008/045380 A2 | 4/2008 |
| WO | WO 2008/095927 | 8/2008 |

OTHER PUBLICATIONS

Kandpal, et al., "A polymerase chain reaction approach for constructing jumping and linking libraries," Nucleic Acid Research, (1990) vol. 18, No. 10, p. 3081.

Liu, et al., "Linking PCR splices small exons into a large DNA molecule amenable to rapid mutation screening," American Journal of Human Genetics, (1997) Poster Presentation Abstracts Supplement 61(4), A223.

*Primary Examiner* — Jim Ketter

(74) *Attorney, Agent, or Firm* — Squire Sanders (US) LLP

(57) ABSTRACT

The present invention provides compositions and methods for rapid assembly of one or more assembled polynucleotides from a plurality of component polynucleotides. The methods of the invention utilize circular nucleic acid vectors that comprise a DNA segment D flanked by an annealable linker sequence, annealable linker sequence pairs LA and LB, or annealable linker sequence/primer binding segment pairs LA and PB or PA and LB. Restriction endonuclease digestion of a plurality of vectors containing the DNA segments to be assembled generates a plurality of DNA fragments comprising the elements PA-D-LB, LA-D-LB, and LA-D-PB or D-LB, LA-D-LB, and LA-D. The sequences of annealable linker sequences LA and LB provide complementary termini to the DNA fragments, which are utilized in host cell mediated homologous recombination or together with primer binding segments PA and PB in a polymerase cycling assembly reaction for the ordered assembly of the various DNA segments into one or more assembled polynucleotides.

18 Claims, 17 Drawing Sheets

Column Purification

Heat Inactivation

COMPOSITIONS AND METHODS FOR THE ASSEMBLY OF POLYNUCLEOTIDES

This application is a continuation of U.S. application Ser. No. 12/622,401, filed on Nov. 19, 2009, which claims benefit under 35 U.S.C. §119(e) of U.S. Provisional Application No. 61/116,109, filed on Nov. 19, 2008, and U.S. Provisional Application No. 61/162,230, filed on Mar. 20, 2009, the contents of which are hereby incorporated by reference in their entireties.

1. FIELD OF THE INVENTION

The present invention relates generally to the field of recombinant DNA technology and, more particularly, to improved methods for the ordered assembly of a plurality of DNA segments into an assembled polynucleotide.

2. BACKGROUND OF THE INVENTION

Recombination of polynucleotides can be carried out using many methods known in the art. Traditional techniques for recombining nucleic acids have utilized restriction enzymes and ligating enzymes for the creation of novel nucleic acid molecules. Recombinant molecules such as cloning and expression vectors can be utilized to integrate a nucleic acid sequence of interest into the genome of a host cell, and/or drive the expression of one or more genes of interest. Utilization of a vector to drive expression of a gene of interest in the cell, for example a yeast cell, requires that the vector contain requisite genetic elements that enable replication and expression of the gene of interest. These elements may include, for example, the gene or genes of interest, a promoter sequence, a terminator sequence, selectable markers, integration loci, and the like.

Assembly of elements into a single vector using traditional restriction and ligation enzyme-based methods can be time-consuming and laborious. Each sub-cloning step, i.e., the introduction of a new nucleic acid fragment into an existing polynucleotide, can require that the resulting clone be screened and characterized before the introduction of additional fragments. Clones produced by blunt end ligation require confirmation that the fragment was introduced in the proper orientation. On the other hand, sticky-end ligation requires that the restriction sites utilized to produce the sticky ends on the acceptor fragment also be present in the donor fragment, but not at a site that would interrupt the sequence of interest within the donor fragment. Thus, the selection of workable restriction sites depends entirely on the compositions of the pieces being joined and must be carefully considered in each case. In addition, these methods often introduce extraneous nucleic acid sequences to the resulting clone that can interfere with the structure and function of the desired gene products. Further limiting the efficiency of restriction-enzyme based cloning methods is the intrinsic limitation on the number of nucleic acid molecules that can be ligated together in a single reaction.

The polymerase chain reaction (PCR) is a powerful technique by which specific polynucleotide sequences, including genomic DNA, cDNA and mRNA, are amplified in vitro. PCR typically comprises contacting separate complementary strands of a target nucleic acid with two oligonucleotide primers under conditions that allow for the formation of complementary primer extension products on both strands. These strands act as templates for the synthesis of copies of the desired nucleic acid sequences. By repeating the separation and synthesis steps in an automated system, exponential duplication of the target sequences can be achieved.

One method of PCR, termed "splicing by overlap extension" ("SOE"; see, e.g., U.S. Pat. No. 5,023,171), facilitates the assembly of DNA molecules at precise junctions without the use of restriction enzymes or ligase. Component fragments to be recombined are generated in separate polymerase chain reactions using uniquely designed primers which produce amplicons having complementary termini to one another. Upon mixing and denaturation of these amplicons, strands having complementary sequences at their 3' ends overlap and act as primers for each other. Extension of this overlap by DNA polymerase produces a nucleic acid molecule in which the original sequences are "spliced" together. Subsequent rounds of PCR amplify the resulting spliced polynucleotide.

SOE, while more efficient than traditional ligation enzyme-based methods for combining a plurality of nucleic acid fragments, does require time to optimize primer sequences and amplification conditions to produce desired products. Each junction between the fragments to be spliced together must be individually considered, and a pair of primers must be designed for each fragment in order to make the ends compatible. Traditional considerations for the design of PCR primers, e.g., melting temperature, G-C content, avoidance of hairpin and dimer formation, and stringency for false priming sites, must be considered even more carefully as the number of fragments to be spliced in the SOE reaction increases.

Thus, despite advances in recombinant DNA technology, there exists a need for improved methods that provide for the rapid and ordered assembly of polynucleotides. Particularly needed are methods which can facilitate the assembly of a number of polynucleotides with minimal manipulation and characterization of intermediate products, and without the need for primer optimization steps. These and other needs can be met by compositions and methods of the present invention.

3. SUMMARY OF THE INVENTION

The compositions and methods provided herein allow for rapid and ordered assembly, or "stitching," of component polynucleotides into assembled polynucleotides. In some embodiments, the methods provided herein utilize circular nucleic acid assembly vectors. In certain embodiments, an assembly vector comprises a component polynucleotide wherein the component polynucleotide comprises a DNA segment flanked by: (i) an annealable linker on the 3' end; (ii) a primer binding segment on the 5' end and an annealable linker on the 3' end; (iii) an annealable linker on both the 3' end and on the 5' end; (vi) an annealable linker on the 5' end and primer binding segment on the 3' end; or (v) an annealable linker on the 5' end.

In some embodiments, a plurality of component polynucleotides can be stitched together by providing a plurality of assembly vectors in a single reaction vessel. In certain embodiments, component polynucleotides can be excised from their assembly vectors within the reaction vessel. In some embodiments, the component polynucleotides can then be denatured, annealable linker sequences can be annealed to complementary strands on an adjacent component polynucleotide, and the component polynucleotides can be stitched together into an assembled polynucleotide by splicing by overlap extension (SOE) followed by PCR. In other embodiments, component polynucleotides excised from assembly vectors can be assembled into an assembled polynucleotide in vivo by homologous recombination within a host cell transformed with the component polynucleotides. Assembled polynucleotides can be further combined in vivo by host cell mediated homologous recombination.

The efficiency of polynucleotide assembly can be enhanced by the provision of a standard set of annealable linker sequences that are used within the assembly vector, for example, those described herein as SEQ ID NOS: 1 to 23. The annealable linker sequences provide sequence overlap between adjacent component polynucleotides in the assembly reaction. Ideally, the annealable linker sequences lack appreciable secondary structure both at the RNA and at the DNA level, do not cross react in an undesirable manner with one another, and have relatively high melting temperatures ($T_m$). Consequently, a number of component polynucleotides can be stitched together without the need for designing unique primers for each component polynucleotide, thereby saving time and labor. Compositions and methods provided herein can be used to assemble many types of polynucleotides, including synthetic genes, constructs, cloning vectors, expression vectors, chromosomes, genomes, peptide libraries, and the like.

In one aspect, provided herein is a vector, i.e., an assembly vector, that can be used in the assembly of one or more assembled polynucleotides from a plurality of component polynucleotides.

In some embodiments, the assembly vector is a circular polynucleotide that comprises, in a 5' to 3' orientation, a restriction site RA, an annealable linker sequence LA, a DNA segment D, an annealable linker sequence LB, and a restriction site RB (i.e., 5'-RA-LA-D-LB-RB-3'). In some embodiments, the assembly vector is a circular polynucleotide that comprises, in a 5' to 3' orientation, a restriction site RA, a DNA segment D, an annealable linker sequence LB, and a restriction site RB (i.e., 5'-RA-D-LB-RB-3'). In some embodiments, the assembly vector is a circular polynucleotide that comprises, in a 5' to 3' orientation, a restriction site RA, an annealable linker sequence LA, a DNA segment D, and a restriction site RB (i.e., 5'-RA-LA-D-RB-3'). In some embodiments, the assembly vector is a circular polynucleotide that comprises, in a 5' to 3' orientation, a restriction site RA, a primer binding segment PA, a DNA segment D, an annealable linker sequence LB, and a restriction site RB (i.e., 5'-RA-PA-D-LB-RB-3'). In some embodiments, the assembly vector is a circular polynucleotide that comprises, in a 5' to 3' orientation, a restriction site RA, an annealable linker sequence LA, a DNA segment D, a primer binding segment PB, and a restriction site RB (i.e., 5'-RA-LA-D-PB-RB-3'). In some embodiments, the assembly vector is a circular polynucleotide that comprises, in a 5' to 3' orientation, a restriction site RA, an annealable linker sequence LA, a DNA segment D, an annealable linker sequence LB, and a restriction site RB (i.e., 5'-RA-LA-D-LB-RB-3'). Exemplary assembly vectors are provided in FIG. 1B and FIG. 2.

In some embodiments, a primer binding segment (i.e., PA or PB) can be any nucleotide sequence that is not complementary with any of the annealable linker sequences that are used to make an assembled polynucleotide. In some embodiments, a primer binding segment includes a restriction endonuclease recognition site and/or cleavage site. In some embodiments, a primer binding segment comprises a nucleic acid sequence of one of the available linker sequences (e.g., one of SEQ ID NOS: 1 to 23), or complements thereof, not being used in the particular assembly reaction. In some embodiments, the nucleic acid sequence of primer binding segment PA is selected from the group consisting of SEQ ID NOS: 24, 25, and complements thereof. In some embodiments, the nucleic acid sequence of primer binding segment PB is selected from the group consisting of SEQ ID NOS: 24, 25, and complements thereof. In preferable embodiments, primer binding segment PA and primer binding segment PB are not identical in sequence.

In some embodiments, the two or more annealable linker sequences are at least 24 nucleotides in length and have a $T_m$ of at least 60° C.

In some embodiments, two or more annealable linker sequences have a G-C content of at least 70% and a $T_m$ of at least 70° C., and do not form appreciable secondary DNA structures. In some embodiments, the nucleic sequence of annealable linker sequence LA is selected from the group consisting of SEQ ID NOS: 1 to 8, and complements thereof. In some embodiments, the nucleic sequence of annealable linker sequence LB is selected from the group consisting of SEQ ID NOS: 1 to 8, and complements thereof. In some embodiments, the nucleic sequences of annealable linker sequence LA and annealable linker sequence LB are selected from the group consisting of SEQ ID NOS: 1 to 8, and complements thereof.

In some embodiments, two or more annealable linker sequences have an A-T content of at least 30% and a $T_m$ of at least 65° C., and do not form appreciable secondary DNA or RNA structures. In some embodiments, two or more annealable linker sequences have a low G-C content and a $T_m$ of at least 65° C., and comprise the sequence motif 5'-ANNNNNNNNANNNAANTANNTTNANA-3' (SEQ ID NO: 248), wherein A stands for adenine, N for any nucleotide, and T for thymine. In some embodiments, the nucleic sequence of annealable linker sequence LA is selected from the group consisting of SEQ ID NOS: 9 to 23, and complements thereof. In some embodiments, the nucleic sequence of annealable linker sequence LB is selected from the group consisting of SEQ ID NOS: 9 to 23, and complements thereof. In some embodiments, the nucleic sequences of annealable linker sequence LA and annealable linker sequence LB are selected from the group consisting of SEQ ID NOS: 9 to 23, and complements thereof.

The ordered assembly of the plurality of component polynucleotides can be controlled by the selection of annealable linker sequences that flank a DNA segment within the assembly vector. Accordingly, in some embodiments, to ensure that component polynucleotides can be assembled in an ordered fashion, the sequences of an annealable linker sequence/annealable linker sequence pair within a particular assembly vector are not complementary. Similarly, in some embodiments, the sequences of a primer binding segment/annealable linker sequence pair within a particular assembly vector are not complementary.

In a particular embodiment, restriction sites RA and RB are cleavable by the same restriction endonuclease so as to facilitate the excision of the component polynucleotide from the assembly vector. In some embodiments, restriction site RA or RB is cleavable by a restriction endonuclease that leaves a 5' or 3' overhang. In other embodiments, restriction site RA or RB is cleavable by a restriction endonuclease that leaves a blunt end. In some embodiments, restriction sites RA and RB are cleavable by the same restriction endonuclease. In still other embodiments, the restriction sites RA and RB are cleavable by a Type IIS restriction endonuclease. In some embodiments, the restriction sites RA and RB are cleavable by the same Type IIS restriction endonuclease. In a particular embodiment, restriction sites RA and RB are cleavable by SapI or LguI restriction endonucleases.

In another aspect, the invention provides an entry vector useful in the preparation of an assembly vector comprising a DNA segment.

In some embodiments, the entry vector is a circular polynucleotide that comprises, in a 5' to 3' orientation, a restriction site RA, a restriction site RY, a DNA segment D, a restriction site RZ, an annealable linker sequence LB, and a restriction site RB (i.e., 5'-RA-RY-D-RZ-LB-RB-3'). In some embodiments, the entry vector is a circular polynucleotide that comprises, in a 5' to 3' orientation, a restriction site RA, an annealable linker sequence LA, a restriction site RY, a DNA segment D, a restriction site RZ, and a restriction site RB (i.e., 5'-RA-LA-RY-D-RZ-RB-3'). In some embodiments, the entry vector is a circular polynucleotide that comprises, in a 5' to 3' orientation, a restriction site RA, an annealable linker sequence LA, a restriction site RY, a DNA segment D, a restriction site RZ, an annealable linker sequence LB, and a restriction site RB (i.e., 5'-RA-LA-RY-D-RZ-LB-RB-3'). In some embodiments, the entry vector is a circular polynucleotide that comprises, in a 5' to 3' orientation, a restriction site RA, a primer binding segment PA, a restriction site RY, a DNA segment D, a restriction site RZ, an annealable linker sequence LB, and a restriction site RB (i.e., 5'-RA-PA-RY-D-RZ-LB-RB-3'). In some embodiments, the entry vector is a circular polynucleotide that comprises, in a 5' to 3' orientation, a restriction site RA, an annealable linker sequence LA, a restriction site RY, a DNA segment D, a restriction site RZ, a primer binding segment PB, and a restriction site RB (i.e., 5'-RA-LA-RY-D-RZ-PB-RB-3'). An exemplary entry vector is provided in FIG. 1A.

Digestion of an entry vector with one or more restriction endonucleases capable of cleaving RY and RZ can create a linearized vector capable of acceptance of a DNA segment. The DNA segment can be ligated into RY and RZ sites using standard cloning techniques to generate an assembly vector of the invention. In some embodiments, restriction sites RY and RZ of the entry vector are cleavable by the same restriction endonuclease. In some embodiments, restriction sites RY and RZ of the entry vector are cleavable by a Type IIS restriction endonuclease. In some embodiments, restriction sites RY and RZ of the entry vector are cleavable by the same Type IIS restriction endonuclease. In particular embodiments, the Type IIS restriction endonuclease is SchI or MlyI.

In some embodiments, restriction sites RA and RB of the entry vector are cleavable by the same restriction endonuclease. In some embodiments, restriction sites RA and RB of the entry vector are cleavable by a Type IIS restriction endonuclease. In some embodiments, restriction sites RA and RB of the entry vector are cleavable by the same Type IIS restriction endonuclease. In particular embodiments, the Type IIS restriction endonuclease is SapI or LguI.

In another aspect, the invention provides an assembly composition comprising a plurality of assembly vectors for use in the assembly of one or more assembled polynucleotides from a plurality of component polynucleotides. In some embodiments, the assembly composition comprises:

(a) one or more first nucleic acid molecules, wherein each first nucleic acid molecule is circular and comprises, in a 5' to 3' orientation, a first restriction site $RA_0$, any DNA segment selected from the group $D_0$, an annealable linker sequence $LB_0$, and a second restriction site $RB_0$;

(b) one or more intermediate nucleic acid molecules wherein each intermediate nucleic acid molecule n is circular and comprises, in a 5' to 3' orientation, a first restriction site $RA_n$, a first annealable linker sequence $LA_n$, any DNA segment selected from the group $D_n$, a second annealable linker sequence $LB_n$, and a second restriction site $RB_n$, and wherein n represents an integer from one to the number of intermediate nucleic acid molecules; and (c) one or more last nucleic acid molecules, wherein each last nucleic acid molecule is circular and comprises, in a 5' to 3' orientation, a first restriction site $RA_m$, an annealable linker sequence $LA_m$, any DNA segment selected from the group $D_m$, a second restriction site $RB_m$ wherein m represents an integer one greater than the number of intermediate nucleic acid molecules;

whereupon cleavage of restriction sites $RA_0$ through $RB_m$ and denaturation of the resulting linear nucleic acid molecules, each annealable linker sequence $LB_{(p-1)}$ is capable of hybridizing to the complement of annealable linker sequence $LA_p$, wherein n is an integer that varies from 1 to (m−1), wherein p represents an integer from 1 to m, and wherein each group $D_0, \ldots D_n, \ldots$ and $D_m$ consists of one or more DNA segments.

In certain embodiments, one or more first nucleic acid molecules further comprises a primer binding segment PA positioned 5' to the DNA segment selected from the group $D_0$. In certain embodiments, one or more last nucleic acid molecules further comprises a primer binding segment PB positioned 3' to the DNA segment selected from the group $D_m$.

In certain embodiments, the assembly composition comprises two or more intermediate nucleic acid molecules. In certain embodiments, the assembly composition comprises three or more intermediate nucleic acid molecules. In certain embodiments, the assembly composition comprises four or more intermediate nucleic acid molecules. In certain embodiments, the assembly composition comprises five or more intermediate nucleic acid molecules. In certain assembly embodiments, the composition comprises six or more intermediate nucleic acid molecules. In certain embodiments, the assembly composition comprises seven or more intermediate nucleic acid molecules. In certain embodiments, the assembly composition comprises eight or more intermediate nucleic acid molecules. In certain embodiments, the assembly composition comprises nine or more intermediate nucleic acid molecules. In certain embodiments, the assembly composition comprises ten or more intermediate nucleic acid molecules. In certain embodiments, the assembly composition comprises fifteen or more intermediate nucleic acid molecules. In certain embodiments, the assembly composition comprises twenty or more intermediate nucleic acid molecules.

In certain embodiments, m is equal to 1. In certain embodiments, m is equal to 2. In certain embodiments, m is equal to 3. In certain embodiments, m is equal to 4. In certain embodiments, m is equal to 5. In certain embodiments, m is equal to 6. In certain embodiments, m is equal to 7. In certain embodiments, m is equal to 8. In certain embodiments, m is equal to 9. In certain embodiments, m is equal to 10. In certain embodiments, m is equal to or greater than 10.

In some embodiments, upon cleavage of restriction sites $RA_0$ through $RB_m$ and denaturation of the resulting linear nucleic acid molecules, each annealable linker sequence $LB_{(p-1)}$ is capable of selectively hybridizing to the complement of annealable linker sequence $LA_p$ compared to the other annealable linker sequences, or their complements, in the assembly composition. In some embodiments, each annealable linker sequence $L_{(p-1)}$ is identical in sequence to annealable linker sequence $LA_p$.

In a particular embodiment, the restriction sites $RA_0$ through $RB_m$ are cleavable by the same restriction endonuclease so as to facilitate excision of the component polynucleotides from the assembly vectors. In some embodiments, the restrictions sites $RA_0$ through $RB_m$ are cleavable by SapI and/or LguI restriction endonucleases.

In another aspect, the invention provides a components composition comprising a plurality of linear nucleic acid molecules wherein the linear nucleic acid molecules can be formed by digesting an assembly composition with one or more restriction endonucleases capable of cleaving restriction sites $RA_0$ through $RB_m$ wherein the assembly composition comprises:
  (a) one or more first nucleic acid molecules, wherein each first nucleic acid molecule is circular and comprises, in a 5' to 3' orientation, a first restriction site $RA_0$, any DNA segment selected from the group $D_0$, an annealable linker sequence $LB_0$, and a second restriction site $RB_0$;
  (b) one or more intermediate nucleic acid molecules wherein each intermediate nucleic acid molecule n is circular and comprises, in a 5' to 3' orientation, a first restriction site $RA_n$, a first annealable linker sequence $LA_n$, any DNA segment selected from the group $D_n$, a second annealable linker sequence $LB_n$, and a second restriction site $RB_n$, and wherein n represents an integer from one to the number of intermediate nucleic acid molecules; and
  (c) one or more last nucleic acid molecules, wherein each last nucleic acid molecule is circular and comprises, in a 5' to 3' orientation, a first restriction site $RA_m$, an annealable linker sequence $LA_m$, any DNA segment selected from the group $D_m$, a second restriction site $RB_m$ wherein m represents an integer one greater than the number of intermediate nucleic acid molecules;
  whereupon cleavage of restriction sites $RA_0$ through $RB_m$ and denaturation of the resulting linear nucleic acid molecules, each annealable linker sequence $LB_{(p-1)}$ is capable of hybridizing to the complement of annealable linker sequence $LA_p$, wherein n is an integer that varies from 1 to (m−1), wherein p represents an integer from 1 to m, and wherein each group $D_0, \ldots D_n, \ldots$ and $D_m$ consists of one or more DNA segments.

In certain embodiments, one or more first nucleic acid molecules further comprises a primer binding segment PA positioned 5' to the DNA segment selected from the group $D_0$. In certain embodiments, one or more last nucleic acid molecules further comprises a primer binding segment PB positioned 3' to the DNA segment selected from the group $D_m$.

In certain embodiments, the components composition comprises two or more intermediate nucleic acid molecules. In certain embodiments, the components composition comprises three or more intermediate nucleic acid molecules. In certain embodiments, the components composition comprises four or more intermediate nucleic acid molecules. In certain embodiments, the components composition comprises five or more intermediate nucleic acid molecules. In certain embodiments, the components composition comprises six or more intermediate nucleic acid molecules. In certain embodiments, the components composition comprises seven or more intermediate nucleic acid molecules. In certain embodiments, the assembly composition comprises eight or more intermediate nucleic acid molecules. In certain embodiments, the assembly composition comprises nine or more intermediate nucleic acid molecules. In certain embodiments, the assembly composition comprises ten or more intermediate nucleic acid molecules. In certain embodiments, the assembly composition comprises fifteen or more intermediate nucleic acid molecules. In certain embodiments, the assembly composition comprises twenty or more intermediate nucleic acid molecules.

In certain embodiments, m is equal to 1. In certain embodiments, m is equal to 2. In certain embodiments, m is equal to 3. In certain embodiments, m is equal to 4. In certain embodiments, m is equal to 5. In certain embodiments, m is equal to 6. In certain embodiments, m is equal to 7. In certain embodiments, m is equal to 8. In certain embodiments, m is equal to 9. In certain embodiments, m is equal to 10. In certain embodiments, m is equal to or greater than 10.

In another aspect, provided herein is a kit useful for assembling a plurality of polynucleotides in accordance with the methods provided herein. In some embodiments, the kit comprises: (a) one or more entry vectors described herein; (b) one or more restriction endonucleases capable of cleaving restriction sites RA and RB of the entry vectors; and (c) one or more restriction endonucleases capable of cleaving restriction sites RY and RZ of the entry vectors.

In another aspect, the invention provides a library of nucleic acid molecules. In some embodiments, a nucleic acid molecule of the library comprises a first restriction site RA, a DNA segment D, an annealable linker sequence LB, and a second restriction site RB. In some embodiments, a nucleic acid molecule of the library comprises a first restriction site RA, a primer binding segment PA, a DNA segment D, an annealable linker sequence LB, and a second restriction site RB. In some embodiments, a nucleic acid molecule of the library comprises a first restriction site RA, an annealable linker sequence LA, a DNA segment D, an annealable linker sequence LB, and a second restriction site RB. In some embodiments, a nucleic acid molecule of the library comprises a first restriction site RA, an annealable linker sequence LA, a DNA segment D, and a second restriction site RB. In some embodiments, a nucleic acid molecule of the library comprises a first restriction site RA, an annealable linker sequence LA, a DNA segment D, a primer binding segment PB, and a second restriction site RB.

In some embodiments, the library comprises at least one of each of the following vectors:
  (a) a vector that consists of a circular polynucleotide that comprises, in a 5' to 3' orientation, a restriction site RA, a DNA segment D, an annealable linker sequence LB, and a restriction site RB;
  (b) a vector that consists of a circular polynucleotide that comprises, in a 5' to 3' orientation, a restriction site RA, an annealable linker sequence LA, a DNA segment D, an annealable linker sequence LB, and a restriction site RB; and
  (c) a vector that consists of a circular polynucleotide that comprises, in a 5' to 3' orientation, a restriction site RA, an annealable linker sequence LA, a DNA segment D, and a restriction site $RB_0$.

In some embodiments, the library comprises at least one of each of the following vectors:
  (a) a vector that consists of a circular polynucleotide that comprises, in a 5' to 3' orientation, a restriction site RA, a primer binding segment PA, a DNA segment D, an annealable linker sequence LB, and a restriction site RB;
  (b) a vector that consists of a circular polynucleotide that comprises, in a 5' to 3' orientation, a restriction site RA, an annealable linker sequence LA, a DNA segment D, an annealable linker sequence LB, and a restriction site RB; and
  (c) a vector that consists of a circular polynucleotide that comprises, in a 5' to 3' orientation, a restriction site RA, an annealable linker sequence LA, a DNA segment D, a primer binding segment PB, and a restriction site $RB_0$.

In some embodiments, the DNA segment D comprises a nucleic sequence selected from the group consisting of a selectable marker, a promoter, genomic targeting sequence, a nucleic acid sequence encoding an epitope tag, and a nucleic acid sequence encoding a gene of interest, a nucleic acid sequence encoding a termination codon and lacZ.

In some embodiments, the library comprises at least one of each of the following nucleic acid molecules:

(a) a first nucleic acid molecule wherein the first nucleic acid molecule is circular and comprises, in a 5' to 3' orientation, a first restriction site $RA_0$, a DNA segment $D_0$, an annealable linker sequence $LB_0$, and a second restriction site $RB_0$;

(b) an intermediate nucleic acid molecule wherein the intermediate nucleic acid molecule n is circular and comprises, in a 5' to 3' orientation, a first restriction site $RA_n$, a first annealable linker sequence $LA_n$, a DNA segment $D_n$, a second annealable linker sequence $LB_n$, and a second restriction site $RB_n$, and wherein n represents an integer from one to the number of intermediate nucleic acid molecules; and (c) a last nucleic acid molecule wherein the last nucleic acid molecule is circular and comprises, in a 5' to 3' orientation, a first restriction site $RA_m$, an annealable linker sequence $LA_m$, a DNA segment $D_m$, a second restriction site $RB_m$ wherein m represents an integer one greater than the number of intermediate nucleic acid molecules;

whereupon cleavage of restriction sites $RA_0$ through $RB_m$ and denaturation of the resulting linear nucleic acid molecules, each annealable linker sequence $LB_{(p-1)}$ is capable of hybridizing to the complement of annealable linker sequence $LA_p$ wherein p represents the integers from 1 to m. In some embodiments, a first nucleic acid molecule further comprises a primer binding segment PA positioned 5' to the DNA segment selected from the group $D_0$. In some embodiments, a last nucleic acid molecules further comprises a primer binding segment PB positioned 3' to the DNA segment selected from the group $D_m$.

In certain embodiments, the library comprises two or more intermediate nucleic acid molecules. In certain embodiments, the library comprises three or more intermediate nucleic acid molecules. In certain embodiments, the library comprises four or more intermediate nucleic acid molecules. In certain embodiments, the library comprises five or more intermediate nucleic acid molecules. In certain embodiments, the library comprises six or more intermediate nucleic acid molecules. In certain embodiments, the library comprises seven or more intermediate nucleic acid molecules. In certain embodiments, the assembly composition comprises eight or more intermediate nucleic acid molecules. In certain embodiments, the assembly composition comprises nine or more intermediate nucleic acid molecules. In certain embodiments, the assembly composition comprises ten or more intermediate nucleic acid molecules. In certain embodiments, the assembly composition comprises fifteen or more intermediate nucleic acid molecules. In certain embodiments, the assembly composition comprises twenty or more intermediate nucleic acid molecules.

In certain embodiments, m is equal to 1. In certain embodiments, m is equal to 2. In certain embodiments, m is equal to 3. In certain embodiments, m is equal to 4. In certain embodiments, m is equal to 5. In certain embodiments, m is equal to 6. In certain embodiments, m is equal to 7. In certain embodiments, m is equal to 8. In certain embodiments, m is equal to 9. In certain embodiments, m is equal to 10. In certain embodiments, m is equal to or greater than 10.

In another aspect, provided herein are methods of assembling one or more assembled polynucleotides from a plurality of component polynucleotides, comprising the steps of:

(a) digesting an assembly composition with one or more restriction endonucleases to generate a components composition, the assembly composition comprising:

(i) one or more first nucleic acid molecules, wherein each first nucleic acid molecule is circular and comprises, in a 5' to 3' orientation, a first restriction site $RA_0$, any primer binding segment selected from the group PA, any DNA segment selected from the group $D_0$, an annealable linker sequence $LB_0$, and a second restriction site $RB_0$;

(ii) one or more intermediate nucleic acid molecules wherein each intermediate nucleic acid molecule n is circular and comprises, in a 5' to 3' orientation, a first restriction site $RA_n$, a first annealable linker sequence $LA_n$, any DNA segment selected from the group $D_n$, a second annealable linker sequence $LB_n$, and a second restriction site $RB_n$, and wherein n represents an integer from one to the number of intermediate nucleic acid molecules; and (iii) one or more last nucleic acid molecules, wherein each last nucleic acid molecule is circular and comprises, in a 5' to 3' orientation, a first restriction site $RA_m$, an annealable linker sequence $LA_m$, a DNA segment selected from the group $D_m$, any primer binding segment selected from the group PB, a second restriction site $RB_m$ wherein m represents an integer one greater than the number of intermediate nucleic acid molecules; whereupon cleavage of restriction sites $RA_0$ through $RB_m$ and denaturation of the resulting linear nucleic acid molecules, each annealable linker sequence $LB_{(p-1)}$ is capable of hybridizing to the complement of annealable linker sequence $LA_p$, wherein n is an integer that varies from 1 to (m−1), wherein p represents an integer from 1 to m, and wherein each group $D_0, \ldots D_n, \ldots$ and $D_m$ consists of one or more DNA segments;

wherein the one or more restriction endonucleases are capable of cleaving the restriction sites $RA_0$ through $RB_m$; and (b) contacting the components composition with DNA polymerase, deoxyribonucleoside triphosphates and one or more first primers and one or more second primers, under conditions suitable for denaturation of the nucleic acid molecules, annealing of annealable linker sequence $LB_{(p-1)}$ to annealable linker sequence $LA_p$, and extension therefrom; wherein each said first primer is capable of hybridizing to one of said primer binding segments selected from the group PA and each said second primer is capable of hybridizing to one of said primer binding segments selected from the group PB; and subjecting the components composition to polymerase chain reaction, wherein a polynucleotide is assembled which comprises, in a 5' to 3' orientation, one DNA segment selected from each of the groups $D_0, \ldots D_n, \ldots$ and $D_m$. In the method, p represents the integers from 1 to m.

In certain embodiments, the assembly composition comprises two or more intermediate nucleic acid molecules. In certain embodiments, the assembly composition comprises three or more intermediate nucleic acid molecules. In certain embodiments, the assembly composition comprises four or more intermediate nucleic acid molecules. In certain embodiments, the assembly composition comprises five or more intermediate nucleic acid molecules. In certain embodiments, the assembly composition comprises six or more intermediate nucleic acid molecules. In certain embodiments, the assembly composition comprises seven or more intermediate nucleic acid molecules. In certain embodiments, the assembly composition comprises eight or more intermediate nucleic acid molecules. In certain embodiments, the assembly composition comprises nine or more intermediate nucleic acid molecules. In certain embodiments, the assembly composition comprises ten or more intermediate nucleic acid molecules. In certain embodiments, the assembly composition comprises fifteen or more intermediate nucleic acid molecules. In certain embodiments, the assembly composition comprises twenty or more intermediate nucleic acid molecules.

In certain embodiments, m is equal to 1. In certain embodiments, m is equal to 2. In certain embodiments, m is equal to 3. In certain embodiments, m is equal to 4. In certain embodiments, m is equal to 5. In certain embodiments, m is equal to 6. In certain embodiments, m is equal to 7. In certain embodiments, m is equal to 8. In certain embodiments, m is equal to 9. In certain embodiments, m is equal to 10. In certain embodiments, m is equal to or greater than 10.

In some embodiments, the assembly composition comprises one first nucleic acid molecule and one last nucleic acid molecule. In other embodiments, the assembly composition comprises more than one first nucleic acid molecule and more than one last nucleic acid molecule, and the assembly methods provide for the ordered assembly of multiple component polynucleotides into a plurality of assembled polynucleotides in a combinatorial fashion. In certain embodiments, the assembly composition comprises comprises at least two nucleic acid molecules that comprise the same annealable linker sequence LA or LB, or the same primer binding segment PA or PB, or the same pair of annealable linker sequences LA and LB, or the same pair of annealable linker sequence/primer binding segment LA and PB, or LB and PA.

In another aspect, provided herein are methods for generating host cells comprising assembled polynucleotides. In some embodiments, the methods comprise transforming a host cell with an assembled polynucleotide generated by the methods of polynucleotide assembly described herein. In other embodiments, the methods comprise transforming a host cell with a plurality of assembled polynucleotides generated by the methods of polynucleotide assembly described herein. In a particular embodiment, the host cell combines two or more assembled polynucleotides into one or more combined polynucleotide by homologous recombination. In yet other embodiments, the methods comprise transforming a host cell with a plurality of component polynucleotides and allowing the host cell to generate one or more assembled or combined polynucleotides by homologous recombination.

In another aspect, the present invention provides methods for generating a plurality of host cells comprising a plurality of assembled polynucleotides. In some embodiments, the plurality of host cells are generated by transforming host cells with a composition comprising a plurality of assembled polynucleotides generated by combinatorial assembly of component polynucleotides. In other embodiments, the plurality of host cells are generated by transforming host cells with a composition comprising a plurality of assembled polynucleotides of which at least two assembled polynucleotides comprise non-functional segments of a selectable marker that upon host cell mediated homologous recombination generate a functional selectable marker, and by selecting host cells comprising a combined polynucleotide. In yet other embodiments, the plurality of host cells are generated by combinatorial methods by transforming host cells with a component composition comprising multiple component polynucleotides of which at least two component polynucleotides comprise the same annealable linker sequence LA or LB or the same pair of annealable linker sequences LA and LB, and by selecting host cells comprising an assembled polynucleotide.

In another aspect, provided herein is a polynucleotide having a sequence selected from the group consisting of SEQ ID NOS: 1 to 25.

In another aspect, provided herein is a polynucleotide comprising one or more sequences selected from the group consisting of SEQ ID NOS: 1 to 25.

4. BRIEF DESCRIPTION OF THE FIGURES

FIG. 1A provides a schematic of an entry vector useful for the preparation of an assembly vector of the invention. The vector contains a restriction site $RA_0$, a primer binding segment PA or an annealable linker sequence LA, a restriction site RY, a DNA segment D, a restriction site RZ, a primer binding segment PB or an annealable linker sequence LB, and a restriction site RB.

FIG. 1B provides an exemplary method of preparing an entry vector for acceptance of a DNA segment to form an assembly vector. In the exemplary, RY=RZ=SchI. Digestion with SchI, a Type IIS restriction endonuclease that is capable of producing blunt ends allows for isolation of the vector with the linker sites open to be fused to the DNA segment (D). Blunt-end ligation of D into the entry vector can be performed by traditional methods using, e.g., T4 DNA ligase.

FIG. 2 presents a schematic of an assembly composition comprising a plurality of assembly vectors (first, intermediate, and last), each comprising a DNA segment of interest ($D_0$, $D_n$, $D_m$). The first nucleic acid molecule comprises a first restriction site $RA_0$, a primer binding segment PA, a DNA segment $D_0$, an annealable linker sequence $LB_0$, and a second restriction site $RB_0$. The one or more intermediate nucleic acid molecules comprise a first restriction site $RA_n$, a first annealable linker sequence $LA_n$, a DNA segment $D_n$, a second annealable linker sequence $LB_n$, and a second restriction site $RB_n$ wherein n represents an integer from one to the number of intermediate nucleic acid molecules; and the last nucleic acid molecule comprises a first restriction site $RA_m$, an annealable linker sequence $LA_m$, a DNA segment $D_m$, a primer binding segment PB, a second restriction site $RB_m$ wherein m represents an integer one greater than the number of intermediate nucleic acid molecules.

FIG. 3 presents an exemplary method of assembling, i.e., "stitching" a assembled polynucleotide from four (4) component polynucleotides. Assembly vectors comprising DNA segments to be assembled are pooled in a single tube and digested with SapI to release component polynucleotide fragments from the assembly vector backbones. Following heat inactivation of SapI, the component polynucleotide fragments are subjected to denaturing conditions, followed by annealing conditions sufficient for hybridization of the complementary annealable linker pairs. Following primer extension in the presence of DNA polymerase and dNTPs, primers complementary to PA and PB are added, followed by traditional PCR amplification. An assembled polynucleotide comprising component polynucleotides $D_0$, $D_1$, $D_2$, and $D_3$ assembled in a 5' to 3' direction is produced as a result of the assembling reaction.

FIG. 4 shows a map of the pRYSE vector.

FIG. 5 shows assembled polynucleotides obtained by assembling 2 to 4 component polynucleotides (Assemblies 1 through 6 in Table 7) using different methods for removing the SapI restriction endonuclease (column purification or heat inactivation), different assembly vector DNA concentrations (5 ng (low DNA concentration) or 50 ng (high DNA concentration) of smallest fragment with equal molar concentration of all other fragments, and different annealing temperatures for PCR amplification (54° C. and 72° C.).

FIG. 6 shows assembled polynucleotides obtained by assembling 6 or 9 component polynucleotides (Assemblies 7, and 13 through 16 in Table 7) using different DNA polymerases (Phusion (New England Biolabs, Ipswich, Mass.) and PfuUltraII (Stratagene/Agilent, La Jolla, Calif.)).

FIG. 7 shows a map of the pMULE vector. The pMULE entry vector differs from the pRYSE entry vector in that it lacks a primer binding segments or annealable linker sequences.

FIG. 8 present an exemplary method of combining assembled polynucleotides into a combined polynucleotide by host cell mediated homologous recombination, and integrating the combined polynucleotide into a chromosome of the host cell. Assembled polynucleotide A comprises a DNA segment $D_{m1}$ encoding a first non-functional segment of a selectable marker and a DNA segment $D_{01}$ encoding an upstream genomic targeting sequence. Assembled polynucleotide B comprises a DNA segment $D_{m2}$ encoding a second non-functional segment of the selectable marker and a DNA segment $D_{02}$ encoding a downstream genomic targeting sequence. The host cell recombines assembled polynucleotide A and assembled polynucleotide B at the region of homology in DNA segments $D_{m1}$ and $D_{m2}$ to form a combined polynucleotide comprising a functional selectable marker, and uses the genomic targeting sequences encoded by DNA segments $D_{01}$ and $D_{02}$ to insert the combined polynucleotide by homologous recombination into its chromosome.

FIG. 9 presents an exemplary method of generating an assembled polynucleotide by homologous recombination in a host cell and integration of the assembled polynucleotide into the chromosome of the host cell. In the first step, an assembly composition comprising assembly vectors is digested with a restriction endonuclease, resulting in the excision of component polynucleotides from the assembly vector backbones. In the second step, the component polynucleotides are introduced into a host cell where they are recombined at the regions of homology in the annealable linker sequences to form an assembled polynucleotide, and the assembled polynucleotide is integrated into the chromosome of the host cell.

FIG. 10 presents an exemplary method of assembling a plurality of assembled polynucleotide from seven (7) component polynucleotides in the same reaction. Assembly vectors comprising DNA segments to be assembled are pooled in a single tube and digested with SapI to release component polynucleotides from the assembly vector backbones. Following heat inactivation of SapI the component polynucleotide fragments are subjected to denaturing conditions, followed by annealing conditions sufficient for hybridization of the complementary annealable linker pairs. Following primer extension in the presence of DNA polymerase and dNTPs, primers complementary to PA and PB are added, followed by traditional PCR amplification. The assembly reaction results in the production of an assembled polynucleotide comprising component polynucleotides $D_{01/02}$, $D_{1/2}$, $D_3$, and $D_{41/42}$ assembled in a 5' to 3' direction.

FIG. 11 presents an exemplary method of generating a plurality of host cells comprising combinatorially combined polynucleotides. Assembled polynucleotides A1 and A2, each comprising the same upstream genomic targeting sequence and the same first non-functional portion of a selectable marker, and assembled polynucleotides B1 and B2, each comprising the same downstream genomic targeting sequence and the same second non-functional portion of a selectable marker, are combinatorially combined by host cell mediated homologous recombination to generate four different combined polynucleotides, A1/B1, A1/B2, A2/B1, and A2/B2, each comprising a functional selectable marker, that can be inserted into a chromosome to generate four different host cells.

FIG. 12A shows the component polynucleotides used in Example 10 for the high-throughput generation of combinatorially assembled polynucleotides and yeast cells comprising combinatorially assembled and combined polynucleotides, and the expected assembled and combined polynucleotides. US=upstream genomic targeting sequence, DS=downstream genomic targeting sequence, P=various promoter sequences, G=various protein coding sequences, URA=5' segment of selectable marker, RA3=3' segment of selectable marker, PA=primer binding segment PmeI-5', PB=primer binding segment PmeI-3', $LB_0$=annealable linker sequence RYSE 2, $LA_{n1}$=annealable linker sequence RYSE 2, $LB_{n1}$=annealable linker sequence RYSE 15, $LA_{n2}$=annealable linker sequence RYSE 3, $LB_{n2}$=annealable linker sequence RYSE16, $LA_{n3}$=annealable linker sequence RYSE 15, $LB_{n3}$=annealable linker sequence RYSE 3, $LA_{n4}$=annealable linker sequence RYSE 16, $LB_{n4}$=annealable linker sequence RYSE 4, $LA_{m1}$=annealable linker sequence RYSE 3, $LA_{m2}$=annealable linker sequence RYSE 4, $LA_{m3}$=annealable linker sequence RYSE 3.

Figure 14:
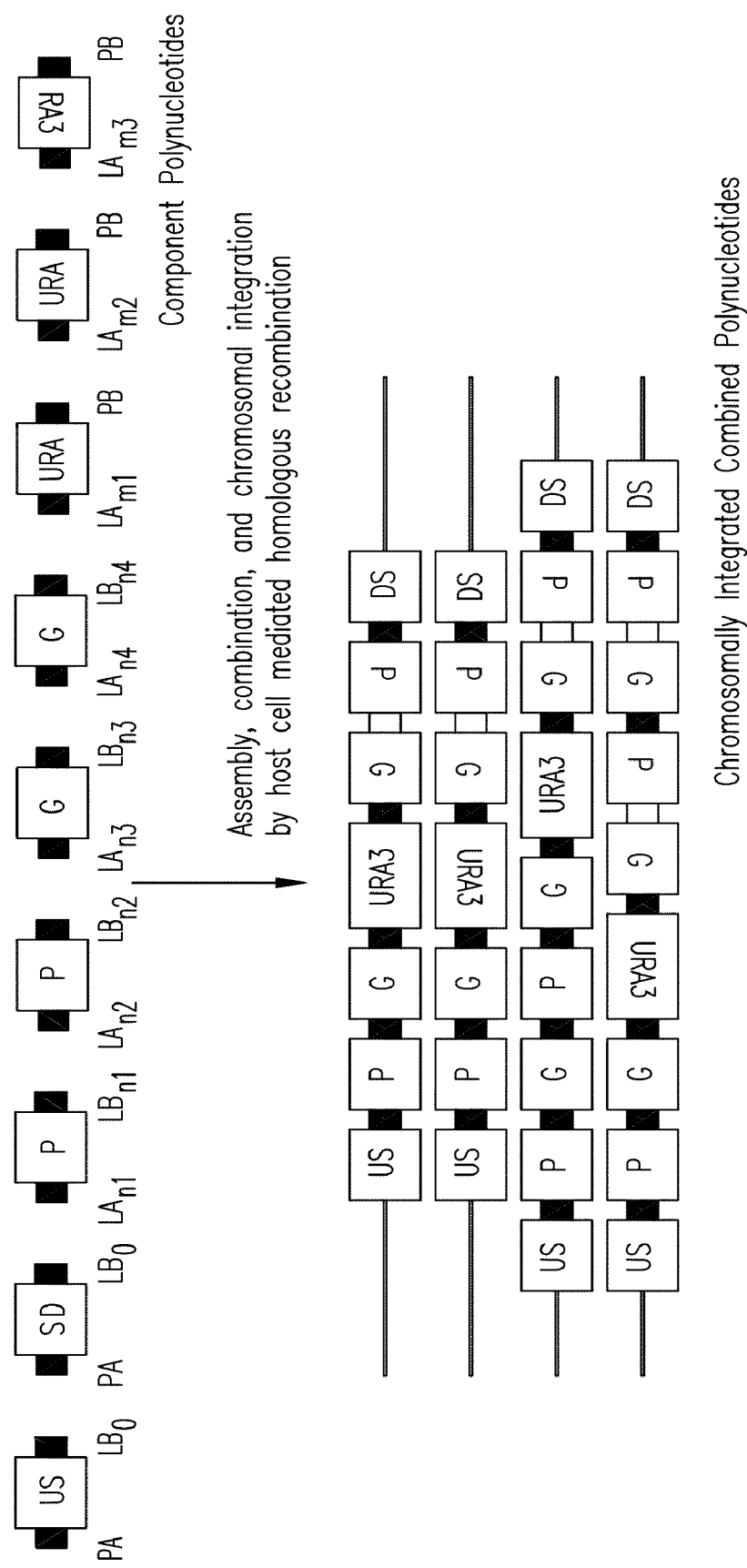

FIG. 14 shows the component polynucleotides used in Example 12 for the high-throughput generation of yeast cells comprising chromosomally integrated combinatorially assembled and combinatorially combined polynucleotides, and the expected combined polynucleotides obtained upon assembly and combination by host cell mediated homologous recombination. US=upstream genomic targeting sequence, DS=downstream genomic targeting sequence, P=various promoter sequences, G=various protein coding sequences, URA=5' segment of selectable marker, RA3=3' segment of selectable marker, PA=primer binding segment PmeI-5', PB=primer binding segment PmeI-3', $LB_0$=annealable linker sequence RYSE 2, $LA_{n1}$=annealable linker sequence RYSE 2, $LB_{n1}$=annealable linker sequence RYSE 15, $LA_{n2}$=annealable linker sequence RYSE 3, $LB_{n2}$=annealable linker sequence RYSE16, $LA_{n3}$=annealable linker sequence RYSE 15, $LB_{n3}$=annealable linker sequence RYSE 3, $LA_{n4}$=annealable linker sequence RYSE 16, $LB_{n4}$=annealable linker sequence RYSE 4, $LA_{m1}$=annealable linker sequence RYSE 3, $LA_{m2}$=annealable linker sequence RYSE 4, $LA_{m3}$=annealable linker sequence RYSE 3.

5. DETAILED DESCRIPTION OF THE EMBODIMENTS

5.1 Definitions

As used herein, the term "polynucleotide" refers to a polymer composed of nucleotide units as would be understood by one of skill in the art. Preferred nucleotide units include but are not limited to those comprising adenine (A), guanine (G), cytosine (C), thymine (T), and uracil (U). Useful modified nucleotide units include but are not limited to those comprising 4-acetylcytidine, 5-(carboxyhydroxylmethyl)uridine, 2-O-methylcytidine, 5-carboxymethylaminomethyl-2-thiouridine, 5-carboxymethylamino-methyluridine, dihydrouridine, 2-O-methylpseudouridine, 2-O-methylguanosine, inosine, N6-isopentyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, 5-methoxyuridine, 5-methoxycarbonylmethyl-2-thiouridine, 5-methoxycarbonylmethyluridine, 2-methylthio-N6-isopentyladenosine, uridine-5-oxyacetic acid-methylester, uridine-5-oxyacetic acid, wybutoxosine, wybutosine, pseudouridine, queuosine, 2-thiocytidine, 5-methyl-2-thiouridine, 2-thiouridine, 4-thiouridine, 5-methyluridine, 2-O-methyl-5-methyluridine, 2-O-methyluridine, and the like. Polynucleotides include naturally occurring nucleic acids, such as deoxyribonucleic acid ("DNA") and ribonucleic acid ("RNA"), as well as nucleic acid analogs. Nucleic acid analogs include those that include non-naturally occurring bases, nucleotides that engage in linkages with other nucleotides other than the naturally occurring phosphodiester bond or that include bases attached through linkages other than phosphodiester bonds. Thus, nucleotide analogs include, for example and without limitation, phosphorothioates, phosphorodithioates, phosphorotriesters, phosphoramidates, boranophosphates, methylphosphonates, chiral-methyl phosphonates, 2-O-methyl ribonucleotides, peptide-nucleic acids (PNAs), and the like.

As used herein, a "component polynucleotide" refers to a polynucleotide sequence that can be assembled together to form a "assembled polynucleotide" using the methods of polynucleotide assembly described herein. When a plurality of assembly vectors are digested with one or more restriction endonucleases capable of excising the component polynucleotides from the assembly vectors, the resulting population of component polynucleotides can comprise the totality of DNA segments to be assembled into a assembled polynucleotide.

As used herein, an "assembled polynucleotide" refers to a polynucleotide produced by the methods of polynucleotide assembly described herein. The assembled polynucleotide can be comprised of the two or more component polynucleotides. In some embodiments, the assembled polynucleotide comprises 2, 3, 4, 5, 6, 7, 8, 9, 10, 11, 12, 13, 14, 15 or more component polynucleotides. Assembled polynucleotide length can range from about 100 to about 20,000 nucleotides, or more. In some embodiments, the assembled polynucleotide length ranges from about 200 to about 10,000, about 200 to about 8000, about 200 to about 5000, about 200 to about 3000, or about 200 to about 1000 nucleotides. In other embodiments, the assembled polynucleotide length can range from about 200 to about 2000, about 2000 to about 5000, about 5000 to about 10,000, about 10,000 to about 20,000, or greater than 20,000 nucleotides.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

As used herein, the term "DNA segment," alternately referred to as "Bits" in the examples below, refers to any isolated or isolatable molecule of DNA. Useful examples include but are not limited to a protein-coding sequence, reporter gene, fluorescent marker coding sequence, promoter, enhancer, terminator, intron, exon, poly-A tail, multiple cloning site, nuclear localization signal, mRNA stabilization signal, selectable marker, integration loci, epitope tag coding sequence, degradation signal, or any other naturally occurring or synthetic DNA molecule. In some embodiments, the DNA segment can be of natural origin. Alternatively, a DNA segment can be completely of synthetic origin, produced in vitro. Furthermore, a DNA segment can comprise any combination of isolated naturally occurring DNA molecules, or any combination of an isolated naturally occurring DNA molecule and a synthetic DNA molecule. For example, a DNA segment may comprise a heterologous promoter operably linked to a protein coding sequence, a protein coding sequence linked to a poly-A tail, a protein coding sequence linked in-frame with a epitope tag coding sequence, and the like.

"Complementary" refers to the topological compatibility or matching together of interacting surfaces of two polynucleotides as understood by those of skill in the art. Thus, two sequences are "complementary" to one another if they are capable of hybridizing to one another to form a stable anti-parallel, double-stranded nucleic acid structure. A first polynucleotide is complementary to a second polynucleotide if the nucleotide sequence of the first polynucleotide is substantially identical to the nucleotide sequence of the polynucleotide binding partner of the second polynucleotide, or if the first polynucleotide can hybridize to the second polynucleotide under stringent hybridization conditions. Thus, the polynucleotide whose sequence 5'-TATAC-3' is complementary to a polynucleotide whose sequence is 5'-GTATA-3'.

"Primer" refers to a polynucleotide sequence that is capable of specifically hybridizing to a polynucleotide template sequence, e.g., a primer binding segment, and is capable of providing a point of initiation for synthesis of a complementary polynucleotide under conditions suitable for synthesis, i.e., in the presence of nucleotides and an agent that catalyzes the synthesis reaction (e.g., a DNA polymerase). The primer is complementary to the polynucleotide template sequence, but it need not be an exact complement of the polynucleotide template sequence. For example, a primer can be at least about 80, 85, 90, 95, 96, 97, 98, or 99% identical to the complement of the polynucleotide template sequence. A primer can be of variable length but generally is at least 15 bases. In some embodiments, the primer is between 15 and 35 bases long. In some embodiments, the primer is more than 35 bases long. In other embodiments, the primer has a melting temperature ($T_m$), i.e., the temperature at which one half of the DNA duplex will dissociate to become single stranded, of at least 50° C. In other embodiments, the primer has a $T_m$ between about 50° C. and 70° C. In still other embodiments, the primer does not form appreciable DNA or RNA secondary structures so as to not impact the efficiency of hybridization to the polynucleotide template sequence.

As used herein, the term "primer binding segment" is a polynucleotide sequence that binds to a primer so as to provide a point of initiation for synthesis of a complementary polynucleotide under conditions suitable for synthesis. In some embodiments, the primer binding sequence is one of the annealable linkers of the present invention. A sequence is a primer binding sequence instead of an annealable linker by the absence of a complementary linker within a given set of assembly vectors or component polynucleotides within an assembly composition. In some embodiments, the primer binding segment can function as a genomic targeting sequence, e.g., an upstream or downstream genomic targeting sequence.

As used herein, the term "linker sequence" and "annealable linker sequence" are used interchangeably and refer to a polynucleotide sequence contained within an entry vector and assembly vector described herein. In particular, an annealable linker sequence flanks a DNA segment within an entry vector or assembly vector. Upon excision of a component polynucleotide from an assembly vector, and denaturation of the component polynucleotide, an annealable linker is capable of specifically hybridizing to a complementary annealable linker sequence of an adjacent component polynucleotide in a polynucleotide assembly reaction, as described herein. An annealable linker, upon annealing with a complementary linker strand, can provide a point of initiation for synthesis of a complementary polynucleotide.

As used herein, the term "vector" is used in reference to extrachromosomal nucleic acid molecules capable of replication in a cell and to which an insert sequence can be operatively linked so as to bring about replication of the insert sequence. Useful examples include but are not limited to circular DNA molecules such as plasmid constructs, phage constructs, cosmid vectors, etc., as well as linear nucleic acid constructs (e.g., lambda phage constructs, bacterial artificial chromosomes (BACs), yeast artificial chromosomes (YACs), etc.). A vector may include expression signals such as a promoter and/or a terminator, a selectable marker such as a gene conferring resistance to an antibiotic, and one or more restriction sites into which insert sequences can be cloned. Vectors can have other unique features (such as the size of DNA insert they can accommodate).

As used herein, the term "entry vector" refers to a cloning vector plasmid that can serve as a parental vector for the preparation of an assembly vector to be used in the polynucleotide assembly methods provided herein. An entry vector comprises two annealable linker sequences, or an annealable linker sequence and a primer binding segment, which flank restriction sites that can be utilized for the introduction of a DNA segment to form an assembly vector. As used herein, an "assembly vector" refers to an entry vector to which a DNA segment has been introduced. An assembly vector can be used in the polynucleotide assembly methods described herein to provide a component polynucleotide to be assembled into a assembled polynucleotide.

As used herein, the term "assembly vector" refers to a vector comprising one annealable linker sequence, two annealable linker sequences, or an annealable linker sequence and a primer binding segment, and a DNA segment.

As used herein, the term "restriction enzyme" or "restriction endonuclease" refers to a member or members of a classification of catalytic molecules that bind a cognate sequence of DNA and cleave the DNA molecule at a precise location within that sequence. Restriction endonucleases include Type IIS restriction endonucleases. This class of enzymes differs from other restriction endonucleases in that the recognition sequence is separate from the site of cleavage. Some examples of Type IIS restriction enzymes include AlwI, BsaI, BbsI, BbuI, BsmAI, BsrI, BsmI, BspMI, EarI, Esp3I, FokI, HgaI, HphI, LguI, MboII, MnlI, PleI, SapI, SchI, SfaNi, and the like. Many of these restriction endonucleases are available commercially and are well known to those skilled in the art.

As used herein, the term "annealable linker sequence duplex" refers to one annealable linker sequence strand aligned with a substantially complementary annealable linker sequence strand in antiparallel association. Complementarity need not be perfect; annealable linker sequence duplexes may contain mismatched base pairs or unmatched bases, although in particular embodiments, the annealable linker sequence duplex comprises two annealable linker sequence strands having perfect complementarity.

As used herein, the term "genomic targeting sequence" refers to a nucleotide sequence that is present in the genome of a host cell at a site at which a polynucleotide of the invention is to be inserted by host cell mediated homologous recombination. The terms "upstream genomic targeting sequence" and "downstream genomic targeting sequence" refer to genomic targeting sequences that are located upstream and downstream of each other in the genome of a host cell.

As used herein, the term "chromosomal targeting sequence" refers to a nucleotide sequence that is present in a chromosome of a host cell at a site at which a polynucleotide of the invention is to be inserted by host cell mediated homologous recombination. The terms "upstream chromosomal targeting sequence" and "downstream chromosomal targeting sequence" refer to chromosomal targeting sequences that are located upstream and downstream of each other in a chromosome of a host cell.

5.2 Methods of Polynucleotide Assembly

Figure 1A:
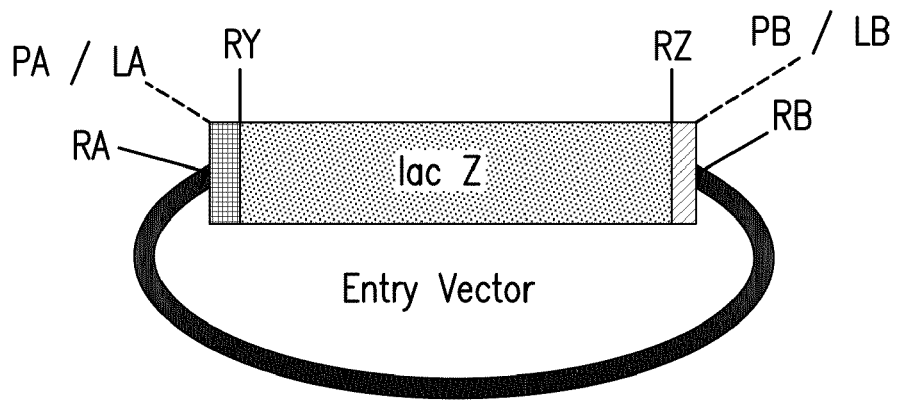
Figure 1B:
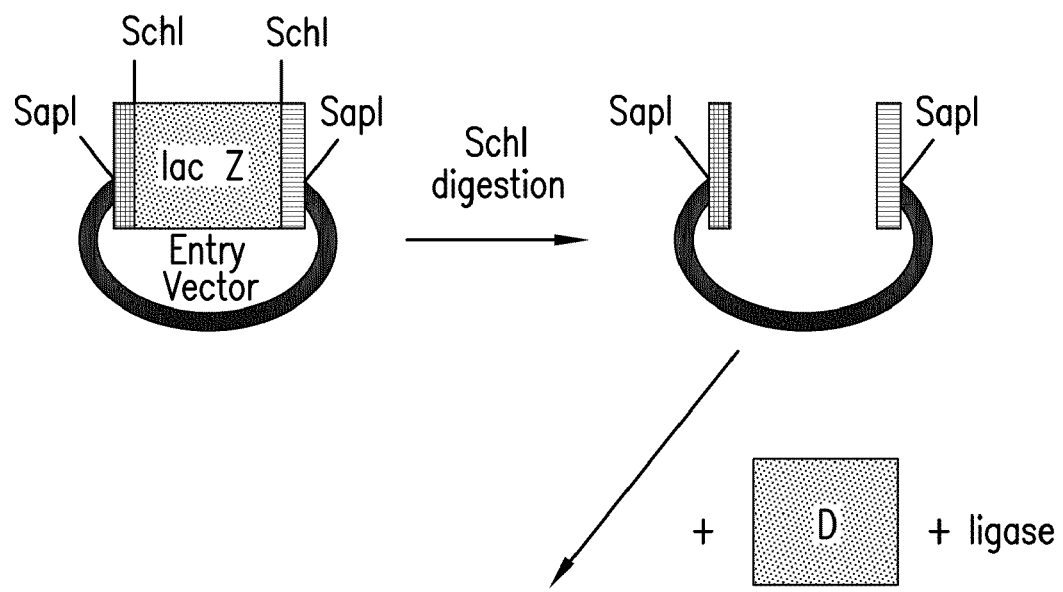
Figure 1B:
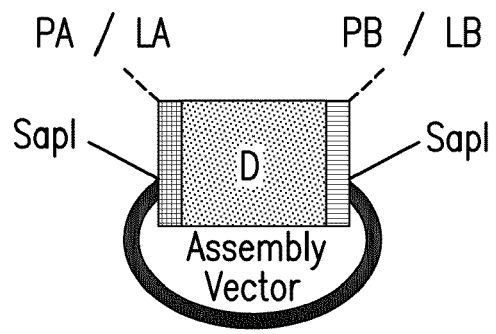
Figure 3:
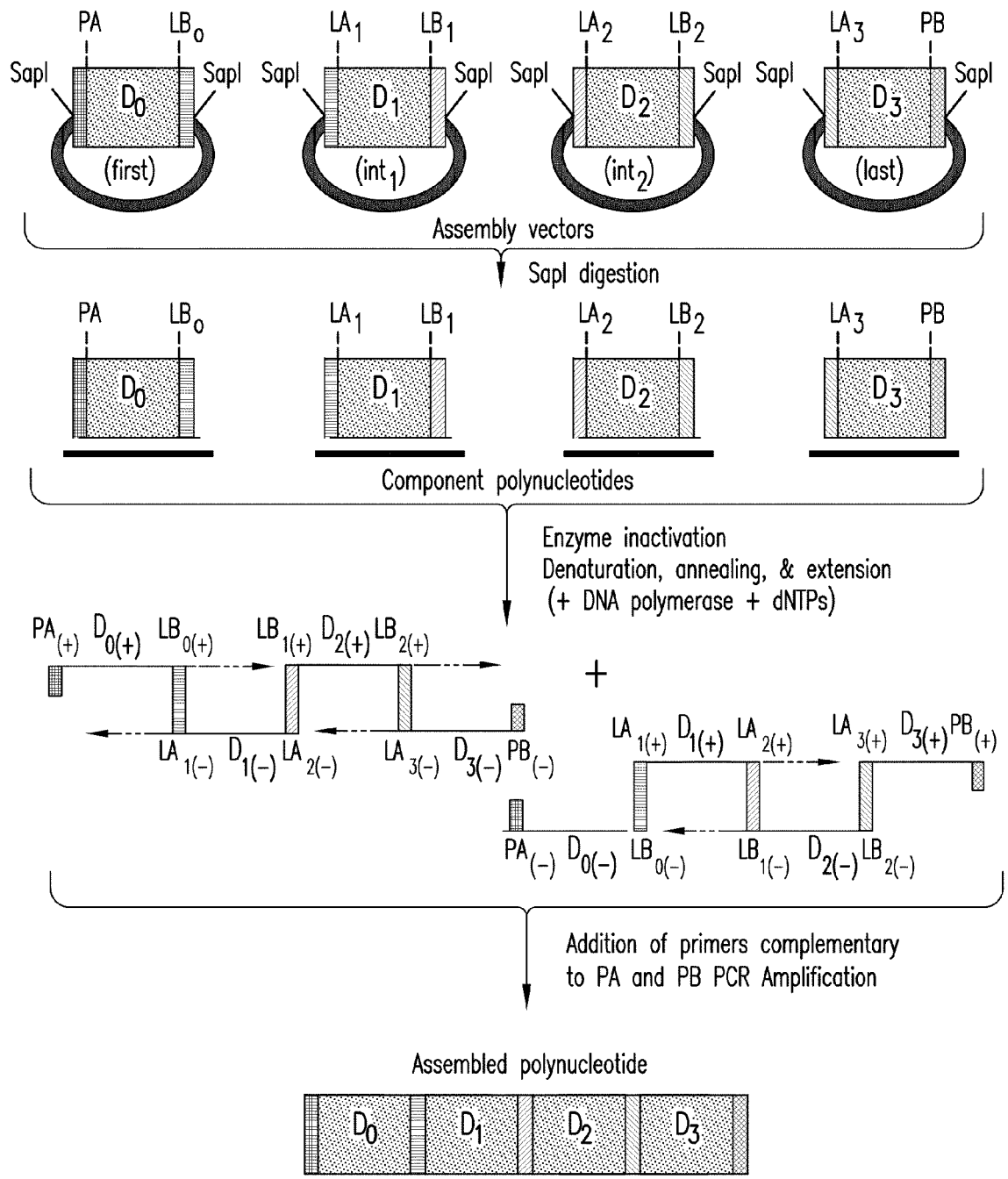

In one aspect, the present invention provides rapid, robust, and high-throughput methods for the ordered assembly of a plurality of component polynucleotides into one or more assembled polynucleotides. The methods of the invention utilize circular nucleic acid vectors, termed assembly vectors, that each comprise a DNA segment, D, flanked by an annealable linker sequence (i.e., LA or LB), a pair of annealable linker sequences (i.e., LA and LB), or an annealable linker sequence and a primer binding segment (i.e., LA and PB or LB and PA), and a pair of restriction sites, RA and RB (FIG. 1B). Restriction endonuclease digestion of a plurality of assembly vectors at restriction sites RA and RB generates a plurality of component polynucleotides comprising the elements 5'-LA-D-3', 5'-D-LB-3', 5'-LA-D-LB-3', 5'-LA-D-PB-3', or 5'-LB-D-PA-3' (FIG. 3). In the methods of the invention annealable linker sequences LA and LB provide the component polynucleotides with complementary termini that are utilized in a splice overlap extension assembly reaction followed by polymerase chain reaction (SOE/PCR) to assemble the component polynucleotides into an assembled polynucleotide with an ordered sequence.

In particular, the methods can provide for assembly into a single assembled polynucleotide of a number of functional DNA elements, including but not limited to protein-coding sequences, reporter genes, fluorescent marker coding sequences, promoters, enhancers, terminators, introns, exons, poly-A tails, multiple cloning sites, nuclear localization signals, mRNA stabilization signals, selectable markers, integration loci, epitope tag coding sequences, and degradation signals. The methods can be used for the assembly of any type of assembled polynucleotide, including but not limited to synthetic genes, constructs, cloning vectors, expression vectors, chromosomes, genomic integration constructs, genomes, and DNA libraries. Furthermore, the methods can be used to assemble DNA segments in a single reaction without need for manipulation and characterization of intermediate products.

In some embodiments, the methods can also provide for the assembly of an assembled polynucleotide from a plurality of component polynucleotides not originating from an assembly vector (i.e., DNA segments obtained by standard procedures known in the art, such as for example, PCR amplification, chemical synthesis, and the like, that are flanked by one or two annealable linker sequences, LA and/or LB, or by an annealable linker sequence and a primer binding segment (i.e., LA and PB or LB and PA). The component polynucleotides not originating from an assembly vector may be added to the assembly reaction at any stage prior to the SOE/PCR reaction or host cell mediated homologous recombination for assembly into the assembled polynucleotide. Thus, in some embodiments, the assembly methods can be used to assemble: (1) component polynucleotides derived from assembly vectors comprising one or two annealable linker sequences, or an annealable linker sequence and a primer binding segment, and generated by digestion of the assembly vectors; (2) vectorless DNA fragments flanked by one or two annealable linker sequences, or by an annealable linker sequence and a primer binding segment; and (3) combinations thereof.

In some embodiments, provided herein are methods of assembling a plurality of component polynucleotides into one or more assembled polynucleotides, comprising the steps of:
 (a) digesting an assembly composition with one or more restriction endonucleases to generate a components composition, the assembly composition comprising:
  (i) one or more first nucleic acid molecules, wherein each first nucleic acid molecule is circular and comprises, in a 5' to 3' orientation, a first restriction site $RA_0$, any primer binding segment selected from the group PA, any DNA segment selected from the group $D_0$, an annealable linker sequence $LB_0$, and a second restriction site $RB_0$;
  (ii) one or more intermediate nucleic acid molecules wherein each intermediate nucleic acid molecule n is circular and comprises, in a 5' to 3' orientation, a first restriction site $RA_n$, a first annealable linker sequence $LA_n$, any DNA segment selected from the group $D_n$, a second annealable linker sequence $LB_n$, and a second restriction site $RB_n$, and wherein n represents an integer from one to the number of intermediate nucleic acid molecules; and
  (iii) one or more last nucleic acid molecules, wherein each last nucleic acid molecule is circular and comprises, in a 5' to 3' orientation, a first restriction site $RA_m$, an annealable linker sequence $LA_m$, a DNA segment selected from the group $D_m$, any primer binding segment selected from the group PB, a second restriction site $RB_m$ wherein m represents an integer one greater than the number of intermediate nucleic acid molecules; whereupon cleavage of restriction sites $RA_0$ through $RB_m$ and denaturation of the resulting linear nucleic acid molecules, each annealable linker sequence $LB_{(p-1)}$ is capable of hybridizing to the complement of annealable linker sequence $LA_p$, wherein n is an integer that varies from 1 to (m−1), wherein p represents an integer from 1 to m, and wherein each group $D_0, \ldots D_n, \ldots$ and $D_m$ consists of one or more DNA segments;
 wherein the one or more restriction endonucleases are capable of cleaving the restriction sites $RA_0$ through $RB_m$; and
 (b) contacting the components composition with DNA polymerase, deoxyribonucleoside triphosphates and one or more first primers and one or more second primers, under conditions suitable for denaturation of the nucleic acid molecules, annealing of annealable linker sequence $LB_{(p-1)}$ to annealable linker sequence $LA_p$, and extension therefrom; wherein each said first primer is capable of hybridizing to one of said primer binding segments selected from the group PA and each said second primer is capable of hybridizing to one of said primer binding segments selected from the group PB; and subjecting the components composition to polymerase chain reaction, wherein a polynucleotide is assembled which comprises, in a 5' to 3' orientation, one DNA segment selected from each of the groups $D_0, \ldots D_n, \ldots$ and $D_m$. In the method, p represents the integers from 1 to m.

FIG. 3 depicts one embodiment of the assembly methods of the invention for illustrative purposes. In this example, a total of four component polynucleotides are assembled to yield an assembled polynucleotide. However, the assembly methods provided herein can be used to assemble any number of component polynucleotides into one or more assembled polynucleotides. In some embodiments, the methods provided herein result in the assembly of 2, 3, 4, 5, 6, 7, 8, 9, 10, 11, 12, 13, 14, 15, or more component polynucleotides into one or more assembled polynucleotides.

In the example illustrated in FIG. 3, the assembly composition from which the assembled polynucleotide is generated comprises four input assembly vectors, denoted "first," "intermediate 1 ($int_1$)," "intermediate 2 ($int_2$)," and "last." Each assembly vector comprises a DNA segment flanked either by an annealable linker sequence and a primer binding segment, or by two annealable linker sequences. Specifically, DNA segment $D_0$ is flanked by 5' primer binding segment PA and 3' annealable linker sequence $LB_0$. DNA segment $D_1$ is flanked by 5' and 3' annealable linker sequences $LA_1$ and $LB_1$, and DNA segment $D_2$ is flanked by 5' and 3' annealable linker sequences $LA_2$ and $LB_2$. DNA segment $D_3$ is flanked by 3' primer binding segment PB and 5' annealable linker sequence $LA_3$. The 5'-PA-D-LB-3', 5'-LA-D-LB-3', or 5'-LA-D-PB-3' elements in the assembly vectors are further flanked by SapI restriction endonuclease sites.

Figure 2:
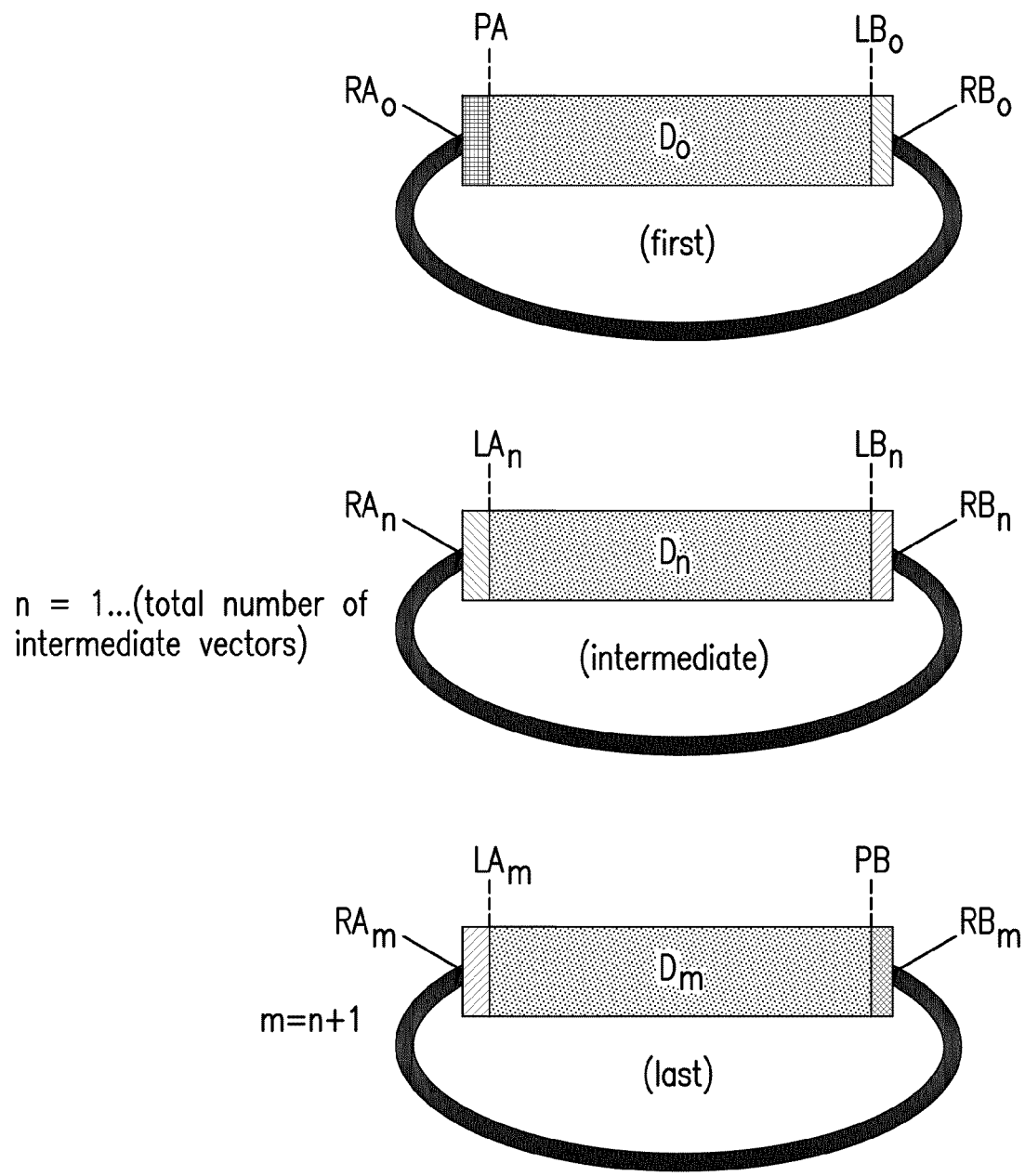

In the first step of the assembly reaction shown in FIG. 3, the assembly composition is digested with SapI, resulting in the excision of component polynucleotides, comprising the elements 5'-PA-D-LB-3', 5'LA-D-LB-3', or 5'-LA-D-PB-3', from the assembly vector backbones into a components composition. Because Sap I is a Type IIS restriction endonuclease, its recognition site is distal to its cleavage site, and cleavage occurs outside of its recognition sequence. This property makes Type IIS restriction endonucleases particularly useful in the assembly of a polynucleotide according to the methods provided herein, since polynucleotides can be assembled which do not comprise a restriction-site scar, which may otherwise result from cleavage of restriction sites RA and RB with a non-Type IIS restriction endonuclease. Referring to FIG. 2, the Type IIS recognition site is 5' of the corresponding cleavage site for each of $RA_0$, $RA_n$, and $RA_m$, and 3' of its cleavage site $RB_0$, $RA_n$, and $RA_m$. Thus, restriction sites $RA_0$ through $RB_m$ are oriented so that cleavage by one or more Type IIS restriction endonucleases capable of cleaving $RA_0$ through $RB_m$ results in separation of $RA_0$ from $D_0$, $LB_0$ from $RB_0$, $RA_n$, from $LA_n$, $LB_n$ from $RB_n$, $RA_m$ from $LA_m$, and $D_m$ from $RB_m$, wherein resultant linearized nucleic acid molecules comprising $D_0$, $LB_0$, $RA_n$, $LB_n$, $LA_m$ or $D_m$ do not comprise any of $RA_0$ through $RB_m$. As a consequence, the resulting component polynucleotides do not include any trace of either the restriction enzyme's recognition or cleavage sites. As a result, the inventive methods of polynucleotide assembly can be used to transform host cells multiple times without the introduction of sequence repeats which may cause genetic instability.

Subsequently, the restriction endonuclease is optionally inactivated. If inactivation is desired, any method known in the art for inactivating endonuclease enzyme activity may be employed, including column or gel-based purification methods. One convenient method is heat inactivation, e.g., at 65° for 20 minutes, which requires little or no manipulation of the components composition outside of the reaction tube.

Assembly of the component polynucleotides into an assembled polynucleotide is enabled by sequence duplexes formed by overlapping strands of complementary termini among the component polynucleotides. Specifically, the annealable linker sequences are designed such that annealable linker sequence $LB_0$ can hybridize to the complement of annealable linker sequence $LA_1$, annealable linker sequence $LB_1$ can hybridize to the complement of annealable linker sequence $LA_2$, and annealable linker sequence $LB_2$ can hybridize to the complement of annealable linker sequence $LA_3$. Thus, in the second step of the assembly reaction, the component polynucleotides are subjected to denaturing conditions (e.g., heat) to generate single-stranded component polynucleotides, which concomitant with or subsequent to the denaturation step of the assembly reaction are contacted with a thermostable DNA polymerase and deoxyribonucleoside triphosphates.

The thermostable DNA polymerase can be any thermostable DNA polymerase deemed suitable by those of skill in the art. Thermostable DNA polymerases suitable for use in the present methods include but are not limited to *Thermus thermophilus* (Tth) DNA polymerase, *Thermus aquaticus* (Taq) DNA polymerase, *Thermotoga neopolitana* (Tne) DNA polymerase, *Thermotoga maritima* (Tma) DNA polymerase, *Therm°C°Ccus litoralis* (Tli or VENT™) DNA polymerase, *Pyr°C°Ccus furiosus* (Pfu or DEEPVENT™) DNA polymerase, *Pyr°C°Ccus woosii* (Pwo) DNA polymerase, *Bacillus sterothermophilus* (Bst) DNA polymerase, *Sulfolobus acid°Caldarius* (SAC) DNA polymerase, *Thermoplasma acidophilum* (Tac) DNA polymerase, *Thermus flavus* (Tfl/Tub) DNA polymerase, *Thermus ruber* (Tru) DNA polymerase, *Thermus br°Ckianus* (DYNAZYME™) DNA polymerase, *Methanobacterium thermoautotrophicum* (Mth) DNA polymerase, and mutants, variants, and derivatives thereof. Thermostable DNA polymerases having high fidelity (i.e., proofreading properties) and low error rates are preferred. In certain embodiments, the DNA polymerase is Phusion™ DNA Polymerase (New England Biolabs, Ipswich, Mass.). In other embodiments, the DNA Polymerase is PfuUltra™ II Fusion DNA Polymerase (Strategene/Agilent, La Jolla, Calif.).

The assembly reaction is then subjected to conditions that allow for strand elongation from the 3'-hydroxyl portions of the overlapping annealable linker sequences, during which the thermostable DNA polymerase fills in the portion between the overlapping annealable linker sequences. The assembly reaction is subjected to a limited number of repeating cycles of denaturation/annealing/extension (e.g., for 5-15 cycles) during which a substantial amount of double-stranded assembled polynucleotides are formed. During this cycling, the component polynucleotides act as both primers and template to generate a full length template for the assembled polynucleotide. In certain embodiments, the annealing and extension steps of the PCR can both be performed at 72° C.

In contrast to the annealable linker sequences LA and LB, the primer binding segments PA and PB are designed to not overlap with each other or any of the annealable linker sequences or DNA segments, but rather serve as binding sites for primers used to amplify the full length assembled polynucleotide. Thus, in steps 4 and 5 of the assembly reaction, primers complementary to primer binding segments PA and PB are added, and the composition is subjected to traditional PCR amplification conditions. The PCR amplification conditions can be any PCR amplification conditions deemed suitable by those of skill in the art, including those described in *PCR Technology: Principles and Applications for DNA Amplification*, ed. H A Erlich, Stockton Press, New York, N.Y. (1989); *PCR Prot°Cols: A Guide to Methods and Applications*, eds. Innis, Gelfland, Snisky, and White, Academic Press, San Diego, Calif. (1990); Mattila et al. (1991)*Nucleic Acids Res.* 19: 4967; Eckert, K. A. and Kunkel, T. A. (1991) PCR Methods and Applications 1: 17; and U.S. Pat. Nos. 4,683,202 and 4,965,188, each of which are incorporated herein by reference. In certain embodiments, the PCR step of the assembly reaction comprises about 35 cycles of denaturation, annealing, and extension in the presence of primers complementary to primer binding segments PA and PB. In certain embodiments, the annealing and extension steps of the PCR can both be performed at 72°. However, one of skill in the art will understand that optimal conditions for successful amplification will depend on the thermostable DNA polymerase and the annealable linker sequences utilized, and these conditions may be adjusted accordingly.

Optionally, the assembled polynucleotide can be purified by any technique apparent to one of skill in the art, e.g., gel electrophoresis purification methods and used for a variety of purposes. For example, the assembled polynucleotide can be inserted into an expression vector backbone for sequence verification.

5.3 Methods of Generating Host Cells Comprising Assembled Polynucleotides

In another aspect, the present invention provides methods for generating host cells comprising assembled polynucleotides. In some embodiments, the assembled polynucleotide is at least 3 kb in size. In other embodiments, the assembled polynucleotide is at least 5 kb in size. In still other embodiments, the assembled polynucleotide is at least 6, 7, 8, 9, or 10 kb in size. In still other embodiments, the assembled polynucleotide is greater than 10 kb in size. In still other embodiments, the assembled polynucleotide is greater than 15 kb in size. In still other embodiments, the assembled polynucleotide is greater than 20 kb in size.

In some embodiments, methods are provided that comprise transforming a host cell with an assembled polynucleotide generated by the methods of polynucleotide assembly described herein. The assembled polynucleotide can be circularized prior to transformation or can be transformed as a linear molecule. The assembled polynucleotide can be maintained in the host cell as an extrachromosomal polynucleotide. Alternatively, the assembled polynucleotide can be integrated into the genome of the host cell, e.g., by host cell mediated homologous recombination. To integrate an assembled polynucleotide into the genome by homologous recombination, the assembled polynucleotide must comprise at one terminus a nucleic acid sequence comprising an upstream genomic targeting sequence and at the other terminus a nucleic acid sequence comprising a downstream genomic targeting sequence. Accordingly, an assembled polynucleotide that is to be integrated into a chromosome of a host cell is generated from an assembly composition comprising a first nucleic acid molecule comprising an upstream chromosomal targeting sequence and a last nucleic acid molecule comprising a downstream chromosomal targeting sequence, each chromosomal targeting sequence being of sufficient length to initiate homologous recombination by the host cell with its chromosome.

In other embodiments, the methods comprise transforming a host cell with a plurality of assembled polynucleotides generated by the methods of polynucleotide assembly described herein. In a particular embodiment, the host cell combines two or more assembled polynucleotides into a single combined polynucleotide by homologous recombination. Host cell transformants comprising the combined polynucleotides are selected by virtue of expressing a selectable marker that is generated in the process of combining the assembled polynucleotides. The method is particularly useful for inserting relatively large pieces of polynucleotide into a target polynucleotide by homologous recombination. For chromosomal integration to occur, the combined polynucleotide must comprise an upstream genomic targeting sequence located 5' or 3' of the coding sequence of the selectable marker and a downstream genomic targeting sequence located 3' or 5' of the coding sequence of the selectable marker, respectively. Genomic integration as used herein includes chromosomal integration, i.e., integration of a polynucleotide into a chromosome of a host cell. Suitable chromosomal integration sites in *Saccharomyces cerevisiae* include but are not limited to the NDT80, HO, GAL2, and GAL1-GAL10-GAL7 locus. The method can also be useful for generating host cells comprising an extrachromosomally maintained polynucleotide, e.g., vectors and expression plasmids. The stability of either a chromosomally integrated or an extrachromosomally maintained combined polynucleotide is increased when the combined polynucleotide does not comprise identical annealable linker sequences or DNA segments arranged as direct repeats that can otherwise initiate additional homologous recombination events resulting in the excision of segments of the component polynucleotide. Therefore, in some embodiments, the assembled polynucleotides comprise unique annealable linker sequences and DNA segments. In other embodiments, the assembled polynucleotides contain one or more identical annealable linker sequences or DNA segments that upon combination of the assembled polynucleotides are arranged as inverted repeats in the combined polynucleotide.

Figure 8:
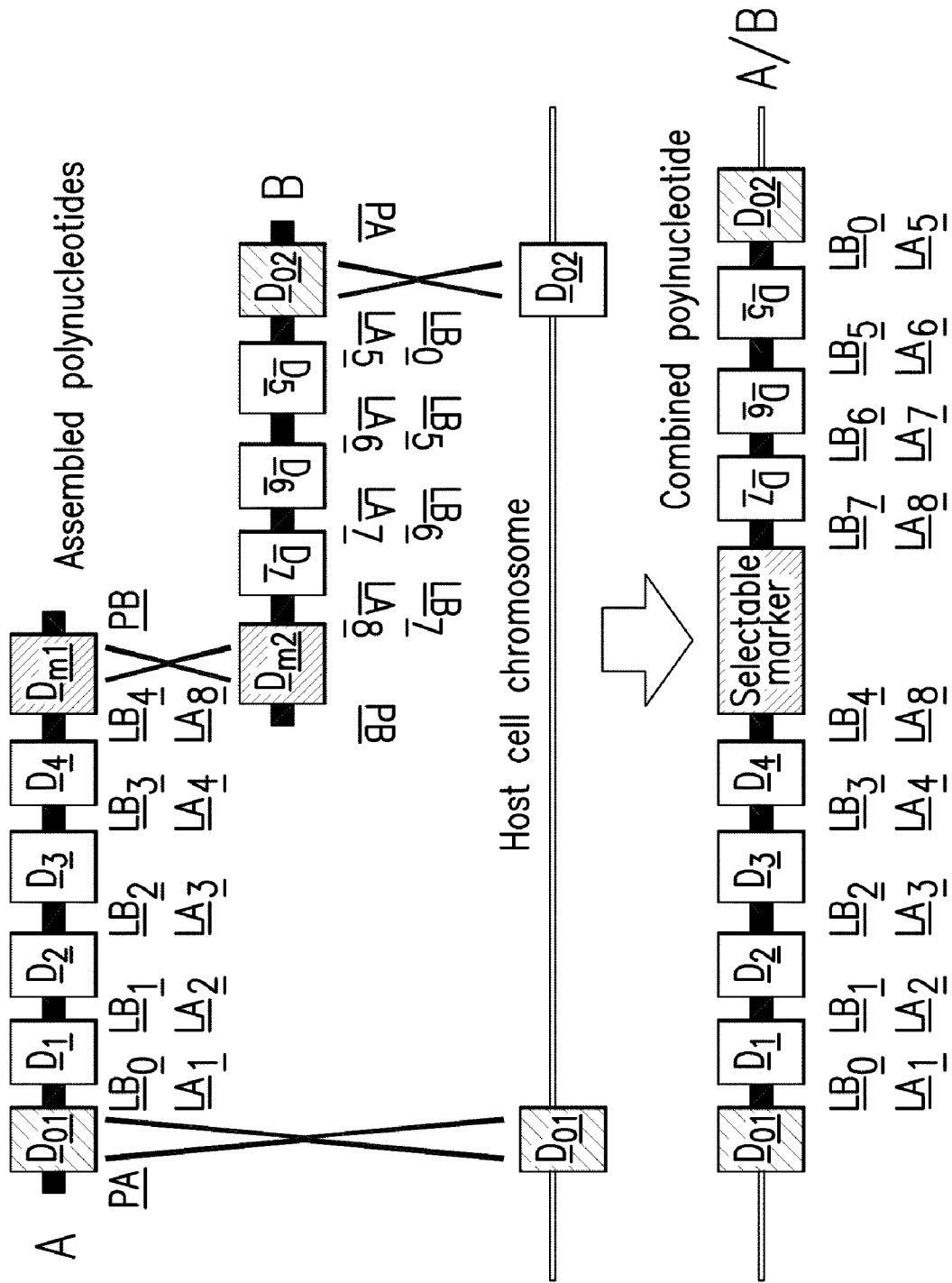

The generation of an exemplary combined polynucleotide and integration of the combined polynucleotide into a chromosome of the host cell by homologous recombination is illustrated in FIG. 8. Two assembled polynucleotides A and B are taken up by a host cell that is capable of homologous recombination. Each assembled polynucleotide comprises a DNA segment $D_m$ that encodes a segment of a selectable marker, wherein DNA segment $D_{m1}$ of assembled polynucleotide A encodes a first segment of a selectable marker and DNA segment $D_{m2}$ of assembled polynucleotide B encodes a second segment of the selectable marker, wherein DNA segment $D_{m1}$ and DNA segment $D_{m2}$ comprise a region of homology sufficient to initiate host cell mediated homologous recombination, and wherein neither DNA segment $D_{m1}$ nor DNA segment $D_{m2}$ produces a functional selectable marker, but whereupon homologous recombination by the host cell a functional selectable marker is generated. Each assembled polynucleotide further comprises a DNA segment $D_0$ encoding a chromosomal targeting sequence of sufficient length to initiate host mediated homologous recombination, wherein DNA segment $D_{01}$ of assembled polynucleotide A encodes an upstream chromosomal targeting sequence and DNA segment $D_{02}$ of assembled polynucleotide B encodes a downstream chromosomal targeting sequence. Once inside the cell, the host cell recombines assembled polynucleotide A and assembled polynucleotide B at the region of homology in DNA segments $D_{m1}$ and $D_{m2}$ to form a combined polynucleotide. Moreover, the host cell uses the chromosomal targeting sequences encoded by DNA segments $D_{01}$ and $D_{02}$ to insert the combined polynucleotide by homologous recombination into its chromosome. Host cells comprising the combined polynucleotide can be readily identified based on the functional selectable marker generated.

Figure 9:
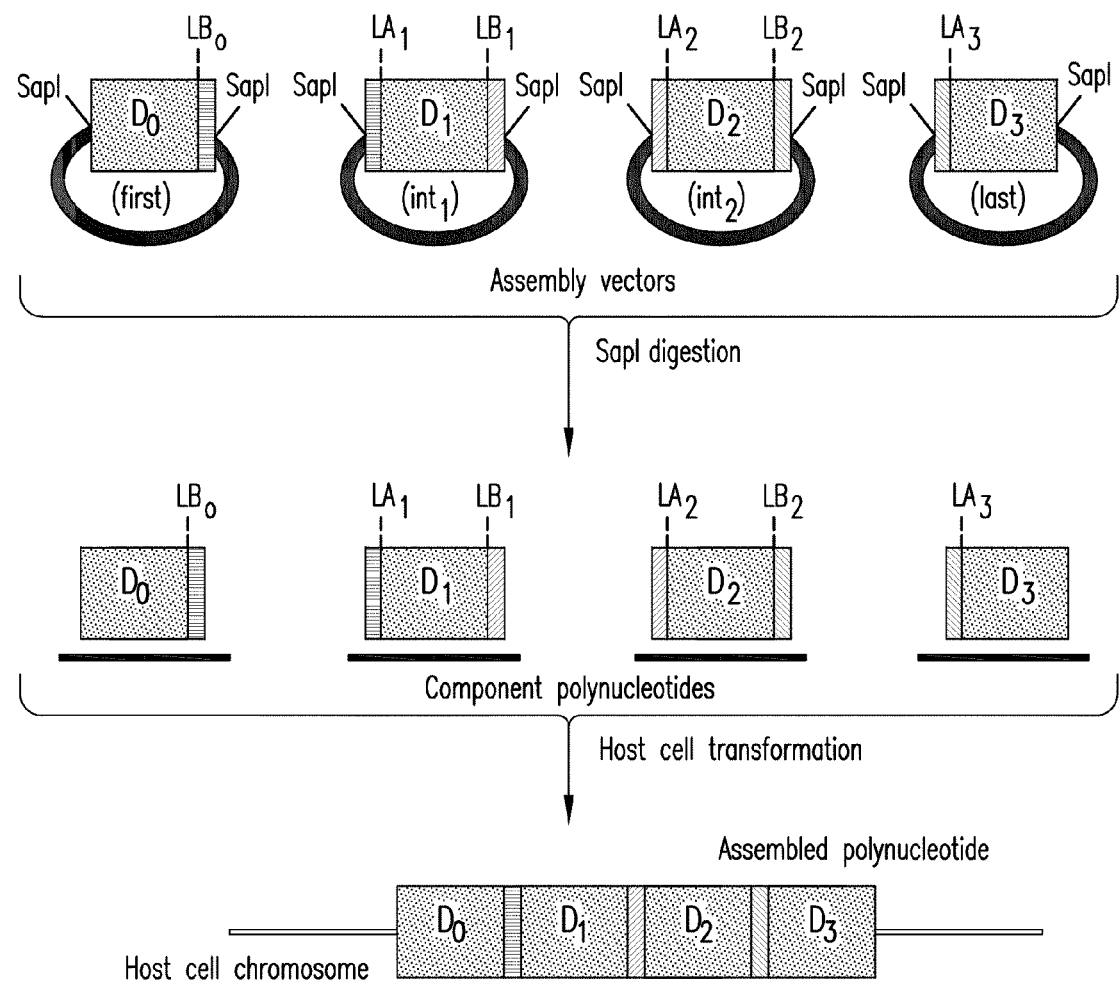

In yet other embodiments, the methods comprise transforming a host cell with a plurality of component polynucleotides and allowing the host cell to generate one or more assembled polynucleotides by homologous recombination. The assembled polynucleotide can be extrachromosomally maintained in the host cell or integrated into the chromosome of the host cell. The generation of an exemplary assembled polynucleotide by homologous recombination in a host cell and integration of the assembled polynucleotide into the chromosome of the host cell is illustrated in FIG. 9. In the first step, an assembly composition comprising assembly vectors is digested with a Type IIS restriction endonuclease such as SapI or LguI, resulting in the excision from the assembly vector backbones of component polynucleotides. In this embodiment, $D_0$ and $D_3$ can be the upstream and downstream chromosomal targeting sequence, in which case the presence of a primer binding segment in the first and last assembly vectors is optional. Alternatively, the two primer binding segments could function as the upstream and downstream genomic targeting sequences.

Once excised, each excised component polynucleotide comprises an annealable linker sequence LB that is homologous to an annealable linker sequence LA of another component polynucleotide and that is of sufficient length to initiate host mediated homologous recombination. The component polynucleotide excised from the first assembly vector further comprises an upstream chromosomal targeting sequence, and the component polynucleotide excised from the last assembly vector further comprises a downstream chromosomal targeting sequence, wherein both chromosomal targeting sequences are of sufficient length to initiate host mediated homologous recombination with a chromosome of the host cell. The restriction endonuclease can subsequently be inactivated. In the second step of the method, the components composition is introduced into a host cell capable of homologous recombination. Once inside the cell, the host cell recombines the component polynucleotides at the regions of homology between the annealable linker sequences to form an assembled polynucleotide, and the assembled polynucleotide is integrated into the chromosome. Host cells comprising the assembled polynucleotide can be readily identified based on a selectable marker encoded by a DNA segment of the assembled polynucleotide.

Any host cell can be used in the methods describe herein. In particular embodiments, suitable host cells are host cells that are capable of recombining polynucleotides based on complementary sequence stretches such as provided by the selectable marker segments, genomic targeting sequences, and annealable linker sequences provided herein. Illustrative examples of such host cells include but are not limited to *Saccharomyces cerevisiae*. Conditions suitable for uptake of DNA by such host cells are well known in the art.

Host cell transformants comprising an assembled or combined polynucleotide can be readily identified by virtue of expressing a selectable marker encoded by the assembled polynucleotide or by the combined polynucleotide that permits selection for or against the growth of the cells. The selectable marker may be encoded by a single DNA segment present in an assembly vector of an assembly composition. Alternatively, non-functional segments of the selectable marker may be encoded by DNA segments present in multiple assembly vectors of an assembly composition or in multiple assembled polynucleotides such that a functional selectable marker is generated only upon generation of an assembled polynucleotide or upon generation of a combined polynucleotide, respectively.

A wide variety of selectable markers are known in the art (see, for example, Kaufinan, *Meth. Enzymol.*, 185:487 (1990); Kaufman, *Meth. Enzymol.*, 185:537 (1990); Srivastava and Schlessinger, *Gene*, 103:53 (1991); Romanos et al., in DNA Cloning 2: Expression Systems, 2nd Edition, pages 123-167 (IRL Press 1995); Markie, *Methods Mol. Biol.*, 54:359 (1996); Pfeifer et al., *Gene*, 188:183 (1997); Tucker and Burke, *Gene*, 199:25 (1997); Hashida-Okado et al., *FEBS Letters*, 425:117 (1998)). In some embodiments, the selectable marker is a drug resistant marker. A drug resistant marker enables cells to detoxify an exogenous drug that would otherwise kill the cell. Illustrative examples of drug resistant markers include but are not limited to those which confer resistance to antibiotics such as ampicillin, tetracycline, kanamycin, bleomycin, streptomycin, hygromycin, neomycin, Zeocin™, and the like. In other embodiments, the selectable marker is an auxotrophic marker. An auxotrophic marker allows cells to synthesize an essential component (usually an amino acid) while grown in media that lacks that essential component. Selectable auxotrophic gene sequences include, for example, hisD, which allows growth in histidine free media in the presence of histidinol. Other selectable markers include a bleomycin-resistance gene, a metallothionein gene, a hygromycin B-phosphotransferase gene, the AURI gene, an adenosine deaminase gene, an aminoglycoside phosphotransferase gene, a dihydrofolate reductase gene, a thymidine kinase gene, a xanthine-guanine phosphoribosyltransferase gene, and the like.

Auxotrophy can also be used to identify host cell transformants comprising a chromosomally integrated assembled or combined polynucleotide when the integration of the assembled or combined polynucleotide results in the disruption of a gene that the host cell requires to synthesize a component essential for cell growth, thus rendering the cell auxotrophic.

Host cell transformants comprising a chromosomally integrated assembled or combined polynucleotide can also be identified by selecting host cell transformants exhibiting other traits encoded by individual DNA segments or by combinations of DNA segments, e.g., expression of peptides that emit light, or by molecular analysis of individual host cell colonies, e.g., by restriction enzyme mapping, PCR amplification, or sequence analysis of isolated assembled polynucleotides or chromosomal integration sites.

5.4 Combinatorial Methods of Polynucleotide Assembly and Host Cell Generation In another aspect, the present invention provides rapid, robust, and high-throughput methods for the ordered assembly of multiple component polynucleotides into a plurality of assembled polynucleotides. The methods rely on the use of an assembly composition comprising assembly vectors that each comprise a DNA segment D, flanked by an annealable linker sequence LA or LB, a pair of annealable linker sequences LA and LB, or by an annealable linker sequence and a primer binding segment, i.e., LA and PB or LB and PA, flanked by a pair of restriction sites RA and RB (FIG. 1B). However, to generate a diversity of assembled polynucleotides using the methods disclosed herein, annealable linker sequences and primer binding segments are chosen such that more than one combination of component polynucleotides can be assembled into an assembled polynucleotide in the reaction. Thus, in some embodiments, the assembly composition comprises at least two assembly vectors that have the same annealable linker sequence LA or LB or the same primer binding segment PA or PB, but differ with respect to the DNA segment. In other 70 embodiments, the assembly composition comprises at least two assembly vectors that have the same pair of annealable linker sequences LA and LB, or the same annealable linker sequence and primer binding segment pair, i.e., LA and PB or LB and PA but differ with respect to the DNA segment.

Figure 10:
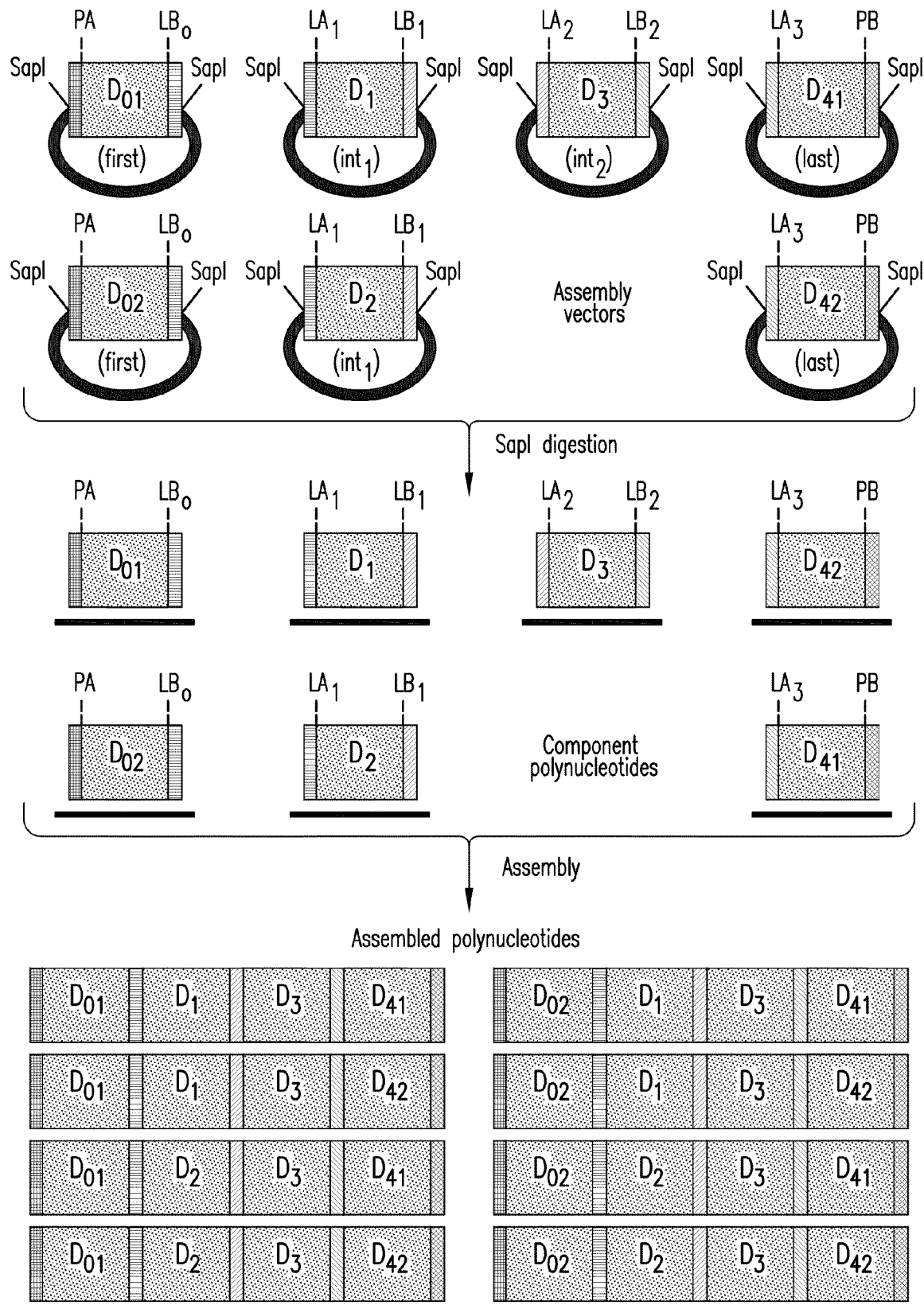

FIG. 10 presents an exemplary method of generating a plurality of assembled polynucleotides from seven (7) component polynucleotides in the same reaction. Assembly vectors comprising DNA segments to be assembled are pooled in a single tube and digested with SapI to release component polynucleotide fragments from the assembly vector backbones. Following heat inactivation of SapI, the component polynucleotides are subjected to denaturing conditions, followed by annealing conditions sufficient for hybridization of the complementary annealable linker pairs. Following primer extension in the presence of DNA polymerase and dNTPs, primers complementary to primer binding segments PA and PB are added to PCR amplify eight (8) different full-length assembled polynucleotides that comprise DNA segments $D_{01/02}$, $D_{1/2}$, $D_3$, and $D_{41/42}$ assembled in various possible combinations. Individual assembled polynucleotides can be isolated from the composition of mixed assembled polynucleotides, e.g., by another round of PCR amplification using primers complementary to regions of DNA segments $D_{01}$, $D_{02}$, $D_{41}$, and $D_{42}$. Alternatively, a set of assembled polynucleotides can be isolated by first and last assembly vectors comprising one of a group of primer binding segments PA and/or PB and using primers for PCR amplification that hybridize to only a select subgroup of primer binding segments PA and PB. The isolated assembled polynucleotides can be used, e.g., to transform host cells to generate a plurality of host cells comprising assembled polynucleotides. Alternatively, host cells can be directly transformed with the composition of mixed assembled polynucleotides and host cell transformants comprising each assembled polynucleotide can be isolated, e.g., by molecular analysis of individual host cell colonies, or by selecting host cell transformants comprising selectable markers or exhibiting other traits encoded by individual DNA segments or by combinations of DNA segments.

Figure 11:
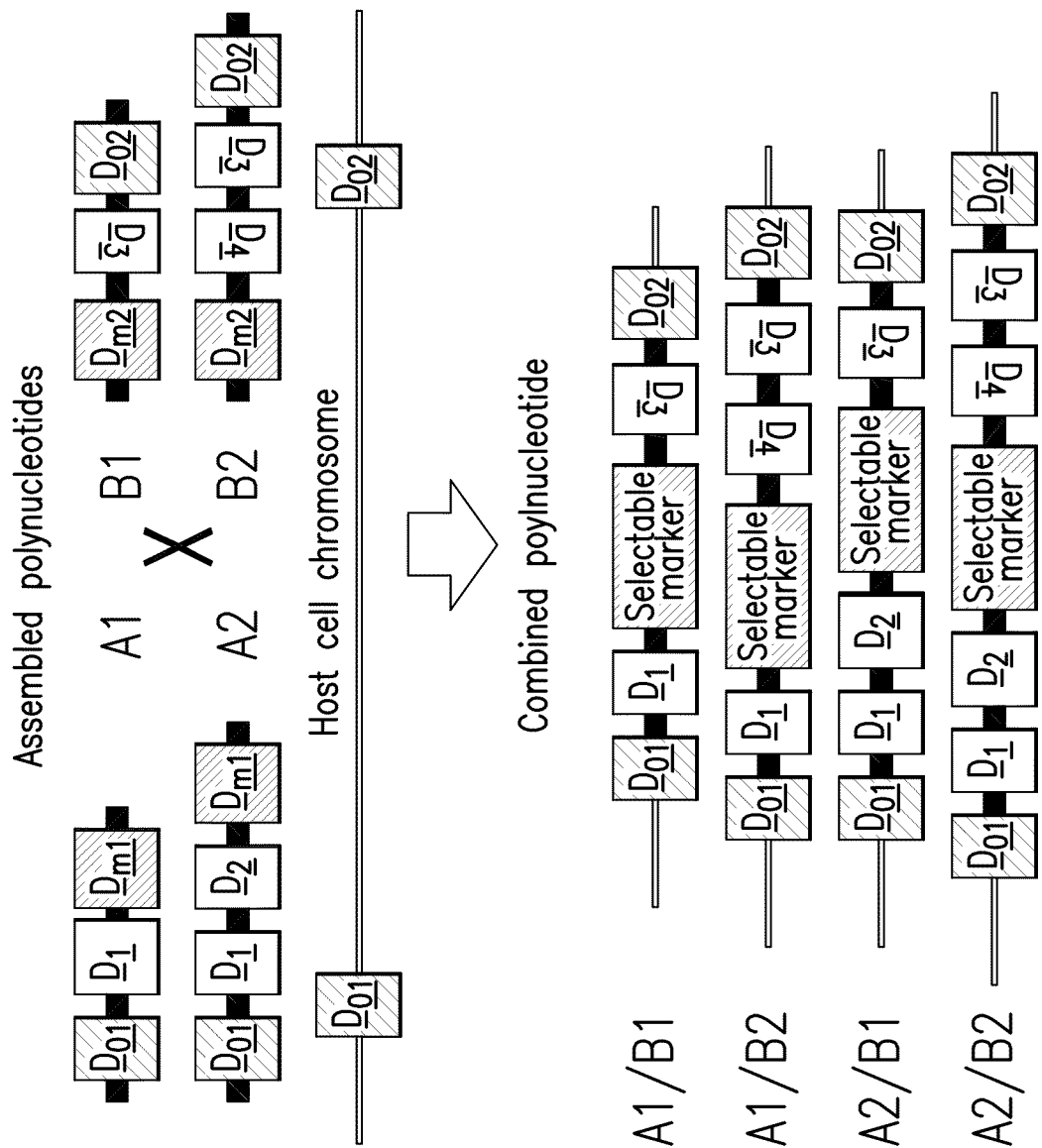

In other embodiments, a plurality of host cells comprising a plurality of polynucleotides assembled by combinatorial methods are generated by transforming host cells with a composition comprising multiple assembled polynucleotides of which at least two assembled polynucleotides comprise non-functional segments of a selectable marker that upon homologous recombination generate a functional selectable marker, and by selecting host cells comprising a combined polynucleotide. FIG. 11 illustrates a combinatorial approach to generating a plurality of host cells comprising combined polynucleotides. In the example, assembled polynucleotides A1 and A2, each comprising the same upstream chromosomal targeting sequence and the same first portion of a selectable marker, and assembled polynucleotides B1 and B2, each comprising the same downstream chromosomal targeting sequence and the same second portion of a selectable marker, are combinatorially combined by host cell mediated homologous recombination to generate four different combined polynucleotides, A1/B1, A1/B2, A2/B1, and A2/B2, that can be inserted into a chromosome to generate four different host cells.

In yet other embodiments, a plurality of host cells comprising a plurality of polynucleotides assembled and combined by combinatorial methods are generated by transforming host cells with a component composition comprising multiple component polynucleotides of which at least two component polynucleotides comprise non-functional segments of a selectable marker that upon host cell mediated homologous recombination generate a functional selectable marker, and by selecting host cells comprising an assembled or combined polynucleotide.

5.5 Entry Vectors

In another aspect, provided herein is a vector, i.e., an entry vector, that can be used to prepare an assembly vector. In some embodiments, an entry vector is a circular polynucleotide that comprises a selectable marker, an origin of replication, and a DNA segment immediately flanked by two restriction sites that facilitate the subcloning of different DNA segments to be assembled in the assembly methods provided herein. The entry vector further comprises one or two annealable linker sequences, or an annealable linker sequence and a primer binding segment, flanking the restriction sites. The entry vector further comprises an additional pair of restriction sites positioned at the outer flanks of the DNA segment, e.g., that flank the one or two annealable linker sequences, or the annealable linker sequence and primer binding segment. Thus, in some embodiments, the entry vector is a circular polynucleotide that comprises, in a 5' to 3' orientation, a restriction site RA, an annealable linker sequence LA, a restriction site RY, a DNA segment D, a restriction site RZ, and a restriction site RB. In other embodiments, the entry vector is a circular polynucleotide that comprises, in a 5' to 3' orientation, a restriction site RA, a restriction site RY, a DNA segment D, a restriction site RZ, an annealable linker sequence LB, and a restriction site RB. In other embodiments, the entry vector is a circular polynucleotide that comprises, in a 5' to 3' orientation, a restriction site RA, a primer binding segment PA or an annealable linker sequence LA, a restriction site RY, a DNA segment D, a restriction site RZ, a primer binding segment PB or an annealable linker sequence LB, and a restriction site RB.

In some embodiments, the sequence of the DNA segment D of the entry vector is the lac Z reporter gene. The lac Z reporter gene is useful for facilitating blue/white selection of colonies transformed with vectors comprising DNA segments other than lac Z, e.g., during the preparation of an assembly vector described herein.

In some embodiments, the entry vector is a circular polynucleotide that comprises, in a 5' to 3' orientation, a restriction site RA, an annealable linker sequence LA, a restriction site RY, a DNA segment D, a restriction site RZ, and a restriction site RB (i.e., 5'-RA-LA-RY-D-RZ-RB-3'). In some embodiments, the entry vector is a circular polynucleotide that comprises, in a 5' to 3' orientation, a restriction site RA, a restriction site RY, a DNA segment D, a restriction site RZ, an annealable linker sequence LB, and a restriction site RB (i.e., 5'-RA-RY-D-RZ-LB-RB-3'). In some embodiments, the entry vector is a circular polynucleotide that comprises, in a 5' to 3' orientation, a restriction site RA, an annealable linker sequence LA, a restriction site RY, a DNA segment D, a restriction site RZ, an annealable linker sequence LB, and a restriction site RB (i.e., 5'-RA-LA-RY-D-RZ-LB-RB-3'). In some embodiments, the entry vector is a circular polynucleotide that comprises, in a 5' to 3' orientation, a restriction site RA, a primer binding segment PA, a restriction site RY, a DNA segment D, a restriction site RZ, an annealable linker sequence LB, and a restriction site RB (i.e., 5'-RA-PA-RY-D-RZ-LB-RB-3'). In some embodiments, the entry vector is a circular polynucleotide that comprises, in a 5' to 3' orientation, a restriction site RA, an annealable linker sequence LA, a restriction site RY, a DNA segment D, a restriction site RZ, a primer binding segment PB, and a restriction site RB (i.e., 5'-RA-LA-RY-D-RZ-PB-RB-3'). An exemplary entry vector is provided in FIG. 1A.

The primer binding segment can be any nucleotide sequence that is not complementary with any of the annealable linker sequences that are used to make an assembled polynucleotide. In some embodiments, the two primer binding segment includes a restriction endonuclease recognition and cleavage site. In some embodiments, the primer binding segment is simply one of the available linker sequences that are not being used in a particular assembly reaction. In some embodiments, the nucleic acid sequence of primer binding segment PA is selected from the group consisting of SEQ ID NOS: 24 and 25. In some embodiments, the nucleic acid sequence of primer binding segment PB is selected from the group consisting of SEQ ID NOS: 24 and 25. In some embodiments, the nucleic acid sequences of primer binding segment PA and primer binding segment PB are selected from the group consisting of SEQ ID NOS: 24 and 25. In preferable embodiments, PA and PB are not identical in sequence.

In some embodiments, the nucleic acid sequence of annealable linker sequence LA or LB is at least 24 nucleotides and has a $T_m$ of at least 60° C. In some embodiments, the nucleic acid sequence of annealable linker sequence LA is selected from the group consisting of SEQ ID NOS: 1 to 23. In some embodiments, the nucleic sequence of annealable linker sequence LB is selected from the group consisting of SEQ ID NOS: 1 to 23. In some embodiments, the nucleic sequences of annealable linker sequence LA and annealable linker sequence LB are selected from the group consisting of SEQ ID NOS: 1 to 23.

The restriction sites RY and RZ can be utilized as cloning sites to introduce various DNA segments for the generation of an assembly vector. In some embodiments, RY and RZ are not identical in sequence. In some embodiments, RY and RZ are cleavable by the same restriction endonuclease. In some embodiments, RY and RZ are identical in sequence. In some embodiments, restriction sites RY and RZ are cleavable by a restriction endonuclease that generates staggered ends, i.e. termini having a 5' or 3' overhang. In other embodiments, restriction sites RY and RZ are cleavable by a restriction endonuclease that generates blunt ends.

Although restriction sites RY and RZ can be any restriction site known in the art, restriction sites recognized by the Type IIS restriction endonucleases are particularly useful. Type IIS restriction endonucleases have DNA binding domains that are distinct from their cleavage domains. Therefore, they recognize a specific sequence but cleave at a defined distance away. For example, the Type IIS restriction endonuclease SchI (which is also known as MlyI) binds to a recognition site containing the sequence GAGTC and cleaves four (4) base pairs away from the recognition site, creating a blunt ended DNA molecule. Type IIS restriction sites are particularly useful for the preparation of an assembly vector from an entry vector. For example, in a subcloning procedure wherein the DNA segment of an entry vector, for example lacZ, is replaced with a DNA segment of interest, excision of lacZ with a Type IIS restriction endonuclease can result in complete removal of the restriction site recognition sequence. As a result, upon ligation of the DNA segment of interest to the linearized entry vector, extraneous sequence between the annealable linker sequence or the primer binding segment and the newly introduced DNA segment is minimized.

Thus, in some embodiments, restriction sites RY and RZ are restriction sites recognizable and cleavable by any Type IIS restriction endonuclease known in the art. Suitable Type IIS restriction endonucleases include but are not limited to the following endonucleases and their isoschizomers, which are indicated in parentheses: Alw26I (BsmAI), AlwI (AclWI, BinI), AsuHPI (HphI), BbvI (Bst71I), BcefI, BstF5I (BseGI, FokI), FauI, HgaI, SapI (LguI), MboII, PleI, SapI, SchI (MlyI), SfaNI, and TspRI, AceIII, BbsI (BbvII, BpiI, BpuAI), Bce83I, BciVI, BfiI (BmrI), BpmI (GsuI), BsaI (Eco31I), BseRI, BsgI, BsmBI (Esp3I), BsmFI, BspMI, BsrDI (Bse3DI), Bsu6I (Eam1104I), EarI, Ksp632I, Eco57I, FauI, MmeI, RleAI, TaqII, and Tth111II. In particular embodiments, restriction sites RY and RZ are recognizable and cleavable by the SchI restriction endonuclease.

In some embodiments, RA and RB are not identical in sequence. In some embodiments, RA and RB are cleavable by the same restriction endonuclease. In some embodiments, RA and RB are identical in sequence. In some embodiments, restriction sites RA and RB are cleavable by a restriction endonuclease that generates staggered ends, i.e. termini having a 5' or 3' overhang. In other embodiments, restriction sites RA and RB are cleavable by a restriction endonuclease that generates blunt ends.

Although restriction sites RA and RB can be any restriction sites known in the art, restriction sites that are relatively infrequent in DNA (e.g., cDNA) of one or more organisms (i.e., an infrequent cutter) are particularly useful. In some embodiments, restriction sites RA and RB are recognizable and cleavable by a restriction endonuclease that has relatively infrequent restriction sites in human DNA. In some embodiments, restriction sites RA and RB are recognizable and cleavable by a restriction endonuclease that has relatively infrequent restriction sites in mouse DNA. In some embodiments, restriction sites RA and RB are recognizable and cleavable by a restriction endonuclease that has relatively infrequent restriction sites in yeast DNA, for example, in the DNA of *Saccharomyces cerevisiae*, *Pichia pastoris*, *Kluyveromyces lactis*, *Arxula adeninivorans*, or *Hansenula polymorpha*. In some embodiments, restriction sites RA and RB are recognizable and cleavable by a restriction endonuclease that has relatively few restriction sites in the DNA of bacteria, for example, in the DNA of *Escherichia coli* or *Bacillus subtilis*.

In some embodiments, restriction sites RA and RB are recognizable and cleavable by a Type IIS restriction endonuclease wherein the recognition site is distal to the polynucleotide sequence comprising, e.g., PA/LA-D-PB/LB. In some embodiments, each restriction site RA and RB is independently recognizable and cleavable by a restriction endonuclease selected from the group consisting of MssI, NruI (Bsp68I, MluB2I, Sbo13I, SpoI), SnaBI (BstSNI, Eco105I), SrfI, and SwaI (BstRZ246I, BstSWI, MspSWI, SmiI), HpaI, HincII, PshAI, OliI, AluI, Alw26I, BalI, DraI, DpnI, EcoR47III, EcoRCRI, EcoRV, FokI, HaeIII, HincII, MboI, MspA1I, NaeI, RsaI, PvuII, ScaI, SmaI, SspI, StuI, XmnI, EcaBC3I, SciI, HincII, DraI, BsaBI, Cac8I, Hpy8I, MlyI, PshAI, SspD51, BfrBI, BsaAI, BsrBI, BtrI, CdiI, CviJI, CviRI, Eco47III, Eco78I, EcoICRI, FnuDII, FspAI, HaeI, LpnI, MlyI, MslI, MstI, NaeI, NlaIV, NruI, NspBII, OliI, PmaCI, PshAI, PsiI, SrfI, StuI, XcaI, XmnI, ZraI, and isoschizomers thereof. In a particular embodiment, restriction sites RA and RB are recognizable and cleavable by the SapI or LguI restriction endonuclease. LguI is an isoschizomer of SapI having the same recognition and cleavage specificity.

In some embodiments, the entry vector provided herein also comprises one or more nucleic acid sequences that generally have some function in the replication, maintenance, or integrity of the vector (e.g., origins of replication) as well as one or more selectable markers. Replication origins are unique polynucleotides that comprise multiple short repeated sequences that are recognized by multimeric origin-binding proteins and that play a key role in assembling DNA replication enzymes at the origin site. Suitable origins of replication for use in the entry and assembly vectors provided herein include but are not limited to *E. coli* oriC, colE1 plasmid origin, 2μ and ARS (both useful in yeast systems), sfl, SV40 EBV oriP (useful in mammalian systems), or those found in pSC101. Selectable markers can be useful elements in vectors as they provide a means to select for or against growth of cells that have been successfully transformed with a vector containing the selectable marker and express the marker.

In some embodiments, any vector may be used to construct the entry vector as provided herein. In particular, vectors known in the art and those commercially available (and variants or derivatives thereof) may be engineered to include a restriction site RA, optionally a primer binding segment PA or an annealable linker sequence LA, a restriction site RY, a DNA segment D, a restriction site RZ, optionally a primer binding segment PB or an annealable linker sequence LB, and a restriction site RB, for use in the methods provided herein. Such vectors may be obtained from, for example, Vector Laboratories Inc., InVitrogen, Promega, Novagen, NEB, Clontech, Boehringer Mannheim, Pharmacia, EpiCenter, OriGenes Technologies Inc., Stratagene, Perkin Elmer, Pharmingen, Life Technologies, Inc., and Research Genetics. General classes of vectors of particular interest include prokaryotic and/or eukaryotic cloning vectors, expression vectors, fusion vectors, two-hybrid or reverse two-hybrid vectors, shuttle vectors for use in different hosts, mutagenesis vectors, transcription vectors, vectors for receiving large inserts, and the like. Other vectors of interest include viral origin vectors (M13 vectors, bacterial phage λ vectors, adenovirus vectors, and retrovirus vectors), high, low and adjustable copy number vectors, vectors that have compatible replicons for use in combination in a single host (PACYC184 and pBR322) and eukaryotic episomal replication vectors (pCDM8).

Figure 4:
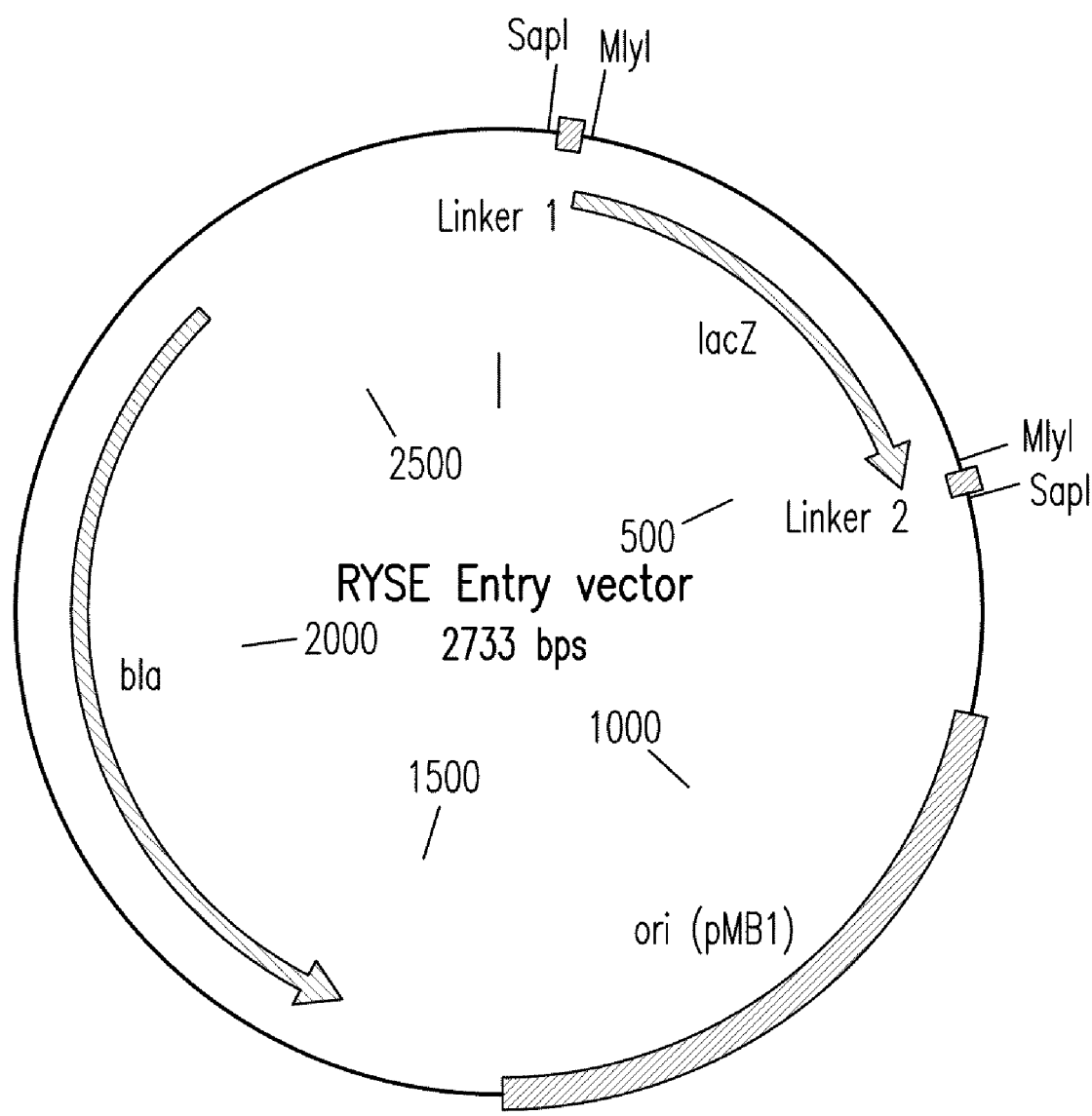
Figure 5:
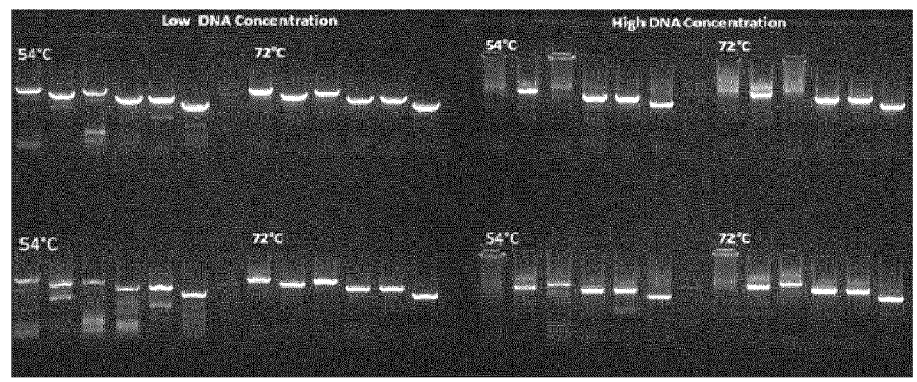
Figure 6:
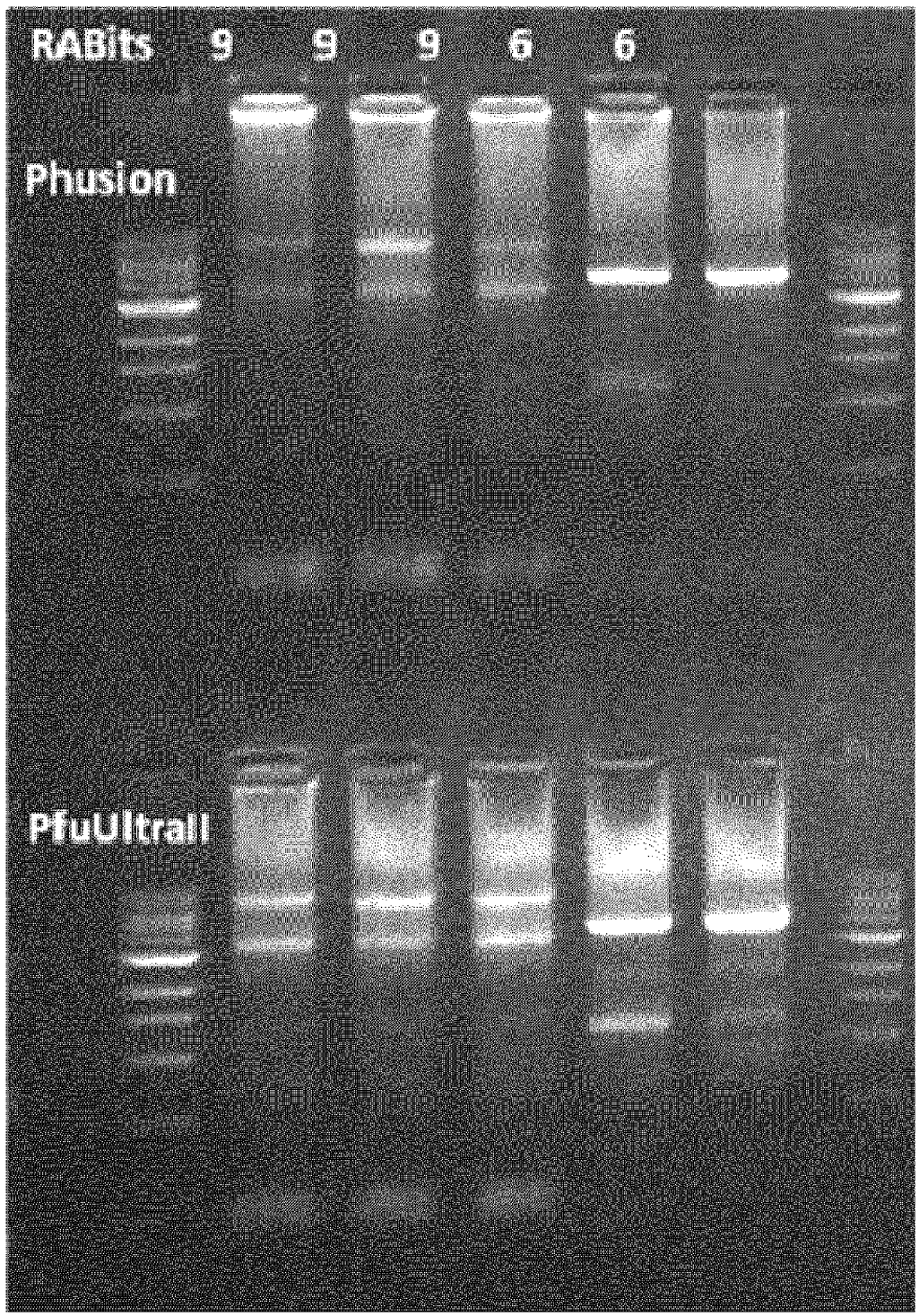

In particular embodiments, entry vectors for use in accordance with the methods provided herein are the pRYSE vectors, having the nucleotide sequences of SEQ ID NO: 207 through 221. A schematic of the pRYSE vectors is provided in FIG. 4, and the preparation of the pRYSE vectors is described in Example 1 below.

5.6 Assembly Vectors

In another aspect, provided herein is a vector, i.e., an assembly vector, that can be used in the assembly of a plurality of component polynucleotides into one or more assembled polynucleotides. In some embodiments, an assembly vector is a circular polynucleotide that comprises a selectable marker, an origin of replication, and a DNA segment flanked by an annealable linker sequence, an annealable linker sequence pair, or by an annealable linker sequence/primer binding segment pair, flanked by a pair of restriction sites. The restriction sites can serve to facilitate excision of the component polynucleotide from the assembly vector backbone during the assembly reaction. Thus, in some embodiments, the assembly vector is a circular polynucleotide that comprises, in a 5' to 3' orientation, a restriction site RA, a primer binding segment PA or an annealable linker sequence LA, a DNA segment D, and a restriction site RB. In some embodiments, the assembly vector is a circular polynucleotide that comprises, in a 5' to 3' orientation, a restriction site RA, a DNA segment D, a primer binding segment PB or an annealable linker sequence LB, and a restriction site RB. In certain embodiments, the assembly vector is a circular polynucleotide that comprises, in a 5' to 3' orientation, a restriction site RA, a primer binding segment PA or an annealable linker sequence LA, a DNA segment D, a primer binding segment PB or an annealable linker sequence LB, and a restriction site RB.

In some embodiments, the assembly vector is a circular polynucleotide that comprises, in a 5' to 3' orientation, a restriction site RA, an annealable linker sequence LA, a DNA segment D, and a restriction site RB (i.e., 5'-RA-LA-D-RB-3'). In some embodiments, the assembly vector is a circular polynucleotide that comprises, in a 5' to 3' orientation, a restriction site RA, a DNA segment D, an annealable linker sequence LB, and a restriction site RB (i.e., 5'-RA-D-LB-RB-3'). In some embodiments, the assembly vector is a circular polynucleotide that comprises, in a 5' to 3' orientation, a restriction site RA, an annealable linker sequence LA, a DNA segment D, an annealable linker sequence LB, and a restriction site RB (i.e., 5'-RA-LA-D-LB-RB-3'). In some embodiments, the assembly vector is a circular polynucleotide that comprises, in a 5' to 3' orientation, a restriction site RA, a primer binding segment PA, a DNA segment D, an annealable linker sequence LB, and a restriction site RB (i.e., 5'-RA-PA-D-LB-RB-3'). In some embodiments, the assembly vector is a circular polynucleotide that comprises, in a 5' to 3' orientation, a restriction site RA, an annealable linker sequence LA, a DNA segment D, a primer binding segment PB, and a restriction site RB (i.e., 5'-RA-LA-D-PB-RB-3'). Exemplary assembly vectors are provided in FIG. 1B and FIG. 2.

In some embodiments, the nucleic acid sequence of primer binding segment PA is selected from the group consisting of SEQ ID NOS: 24 and 25. In some embodiments, the nucleic acid sequence of primer binding segment PB is selected from the group consisting of SEQ ID NOS: 24 and 25. In some embodiments, the nucleic acid sequences of primer binding segment PA and primer binding segment PB are selected from the group consisting of SEQ ID NOS: 24 and 25. In preferable embodiments, the nucleic acid sequences of primer binding segment PA and primer binding segment PB are not identical.

In some embodiments, the nucleic acid sequence of annealable linker sequence LA or LB is at least 24 nucleotides and has a $T_m$ of at least 60° C. In some embodiments, the nucleic acid sequence of annealable linker sequence LA is selected from the group consisting of SEQ ID NOS: 1 to 23. In some embodiments, the nucleic acid sequence of annealable linker sequence LB is selected from the group consisting of SEQ ID NOS: 1 to 23. In some embodiments, the nucleic acid sequences of annealable linker sequence LA and annealable linker sequence LB are selected from the group consisting of SEQ ID NOS: 1 to 23.

In some embodiments, RA and RB are not identical in sequence. In some embodiments, RA and RB are cleavable by the same restriction endonuclease. In some embodiments, RA and RB are identical in sequence. In some embodiments, restriction sites RA and RB are cleavable by a restriction endonuclease that generates staggered ends, i.e. termini having a 5' or 3' overhang. In other embodiments, restriction sites RA and RB are cleavable by a restriction endonuclease that generates blunt ends.

Although restriction sites RA and RB can be any restriction sites known in the art, restriction sites that are relatively infrequent in DNA (e.g., cDNA) of one or more organisms (i.e., an infrequent cutter) are particularly useful. In some embodiments, restriction sites RA and RB are recognizable and cleavable by a restriction endonuclease that has relatively infrequent restriction sites in human DNA. In some embodiments, restriction sites RA and RB are recognizable and cleavable by a restriction endonuclease that has relatively infrequent restriction sites in mouse DNA. In some embodiments, restriction sites RA and RB are recognizable and cleavable by a restriction endonuclease that has relatively infrequent restriction sites in yeast DNA, for example, in the DNA of *Saccharomyces cerevisiae, Pichia pastoris, Kluyveromyces lactis, Arxula adeninivorans*, or *Hansenula polymorpha*. In some embodiments, restriction sites RA and RB are recognizable and cleavable by a restriction endonuclease that has relatively few restriction sites in the DNA of bacteria, for example, in the DNA of *Escherichia coli* or *Bacillus subtilis*.

In some embodiments, restriction sites RA and RB are recognizable and cleavable by a Type IIS restriction endonuclease. Illustrative examples of suitable Type IIS restriction endonucleases include but are not limited to: MssI, NruI (Bsp68I, MluB2I, Sbo13I, SpoI), SnaBI (BstSNI, Eco105I), SrfI, and SwaI (BstRZ246I, BstSWI, MspSWI, SmiI), HpaI, HincII, PshAI, OliI, AluI, Alw26I, BalI, DraI, DpnI, EcoR47III, EcoRCRI, EcoRV, FokI, HaeIII, HincII, MboI, MspA1I, NaeI, RsaI, PvuII, ScaI, SmaI, SspI, StuI, XmnI, EcaBC3I, SciI, HincII, DraI, BsaBI, Cac8I, Hpy8I, MlyI, PshAI, SspD51, BfrBI, BsaAI, BsrBI, BtrI, CdiI, CviJI, CviRI, Eco47III, Eco78I, EcoICRI, FnuDII, FspAI, HaeI, LpnI, MlyI, MslI, MstI, NaeI, NlaIV, NruI, NspBII, OliI, PmaCI, PshAI, PsiI, SrfI, StuI, XcaI, XmnI, ZraI, or isoschizomers thereof. In a particular embodiment, restriction sites RA and RB are recognizable and cleavable by the SapI or LguI restriction endonuclease.

Preferably, the DNA segment of an assembly vector does not comprise a nucleic acid sequence that can be recognized and cleaved by a restriction endonuclease that can cleave any of restriction sites RA and RB within the assembly vector. This ensures that the DNA segment remains intact during the first stage of the assembly reaction, during which the component polynucleotide is excised from the assembly vector backbone. In particular embodiments, the DNA segment does not comprise a SapI/LguI site and RA and RB are cleavable by SapI or LguI. Site-directed mutagenesis (see Carter, *Bi°Chem. J.* 237:1-7 (1986); Zoller and Smith, *Methods Enzymol.* 154:329-50 (1987)), cassette mutagenesis, restriction selection mutagenesis (Wells et al., *Gene* 34:315-323 (1985)), oligonucleotide-mediated (site-directed) mutagenesis, PCR mutagenesis, or other known techniques can be performed to modify any such sequence within the DNA segment either before or after ligation of the DNA segment to the entry vector.

In some embodiments, the assembly vector provided herein also comprises one or more nucleic acid sequences that generally have some function in the replication, maintenance, or integrity of the vector (e.g., origins of replication) as well as one or more selectable markers. Replication origins are unique polynucleotides that comprise multiple short repeated sequences that are recognized by multimeric origin-binding proteins and that play a key role in assembling DNA replication enzymes at the origin site. Suitable origins of replication for use in the entry and assembly vectors provided herein include but are not limited to *E. coli* oriC, colE1 plasmid origin, 2μ and ARS (both useful in yeast systems), sfl, SV40 EBV oriP (useful in mammalian systems), or those found in pSC101. Selectable markers can be useful elements in vectors as they provide a means to select for or against growth of cells that have been successfully transformed with a vector containing the selectable marker and express the marker.

In some embodiments, any vector may be used to construct the assembly vector as provided herein. In particular, vectors known in the art and those commercially available (and variants or derivatives thereof) may be engineered to include a restriction site RA, a primer binding segment PA or an annealable linker sequence LA, a DNA segment D, a primer binding segment PB or an annealable linker sequence LB, and a restriction site RB, for use in the methods provided herein. Such vectors may be obtained from, for example, Vector Laboratories Inc., InVitrogen, Promega, Novagen, NEB, Clontech, Boehringer Mannheim, Pharmacia, EpiCenter, OriGenes Technologies Inc., Stratagene, Perkin Elmer, Pharmingen, Life Technologies, Inc., and Research Genetics. General classes of vectors of particular interest include prokaryotic and/or eukaryotic cloning vectors, expression vectors, fusion vectors, two-hybrid or reverse two-hybrid vectors, shuttle vectors for use in different hosts, mutagenesis vectors, transcription vectors, vectors for receiving large inserts, and the like. Other vectors of interest include viral origin vectors (M13 vectors, bacterial phage λ vectors, adenovirus vectors, and retrovirus vectors), high, low and adjustable copy number vectors, vectors that have compatible replicons for use in combination in a single host (PACYC184 and pBR322) and eukaryotic episomal replication vectors (pCDM8).

An assembly vector can be prepared from an entry vector. To prepare an assembly vector from an entry vector, the entry vector can be digested with one or more restriction endonucleases capable of cleaving RY and RZ thereby linearizing the vector such that it can accept a DNA segment. The DNA segment can be ligated into RY and RZ sites using standard cloning techniques to generate an assembly vector of the invention. For example, the DNA segment may be obtained by standard procedures known in the art from cloned DNA (e.g., a DNA "library"), by chemical synthesis, by cDNA cloning, or by the cloning of genomic DNA, or fragments thereof, purified from the desired cell, or by PCR amplification and cloning. See, for example, Sambrook et al., *Molecular Cloning, A Laboratory Manual*, 3d. ed., Cold Spring Harbor Laboratory Press, Cold Spring Harbor, N.Y. (2001); Glover, D. M. (ed.), *DNA Cloning: A Practical Approach*, 2d. ed., MRL Press, Ltd., Oxford, U.K. (1995).

An assembly vector can also be prepared from another vector that does not comprise an annealable linker sequence, an annealable linker sequence pair, or an annealable linker sequence/primer binding segment pair flanking the site of insertion of the DNA segment. To prepare an assembly vector from such a vector, the vector can be digested with one or more restriction endonucleases capable of cleaving the vector at a site suitable for insertion of a DNA fragment, e.g., at a multiple cloning site, thereby linearizing the vector such that it can accept a DNA fragment. The DNA fragment to be inserted can be obtained by standard procedures known in the art such as, for example, cloning, chemical synthesis, or PCR amplification. The DNA fragment comprises a DNA segment flanked by an annealable linker sequence, an annealable linker sequence pair or an annealable linker sequence/primer binding segment pair. Thus, in some embodiments, the DNA fragment comprises, in a 5' to 3' orientation, an annealable linker sequence LA or a primer binding segment PA, a DNA segment D, and an annealable linker sequence LB or a primer binding segment PB (i.e., 5'-LA-D-LB-3' or 5'-PA-D-LB-3' or 5'-LA-D-PB-3'). In some embodiments, the DNA fragment comprises, in a 5' to 3' orientation, a DNA segment D, and an annealable linker sequence LB or a primer binding segment PB (i.e., 5'-D-LB-3' or 5'-D-PB-3'). In some embodiments, the DNA fragment comprises, in a 5' to 3' orientation, an annealable linker sequence LA or a primer binding segment PA, and a DNA segment D, (i.e., 5'-LA-D-3' or 5'-PA-D-3'). The DNA fragment can further comprise a pair of restriction sites that flank the annealable linker sequence, the annealable linker sequence pair or the annealable linker sequence/primer binding segment pair and that upon cleavage by a restriction endonuclease produce termini that are compatible with termini produced by linearising the vector into which the DNA fragment is to be inserted. Alternatively, the DNA fragment can generated such that it contains such compatible termini and does not require additional digestion with a restriction endonuclease to produce the compatible termini. Upon ligation of the DNA fragment with the linearized vector to generate an assembly vector, the restriction sites used to generate the compatible termini may be preserved to serve as restriction sites RA and RB of the assembly vector. Alternatively, the ligation may remove the original restriction sites but additional restriction sites may be present in the linearised vector that can serve as restriction sites RA and RB of the assembly vector.

Exemplary methods for generating an assembly vector from an entry vector (i.e., a pRYSE vector) or from another vector (i.e., a pMULE vector) are provided in Example 6 below.

5.7 Annealable Linker Sequences

In another aspect, provided herein are annealable linker sequences that flank the DNA segment located within entry vectors and assembly vectors. Annealable linker sequences provide sequence overlap between adjacent component polynucleotides in an assembly reaction, and thus serve to prime a component polynucleotide for assembly into an assembled polynucleotide. Thus, in preferred embodiments, the annealable linker sequences LA and LB of the entry and assembly vectors are optimized to provide efficient and accurate priming to complementary annealable linker sequences during an assembly reaction.

In some embodiments, the length of an annealable linker sequence is long enough to provide adequate specificity with its complement annealable linker sequence, yet short enough to readily anneal to its complement annealable linker sequence at the annealing temperature of the assembly reaction. In some embodiments the length of an annealable linker sequence is long enough to allow for host cell mediated homologous recombination with its complement annealable linker sequence.

In some embodiments, the annealable linker sequence is about 5, 10, 15, 20, 25, 30, 35, 40, 45, 50, 55, 60, 65, 70, 75, or 80 nucleotides in length. In some embodiments, the annealable linker sequence is at least 10, 12, 14, 16, 18, 20, 22, 24, 26, 28, or 30 nucleotides in length. In some embodiments, the annealable linker sequence is greater than 30, 40, 50, 60, 70, 80, 90, 100, 500, 1000, 5000, or 10,000 nucleotides in length. In some embodiments, the annealable linker is at least 18 nucleotides in length and is a number divisible by three, so as to facilitate read-through transcription of the linker when ligated to an encoding DNA segment. In particular embodiments, the annealable linker is 18, 21, 24, 27, 30, 33, 36, 39, 42, 45, 48, 51, 54, 57, or 60 nucleotides in length.

In some embodiments, an annealable linker sequence has a relatively high melting temperature ($T_m$), i.e., the temperature at which one half of an annealed annealable linker sequence duplex will dissociate to become single stranded. The $T_m$ of an annealable linker can be calculated according to SantaLucia, PNAS, 95:-1460-1465 (1998) using a nearest neighbor algorithm. A relatively high $T_m$ may provide for more specific priming during an assembly reaction. A relatively high $T_m$ may also allow combination of the annealing and extension steps of PCR or reduce the amount of time needed to adjust temperatures between the annealing and extension steps of PCR and thus enable greater efficiency in using the assembly methods of the invention. Thus, in some embodiments, an annealable linker sequence duplex has a $T_m$ of about 60° C.-80° C. In some embodiments, an annealable linker sequence duplex has a $T_m$ of about 65° C.-75° C. In some embodiments, an annealable linker sequence duplex has a $T_m$ of greater than 50° C., 55° C., 60° C., 65° C., 70° C., 75° C., 80° C., 85° C., or 90° C.

In some embodiments, annealable linker sequences do not form appreciable secondary structures (e.g., hairpins, self-dimers) produced via intramolecular (i.e., within the same molecule) interactions under the conditions of the methods described herein, either at the DNA level or at the RNA level or at both the DNA and the RNA level. The presence of secondary structures in DNA can lead to poor or no assembled polynucleotide yield of the assembly reaction. The presence of secondary structures in RNA can lead to decreased translation efficiencies, which are of particular concern when the annealable linker sequence is used to assemble component polynucleotides comprising a promoter and a protein coding sequence into a assembled polynucleotide in which the annealable linker sequence is positioned between the promoter and the protein coding sequence. Accordingly, annealable linker sequences useful in the assembly methods of the invention are designed to not form secondary RNA and/or DNA structures. The ability of an annealable linker sequence to form secondary RNA or DNA structures can be determined using software tools such as, for example, IDT Oligo Analyzer (Integrated DNA Technologies, Coralville, Iowa), mFold (Zuker 2003 *Nucleic Acids Res.* 31 (13), 3406-15), or RNAfold (Hofacker & Stadler (2006) *Bioinformatics* 22 (10): 1172-6). In general, these tools calculate the Gibbs free energy ($\Delta G$) for transition of a sequence from the linear to the folded state. The larger $\Delta G$, the less likely that the sequence will form a secondary structure. Accordingly, in some embodiments, annealable linker sequences are designed to have large $\Delta G$ values for the transition from linear to folded states. In some embodiments, annealable linker sequences are designed to have $\Delta G$ values for the transition from linear to folded states that are equal to or greater than the $\Delta G$ values for the transition from linear to folded states of the n-bases that lie immediately upstream of the coding sequences of highly expressed genes in the *Saccharomyces cerevisiae* genome, wherein n represents an integer that corresponds to the number of bases in the annealable linker sequence. In some embodiments, annealable linker sequences are 36 bases long and have a $\Delta G$ value for the transition from linear to folded states of −1 or greater.

In some embodiments, annealable linker sequences are also designed to avoid unintended intermolecular interactions (i.e., between different molecules). Thus, in some embodiments, an annealable linker sequence does not anneal substantially with any other sequences within the assembly vector that contains the annealable linker sequence (e.g., vector backbone sequences) and/or with any other sequences within other assembly vectors of the assembly compositions aside from the complementary annealable linker sequences required for polynucleotide assembly by the methods provided herein. In some embodiments, an annealable linker sequence does not anneal substantially with other annealable linker sequences within assembly vectors of the assembly compositions provided herein.

In some embodiments, an annealable linker sequence has a high G-C content, i.e., the number of guanine and cytosine nucleotides in the annealable linker sequence as a percentage of the total number of bases in the annealable linker sequence Annealable linker sequences that have a high G-C content are generally useful in the methods of the invention because a high G-C content generally provides for a high $T_m$, which in turn may provide for more specific priming during an assembly reaction and for time and process savings by allowing combination of the annealing and extension steps of SOE/PCR. In some embodiments, the G-C content of the annealable linker sequence is between about 20-80%. In some embodiments, the G-C content of the annealable linker sequence is between about 40-60%. In some embodiments, the G-C content of the annealable linker sequence is about 40, 45, 50, 55, 60, or 70%. In particular embodiments, an annealable linker sequence has a G-C content of greater than 70%. Illustrative examples of annealable linker sequences that have a high G-C content, do not form appreciable secondary DNA structures, and have a $T_m$ of 70° C. or greater are SEQ ID NOS: 1 to 8.

In some embodiments, an annealable linker sequence has a high A-T content, i.e., the number of adenine and thymine nucleotides in the annealable linker sequence as a percentage of the total number of bases in the annealable linker sequence. A high A-T content may provide for reduced propensity of the annealable linker sequence to form substantial secondary structures, which may be of particular concern when the annealable linker sequence is used to assemble component polynucleotides comprising a promoter and a protein coding sequence into a assembled polynucleotide in which the annealable linker sequence is positioned between the promoter and the protein coding sequence. In some embodiments, the A-T content of the annealable linker sequence is between about 20-80%. In some embodiments, the A-T content of the annealable linker sequence is between about 40-60%. In some embodiments, the A-T content of the annealable linker sequence is about 30, 35, 40, 45, 50, 55, or 60%. In some embodiments, the annealable linker sequence has an A-T content of greater than 30%. In some embodiments, the sequence of the 3'-most 26 bases of an annealable linker sequence fulfills the following consensus motif: 5'ANNNNNNNNANNNAANTANNTTNANA-3' (SEQ ID NO: 248), wherein A stands for adenine, N for any motif, have a relatively high A-T content, do not form appreciable secondary RNA or DNA structures, nucleotide, and T for thymine. This consensus motif is frequently found in the 26 bases that lie upstream of the start codons of highly expressed genes in the genome of *Saccharomyces cerevisiae*. Illustrative examples of annealable linker sequences that comprise this consensus motif, have a relatively high A-T content, do not form appreciable secondary RNA or DNA structures, and have a $T_m$ of 65° C. or greater are SEQ ID NOS: 9 to 23.

In some embodiments, an annealable linker sequence comprises one or more restriction sites. Incorporation of restriction sites into an annealable linker sequence allows for the excision of a DNA segment from an entry or assembly vector while maintaining the restriction sites RA and RB within the entry vector or assembly vector. Restriction sites within the annealable linker sequence also facilitate directional subcloning of DNA segments into other entry or assembly vectors. This feature facilitates the efficient construction of assembly vectors comprising the same DNA segment but having different annealable linker sequence pairs or primer binding segment/annealable linker sequence pairs, for instance, to generate a library of assembly vectors comprising different annealable linker sequence pairs as described below. This feature can also obviate the need to re-amplify and sequence a DNA segment to create additional assembly vectors comprising the DNA segment. Thus, in some embodiments, the annealable linker sequence comprises a unique restriction site. In some embodiments, the restriction site is a 7-base pair restriction site, i.e., is cleavable by a restriction endonuclease that recognizes a 7-base pair nucleotide sequence. In some embodiments, the restriction site is a 8-base pair restriction site. In particular embodiments, the restriction site within the annealable linker sequence is recognized and cleavable by MreI, FseI, SbfI, AsiSI, NotI, AscI, or BbvCI.

In some embodiments, the annealable linker sequence comprises a sequence that allows for read-through transcription once the linker is ligated to an encoding DNA segment. In some embodiments, an annealable linker sequence allows for read-through transcription in both the 5' to 3' and 3' to 5' orientation. In these embodiments, the length of the annealable linker sequence, preferably, is a number of nucleotides divisible by three (3).

In particular embodiments, an annealable linker sequence does not comprise codons that are rarely used in *Escherichia coli* (*E. coli*) or *Saccharomyces cerevisiae* (*S. cerevisiae*). Efficient expression of heterologous genes in *E. coli* or *S. cerevisiae* can be adversely affected by the presence of infrequently used codons, and expression levels of the heterologous protein often rise when rare codons are replaced by more common ones. See, e.g., Williams et al., *Nucleic Acids Res.* 16: 10453-10467, 1988 and Hoog et al., *Gene* 43: 13-21, 1986. Accordingly, an annealable linker sequence that comprises a read-through sequence preferably does not comprise rare codons used in *E. coli* or *S. cerevisiae*, so as to enable efficient expression of proteins encoded by a assembled polynucleotide comprising the annealable linker sequence.

In some embodiments, the set of annealable linker sequences are unique sequences that are not found in an intended host organism. In some embodiments, the set of annealable linker sequences are unique sequences that are not found in *E. coli*. In other embodiments, the set of annealable linker sequences are unique sequences that are not found in *S. cerevisiae*.

In some embodiments, suitable annealable linker sequences are identified in a test assembled polynucleotide. A test assembled polynucleotide comprises the annealable linker sequence to be tested and additional elements that permit testing of the annealable linker sequence. For example, to test whether an annealable linker is suitable for assembling a first component polynucleotide comprising a promoter sequence and a second component polynucleotide comprising a protein coding sequence to be put under the control of the promoter in the assembled polynucleotide, a test assembled polynucleotide can be assembled from the first component polynucleotide comprising, in a 5' to 3' orientation, a primer binding segment or an annealable linker sequence, a DNA segment comprising the promoter, and the annealable linker sequence to be tested, and the second component polynucleotide comprising, in a 5' to 3' orientation, the annealable linker sequence to be tested, a DNA segment encoding a reporter gene (e.g., green fluorescent protein (GFP)), and a primer binding segment or annealable linker sequence. The test assembled polynucleotide can be tested in vivo or in vitro for the efficiency of expression of the reporter gene. Similar test assembled polynucleotides can be assembled to test the suitability of annealable linker sequences for assembling component polynucleotides comprising DNA segments comprising other elements, such as an enhancer, terminator, poly-A tail, nuclear localization signal, mRNA stabilization signal, selectable marker, epitope tag coding sequence, degradation signal, and the like. The test assembled polynucleotide may comprise additional component polynucleotides that enable testing, such as for example, genomic targeting sequences and selectable markers that enable introduction of the test assembled polynucleotide into host cells and selection of positive transformants for in vivo testing.

Table 1 presents the $T_m$, restriction sites, and read-through amino acids of exemplary annealable linker sequences corresponding to SEQ ID NOS: 1-23.

TABLE 1

Sequence and Characteristics of Annealable Linker Sequences

| Annealable Linker Sequence | Seq. Name | Length (bases) | % G-C | % A-T | Melt Temp. ($T_m$) | Restriction Enzyme Site | Read-Through Amino Acids Fwd | Rev |
|---|---|---|---|---|---|---|---|---|
| SEQ ID NO: 1 | RYSE 1 | 24 | 79.2 | 20.8 | 72.4 | | | |
| SEQ ID NO: 2 | RYSE 2 | 24 | 75.0 | 25.0 | 71.4 | MreI | | |
| SEQ ID NO: 3 | RYSE 3 | 24 | 75.0 | 25.0 | 73.7 | FseI | | TAGQARGD (SEQ ID NO: 249) |
| SEQ ID NO: 4 | RYSE 4 | 24 | 70.8 | 29.2 | 71.5 | SbfI | NLQAASAD (SEQ ID NO: 250) | IGARGLQV (SEQ ID NO: 251) |
| SEQ ID NO: 5 | RYSE 5 | 24 | 70.8 | 29.2 | 71.2 | AsiSI | NAIADAAD (SEQ ID NO: 252) | IGGVGDRV (SEQ ID NO: 253) |
| SEQ ID NO: 6 | RYSE 6 | 24 | 70.8 | 29.2 | 70.9 | NotI | KAAAGEGD (SEQ ID NO: 254) | ISLASGRL (SEQ ID NO: 255) |
| SEQ ID NO: 7 | RYSE 7 | 24 | 70.8 | 29.2 | 71.5 | AscI | KARHGRRD (SEQ ID NO: 256) | |
| SEQ ID NO: 8 | RYSE 8 | 24 | 75.0 | 25.0 | 70.7 | BbvCI | | |
| SEQ ID NO: 9 | RYSE 9 | 36 | 50.0 | 50.0 | 67.4 | | | |
| SEQ ID NO: 10 | RYSE 10 | 36 | 52.8 | 47.2 | 67.7 | | | |
| SEQ ID NO: 11 | RYSE 11 | 36 | 58.3 | 41.7 | 69.2 | | | |
| SEQ ID NO: 12 | RYSE 12 | 36 | 50.0 | 50.0 | 67.4 | | | |
| SEQ ID NO: 13 | RYSE 13 | 36 | 58.3 | 41.7 | 69.4 | | | |
| SEQ ID NO: 14 | RYSE 14 | 36 | 52.8 | 47.2 | 67.4 | | | |
| SEQ ID NO: 15 | RYSE 15 | 36 | 52.8 | 47.2 | 67.8 | | | |
| SEQ ID NO: 16 | RYSE 16 | 36 | 52.8 | 47.2 | 67.8 | | | |
| SEQ ID NO: 17 | RYSE 17 | 36 | 52.8 | 47.2 | 68.4 | | | |

TABLE 1-continued

Sequence and Characteristics of Annealable Linker Sequences

| Annealable Linker Sequence | Seq. Name | Length (bases) | % G-C | % A-T | Melt Temp. ($T_m$) | Restriction Enzyme Site | Read-Through Amino Acids Fwd | Rev |
|---|---|---|---|---|---|---|---|---|
| SEQ ID NO: 18 | RYSE 18 | 36 | 50.0 | 50.0 | 67.8 | | | |
| SEQ ID NO: 19 | RYSE 19 | 36 | 52.8 | 47.2 | 68.1 | | | |
| SEQ ID NO: 20 | RYSE 20 | 36 | 55.6 | 44.4 | 68.3 | | | |
| SEQ ID NO: 21 | RYSE 21 | 36 | 55.6 | 44.4 | 67.9 | | | |
| SEQ ID NO: 22 | RYSE 22 | 36 | 52.8 | 47.2 | 67.4 | | | |
| SEQ ID NO: 23 | RYSE 23 | 36 | 55.6 | 44.4 | 68.8 | | | |

5.8 Libraries

In another aspect, provided herein is a library comprising a plurality of assembly vectors. The library can serve to facilitate the efficient assembly of a plurality of component polynucleotides into one or more assembled polynucleotides that are functional in prokaryotes or eukaryotes, and thus facilitate the generation of unique organisms, e,g, recombinant strains of bacteria or yeast, without the need for time-consuming restriction endonuclease and ligase enzyme based cloning techniques. The assembly methods and compositions provided herein can facilitate the efficient replacement or introduction of functional DNA units, e.g., promoters, enhancers, origins of replication, etc., within an expression construct, and thus can provide for efficient optimization of the replication of, and/or expression from, the expression construct within a host organism.

The library may comprise a plurality of assembly vectors assembled within a single composition or container, e.g., a composition or container suitable for performing the assembly methods provided herein. Alternatively, the library may comprise a plurality of assembly vectors that are not assembled within the same composition or container. In some embodiments, the library comprises at least 3, at least 6, at least 10, at least 20, at least 50, or more than 50 assembly vectors, each comprising a DNA segment.

In some embodiments, the library comprises a plurality of assembly vectors wherein each of the assembly vectors comprises, in a 5' to 3' orientation, a first restriction site RA, a DNA segment D, an annealable linker sequence LB, and a second restriction site RB. In some embodiments, the library comprises a plurality of assembly vectors wherein each of the assembly vectors comprises, in a 5' to 3' orientation, a first restriction site RA, a primer binding segment PA or a first annealable linker sequence LA, a DNA segment D, and a second restriction site RB. In some embodiments, the library comprises a plurality of assembly vectors wherein each of the assembly vectors comprises, in a 5' to 3' orientation, a first restriction site RA, a first annealable linker sequence LA, a DNA segment D, an annealable linker sequence LB or a primer binding segment PB, and a second restriction site RB. In some embodiments, the annealable linker sequence pair or annealable linker sequence/primary binding segment pair within each assembly vector of the library does not comprise the same sequence. In some embodiments, the nucleic acid sequence of the annealable linker sequence LA and/or LB within each assembly vector is selected from the group consisting of SEQ ID NOS: 1 to 23. In some embodiments, the nucleic acid sequence of the primer binding segment PA or PB within each assembly vector is selected from the group consisting of SEQ ID NOS: 24 and 25.

In some embodiments, the library comprises at least one of each of the following vectors:
(a) a vector that consists of a circular polynucleotide that comprises, in a 5' to 3' orientation, a restriction site RA, a DNA segment D, an annealable linker sequence LB, and a restriction site RB;
(b) a vector that consists of a circular polynucleotide that comprises, in a 5' to 3' orientation, a restriction site RA, an annealable linker sequence LA, a DNA segment D, an annealable linker sequence LB, and a restriction site RB; and
(c) a vector that consists of a circular polynucleotide that comprises, in a 5' to 3' orientation, a restriction site RA, an annealable linker sequence LA, a DNA segment D, and a restriction site $RB_0$.

In some embodiments, the library comprises at least one of each of the following vectors:
(a) a vector that consists of a circular polynucleotide that comprises, in a 5' to 3' orientation, a restriction site RA, a primer binding segment PA, a DNA segment D, an annealable linker sequence LB, and a restriction site RB;
(b) a vector that consists of a circular polynucleotide that comprises, in a 5' to 3' orientation, a restriction site RA, an annealable linker sequence LA, a DNA segment D, an annealable linker sequence LB, and a restriction site RB; and
(c) a vector that consists of a circular polynucleotide that comprises, in a 5' to 3' orientation, a restriction site RA, an annealable linker sequence LA, a DNA segment D, a primer binding segment PB, and a restriction site $RB_0$.

In some embodiments, the nucleic acid sequence of primer binding segment PA is selected from the group consisting of SEQ ID NOS: 24 and 25. In some embodiments, the nucleic acid sequence of primer binding segment PB is selected from the group consisting of SEQ ID NOS: 24 and 25. In some embodiments, the nucleic acid sequences of primer binding segment PA and primer binding segment PB are selected from the group consisting of SEQ ID NOS: 24 and 25.

In some embodiments, the nucleic acid sequence of any of the annealable linker sequences LA and annealable linker sequences LB in the library are selected from the group consisting of SEQ ID NOS: 1 to 23. In some embodiments, the nucleic acid sequences of at least one of the annealable linker sequences LA and at least one of the annealable linker sequences LB in the library are selected from the group consisting of SEQ ID NOS: 1 to 23. In some embodiments, the nucleic acid sequence of each of the annealable linker sequences LA and annealable linker sequences LB in the library is selected from the group consisting of SEQ ID NOS: 1 to 23.

In some embodiments, the DNA segment D comprises a nucleic sequence selected from the group consisting of a selectable marker, a promoter, a genomic targeting sequence, a nucleic acid sequence encoding an epitope tag, a nucleic acid sequence encoding a gene of interest, a nucleic acid sequence encoding a termination codon, and lacZ.

In some embodiments, the library comprises at least one of each of the following nucleic acid molecules:
- (a) a first nucleic acid molecule wherein the first nucleic acid molecule is circular and comprises, in a 5' to 3' orientation, a first restriction site $RA_0$, any DNA segment selected from the group $D_0$, an annealable linker sequence $LB_0$, and a second restriction site $RB_0$;
- (b) an intermediate nucleic acid molecule wherein the intermediate nucleic acid molecule n is circular and comprises, in a 5' to 3' orientation, a first restriction site $RA_n$, a first annealable linker sequence $LA_n$, any DNA segment selected from the group $D_n$, a second annealable linker sequence $LB_n$, and a second restriction site $RB_n$, and wherein n represents an integer from one to the number of intermediate nucleic acid molecules; and
- (c) a last nucleic acid molecule wherein the last nucleic acid molecule is circular and comprises, in a 5' to 3' orientation, a first restriction site $RA_m$, an annealable linker sequence $LA_m$, any DNA segment selected from the group $D_m$, a second restriction site $RB_m$ wherein m represents an integer one greater than the number of intermediate nucleic acid molecules;

whereupon cleavage of restriction sites $RA_0$ through $RB_m$ and denaturation of the resulting linear nucleic acid molecules, each annealable linker sequence $LB_{(p-1)}$ is capable of hybridizing to the complement of annealable linker sequence $LA_p$ wherein p represents the integers from 1 to m, and wherein each group $D_0, \ldots D_n, \ldots$ and $D_m$ consists of one or more DNA segments. In some embodiments, a first nucleic acid molecule further comprises a primer binding segment PA positioned 5' to the DNA segment selected from the group $D_0$. In some embodiments, a last nucleic acid molecules further comprises a primer binding segment PB positioned 3' to the DNA segment selected from the group $D_m$.

In some embodiments, upon cleavage of restriction sites $RA_0$ through $RB_m$ and denaturation of the resulting linear nucleic acid molecules, each annealable linker sequence $LB_{(p-1)}$ is capable of selectively hybridizing to the complement of annealable linker sequence $LA_p$ compared to the other annealable linker sequences, or their complements, in the components composition. In some embodiments, each annealable linker sequence $LB_{(p-1)}$ is identical in sequence to annealable linker sequence $LA_p$.

In a particular embodiment, the restriction sites $RA_0$ through $RB_m$ are cleavable by the same restriction endonuclease so as to facilitate excision of the component polynucleotides from the assembly vectors. In some embodiments, the restrictions sites $RA_0$ through $RB_m$ are cleavable by SapI and LguI restriction endonucleases.

In some embodiments, the nucleic acid sequence of primer binding segment PA is selected from the group consisting of SEQ ID NOS: 24 and 25. In some embodiments, the nucleic acid sequence of primer binding segment PB is selected from the group consisting of SEQ ID NOS: 24 and 25. In some embodiments, the nucleic acid sequences of primer binding segment PA and primer binding segment PB are selected from the group consisting of SEQ ID NOS: 24 and 25. In preferable embodiments, the nucleic acid sequences of primer binding segment PA and primer binding segment PB are not identical.

In some embodiments, the nucleic acid sequence of any of the annealable linker sequences LA and annealable linker sequences LB in the library is selected from the group consisting of SEQ ID NOS: 1 to 23. In some embodiments, the nucleic acid sequences of at least one of the annealable linker sequences LA and at least one of the annealable linker sequences LB in the library are selected from the group consisting of SEQ ID NOS: 1 to 23. In some embodiments, the nucleic acid sequence of each of the annealable linker sequences LA and annealable linker sequences LB in the library is selected from the group consisting of SEQ ID NOS: 1 to 23. In some embodiments, the nucleic acid sequence of each of the annealable linker sequences LA in the composition are not identical to one another. In some embodiments, the nucleic acid sequence of each of the annealable linker sequences LB in the composition are not identical to one another.

In a particular embodiment, the library comprises the following nucleic acid molecules:
- (a) two first nucleic acid molecules, wherein one first nucleic acid molecule comprises, in a 5' to 3' orientation, a first restriction site $RA_0$, a primer binding segment PA, a DNA segment $D_{01}$, an annealable linker sequence $LB_0$, and a second restriction site $RB_0$, wherein another first nucleic acid molecule comprises, in a 5' to 3' orientation, a first restriction site $RA_0$, a primer binding segment PA, a DNA segment $D_{02}$, an annealable linker sequence $LB_0$, and a second restriction site $RB_0$, wherein DNA segment $D_{01}$ encodes a first genomic targeting sequence, wherein DNA segment $D_{02}$ encodes a second genomic targeting sequence located downstream of the first genomic targeting sequence in a target genome, and wherein DNA segment $D_{02}$ is positioned in opposite orientation as DNA segment $D_{01}$ relative to primer binding segment PA and annealable linker sequence $LB_0$;
- (b) at least one intermediate nucleic acid molecule comprising, in a 5' to 3' orientation, a first restriction site $RA_n$, a first annealable linker sequence $LA_n$, a DNA segment $D_n$, a second annealable linker sequence $LB_n$, and a second restriction site $RB_n$, wherein n represents an integer from one to the number of intermediate nucleic acid molecules; and
- (c) two last nucleic acid molecules, wherein one last nucleic acid molecule comprises, in a 5' to 3' orientation, a first restriction site $RA_m$, an annealable linker sequence $LA_m$, a DNA segment $D_{m1}$, a primer binding segment PB, and a second restriction site $RB_m$, wherein another last nucleic acid molecule comprises, in a 5' to 3' orientation, a first restriction site $RA_m$, an annealable linker sequence $LA_m$, a DNA segment $D_{m2}$, a primer binding segment PB, and a second restriction site $RB_m$, wherein m represents an integer one greater than the number of intermediate nucleic acid molecules, wherein DNA segment $D_{m1}$ encodes a first segment of a selectable marker, wherein DNA segment $D_{m2}$ encodes a second segment of the selectable marker, wherein DNA segment $D_{m2}$ is positioned in opposite orientation as DNA segment $D_{m1}$ relative to annealable linker sequence $LA_m$ and primer binding segment PB, wherein neither DNA segment $D_{m1}$ nor DNA segment $D_{m2}$ produces a functional selectable marker but whereupon homologous recombination of DNA segments $D_{m1}$ and $D_{m2}$ a functional selectable marker is generated;

wherein each annealable linker sequence $LB_{(p-1)}$ is identical to annealable linker sequence $LA_p$, wherein p represents the integers from 1 to m.

In some embodiments, the library comprises a plurality of assembly vectors wherein each assembly vector comprises the same annealable linker sequence, annealable linker sequence pair or annealable linker sequence/primary binding segment pair but differs in the sequence of their respective DNA fragment D.

In other embodiments, the library comprises a plurality of assembly vectors wherein each assembly vector comprises the same DNA segment D flanked by a unique annealable linker sequence, annealable linker sequence pair or annealable linker sequence/primer binding segment pair. Such a library may serve to facilitate the rapid assembly of DNA segment D into a particular position or orientation relative to the other DNA segments being assembled into the assembled polynucleotide.

In some embodiments, the members of the library comprise DNA segments that have shared structural or functional characteristics. For example, a library can comprise a plurality of assembly vectors comprising the same functional DNA unit. Exemplary functional DNA units include but are not limited to protein-coding sequences, reporter genes, fluorescent markers, promoters, enhancers, terminators, introns, exons, poly-A tails, multiple cloning sites, nuclear localization signals, nuclear export signals, mRNA stabilization signals, selectable markers, integration loci, epitope tags, and degradation signals. In some embodiments, the library comprises a plurality of assembly vectors wherein each assembly vector comprises the same promoter. The assembly vectors can comprise any prokaryotic or eukaryotic promoter sequence known in the art. Exemplary eukaryotic promoters include but are not limited to a metallothionein promoter, a constitutive adenovirus major late promoter, a dexamethasone-inducible MMTV promoter, a SV40 promoter, a MRP pol III promoter, a constitutive MPSV promoter, an RSV promoter, a tetracycline-inducible CMV promoter (such as the human immediate-early CMV promoter), and a constitutive CMV promoter. In particular embodiments, the assembly vectors comprise a yeast promoter sequence. Exemplary yeast promoters include but are not limited to PGAL3, PGAL7, PCTR3, PMET3, PPGK1, PTDH1, PTDH3, PFBA1, PTEF1, PENO1, PENO2, PCYC1, PTDH2, PCUP1, PGAL80, PGAL2, PBNA6, PTMA29, PSBP1, PPUP3, PACS2, PTPO1, PRPT1, PAAT2, PAHP1, PSSE1, PTEF2, PNPL3, PPET9, PTUB2, POLE1, PCPR1, PIPPP1, and PSOD1.

In some embodiments, the library comprises a plurality of assembly vectors wherein each assembly vector comprises the same terminator sequence. The assembly vectors can comprise any prokaryotic or eukaryotic terminator sequence known in the art. In particular embodiments, the assembly vectors comprise a yeast terminator sequence. Exemplary yeast terminators include but are not limited to TADH1, TENO1, TENO2, TCYC1, TNDT80, TTDH3, TTDH1, and TPGK1.

In some embodiments, the library comprises a plurality of assembly vectors wherein each assembly vector comprises the same selectable marker. The assembly vectors can comprise any prokaryotic or eukaryotic selectable marker known in the art. Examples of selectable markers include but are not limited to antibiotic resistance markers (e.g., genes encoding resistance to kanamycin, ampicillin, chloramphenicol, gentamycin, or trimethoprim) and metabolic markers (e.g., amino acid synthesis genes or transfer RNA genes).

5.9 Kits

In another aspect, provided herein is a kit for the assembly of a polynucleotide, said kit comprising two or more of the following: (a) one or more entry vectors described herein; (b) one or more restriction endonucleases capable of cleaving the restriction sites RA and RB of said one or more entry vectors; (c) one or more restriction endonucleases capable of cleaving the restriction sites RY and RZ of said entry vectors; and (d) oligonucleotide primers capable of annealing to primer binding segments PA and PB of said one or more entry vectors.

In some embodiments, restriction sites RA and RB of each entry vector of the kit are recognizable and cleavable by SapI restriction endonuclease, and the kit comprises SapI restriction endonuclease. In some embodiments, restriction sites RY and RZ of each entry vector of the kit are recognizable and cleavable by SchI (or MlyI) restriction endonuclease, and the kit comprises SchI (or MlyI) restriction endonuclease.

In some embodiments, the nucleic acid sequence of primer binding segment PA of one or more entry vectors in the kit is selected from the group consisting of SEQ ID NOS: 24 and 25. In some embodiments, the nucleic acid sequence of primer binding segment PB one or more entry vectors in the kit is selected from the group consisting of SEQ ID NOS: 24 and 25. In preferable embodiments, the nucleic acid sequences of primer binding segment PA and primer binding segment PB are not identical.

In some embodiments, the nucleic sequence of annealable linker sequence LA of one or more entry vectors in the kit is selected from the group consisting of SEQ ID NOS: 1 to 23. In some embodiments, the nucleic sequence of annealable linker sequence LB one or more entry vectors in the kit is selected from the group consisting of SEQ ID NOS: 1 to 23. In some embodiments, the nucleic sequences of annealable linker sequence LA and annealable linker sequence LB of all the entry vectors in the kit are selected from the group consisting of SEQ ID NOS: 1 to 23.

In some embodiments, the kit comprises pRYSE vector #1, the sequence of which is provided herein as SEQ ID NO: 221. In some embodiments, the kit comprises pRYSE vector #2, the sequence of which is provided herein as SEQ ID NO: 207. In some embodiments, the kit comprises pRYSE vector #3, the sequence of which is provided herein as SEQ ID NO: 208. In some embodiments, the kit comprises pRYSE vector #4, the sequence of which is provided herein as SEQ ID NO: 209. In some embodiments, the kit comprises pRYSE vector #5, the sequence of which is provided herein as SEQ ID NO: 210. In some embodiments, the kit comprises pRYSE vector #6, the sequence of which is provided herein as SEQ ID NO: 211. In some embodiments, the kit comprises pRYSE vector #7, the sequence of which is provided herein as SEQ ID NO:212. In some embodiments, the kit comprises pRYSE vector #8, the sequence of which is provided herein as SEQ ID NO: 213. In some embodiments, the kit comprises pRYSE vector #9, the sequence of which is provided herein as SEQ ID NO: 214. In some embodiments, the kit comprises pRYSE vector #10, the sequence of which is provided herein as SEQ ID NO: 215. In some embodiments, the kit comprises pRYSE vector #11, the sequence of which is provided herein as SEQ ID NO: 216. In some embodiments, the kit comprises pRYSE vector #12, the sequence of which is provided herein as SEQ ID NO: 217. In some embodiments, the kit comprises pRYSE vector #13, the sequence of which is provided herein as SEQ ID NO: 218. In some embodiments, the kit comprises pRYSE vector #14, the sequence of which is provided herein as SEQ ID NO:219. In some embodiments, the kit comprises pRYSE vector #15, the sequence of which is provided herein as SEQ ID NO: 220.

In some embodiments, the kit further comprises instructions for use that describe the polynucleotide assembly method disclosed herein. In some embodiments, a polynucleotide polymerase, such as a thermostable DNA polymerase (e.g., Pfu DNA polymerase), and deoxyribonucleoside triphosphates (dNTPs) are also present in the kit. In some embodiments, two or more assembly vectors each comprising a component polynucleotide to be assembled into an assembled polynucleotide may be provided in the kit. For example, assembly vectors may be provided that comprise a component polynucleotide useful for calibration and/or for use as a positive control to verify correct performance of the kit. Other examples include but are not limited to assembly vectors comprising as a component polynucleotide a protein-coding sequence, reporter gene, fluorescent marker coding sequence, promoter, enhancer, terminator, intron, exon, poly-A tail, multiple cloning site, nuclear localization signal, mRNA stabilization signal, selectable marker, integration loci, epitope tag coding sequence, and degradation signal.

6. EXAMPLES

The invention is illustrated by the following examples, which are not intended to be limiting in any way. The *Saccharomyces cerevisiae* constructs described in the Examples were derived from *Saccharomyces cerevisiae* strain CEN.PK2. Unlike *Saccharomyces cerevisiae* strain S288c, the genomic sequence of strain CEN.PK2 is not publicly available. Some of the constructs described were sequence-verified, and so the sequences provided are those of the actual CEN.PK2-derived constructs. For constructs that were not sequence-verified, the sequences provided are based on the published genomic sequence of strain S288c, and thus may include polymorphic differences to the sequences of the actual CEN.PK2-derived constructs.

Example 1

This example describes methods for making pRYSE vectors. pRYSE vectors comprise, in a 5' to 3' orientation, a first SapI restriction enzyme recognition site, a first annealable linker sequence or primer binding segment, a first SchI restriction enzyme recognition site, a green fluorescent protein (GFP) or lacZ marker gene, a second SchI restriction enzyme recognition site, a second annealable linker sequence or primer binding segment, and a second SapI restriction enzyme recognition site.

A DNA fragment encoding β-lactamase was PCR amplified from the pUC19 vector (GenBank accession L09137) using primers JCB158-17C (SEQ ID NO: 229) and JCB158-17D (SEQ ID NO: 230) after the SchI restriction enzyme recognition site in the bla gene of pUC19 had been removed by site-directed mutagenesis of pUC19 using PCR primers JCB158-17A (SEQ ID NO: 227) and JCB158-17B (SEQ ID NO: 228). The PCR product was gel purified, and then ligated into the TOPO vector (Invitrogen, Carlsbad, Calif.), from which it was liberated again by digesting the construct to completion using SphI and MfeI restriction enzymes, yielding the "bla DNA fragment".

DNA fragments 1040 (SEQ ID NO: 224), 1041 (SEQ ID NO: 225), and 1042 (SEQ ID NO: 226) were generated synthetically (Biosearch Technologies, Novato, Calif.). DNA fragments 1040 and 1041 were digested to completion using BstXI restriction enzyme, and each digested fragment was ligated with the 2.65 kb vector backbone that was generated by cutting to completion pAM1466 (SEQ ID NO: 223; generated synthetically by Biosearch Technologies, Novato, Calif.) using restriction enzymes SacI and KpnI. The 1040_pAM1466 DNA construct was digested to completion using BsmBI and BstXI restriction enzymes, the reaction mixture was resolved by gel electrophoresis, and an approximately 3.5 kb DNA fragment comprising the 1040 DNA fragment was gel purified. The 1041_pAM1466 DNA construct was digested to completion using BsaI and BstXI restriction enzymes, the reaction mixture was resolved by gel electrophoresis, and an approximately 0.9 kb 1041 DNA fragment comprising the 1041 DNA fragment was gel purified. The purified DNA fragments were ligated, yielding DNA construct 1040_1041_pAM1466. DNA fragment 1042 was joined to DNA construct 1040_1041 by a PCR "stitching" reaction using primers JO36 (SEQ ID NO: 69) and JO37 (SEQ ID NO: 70) to generate the 1040_1041 DNA fragment, primers JO38 (SEQ ID NO: 71) and JO39 (SEQ ID NO: 72) to generate the 1042 DNA fragment with a terminal sequence that overlapped a terminal sequence of the 1040_1041 DNA fragment, and primers JO39 (containing a SphI restriction enzyme recognition site) (SEQ ID NO: 72) and JO36 (containing a MfeI restriction enzyme recognition site) (SEQ ID NO: 69) to join the two PCR products. The 1040_1041_1042 PCR product was digested to completion using SphI and MfeI restriction enzymes, the reaction mixture was resolved by gel electrophoresis, the approximately 2.4 kb 1040_1041_1042 DNA fragment was gel purified, and the purified DNA fragment was ligated to the gel purified bla fragment, yielding the "1040_1041_1042_bla" DNA construct.

The segment of the 1040_1041_1042 bla DNA construct encoding the GFP gene was PCR amplified using PCR primers 1 and 2 (see Table 2). To the amplified GFP fragment terminal SacI and XhoI restriction enzymes recognition sites were added by PCR amplification using as templates the gel-extracted GFP fragments generated in the first round of PCR reactions, and PCR primers 3 and 4 (see Table 2). The amplified PCR products were gel extracted, then digested to completion using XhoI and SacI restriction enzymes, the restriction enzymes were heat inactivated for 20 minutes at 65° C., and the digested PCR products were column purified and then ligated with the gel purified approximately 2.2 kb DNA fragment that resulted from digesting the 1040_1041_1042 bla DNA construct to completion using XhoI and SacI restriction enzymes. The resulting vectors were PCR amplified using PCR primers 5 and 6 (see Table 3), the reaction mixtures were resolved by gel electrophoresis, and the approximately 2.2 kb "pRYSE vector backbones" were gel purified.

TABLE 2

PCR Primers used to Generate GFP Inserts Flanked by Annealable Linker Pairs or Annealable Linker/Primer Binding Segment Pairs and SacI and XhoI Restriction Enzyme Sites

| GFP Fragment | Annealable Linker or Primer Binding Segment 1 | Annealable Linker or Primer Binding Segment 2 | Primer 1 | Primer 2 | Primer 3 | Primer 4 |
|---|---|---|---|---|---|---|
| 1 | Pme1-5' | RYSE 1 | J018 (SEQ ID NO: 73) | J073 (SEQ ID NO: 106) | J055 (SEQ ID NO: 88) | J064 (SEQ ID NO: 97) |

TABLE 2-continued

PCR Primers used to Generate GFP Inserts Flanked by Annealable Linker Pairs or Annealable Linker/Primer Binding Segment Pairs and SacI and XhoI Restriction Enzyme Sites

| GFP Fragment | Annealable Linker or Primer Binding Segment 1 | Annealable Linker or Primer Binding Segment 2 | Primer 1 | Primer 2 | Primer 3 | Primer 4 |
|---|---|---|---|---|---|---|
| 2 | RYSE 1 | RYSE 2 | J019 (SEQ ID NO: 74) | J074 (SEQ ID NO: 107) | J056 (SEQ ID NO: 89) | J065 (SEQ ID NO: 98) |
| 3 | RYSE 2 | RYSE 3 | J020 (SEQ ID NO: 75) | J029 (SEQ ID NO: 82) | J057 (SEQ ID NO: 90) | J066 (SEQ ID NO: 99) |
| 4 | RYSE 3 | RYSE 4 | J021 (SEQ ID NO: 76) | J030 (SEQ ID NO: 83) | J058 (SEQ ID NO: 91) | J067 (SEQ ID NO: 100) |
| 5 | RYSE 4 | RYSE 5 | J022 (SEQ ID NO: 77) | J031 (SEQ ID NO: 84) | J059 (SEQ ID NO: 92) | J068 (SEQ ID NO: 101) |
| 6 | RYSE 5 | RYSE 6 | J023 (SEQ ID NO: 78) | J032 (SEQ ID NO: 85) | J060 (SEQ ID NO: 93) | J069 (SEQ ID NO: 102) |
| 7 | RYSE 6 | RYSE 7 | J024 (SEQ ID NO: 79) | J033 (SEQ ID NO: 86) | J061 (SEQ ID NO: 94) | J070 (SEQ ID NO: 103) |
| 8 | RYSE 7 | RYSE 8 | J025 (SEQ ID NO: 80) | J034 (SEQ ID NO: 87) | J062 (SEQ ID NO: 95) | J071 (SEQ ID NO: 104) |
| 9 | RYSE 2 | Pme1-3' | J020 (SEQ ID NO: 75) | J075 (SEQ ID NO: 108) | J057 (SEQ ID NO: 90) | J072 (SEQ ID NO: 105) |
| 10 | RYSE 3 | Pme1-3' | J021 (SEQ ID NO: 76) | J075 (SEQ ID NO: 108) | J058 (SEQ ID NO: 91) | J072 (SEQ ID NO: 105) |
| 11 | RYSE 4 | Pme1-3' | J022 (SEQ ID NO: 77) | J075 (SEQ ID NO: 108) | J059 (SEQ ID NO: 92) | J072 (SEQ ID NO: 105) |
| 12 | RYSE 5 | Pme1-3' | J023 (SEQ ID NO: 78) | J075 (SEQ ID NO: 108) | J060 (SEQ ID NO: 93) | J072 (SEQ ID NO: 105) |
| 13 | RYSE 6 | Pme1-3' | J024 (SEQ ID NO: 79) | J075 (SEQ ID NO: 108) | J061 (SEQ ID NO: 94) | J072 (SEQ ID NO: 105) |
| 14 | RYSE 7 | Pme1-3' | J025 (SEQ ID NO: 80) | J075 (SEQ ID NO: 108) | J062 (SEQ ID NO: 95) | J072 (SEQ ID NO: 105) |
| 15 | RYSE 8 | Pme1-3' | J026 (SEQ ID NO: 81) | J075 (SEQ ID NO: 108) | J063 (SEQ ID NO: 96) | J072 (SEQ ID NO: 105) |

TABLE 3

Annealable Linker Sequence Pairs or Annealable Linker Sequnece/Primer Binding Segment Pairs Present in pRYSE Vectors, and PCR Primers Used to Generate pRYSE Vector Backbones

| pRYSE vector | Annealable Linker or Primer Binding Segment 1 (see Table 1) | Annealable Linker or Primer Binding Segment 2 (see Table 1) | Primer 5 | Primer 6 |
|---|---|---|---|---|
| 1 | Pme1-5' | RYSE 1 | S001 (SEQ ID NO: 46) | S002 (SEQ ID NO: 47) |
| 2 | RYSE 1 | RYSE 2 | S003 (SEQ ID NO: 48) | S004 (SEQ ID NO: 49) |
| 3 | RYSE 2 | RYSE 3 | S005 (SEQ ID NO: 50) | S006 (SEQ ID NO: 51) |
| 4 | RYSE 3 | RYSE 4 | S007 (SEQ ID NO: 52) | S008 (SEQ ID NO: 53) |
| 5 | RYSE 4 | RYSE 5 | S009 (SEQ ID NO: 54) | S010 (SEQ ID NO: 55) |

TABLE 3-continued

Annealable Linker Sequence Pairs or Annealable Linker Sequnece/Primer Binding
Segment Pairs Present in pRYSE Vectors, and PCR Primers Used to Generate
pRYSE Vector Backbones

| pRYSE vector | Annealable Linker or Primer Binding Segment 1 (see Table 1) | Annealable Linker or Primer Binding Segment 2 (see Table 1) | Primer 5 | Primer 6 |
|---|---|---|---|---|
| 6 | RYSE 5 | RYSE 6 | S011 (SEQ ID NO: 56) | S012 (SEQ ID NO: 57) |
| 7 | RYSE 6 | RYSE 7 | S013 (SEQ ID NO: 58) | S014 (SEQ ID NO: 59) |
| 8 | RYSE 7 | RYSE 8 | S015 (SEQ ID NO: 60) | S016 (SEQ ID NO: 61) |
| 9 | RYSE 2 | Pme1-3' | S005 (SEQ ID NO: 50) | S018 (SEQ ID NO: 63) |
| 10 | RYSE 3 | Pme1-3' | S007 (SEQ ID NO: 52) | S018 (SEQ ID NO: 63) |
| 11 | RYSE 4 | Pme1-3' | S009 (SEQ ID NO: 54) | S018 (SEQ ID NO: 63) |
| 12 | RYSE 5 | Pme1-3' | S011 (SEQ ID NO: 56) | S018 (SEQ ID NO: 63) |
| 13 | RYSE 6 | Pme1-3' | S013 (SEQ ID NO: 58) | S018 (SEQ ID NO: 63) |
| 14 | RYSE 7 | Pme1-3' | S015 (SEQ ID NO: 60) | S018 (SEQ ID NO: 63) |
| 15 | RYSE 8 | Pme1-3' | S017 (SEQ ID NO: 62) | S018 (SEQ ID NO: 63) |

The lacZ gene was PCR amplified from the pUC19 vector using primers S027 (SEQ ID NO: 65) and S028 (SEQ ID NO: 66), which each comprise a SchI restriction enzyme recognition site. The reaction mixture was resolved by gel electrophoresis, the approximately 0.5 kb PCR product was gel purified, and the purified PCR product was ligated with each of the pRYSE vector backbones. Site-directed mutagenesis was performed on the resulting vectors using PCR primers L012 (SEQ ID NO: 231) and L013 (SEQ ID NO: 232) to remove a SchI restriction enzyme recognition site from the origin of replication. Finally, a second site-directed mutagenesis was performed using PCR primers 5036 (SEQ ID NO: 67) and S037 (SEQ ID NO: 68) to remove the SchI restriction enzyme recognition site from the lacZ fragment, thus yielding pRYSE vectors 1 through 15 (see FIG. 4 for a plasmid map of the pRYSE vectors, and SEQ ID NOS: 207 through 221 for the nucleotide sequence of pRYSE vectors 1 through 15).

Example 2

This example describes alternative methods for making pRYSE vectors.

pRYSE vectors 1 through 15 can be generated synthetically using as template SEQ ID NOS: 207 through 221 (e.g., by Biosearch Technologies, Novato, Calif.). Additional pRYSE vectors comprising different annealable linker sequences can be generated synthetically using as template SEQ ID NO: 221 in which the Pme1-5' primer binding segment and/or the RYSE 1 annealable linker sequence are changed to another suitable annealable linker sequence or primer binding segment (see Table 1).

Example 3

This example describes methods for making a pMULE vector, comprising, in a 5' to 3' orientation, a first SapI restriction enzyme recognition site, a first SchI restriction enzyme recognition site, a lacZ marker gene, a second SchI restriction enzyme recognition site, and a second SapI restriction enzyme recognition site. The pMULE vector can be used to clone Mules.

Figure 7:
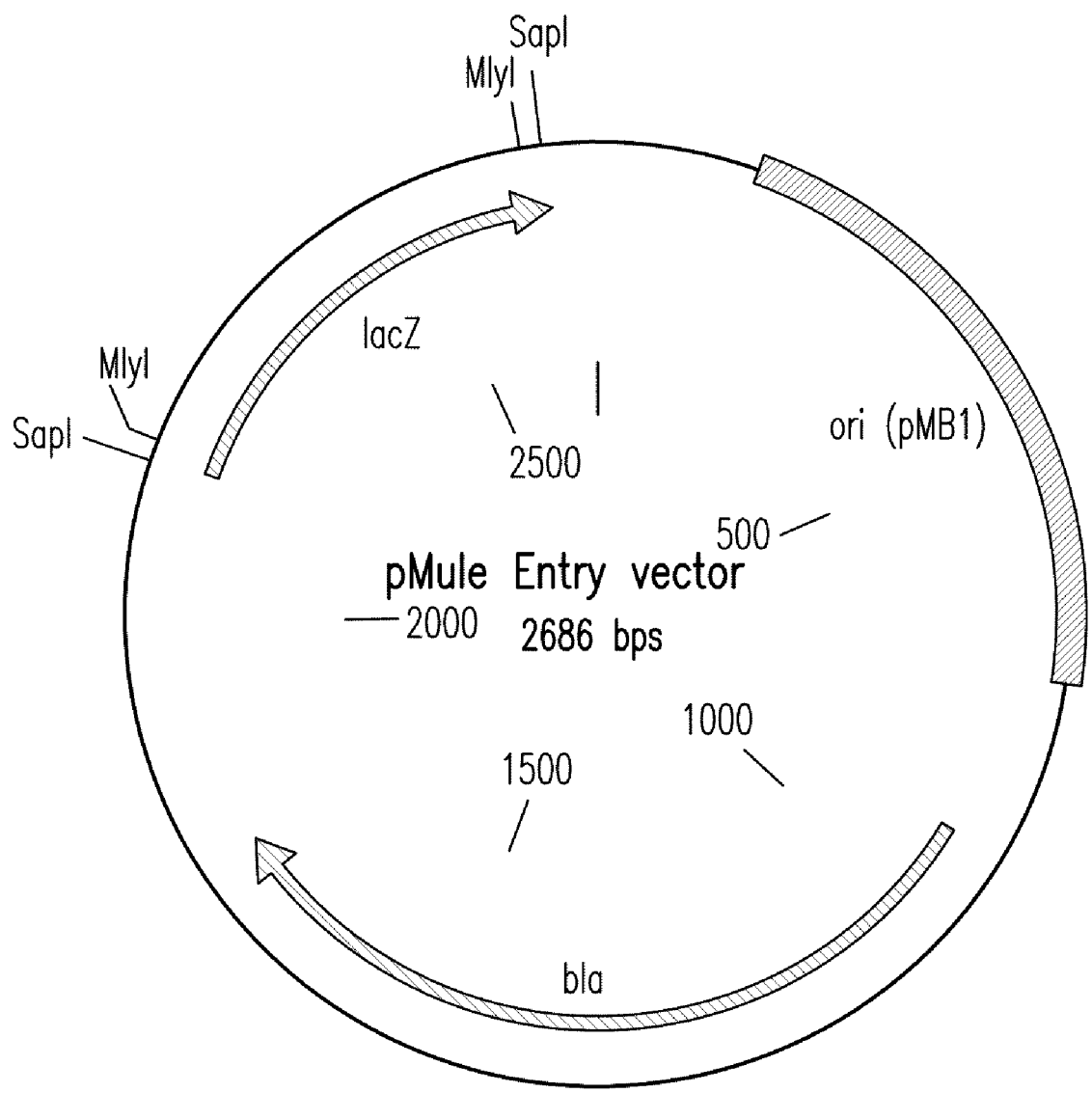

The backbone of pRYSE vector 8 was PCR amplified using primers K162 (SEQ ID NO: 109) and K163 (SEQ ID NO: 110). The reaction mixture was resolved by gel electrophoresis, and the approximately 2.2 kb vector backbone was gel purified. A DNA fragment comprising the lacZ gene was generated by digesting to completion pRYSE vector 8 using SchI restriction enzyme, heat inactivating the enzyme at 65° C. for 20 minutes, resolving the reaction mixture by gel electrophoresis, and gel purifying the approximately 0.5 kb DNA fragment. The purified DNA fragment comprising the lacZ gene was ligated with the purified vector backbone, yielding the pMULE vector (see FIG. 7 for a plasmid map).

Example 4

This example describes methods for making "Bits". Bits are DNA fragments that can be inserted into pRYSE vectors to generate assembly vectors comprising component polynucleotides that can be assembled into assembled polynucleotides using methods disclosed herein. Bits may encode genes or genetic elements of interest (e.g., promoters, terminators, selectable markers, integration loci, epitope tags, localization signals, degradation signals, fluorescent markers, multiple cloning sites). Bits were PCR amplified from a template using primers as described in Table 4.

TABLE 4

| | | | Size | |
|---|---|---|---|---|
| Bit | Type* | Primers | (bp) | Template |
| atoB | Gs | L229 (SEQ ID NO: 40) L230 (SEQ ID NO: 41) | 1185 | plasmid DNA comprising the atoB gene from *Escherichia coli* (GenBank accession number NC_000913 REGION: 2324131 . . . 2325315) |
| mvaS | Gs | L235 (SEQ ID NO: 42) L236 (SEQ ID NO: 43) | 1152 | synthetic DNA fragment comprising mvaS gene from Enter°C.°Ccus *faecalis* (GenBank accession number AF290092 REGION: 142 . . . 1293) codon-optimized for expression in *Saccharomyces cerevisiae* and comprising at position 110 an alanine to glycine modification to increase enzyme activity (see Steussy et al. (2006) Bi°Chemistry 45(48): 14407-14414) |
| ERG13-1 | GsT | L109 (SEQ ID NO: 235) L110 (SEQ ID NO: 26) | 1726 | *Saccharomyces cerevisiae* strain CEN.PK2 genomic DNA |
| 3' NDT80 | D | L221 (SEQ ID NO: 34) L222 (SEQ ID NO: 35) | 516 | *Saccharomyces cerevisiae* strain CEN.PK2 genomic DNA |
| 5' NDT80 | U | L219 (SEQ ID NO: 32) L220 (SEQ ID NO: 33) | 495 | *Saccharomyces cerevisiae* strain CEN.PK2 genomic DNA |
| tP$_{FBA1}$ | P | L225 (SEQ ID NO: 37) L057 (SEQ ID NO: 234) | 526 | *Saccharomyces cerevisiae* strain CEN.PK2 genomic DNA |
| tP$_{TDH3}$ | P | L224 (SEQ ID NO: 36) L054 (SEQ ID NO: 233) | 559 | *Saccharomyces cerevisiae* strain CEN.PK2 genomic DNA |
| ERG10-1 | Gs | L226 (SEQ ID NO: 38) L227 (SEQ ID NO: 39) | 1182 | synthesized fragment encoding the acetyl-CoA acetyltransferase of Ralstonia eutropha (GenBank accession NC_008313 REGION: 183291 . . . 184469) codon-optimized for expression in *Saccharomyces cerevisiae* and followed by an additional stop codon |
| tENO1 | T | L248 (SEQ ID NO: 44) L176 (SEQ ID NO: 27) | 265 | *Saccharomyces cerevisiae* strain CEN.PK2 genomic DNA |
| tTDH3 | T | L185 (SEQ ID NO: 28) L186 (SEQ ID NO: 29) | 260 | *Saccharomyces cerevisiae* strain CEN.PK2 genomic DNA |
| HphA | M | TRIX_L_193 (SEQ ID NO: 184) TRIX_L_194 (SEQ ID NO: 185) | 1912 | plasmid DNA comprising the TEF1 promoter and terminator of *Kluyveromyces lactis* (GenBank accession CR382122 REGIONS: 788874 . . . 789380 and 787141 . . . 787496, respectively) and the hph gene of *Klebsiella pneumonia* |
| tHMG1 | GsT | TRIX_L_232 (SEQ ID NO: 186) TRIX_L_233 (SEQ ID NO: 187) | 1742 | *Saccharomyces cerevisiae* strain CEN.PK2 genomic DNA |
| tP$_{GAL1,10}$ | P | TRIX_L_266 (SEQ ID NO: 190) TRIX_L_267 (SEQ ID NO: 191) | 620 | *Saccharomyces cerevisiae* strain CEN.PK2 genomic DNA |
| ERG10-2 | GsT | TRIX_L_106 (SEQ ID NO: 170) TRIX_L_107 (SEQ ID NO: 171) | 1467 | *Saccharomyces cerevisiae* strain CEN.PK2 genomic DNA |
| ERG13-2 | GsT | TRIX_L_109 (SEQ ID NO: 172) TRIX_L_110 (SEQ ID NO: 173) | 1726 | *Saccharomyces cerevisiae* strain CEN.PK2 genomic DNA |
| GAL80US | U | JU-218-168-130-GAL80US-F (SEQ ID NO: 134) JU-219-168-130-GAL80US-R (SEQ ID NO: 135) | 500 | *Saccharomyces cerevisiae* strain CEN.PK2 genomic DNA |
| GAL80DS | D | JU-220-168-130-GAL80DS-F (SEQ ID NO: 136) JU-221-168-130-GAL80DS-R (SEQ ID NO: 137) | 500 | *Saccharomyces cerevisiae* strain CEN.PK2 genomic DNA |
| P$_{TDH3}$ | P | L224 (SEQ ID NO: 36) TRIX_L_053 (SEQ ID NO: 169) | 583 | *Saccharomyces cerevisiae* strain CEN.PK2 genomic DNA |

TABLE 4-continued

Amplified Bits

| Bit | Type* | Primers | Size (bp) | Template |
|---|---|---|---|---|
| NatA | M | TRIX_L_193 (SEQ ID NO: 184) TRIX_L_194 (SEQ ID NO: 185) | 1456 | plasmid DNA comprising the TEF1 promoter and terminator of *Kluyveromyces lactis* (GenBank accession CR382122 REGIONS: 788874 . . . 789380 and 787141 . . . 787496, respectively) and the nat1 gene of *S. noursei* |
| ERG12 | GsT | TRIX_L_112 (SEQ ID NO: 174) TRIX_L_113 (SEQ ID NO: 175) | 1582 | *Saccharomyces cerevisiae* strain CEN.PK2 genomic DNA |
| ERG8 | GsT | TRIX_L_118 (SEQ ID NO: 178) TRIX_L_119 (SEQ ID NO: 179) | 1616 | *Saccharomyces cerevisiae* strain CEN.PK2 genomic DNA |
| $P_{GAL4oc}$ | P | TRIX_K_131 (SEQ ID NO: 165) PW-91-093-CPK422-G (SEQ ID NO: 162) | 270 | plasmid DNA comprising an "operative constitutive" version of the promoter of the GAL4 gene of *Saccharomyces cerevisiae* strain CEN.PK2 (Griggs & Johnston (1991) PNAS 88(19): 8597-8601) |
| GAL4-1 | G | JU-286-275-31-GAL4-F (SEQ ID NO: 140) JU-285-275-31-GAL4-FIX-R2 (SEQ ID NO: 139) | 526 | *Saccharomyces cerevisiae* strain CEN.PK2 genomic DNA |
| GAL4-2 | G | JU-284-275-31-GAL4-FIX-F2 (SEQ ID NO: 138) JU-287-275-31-GAL4-R (SEQ ID NO: 141) | 2414 | *Saccharomyces cerevisiae* strain CEN.PK2 genomic DNA |
| KanA | M | TRIX_L_193 (SEQ ID NO: 184) TRIX_L_194 (SEQ ID NO: 185) | 1696 | plasmid DNA comprising the TEF1 promoter and terminator of *Kluyveromyces lactis* (GenBank accession CR382122 REGIONS: 788874 . . . 789380 and 787141 . . . 787496, respectively) and the kanR gene of Tn903 transposon |
| ERG19 | GsT | TRIX_L_115 (SEQ ID NO: 176) TRIX_L_116 (SEQ ID NO: 177) | 1441 | *Saccharomyces cerevisiae* strain CEN.PK2 genomic DNA |
| ERG20 | GsT | TRIX_L_124 (SEQ ID NO: 182) TRIX_L_125 (SEQ ID NO: 183) | 1319 | *Saccharomyces cerevisiae* strain CEN.PK2 genomic DNA |
| $P_{GAL7}$ | P | TRIX_L_34 (SEQ ID NO: 166) TRIX_L_35 (SEQ ID NO: 167) | 500 | *Saccharomyces cerevisiae* strain CEN.PK2 genomic DNA |
| $tP_{GAL7}$ | P | TRIX_L_34 (SEQ ID NO: 166) TRIX_L_36 (SEQ ID NO: 168) | 476 | *Saccharomyces cerevisiae* strain CEN.PK2 genomic DNA |
| IDI1 | GsT | TRIX_L_121 (SEQ ID NO: 180) TRIX_L_122 (SEQ ID NO: 181) | 1127 | *Saccharomyces cerevisiae* strain CEN.PK2 genomic DNA |
| $tP_{CTR3}$ | P | TRIX_K_0142 (SEQ ID NO: 163) TRIX_K_0143 (SEQ ID NO: 164) | 710 | plasmid DNA comprising promoter of the CTR3 gene of *Saccharomyces cerevisiae* strain CEN.PK2 |
| LEU2US | U | JU-164-168-110-LEU2US-f (SEQ ID NO: 129) JU-165-168-110-LEU2US-r (SEQ ID NO: 130) | 500 | *Saccharomyces cerevisiae* strain CEN.PK2 genomic DNA |
| LEU2DS | D | JU-162-168-110-LEU2DS-f (SEQ ID NO: 127) JU-163-168-110-LEU2DS-r (SEQ ID NO: 128) | 500 | *Saccharomyces cerevisiae* strain CEN.PK2 genomic DNA |
| ERG9US | U | JU-108-168-110-ERG9US-f (SEQ ID NO: 126) JU-172-168-110-ERG9US-r1 (SEQ ID NO: 133) | 499 | *Saccharomyces cerevisiae* strain CEN.PK2 genomic DNA |

TABLE 4-continued

Amplified Bits

| Bit | Type* | Primers | Size (bp) | Template |
|---|---|---|---|---|
| ERG9CDS | G | JU-106-168-110-ERG9CDS-f (SEQ ID NO: 124) JU-107-168-110-ERG9CDS-r (SEQ ID NO: 125) | 501 | *Saccharomyces cerevisiae* strain CEN.PK2 genomic DNA |
| STE5US | U | TRIX_RN017 (SEQ ID NO: 192) TRIX_RN018 (SEQ ID NO: 193) | 600 | *Saccharomyces cerevisiae* strain CEN.PK2 genomic DNA |
| STE5DS | D | TRIX_RN019 (SEQ ID NO: 194) TRIX_RN020 (SEQ ID NO: 195) | 600 | *Saccharomyces cerevisiae* strain CEN.PK2 genomic DNA |
| URA3 | M | JU-169-168-110-URA3-f (SEQ ID NO: 131) JU-170-168-110-URA3-r (SEQ ID NO: 132) | 1554 | *Saccharomyces cerevisiae* strain CEN.PK2 genomic DNA |

*G = gene; s = stop codon; T = terminator; M = marker; D = downstream integration region; U = upstream integration region; P = promoter.

PCR amplifications were done using the Phusion DNA polymerase (New England Biolabs, Ipswich, Mass.) as per manufacturer's suggested protocol. The PCR reactions were resolved by gel electrophoresis, the bits were gel purified, and the purified bits were treated with T4 polynucleotide kinase (PNK) (New England Biolabs, Ipswich, Mass.) as per manufacturer's suggested protocol. The PNK was heat inactivated at 65° C. for 20 minutes, and the samples were stored at −20° C.

Example 5

This example describes methods for making "MULEs." MULEs are DNA fragments that can be inserted into pMULE vectors to generate assembly vectors comprising components polynucleotides that can be assembled into assembled polynucleotides using methods disclosed herein. MULEs may encode genes or genetic elements of interest (e.g., promoters, terminators, selectable markers, integration loci, epitope tags, localization signals, degradation signals, fluorescent markers, multiple cloning sites) flanked by annealable linker sequence pairs or annealable linker sequence/primer binding segment pairs. MULEs were PCR amplified from a template using primers of which the 3' end anneals to the target sequence and the 5' end comprises an annealable linker sequence or a primer binding segment (see Table 1 for suitable annealable linker sequences), as described in Table 5.

TABLE 5

Amplified MULEs

| MULE | Type* | Primers | Size (bp) | Template |
|---|---|---|---|---|
| tHMG1-a | G | KMH8-276-1-linker4.tHMG1.fwd (SEQ ID NO: 157) KMH9-276-1-linker9.tHMG1.rev (SEQ ID NO: 160) | 1794 | RABit 254 plasmid DNA |
| ERG12 | G | KMH46-276-43-ERG12linker4.fwd (SEQ ID NO: 151) KMH14-276-4-liniker9.ERG12.rev (SEQ ID NO: 145) | 1634 | RABit 250 plasmid DNA |
| ERG19 | G | KMH47-276-43-ERG19linker4.fwd (SEQ ID NO: 152) KMH15-276-4-linker9.ERG19.rev (SEQ ID NO: 146) | 1493 | RABit 241 plasmid DNA |
| $P_{TDH3}$-a | P | KMH81-276-116-TDH3.rev.tHMG1 (SEQ ID NO: 155) S004 (SEQ ID NO: 49) | 626 | RABit 54 plasmid DNA |
| $P_{TDH3}$-b | P | KMH91-276-116-TDH3.rev.FS (SEQ ID NO: 158) S004 (SEQ ID NO: 49) | 546 | RABit 54 plasmid DNA |
| tHMG1-b | G | KMH82-276-116-tHMG1.fwd.TDH3 (SEQ ID NO: 156) S009 (SEQ ID NO: 54) | 1801 | RABit 20 plasmid DNA |

TABLE 5-continued

Amplified MULEs

| MULE | Type* | Primers | Size (bp) | Template |
|------|-------|---------|-----------|----------|
| IME1US | U | KB454-266-53 (SEQ ID NO: 142) KB455-266-53 (SEQ ID NO: 143) | 578 | *Saccharomyces cerevisiae* strain CEN.PK2 genomic DNA |
| IME1DS | D | KMH93-276-130-3'IME.linker4.fwd (SEQ ID NO: 161) KB457-266-53 (SEQ ID NO: 144) | 554 | *Saccharomyces cerevisiae* strain CEN.PK2 genomic DNA |
| LEU2 | M | VH296-235-55-Leu2 12-1 F (SEQ ID NO: 30) VH296-235-55-Leu2 12-1 R (SEQ ID NO: 31) | 1795 | plasmid DNA comprising LEU2 locus of *Saccharomyces cerevisiae* strain CEN.PK2 (Sikorski RS, Hieter (1989) Genetics 122(1): 19-27) |
| FS-a | G | KMH5-276-1-linker3.FS(Kozak).fwd (SEQ ID NO: 153) KMH7-276-1-linker4.TCYC1.rev (SEQ ID NO: 154) | 1981 | plasmid DNA comprising coding sequence of farnesene synthase of *Artemisia annua* (GenBank accession number AY835398) codon-optimized for expression in *Saccharomyces cerevisiae* and terminator of CYC1 gene of *Saccharomyces cerevisiae* strain CEN.PK2 |
| FS-b | G | KMH92-276-116-FS.fwd.TDH3 (SEQ ID NO: 159) KMH7-276-1-linker4.TCYC1.rev (SEQ ID NO: 154) | 1976 | plasmid DNA comprising coding sequence of farnesene synthase of *Artemisia annua* (GenBank accession number AY835398) codon-optimized for expression in *Saccharomyces cerevisiae* and terminator of CYC1 gene of *Saccharomyces cerevisiae* strain CEN.PK2 |
| URA3b laster | M | VH228-235-7-URA3LOF3RYSE12-1F (SEQ ID NO: 204) VH229-235-7-URA3LOF3RYSE12-1R (SEQ ID NO: 205) | 1565 | URA-3 blaster template** |

*G = gene; s = stop codon; T = terminator; M = marker; D = downstream integration region; U = upstream integration region; P = promoter.
**The URA-3 blaster template was made by first generating DNA fragments flanking sequence A (generated from a synthetic DNA fragment comprising SEQ ID NO: 206 using PCR primers TRIX_Z025 (SEQ ID NO: 196) and TRIX_Z026 (SEQ ID NO: 197)), flanking sequence B (generated from a synthetic DNA fragment comprising SEQ ID NO: 206 using PCR primers TRIX_Z027 (SEQ ID NO: 198) and TRIX_Z028 (SEQ ID NO: 199)), URA3-c (generated from *Saccharomyces cerevisiae* strain CEN.PK2 genomic DNA using PCR primers TRIX_Z033 (SEQ ID NO: 200) and TRIX_Z036 (SEQ ID NO: 203)), and URA3-d (generated from *Saccharomyces cerevisiae* strain CEN.PK2 genomic DNA using PCR primers TRIX_Z034 (SEQ ID NO: 201) and TRIX_Z035 (SEQ ID NO: 202)). DNA fragments flanking sequence A, URA3-c, and URA-3-d were then stitched together into DNA fragment A using PCR primers TRIX_Z025 and TRIX_Z034, and DNA fragments URA3-c, URA3-d, and flanking sequence B were stitched together into DNA fragment B using PCR primers TRIX_Z028 and TRIX_Z033. Finally, DNA fragments A and B were stitched together using PCR primers TRIX_Z025 and TRIX_Z028, yielding the URA-3 blaster template.

PCR amplifications were done using the Phusion DNA polymerase (New England Biolabs, Ipswich, Mass.) as per manufacturer's suggested protocol. The PCR reactions were resolved by gel electrophoresis, the MULEs were gel purified, and the purified MULEs were treated with T4 polynucleotide kinase (PNK) (New England Biolabs, Ipswich, Mass.) as per manufacturer's suggested protocol. The PNK was heat inactivated at 65° C. for 20 minutes, and the samples were stored at −20° C.

Example 6

This example describes methods for inserting Bits into pRYSE vectors or MULEs into the pMULE vector to generate assembly vectors.

pRYSE vectors 1 through 8 and pRYSE vector 15 were digested to completion using SchI restriction enzyme, and the digested DNA fragments were treated with Antarctic Phosphatase (New England Biolabs, Ipswich, Mass.). The phosphatase was heat inactivated at 65° C. for 20 minutes, the reaction mixtures were resolved by gel electrophoresis, and the approximately 2.2 kb pRYSE vector backbones (lacking lacZ) were gel purified. Purified pRYSE vector backbones were ligated with Bits as detailed in Table 6, thus yielding assembly vectors.

The pMULE vector is digested to completion using SchI restriction enzyme, the reaction mixture is resolved by gel electrophoresis, and the approximately 2.2 kb pMULE vector backbone (lacking lacZ) is gel purified. The purified pMULE vector backbone is treated with a phosphatase (e.g., Antarctic Phosphatase (New England Biolabs, Ipswich, Mass.), CIAP (New England Biolabs, Ipswich, Mass.), SAP (New England Biolabs, Ipswich, Mass.; Fermentas, Glen Burnie, Md.), or FastAP (Fermentas, Glen Burnie, Md.)), the phosphatase is heat inactivated (e.g., 20 min at 65° C.), and the pMULE vector backbone is ligated with MULEs, thus yielding assembly vectors.

TABLE 6

Assembly Vectors Generated

| Bit (see Table 4) | pRYSE Vector (see Table 3) | Assembly Vector |
|---|---|---|
| atoB | 4 | 2 |
| mvaS | 7 | 5 |
| ERG13-1 | 7 | 12 |
| 3' NDT80 | 15 | 29 |
|  | 10 | 24 |
| 5' NDT80 | 1 | 30 |
|  | 1 | 97 |
| tP$_{FBA1}$ | 6 | 35 |
| tP$_{TDH3}$ | 3 | 53 |
| ERG10-1 | 4 | 60 |
| tENO1 | 8 | 62 |
| tTDH3 | 5 | 64 |
| GAL80US | 1 | 270 |
| HphA | 2 | 22 |
| tHMG1 | 3 | 254 |
| tP$_{GAL1,10}$ | 4 | 229 |
| ERG10-2 | 5 | 244 |
| ERG13-2 | 6 | 253 |
| tP$_{GAL1,10}$ | 7 | 228 |
| tHMG1 | 8 | 255 |
| GAL80DS | 15 | 271 |
| LEU2US | 1 | 187 |
| NatA | 2 | 262 |
| ERG12 | 3 | 250 |
| ERG8 | 5 | 252 |
| P$_{GAL4oc}$ | 6 | 268 |
| GAL4* | 7 | 265 |
| LEU2DS | 14 | 263 |
| ERG9US | 1 | 186 |
| KanA | 2 | 261 |
| ERG19 | 3 | 241 |
| ERG20 | 5 | 251 |
| tP$_{GAL7}$ | 6 | 249 |
| IDI1 | 7 | 237 |
| tP$_{CTR3}$ | 8 | 269 |
| ERG9CDS | 15 | 185 |
| P$_{GAL7}$ | 3 | 44 |
| STE5US | 1 | 567 |
| URA3 | 2 | 556 (orientation 1) |
|  |  | 555 (orientation 2) |
| P$_{TDH3}$ | 3 | 54 |
| tHMG1 | 4 | 20 |
| STE5DS | 11 | 563 |

Ligations were performed using 50 ng vector backbone, 3 molar excess Bit, and a ligase (e.g., Quick Ligase (New England Biolabs, Ipswich, MA), T4 DNA ligase (regular and high concentration; vendor, Fermentas, Glen Burnie, MD), Fast Ligase (Fermentas, Glen Burnie, MD)) as per manufacturer's suggested protocol.
*Bit GAL4 was generated by stitching together Bits GAL4-1 and GAL4-2 (see Table 4) using primers JU-286-275-31-GAL4-F (SEQ ID NO: 140) and JU-287-275-31-GAL4-R (SEQ ID NO: 141).

Assembly vectors were transformed into chemically competent TOP10 *Escherichia coli* parent cells (Invitrogen, Carlsbad, Calif.). Host cell transformants were selected on Luria Bertoni (LB) agar containing 100 ug/mL carbenicillin and 40 ug/mL X-gal. Single white colonies were transferred from LB agar to culture tubes containing 5 mL of LB liquid medium and carbenicillin, and the cultures were incubated overnight at 37° C. on a rotary shaker at 250 rpm. Plasmid DNAs were extracted and sequenced to identify clones containing the correct sequence in the correct orientation. The cells were stored at −80° C. in cryo-vials in 1 mL stock aliquots made up of 400 uL sterile 50% glycerol and 600 uL liquid culture.

Example 7

This example describes methods for assembling component polynucleotides into a assembled polynucleotide using assembly vectors and/or MULEs.

Assembly vectors (see Table 7) were placed together in one tube (333 fmole of each RABit) and digested using LguI restriction enzyme (Fermentas, Glen Burnie, Md.). The restriction enzyme was removed by column centrifugation or heat inactivated for 20 minutes at 65° C. For assembly reactions involving MULEs or assembled polynucleotides, 333 fmole of each MULE or assembled polynucleotide (see Table 7) were placed together in one tube or were added to the digested assembly vectors. The samples were split into three 30 uL reactions; water, buffer, dNTPs, and DNA polymerase were added to each reaction mixture, and a first round of PCR amplification was initiated. Samples were placed on ice, 0.5 uM of each terminal primer (Table 7) were added to the reaction mixtures, and a second round of PCR amplification was performed. The three PCR reaction mixtures were combined in one tube, the reaction mixtures were resolved by gel electrophoresis, and the PCR products were gel purified.

TABLE 7

Terminal Primers for Assembly of Assembled polynucleotides

| Assembly | Assembly Vectors (see Table 6) or MULEs (see Table 5) To Be Combined* | Assembled polynucleotide Size (kb) (Sequence) | Terminal Primer 1 | Terminal Primer 2 |
|---|---|---|---|---|
| 1 | 30_22_53_60 | 4.3 | S000 (SEQ ID NO: 45) | S009 (SEQ ID NO: 54) |
| 2 | 30_22_53 | 3.1 | S000 (SEQ ID NO: 45) | S007 (SEQ ID NO: 52) |
| 3 | 22_53_60 | 3.7 | S002 (SEQ ID NO: 47) | S009 (SEQ ID NO: 54) |
| 4 | 30_22 | 2.5 | S000 (SEQ ID NO: 45) | S005 (SEQ ID NO: 50) |

TABLE 7-continued

Terminal Primers for Assembly of Assembled polynucleotides

| Assembly | Assembly Vectors (see Table 6) or MULEs (see Table 5) To Be Combined* | Assembled polynucleotide Size (kb) (Sequence) | Terminal Primer 1 | Terminal Primer 2 |
|---|---|---|---|---|
| 5 | 22_53 | 2.5 | S002 (SEQ ID NO: 47) | S007 (SEQ ID NO: 52) |
| 6 | 53_60 | 1.8 | S004 (SEQ ID NO: 49) | S009 (SEQ ID NO: 54) |
| 7 | 30_22_53_60_64_35_12_62_29 | 7.7 (SEQ ID NO: 222) | S000 (SEQ ID NO: 45) | S019 (SEQ ID NO: 64) |
| 8 | 30_22_53_60_64_35_5_62_29 | 7.1 | S000 (SEQ ID NO: 45) | S019 (SEQ ID NO: 64) |
| 9 | 30_22_53_2_64_35_5_62_29 | 7.1 | S000 (SEQ ID NO: 45) | S019 (SEQ ID NO: 64) |
| 10 | 60_64_35_5_62_29 | 4.1 | S006 (SEQ ID NO: 51) | S019 (SEQ ID NO: 64) |
| 11 | 2_64_35_5_62_29 | 4.1 | S006 (SEQ ID NO: 51) | S019 (SEQ ID NO: 64) |
| Phase I-A | 270_22_254_229_244_253 | 8.1 (SEQ ID NO: 111) | S000 (SEQ ID NO: 45) | S013 (SEQ ID NO: 58) |
| Phase I-B | 228_255_271 | 3.0 (SEQ ID NO: 112) | S013 (SEQ ID NO: 58) | S019 (SEQ ID NO: 64) |
| Phase II complete | 187_262_250_229_252_268_265_263 | 9.7 (SEQ ID NO: 113) | S000 (SEQ ID NO: 45) | S019 (SEQ ID NO: 64) |
| Phase III-A | 186_261_241_229 | 4.4 (SEQ ID NO: 114) | S000 (SEQ ID NO: 45) | S008 (SEQ ID NO: 53) |
| Phase III-B | 251_249_237_269_185 | 4.3 (SEQ ID NO: 115) | S009 (SEQ ID NO: 54) | S018 (SEQ ID NO: 63) |
| Phase I marker recycling | 270_URA3blaster_44_FS-a_tHMG1-a | 6.3 (SEQ ID NO: 116) | S000 (SEQ ID NO: 45) | S019 (SEQ ID NO: 64) |
| Phase II marker recycling | 187_URA3blaster_44_FS-a_ERG12 | 6.2 (SEQ ID NO: 117) | S000 (SEQ ID NO: 45) | S019 (SEQ ID NO: 64) |
| Phase III marker recycling | 186_URA3blaster_44_FS-a_ERG19 | 6.0 (SEQ ID NO: 118) | S000 (SEQ ID NO: 45) | S019 (SEQ ID NO: 64) |
| STE5 knockout | 567_556_P$_{TDH3}$-a_tHMG1-b_563 | 5.2 (SEQ ID NO: 119) | S000 (SEQ ID NO: 45) | S019 (SEQ ID NO: 64) |
| IME1 knockout | IME1US_LEU2_P$_{TDH3}$-b_FS-b_IME1DS | 5.4 (SEQ ID NO: 120) | S000 (SEQ ID NO: 45) | S019 (SEQ ID NO: 64) |

The first round of PCR amplification was performed as follows: one cycle of denature at 98° C. for 2 minutes; 5 cycles of denature at 98° C. for 30 seconds and anneal/extend at 72° C. for 30 seconds per kilobase PCR product.
The second round of PCR amplification was performed as follows: one cycle of denature at 98° C. for 2 minutes; 35 rounds of denature at 98° C. for 12 seconds and anneal/extend at 72° C. for 20-25 seconds per kilobase PCR product; one cycle of final extend at 72° C. for 7 minutes; and a final hold at 4° C.
When the annealing temperature was not 72° C. (i.e., when it was either 54° C. or 65° C.), in the first round of PCR amplification a 1 minute annealing step followed by a 30 seconds per kilobase PCR product extension step at 72° C. was used, and for the second round of PCR amplification a 15 seconds annealing step followed by a 20 seconds per kilobase PCR product extension step at 72° C. was used.
*Assembly vectors are designated with numbers, and MULEs with names.

As shown in FIGS. 5 and 6, 2 to 9 component polynucleotides were correctly assembled into up to 7.7 kb long assembled polynucleotides.

Example 8

This example describes methods for generating genetically altered host microorganisms using assembled polynucleotides assembled by the methods disclosed herein.

Phase I-A and Phase I-B assembled polynucleotides (see Table 7) were cloned into the TOPO Zero Blunt II cloning vector (Invitrogen, Carlsbad, Calif.), yielding plasmids TOPO-Phase I-A and TOPO-Phase I-B, respectively. The constructs were propagated in TOP10 cells (Invitrogen, Carlsbad, Calif.) grown on LB agar containing 50 µg/ml kanamycin. Each plasmid was digested to completion using NotI restriction endonuclease, the Phase I-A and Phase I-B inserts were gel extracted using a gel purification kit (Qiagen, Valencia, Calif.), and equal molar ratios of the purified DNA fragments were ligated using T4 DNA ligase (New England Biolabs, Ipswich, Mass.), yielding the Phase I complete assembled polynucleotide. The Phase I complete assembled polynucleotide was cloned into the TOPO Zero Blunt II cloning vector (Invitrogen, Carlsbad, Calif.), yielding plasmid TOPO-Phase I. The construct was propagated in TOP10 cells (Invitrogen, Carlsbad, Calif.) grown on LB agar containing 50 µg/ml kanamycin.

The Phase II complete assembled polynucleotide (see Table 7) was cloned into the TOPO Zero Blunt II cloning vector (Invitrogen, Carlsbad, Calif.), yielding plasmid TOPO-Phase II. The construct was propagated in TOP10 cells (Invitrogen, Carlsbad, Calif.) grown on LB agar containing 50 µg/ml kanamycin.

The Phase III-A and Phase III-B assembled polynucleotides (see Table 7) were cloned into the TOPO Zero Blunt II cloning vector (Invitrogen, Carlsbad, Calif.), yielding plasmids TOPO-Phase III-A and TOPO-Phase III-B, respectively. The constructs were propagated in TOP10 cells (Invitrogen, Carlsbad, Calif.) grown on LB agar containing 50 µg/ml kanamycin. Each plasmid was digested to completion using BamHI and SbfI restriction endonuclease, the Phase III-A and Phase III-B inserts were gel extracted using a gel purification kit (Qiagen, Valencia, Calif.), and equal molar ratios of the purified DNA fragments were ligated using T4 DNA ligase (New England Biolabs, Ipswich, Mass.), yielding the Phase III complete assembled polynucleotide. The Phase III complete assembled polynucleotide was cloned into the TOPO Zero Blunt II cloning vector (Invitrogen, Carlsbad, Calif.), yielding plasmid TOPO-Phase III. The construct was propagated in TOP10 cells (Invitrogen, Carlsbad, Calif.) grown on LB agar containing 50 µg/ml kanamycin.

For yeast cell transformations, 25 ml of Yeast Extract Peptone Dextrose (YPD) medium was inoculated with a single colony of a starting host strain. The culture was grown overnight at 30° C. on a rotary shaker at 200 rpm. The OD600 of the culture was measured, and the culture was then used to inoculate 50 ml of YPD medium to an OD600 of 0.15. The newly inoculated culture was grown at 30° C. on a rotary shaker at 200 rpm up to an OD600 of 0.7 to 0.9, at which point the cells were transformed with 1 µg of DNA. The cells were allowed to recover in YPD medium for 4 hours before they were plated on agar containing a selective agent to identify the host cell transformants.

Starter host strain Y1198 was generated by resuspending active dry PE-2 yeast (isolated in 1994 at Santelisa Vale, Sertãozinho, Brazil) in 5 mL of YPD medium containing 100 ug/mL carbamicillin and 50 ug/mL kanamycin. The culture was incubated overnight at 30° C. on a rotary shaker at 200 rpm. An aliquot of 10 uL of the culture was then plated on a YPD plate and allowed to dry. The cells were serially streaked for single colonies, and incubated for 2 days at 30° C. Twelve single colonies were picked, patched out on a new YPD plate, and allowed to grow overnight at 30° C. The strain identities of the colonies were verified by analyzing their chromosomal sizes on a Bio-Rad CHEF DR II system (Bio-Rad, Hercules, Calif.) using the Bio-Rad CHEF Genomic DNA Plug Kit (Bio-Rad, Hercules, Calif.) according to the manufacturer's specifications. One colony was picked and stocked as strain Y1198.

Strains Y1661, Y1662, Y1663, and Y1664 were generated from strain Y1198 by rendering the strain haploid. Strain Y1198 was grown overnight in 5 mL of YPD medium at 30° C. in a glass tube in a roller drum. The OD600 was measured, and the cells were diluted to an OD600 of 0.2 in 5 mL of YP medium containing 2% potassium acetate. The culture was grown overnight at 30° C. in a glass tube in a roller drum. The OD600 was measured again, and 4 OD600*mL of cells was collected by centrifugation at 5,000 g for 2 minutes. The cell pellet was washed once with sterile water, and then resuspended in 3 mL of 2% potassium acetate containing 0.02% raffinose. The cells were grown for 3 days at 30° C. in a glass tube in a roller drum. Sporulation was confirmed by microscopy. An aliquot of 33 uL of the culture was transferred to a 1.5 mL microfuge tube and was centrifuged at 14,000 rpm for 2 minutes. The cell pellet was resuspended in 50 uL of sterile water containing 2 uL of 10 mg/mL Zymolyase 100T (MP Biomedicals, Solon, Ohio), and the cells were incubated for 10 minutes in a 30° C. waterbath. The tube was transferred to ice, and 150 uL of ice cold water was added. An aliquot of 10 uL of this mixture was added to a 12 mL YPD plate, and tetrads were dissected on a Singer MSM 300 dissection microscope (Singer, Somerset, UK). The YPD plate was incubated at 30° C. for 3 days, after which spores were patched out onto a fresh YPD plate and grown overnight at 30° C. The mating types of each spore from 8 four-spore tetrads were analyzed by colony PCR. A single 4 spore tetrad with 2 MATA and 2 MATalpha spores was picked and stocked as strains Y1661 (MATA), Y1662 (MATA), Y1663 (MATalpha), and Y1664 (MATalpha).

Host strain 1515 was generated by transforming strain Y1664 with plasmid TOPO-Phase I digested to completion using PmeI restriction endonuclease. Host cell transformants were selected on YPD medium containing 300 ug/mL hygromycin B.

Host strain 1762 was generated by transforming strain Y1515 with plasmid TOPO-Phase II digested to completion using PmeI restriction endonuclease. Host cell transformants were selected on YPD medium containing 100 ug/mL nourseothricin.

Host strain 1770 was generated by transforming strain Y1762 in two steps with expression plasmid pAM404 and plasmid TOPO-Phase III digested to completion using PmeI restriction endonuclease. Expression plasmid pAM404 was derived from plasmid pAM353, which was generated by inserting a nucleotide sequence encoding a β-farnesene synthase into the pRS425-Gal1 vector (Mumberg et. al. (1994) *Nucl. Acids. Res.* 22(25): 5767-5768). The nucleotide sequence insert was generated synthetically, using as a template the coding sequence of the β-farnesene synthase gene of *Artemisia annua* (GenBank accession number AY835398) codon-optimized for expression in *Saccharomyces cerevisiae* (SEQ ID NO: 121). The synthetically generated nucleotide sequence was flanked by 5' BamHI and 3' XhoI restriction sites, and could thus be cloned into compatible restriction sites of a cloning vector such as a standard pUC or pACYC origin vector. The synthetically generated nucleotide sequence was isolated by digesting to completion the DNA synthesis construct using BamHI and XhoI restriction enzymes. The reaction mixture was resolved by gel electrophoresis, the approximately 1.7 kb DNA fragment comprising the β-farnesene synthase coding sequence was gel extracted, and the isolated DNA fragment was ligated into the BamHI XhoI restriction site of the pRS425-Gal1 vector, yielding expression plasmid pAM353. The nucleotide sequence encoding the β-farnesene synthase was PCR amplified from pAM353 using primers GW-52-84 pAM326 BamHI (SEQ ID NO: 188) and GW-52-84 pAM326 NheI (SEQ ID NO: 189). The resulting PCR product was digested to completion using BamHI and NheI restriction enzymes, the reaction mixture was resolved by gel electrophoresis, the approximately 1.7 kb DNA fragment comprising the β-farnesene synthase coding sequence was gel extracted, and the isolated DNA fragment was ligated into the BamHI NheI restriction site of vector pAM178 (SEQ ID NO: 122), yielding expression plasmid pAM404. Host cell transformants with pAM404 were selected on Complete Synthetic Medium (CSM) lacking methionine and leucine. Host cell transformants with pAM404 and Phase III complete assembled polynucleotide were selected on CSM lacking methionine and leucine and containing 200 ug/mL G418.

Host strain 1793 was generated by transforming strain Y1770 with a URA3 knockout construct (SEQ ID NO: 123). The knockout construct was generated by first generating DNA fragments URA3US (generated from *Saccharomyces cerevisiae* strain CEN.PK2 genomic DNA using PCR primers KMH33-276-21-URA3 5'.fwd (SEQ ID NO: 147) and KMH34-276-21-URA3 5'.rev (SEQ ID NO: 148)) and URA3DS (generated from *Saccharomyces cerevisiae* strain CEN.PK2 genomic DNA using PCR primers KMH35-276-21-URA3 3'.fwd (SEQ ID NO: 149) and KMH36-276-21-URA3 3'.rev (SEQ ID NO: 150); followed by stitching the two DNA fragments together using PCR primers KMH33-276-21-URA3 5'.fwd and KMH36-276-21-URA3 3'.rev. Host cell transformants were selected on YPD medium containing 5-FOA.

Host strain YAAA was generated by transforming strain Y1793 with the Phase I marker recycling assembled polynucleotide (see Table 7). Host cell transformants were selected on CSM lacking methionine and uracil. The URA3 marker was excised by growing the cells overnight in YPD medium at 30° C. on a rotary shaker at 200 rpm, and then plating the cells onto agar containing 5-FOA. Marker excision was confirmed by colony PCR.

Host strain YBBB was generated by transforming strain YAAA with the Phase II marker recycling assembled polynucleotide (see Table 7). Host cell transformants were selected on CSM lacking methionine and uracil. The URA3 marker was excised by growing the cells overnight in YPD medium at 30° C. on a rotary shaker at 200 rpm, and then plating the cells onto agar containing 5-FOA. Marker excision was confirmed by colony PCR.

Host strain Y1912 was generated by transforming strain YBBB with the Phase III marker recycling assembled polynucleotide (see Table 7). Host cell transformants were selected on CSM lacking methionine and uracil. The URA3 marker was excised by growing the cells overnight in YPD medium at 30° C. on a rotary shaker at 200 rpm, and then plating the cells onto agar containing 5-FOA. Marker excision was confirmed by colony PCR.

Host strain Y1913 was generated by transforming strain Y1912 with the STE5 knockout assembled polynucleotide (see Table 7). Host cell transformants were selected on CSM lacking methionine and uracil.

Host strain Y1915 was generated from strain Y1913 by curing the strain from pAM404 and transforming the resulting strain with the IME1 knockout assembled polynucleotide (see Table 7). Strain Y1913 was propagated in non-selective YPD medium at 30° C. on a rotary shaker at 200 rpm. Approximately 100 cells were plated onto YPD solid media and allowed to grow for 3 days at 30° C. before they were replica-plated no CSM plates lacking methionine and leucine where they were grown for another 3 days at 30° C. Cured cells were identified by their ability to grow on minimal medium containing leucine and their inability to grow on medium lacking leucine. A single such colony was picked and transformed with the IME1 knockout assembled polynucleotide. Host cell transformants were selected on CSM lacking methionine and uracil.

Example 9

This example describes methods for selecting annealable linker sequences to be used to assemble component polynucleotides encoding a promoter and a protein coding sequence into a assembled polynucleotide by the inventive methods disclosed herein.

MULEs encoding promoters followed by two different candidate annealable linker sequences, annealable linker sequence RYSE 15 (R15; SEQ ID NO: 15) and annealable linker sequence RYSE 7 (R7; SEQ ID NO: 7), as well as MULEs encoding GFP preceded by the two annealable linker sequences, were PCR amplified as described in Table 8.

TABLE 8

Amplified MULEs Encoding Promoters and GFP with Annealable Linker Sequences RYSE 15 (R15) or Annealable Linker Sequence RYSE 7 (R7)

| MULE | Type* | Primers | Size (bp) | Template |
|---|---|---|---|---|
| pGAL1-R15 | P | Plan X19 (SEQ ID NO: 236) Plan X20 (SEQ ID NO: 237) | 698 | *S. cerevisiae* strain CEN.PK2 genomic DNA |
| pTDH3-R15 | P | Plan X47 (SEQ ID NO: 238) Plan X48 (SEQ ID NO: 239) | 613 | *S. cerevisiae* strain CEN.PK2 genomic DNA |
| pCYC1-R15 | P | Plan X11 (SEQ ID NO: 240) Plan X12 (SEQ ID NO: 241) | 645 | *S. cerevisiae* strain CEN.PK2 genomic DNA |
| pGAL1-R7 | P | Plan X19 (SEQ ID NO: 236) Plan X64 (SEQ ID NO: 242) | 692 | *S. cerevisiae* strain CEN.PK2 genomic DNA |
| pTDH3-R7 | P | Plan X47 (SEQ ID NO: 238) Plan X71 (SEQ ID NO: 243) | 607 | *S. cerevisiae* strain CEN.PK2 genomic DNA |
| pCYC1-R7 | P | Plan X11 (SEQ ID NO: 240) Plan X78 (SEQ ID NO: 244) | 639 | *S. cerevisiae* strain CEN.PK2 genomic DNA |
| R7-GFP | GsT | Plan X96 (SEQ ID NO: 247) Plan X88 (SEQ ID NO: 245) | 1378 | RABit 634 plasmid DNA** |

TABLE 8-continued

Amplified MULEs Encoding Promoters and GFP with Annealable Linker Sequences RYSE 15 (R15) or Annealable Linker Sequence RYSE 7 (R7)

| MULE | Type* | Primers | Size (bp) | Template |
|---|---|---|---|---|
| A-GFP | GsT | Plan X89 (SEQ ID NO: 246) Plan X88 (SEQ ID NO: 245) | 1385 | RABit 634 plasmid DNA** |

PCR reactions contained: 67 uL ddH2O, 20 uL 5x HF Buffer, 2 uL of each Primer (10 uM), 1 uL dNTP mix (200 uM), 1 uL Phusion DNA Polymerase (New England Biolabs, Ipswich, MA), and 9 uL Y002 genomic DNA or RABit 634 plasmid DNA.
PCR amplification was performed as follows: 1 cycle of denature at 98° C. for 2 minutes; 9 cycles of denature at 98° C. for 15 seconds, anneal at 61° C. for 30 seconds decreasing by 1° C. each cycle, and extend at 72° C. for 1 minute; 26 rounds of denature at 98° C. for 15 seconds, anneal at 52° C. for 30 seconds, and extend at 72° C. for 1 minute; 1 cycle of final extend at 72° C. for 7 minutes; and a final hold at 4° C.
*G = gene; s = stop codon; T = terminator; P = promoter.
**RABit 634 comprises the coding sequence of the green fluourescent protein (GFP) followed by the terminator of the ADH1 gene of Saccharomyces cerevisiae.

The PCR reactions were resolved by gel electrophoresis, the MULEs were gel purified, and the purified MULEs were used to assemble test assembled polynucleotides. To this end, MULEs and assembly vectors (see Table 6) to be assembled (see Table 9) were placed together in a tube (333 fmole of each assembly vector, 667 fmole for each MULE) and digested using LguI restriction enzyme (Fermentas, Glen Burnie, Md.). The restriction enzyme was heat inactivated for 20 minutes at 65° C. The samples were split into three 30 uL reactions; water, buffer, dNTPs, and DNA polymerase were added to each reaction mixture, and a first round of PCR amplification was initiated. Terminal primers were then added to the reaction mixtures, and a second round of PCR amplification was performed (see Table 9). The three PCR reaction mixtures were combined in one tube, the reaction mixtures were resolved by gel electrophoresis, and the PCR products were gel purified.

genomic integration of the assembled polynucleotide was confirmed by colony PCR. Two verified colonies from each transformation were picked into 360 uL Bird Seed Medium (BSM) containing 2% sucrose, and the cultures were incubated for 48 hours at 30° C. on a rotary shaker at 999 rpm. An aliquot of 14.4 uL was taken from each well and transferred to 1.1 mL BSM containing 4% sucrose on a 96-well block plate, and cultured for another 6 hours at 30° C. on a rotary shaker at 999 rpm, at which point 100 uL of each culture was transferred to a well of a clear bottom 96-well plate for analysis of GFP expression. GFP expression in each well was analyzed by measuring 515 nm emission after 485 nm excitation on an M5 Plate reader spectrophotometer (Molecular Devices, Sunnyvale, Calif.). Measured GFP concentrations were normalized for cell culture growth by dividing by the OD600 reading for each culture.

TABLE 9

Terminal Primers for Assembly of Test Assembled polynucleotides

| Assembly | MULEs (see Table 8) and Assembly Vectors (see Table 6) To Be Combined* | Assembled polynucleotide Size (kb) | Terminal Primer 1 | Terminal Primer 2 |
|---|---|---|---|---|
| 1 | 97__555__pGAL1-A__A-GFP__24 | 4.7 | S000 | S019 |
| 2 | 97__555__pTDH3-A__A-GFP__24 | 4.6 | (SEQ ID NO: 45) | (SEQ ID NO: 64) |
| 3 | 97__555__pCYC1-A__A-GFP__24 | 4.7 | | |
| 7 | 97__555__pGAL1-R7__R7-GFP__24 | 4.7 | | |
| 8 | 97__555__pTDH3-R7__R7-GFP__24 | 4.6 | | |
| 9 | 97__555__pCYC1-R7__R7-GFP__24 | 4.6 | | |

PCR reactions contained: 41 uL ddH2O, 20 uL 5x HF Buffer, 5 uL of each terminal primer (1 uM), 2 uL dNTP mix (200 uM), 1.8 uL Phusion DNA Polymerase, and 30 uL MULE or LguI digested assembly vector.
The first round of PCR amplification was performed as follows: 1 cycle of denature at 98° C. for 2 minutes; 5 cycles of denature at 98° C. for 30 seconds, anneal at 60° C. for 30 seconds, and extend at 72° C. for 2.5 minutes; followed by a hold at 4° C. for addition of the two terminal primers. The second round of PCR amplification was performed as follows: 1 cycle of denature at 98° C. for 2 minutes; 35 rounds of denature at 98° C. for 12 seconds, anneal at 60° C. for 30 seconds, and extend at 72° C. for 2.5 minutes; 1 cycle of final extend at 72° C. for 7 minutes; and a final hold at 4° C.
*Assembly vectors are designated with numbers, and MULEs with names.

The test assembled polynucleotides were used to transform a Saccharomyces cerevisiae host strain that was URA3 deficient and had a deletion of the GAL80 locus. Host cell transformants were selected on CSM lacking uracil, and correct As shown in Table 10, annealable linker sequence RYSE 15 enabled increased GAL1, TDH3, and CYC1 promoter driven expression of the GFP reporter gene in the test assembled polynucleotides compared to annealable linker sequence RYSE 7.

TABLE 10

GFP Expression in Host Cells Harboring Test Assembled polynucleotides Comprising Either Annealable Linker Sequence RYSE 15 (R15) or Annealable Linker Sequence RYSE 7 (R7) Between Promoter and GFP Reporter

| Annealable linker sequence positioned between promoter and GFP reporter gene in | Average % GFP expression (compared to average % GFP expression obtained with host cells harboring one of 3 seamless control constructs*; average for 2 independent host cell isolates) | | | |
|---|---|---|---|---|
| test assembled polynucleotide | GAL1 promoter | TDH3 promoter | CYC1 promoter | Average across all three promoters |
| R15 | 79.34 | 91.42 | 81.92 | 84.22 |
| R7 | 27.43 | 54.68 | 46.31 | 42.81 |

*The seamless control constructs had an identical structure as the test assembled polynucleotides except that the promoter sequences were seamlessly linked to the GFP reporter gene (i.e., without an intervening annealable linker sequence).

Example 10

This example describes methods for the high-throughput combinatorial assembly of polynucleotides, and methods for the high-throughput generation of host cells comprising combinatorially combined polynucleotides.

Figure 12A:
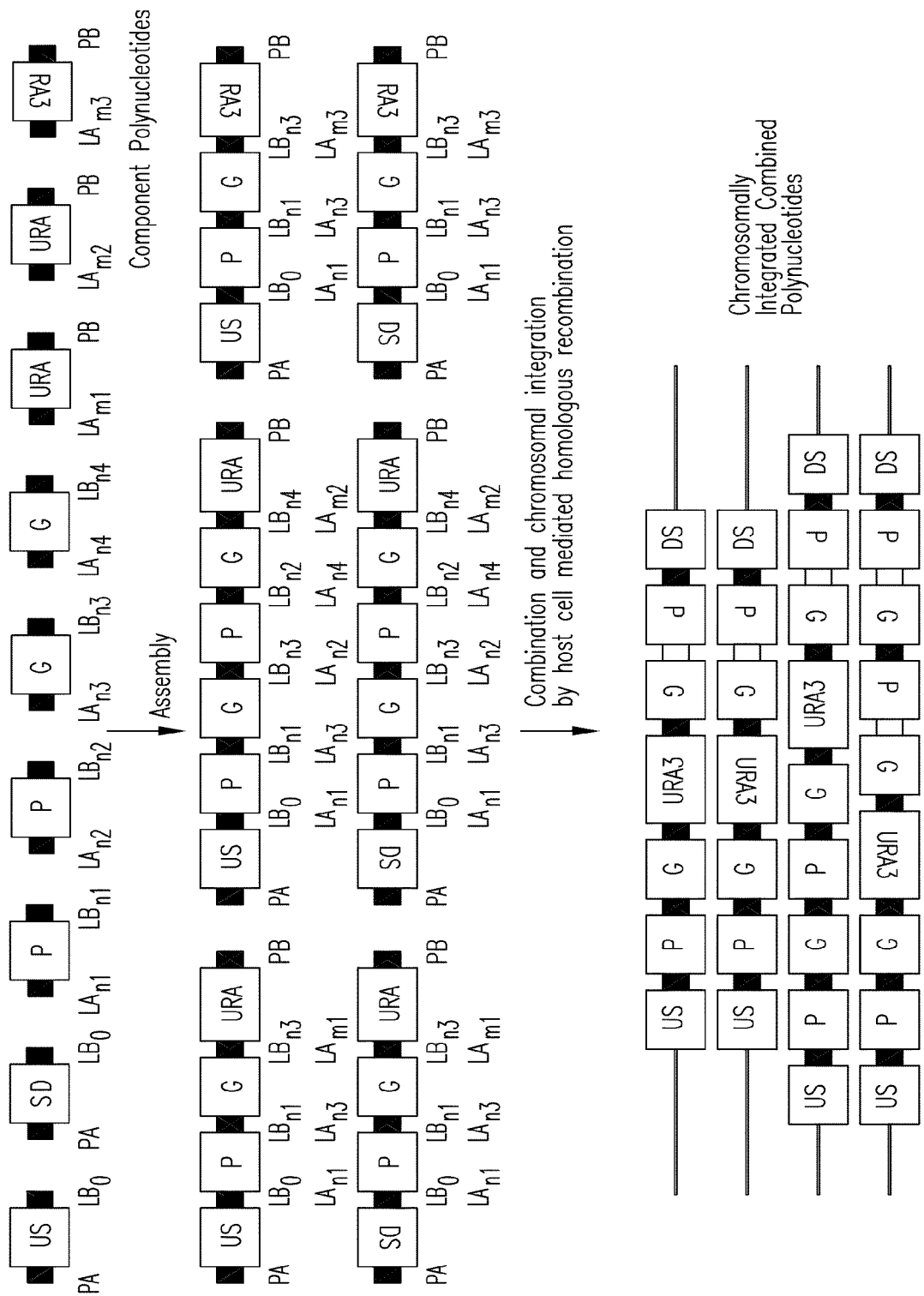
FIG. 12B shows exemplary assembled polynucleotides (boxed) generated as described in Example 10 and resolved on a 1% agarose gel.
FIG. 12C shows restriction analysis for exemplary cell colonies obtained as described in Example 10.

The component polynucleotides used in this example, and the expected assembled and combined polynucleotides generated from these component polynucleotides, are schematically illustrated in FIG. 12A. The component polynucleotides comprised DNA segments encoding an upstream and a downstream chromosomal targeting sequence (US and DS), 6 different promoters (P), 35 different proteins (G), and a 5' and a 3' segment of the URA3 selectable marker (URA and RA3, respectively), flanked by annealable linker sequences pairs or primer binding segment/annealable linker sequence pairs.

Component polynucleotides were released from assembly vectors by digesting RABits or MULES using LguI restriction endonuclease. To this end, 96-well plates ("LguI Digestion Plates") were set up as shown in the table below, and the plates were incubated at 37° C. for 75 min, after which the LguI restriction endonuclease was heat inactivated at 65° C. for 20 min in a PCR machine.

| LguI Digestion Plates | |
|---|---|
| Component (per well) | Volume (uL) |
| 667 fMoles RABit or MULE | Variable |
| 10x Tango Buffer (Fermentas, Glen Burnie, MD) | 10 |
| LguI (Fermentas, Glen Burnie, MD) | 2.5 |
| ddH2O | to 100 |

Component polynucleotides were assembled by SOE. For each LguI Digestion Plate, triplicate 96-well plates ("SOE/PCR Plates") were set up and thermocycled in a PCR machine as shown in the table below.

| SOE/PCR Plates | |
|---|---|
| Component (per well) | Volume (uL) |
| ddH2O | 41 |
| 5x Phusion HF Buffer (New England Biolabs, Ipswich, MA) | 20 |
| 10 mM dNTP mix | 2 |
| Phusion DNA polymerase (New England Biolabs, Ipswich, MA) | 1.8 |
| | 30 |
| LguI-digested RABits or MULEs to be assembled | 30 |
| | Total: 95 |

| Thermocycling conditions | | | |
|---|---|---|---|
| Initial Denature | | 98° C. | 2 min |
| 7 cycles | Denature | 98° C. | 30 sec |
| | Anneal | 67° C. | 30 sec |
| | Extend | 72° C. | 5 min |
| Hold | | 4° C. | ∞ |

Assembled polynucleotides were PCR amplified. Each SOE/PCR Plate received additional reagent and was thermocycled in a PCR machine as shown in the table below. Corresponding wells on SOE/PCR plates were pooled into 96-deep well blocks, and assembled polynucleotides were purified using the Omega Biotek E-Z 96® Cycle-Pure Kit (Omega Bio-Tek Inc., Norcross, Ga.) as per manufacturer's suggested protocol (approximate end-volumes of 45 uL).

| SOE/PCR Plates | |
|---|---|
| Additional Component (per well) | Volume (uL) |
| 10 mM stock of terminal primers S000 (SEQ ID NO: 45) and S019 (SEQ ID NO: 64) | 10 |

| Thermocycling conditions | | | |
|---|---|---|---|
| Initial Denature | | 98° C. | 2 min |
| 35 cycles | Denature | 98° C. | 12 sec |
| | Anneal | 67° C. | 30 sec |
| | Extend | 72° C. | 4.5 min |
| Final Extend | | 72° C. | 7 min |
| Hold | | 4° C. | ∞ |

Figure 12B:
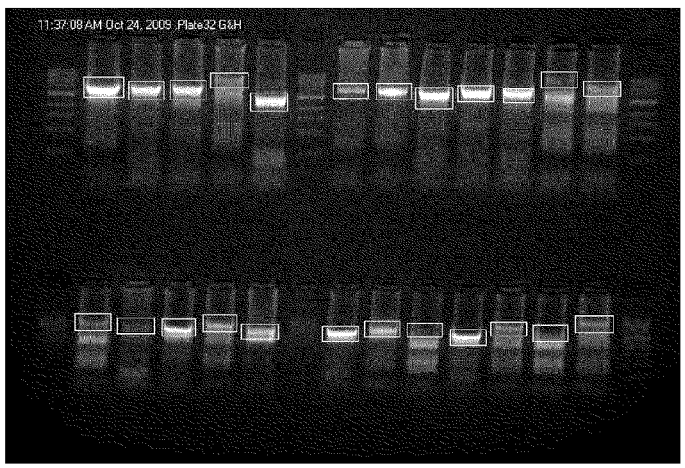

FIG. 12B shows exemplary assembled polynucleotides (boxed) resolved on a 1% agarose gel.

Purified assembled polynucleotides were digested with LguI restriction endonuclease to generate sticky ends for cloning. To this end, 96-well plates ("LguI Assembled Polynucleotide Digestion Plates") were set up as shown in the table below, and the plates were incubated at 37° C. for 60 min, after which the LguI restriction endonuclease was heat inactivated at 65° C. for 20 min in a PCR machine. LguI digested assembled polynucleotides were gel purified using the ZR-96 Zymoclean™ Gel DNA Recovery Kit (Zymo Research Corporation, Orange, Calif.) as per manufacturer's recommended protocol.

| LguI Assembled Polynucleotide LguI Digestion Plates | |
|---|---|
| Component (per well) | Volume (uL) |
| Purified assembled polynucleotide | 43 |
| 10x Tango Buffer | 5 |
| LguI | 2 |

Assembled polynucleotides were ligated into a pUC-19 based vector backbone. When no insert is ligated into this vector, a pTRC promoter (i.e., promoter of the TRC gene of *Saccharomyces cerevisiae*) drives expression of GluRS and kills the host cell. 96-well plates ("Ligation Plates") were set up as shown in the table below, and the plates were incubated at 24° C. for 15 min, and then at 16° C. overnight. Ligation products were purified using the ZR-96 DNA Clean & Concentrator™-5 (Zymo Research Corporation, Orange, Calif.) as per manufacturer's suggested protocol.

| Ligation Plates | |
|---|---|
| Component (per well) | Volume (uL) |
| ddH2O | 5 |
| 10x T4 DNA Ligase Buffer | 2 |
| Vector backbone | 2 |
| Purified assembled polynucleotide | 10 |
| T4 DNA ligase (NEB, Ipswich, MA) | 1 |

Ligation products were electroporated into *E. coli* competent cells. Pre-chilled 96-well electroporation plates were set up and electroporations were carried out as shown in the table below.

| Electroporation Plates | |
|---|---|
| Component (per well) | Volume (uL) |
| Purified ligation products | 10 |
| Lucigen 10G competent cells (Lucigen Corporation, Middleton, WI) | 25 |

| Electroporation settings | | |
|---|---|---|
| 2400 V | 750 Ω | 25 uF |

Figure 12C:

1.1 mL 96-well culture plates ("Culture Plates") containing 250 uL of pre-warmed SOC were set up, and 100 uL SOC was taken from each well and added to the electroporated cells immediately after electroporation. The SOC and cells were mixed, and 100 uL of each mixture was transferred back to the Culture Plates. The Culture Plates were incubated at 37° C. for 1 hour in a Multitron II Incubator Shaker (ATR Biotech, Laurel, Md.). Two dilutions of cells (3 ul and 240 ul) were plated on LB agar comprising 50 ug/mL kanamycin, and incubated overnight at 37° C. Colonies were picked and grown in 96 deep well plates comprising 1 mL LB medium with kanamycin per well, and DNA was extracted for restriction analysis using LguI restriction endonuclease. Results of such restriction analysis for 22 of 24 exemplary colonies comprising an approximately 8 kb combined polynucleotide are shown in FIG. 12C.

Yeast cells comprising chromosomally integrated combined polynucleotides were generated by host cell mediated homologous recombination between terminal chromosomal targeting sequences and selectable marker segments of the assembled polynucleotides. To this end, 96-well PCR plates ("Yeast Transformation Plates") were set up and heat shock transformations were carried out in a PCR machine as shown in the table below.

| Yeast Transformation Plates | |
|---|---|
| Component (per well) | Volume (uL) |
| Miniprep DNA (20 ng/uL) | 10 |
| Competent yeast cells* | 40 |
| PEG/SS/LiAc master mix** | 200 |

| Heat shock | |
|---|---|
| 30° C. | 30 min |
| 42° C. | 45 min |
| 24° C. (optional) | 30 min |

*Prepared by growing cells in 100 mL YPD overnight, diluting the culture and growing to an OD600 of about 0.8 overnight, spinning the cultures at 3,000 g for 5 min, washing the cell pellet with 1 L ddH2O, washing the cell pellet with 1 L 100 mM lithium acetate (LiAc), and resuspending the cell pellet to a total volume of 18 mL in 100 mM LiAc.
**Master mix sufficient for 4 PCR plates contains 100 mL 50% PEG, 4 mL boiled (95° C. for at least 10 min) single-stranded DNA, 15 mL 1M LiAc.

The Yeast Transformation Plates were spun at 2,000 g for 2 min, supernatants were removed, and cell pellets were washed three times with 200 uL ddH2O. Cell pellets were resuspended with 100 uL cold Bird Seed Media (BSM) taken from previously prepared pre-chilled 96-well culture plates ("Seed Plates") containing 360 uL cold BSM per well. The suspended cells were transferred to the Seed Plates, and were grown overnight at 30° C. in a Multitron II Incubator Shaker. The Seed Plates were spun at 3,000 g for 5 min, all but 60 uL of the liquid was removed, and covered Seed Plates were shaken at 1,000 rpm to resuspend the cell pellets.

Example 11

This example describes methods for generating yeast cells comprising assembled polynucleotides generated by host cell mediated homologous recombination.

Figure 13A:
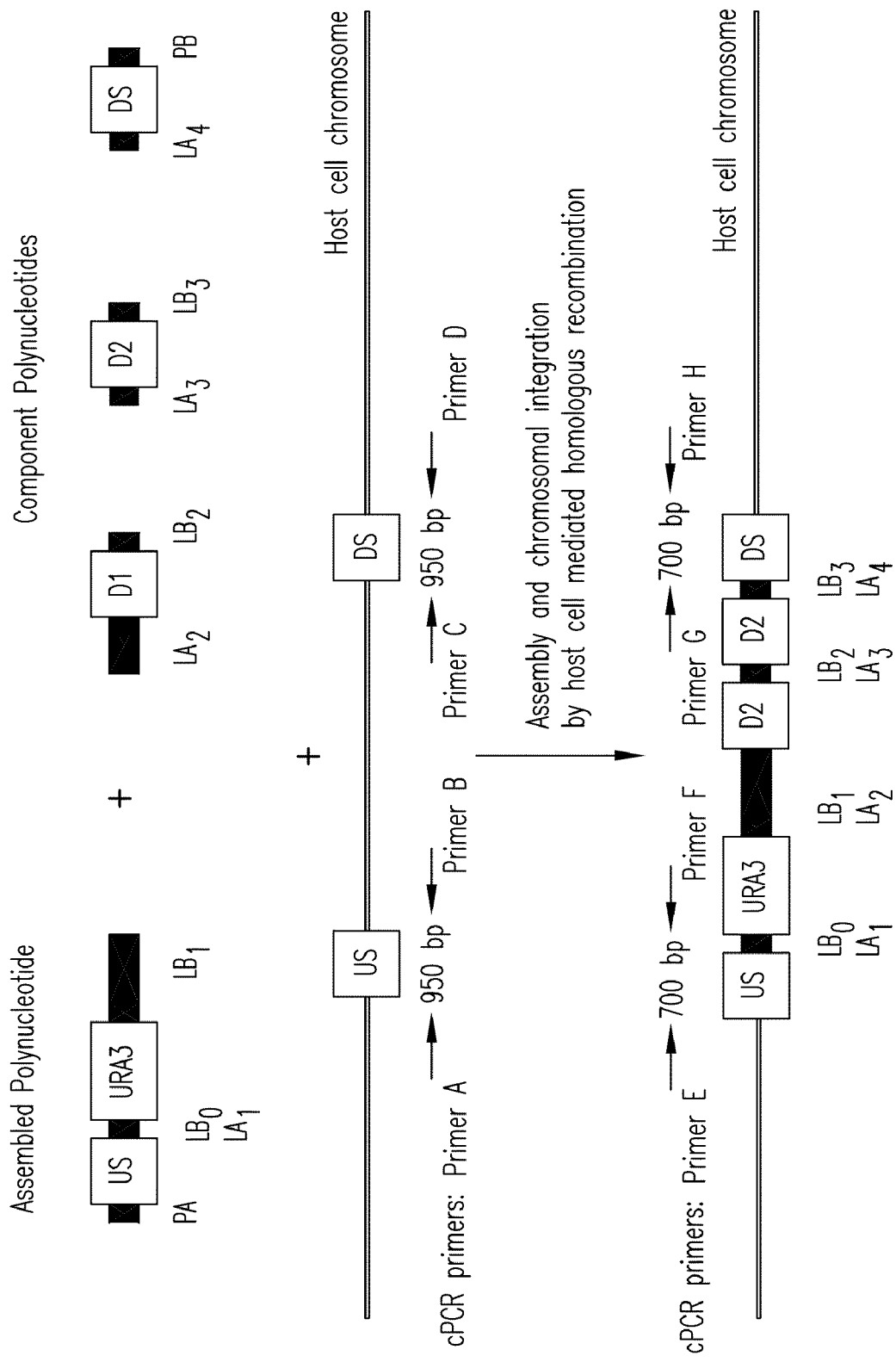
FIG. 13A shows the assembled polynucleotide and component polynucleotides used in Example 11, and the expected chromosomal locus obtained upon assembly and chromosomal integration by the host cells.

The assembled polynucleotide and component polynucleotides used in this example, and the expected chromosomal locus obtained upon assembly and chromosomal integration, are schematically illustrated in FIG. 13A.

Yeast cell transformations were carried out as described in the table below. Following heat shock, the cells were spun down, supernatant was removed, cells were resuspended in 400 uL ddH2O, and host cell transformants were selected for by plating 100-200 uL of the cell suspension on agar lacking uracil.

| Yeast Transformation | |
| --- | --- |
| Component | Volume (uL) |
| Component and assembled polynucleotides (300-500 ng each) | 20 |
| Competent yeast cells* | cell pellet* |
| 50% PEG solution | 240 |
| 1 M LiAc pH 8.4-8.9 | 36 |
| Boiled (95° C. for 5 min) single-stranded DNA (10 mg/mL) (Invitrogen, Carlsbad, CA) | 10 |
| ddH2O | 54 |
| Heat shock | |
| 42° C. | 40 min |

*Prepared by growing cells from a colony in 25 mL YPD overnight at 30° C. to an OD600 of 0.7-0.9, spinning down the cells, washing the cell pellet with 5-10 mL ddH2O, washing the cell pellet with 1 mL ddH2O, washing the cell pellet with 1 mL 100 mM lithium acetate (LiAc), spinning in microcentrifuge for 30 sec to pellet the cells, and discarding the supernatant.

Figure 13B:
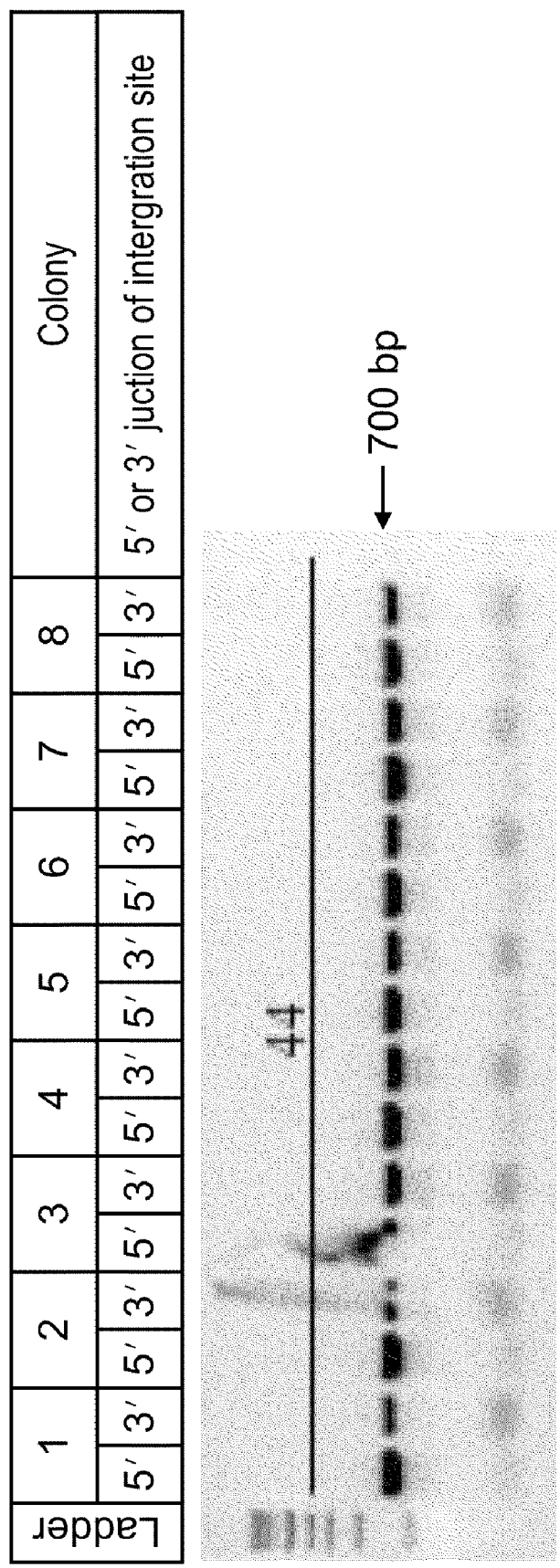
FIG. 13B shows cPCR analysis results obtained for yeast cell transformants generated in Example 11 that comprise chromosomally integrated assembled polynucleotides.

Successful integration of assembled polynucleotides was determined by cPCR using cPCR primers A, B, E, and F (5' junction of chromosomal integration site) or cPCR primers C, D, G, and H (3' junction of chromosomal integration site) (FIG. 13A). As shown in FIG. 13B, all 8 colonies analyzed produced the 700 bp PCR band indicative of a positive chromosomal integration event of the expected assembled polynucleotide and lacked the 950 bp PCR band that the native locus would have produced.

Example 12

This example describes methods for the high-throughput generation of yeast cells comprising combinatorially assembled and combinatorially combined polynucleotides generated by host cell mediated homologous recombination.

The component polynucleotides used in this example, and the expected combined polynucleotides obtained upon assembly and combination by host cell mediated homologous recombination, are schematically illustrated in FIG. 14A. The component polynucleotides comprised DNA segments encoding an upstream and a downstream chromosomal targeting sequence (US and DS), 6 different promoters (P), 35 different proteins (G), and a 5' and a 3' segment of the URA3 selectable marker (URA and RA3, respectively), flanked by annealable linker sequences pairs or primer binding segment/annealable linker sequence pairs.

Component polynucleotides were released from assembly vectors by digesting RABits or MULES using LguI restriction endonuclease. To this end, 96-well plates ("LguI Digestion Plates") were set up as shown in the table below, and the plates were incubated at 37° C. for 75 min, after which the LguI restriction endonuclease was heat inactivated at 65° C. for 20 min in a PCR machine.

| LguI Digestion Plates | |
| --- | --- |
| Component (per well) | Volume (uL) |
| 667 fMoles RABit or MULE | Variable |
| 10x Tango Buffer (Fermentas, Glen Burnie, MD) | 5 |
| LguI (Fermentas, Glen Burnie, MD) | 2.5 |
| ddH2O | to 50 |

To generate yeast cells comprising chromosomally integrated combinatorially assembled and combinatorially combined polynucleotides 96-well PCR plates ("Yeast Transformation Plates") were set up and heat shock transformations were carried out in a PCR machine as shown in the table below.

| Yeast Transformation Plates | |
| --- | --- |
| Component (per well) | Volume (uL) |
| Component polynucleotides | 10 |
| Competent yeast cells* | 40 |
| PEG/SS/LiAc master mix** | 200 |
| Heat shock | |
| 30° C. | 30 min |
| 42° C. | 45 min |
| 24° C. (optional) | 30 min |

*Prepared by growing cells in 100 mL YPD overnight, diluting the culture and growing to an OD600 of about 0.8 overnight, spinning the cultures at 3,000 g for 5 min, washing the cell pellet with 1 L ddH2O, washing the cell pellet with 1 L 100 mM lithium acetate (LiAc), and resuspending the cell pellet to a total volume of 18 mL in 10 mM LiAc.
**Master mix sufficient for 4 PCR plates contains 100 mL 50% PEG, 4 mL boiled (95° C. for at least 10 min) single-stranded DNA, 15 mL 1M LiAc.

The Yeast Transformation Plates were spun at 2,000 g for 2 min, supernatants were removed, and cell pellets were washed three times with 200 uL ddH2O. Cell pellets were resuspended with 100 uL cold Bird Seed Media (BSM) taken from previously prepared pre-chilled 96-well culture plates ("Seed Plates") containing 360 uL cold BSM per well. The suspended cells were transferred to the Seed Plates, and were grown overnight at 30° C. in a Multitron II Incubator Shaker. The Seed Plates were spun at 3,000 g for 5 min, all but 60 uL of the liquid was removed, and covered Seed Plates were shaken at 1,000 rpm to resuspend the cell pellets. Various dilutions of cells were plated on agar lacking uracil, and incubated overnight at 37° C. Colonies of yeast cell transformants harboring a functional URA3 selectable marker were picked and analyzed.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications can be made thereto without departing from the spirit or scope of the appended claims. The embodiments of the present invention described above are intended to be merely exemplary, and those skilled in the art will recognize, or be able to ascertain using no more than routine experimentation, numerous equivalents to the specific procedures described herein. All such equivalents are considered to be within the scope of the present invention and are covered by the following claims. Furthermore, as used in this specification and claims, the singular forms "a," "an" and "the" include plural forms unless the content clearly dictates otherwise.

What is claimed is:

1. A composition comprising:
   (a) one or more first nucleic acid molecules, wherein each first nucleic acid molecule is circular and comprises, in a 5' to 3' orientation, a first restriction site $RA_0$, any DNA segment selected from the group $D_0$, an annealable linker sequence $LB_0$, and a second restriction site $RB_0$;
   (b) one or more intermediate nucleic acid molecules, wherein each intermediate nucleic acid molecule n is circular and comprises, in a 5' to 3' orientation, a first restriction site $RA_n$, a first annealable linker sequence $LA_n$, any DNA segment selected from the group $D_n$, a second annealable linker sequence $LB_n$, and a second restriction site $RB_n$, and wherein n represents an integer from one to the number of intermediate nucleic acid molecules; and
   (c) one or more last nucleic acid molecules, wherein each last nucleic acid molecule is circular and comprises, in a 5' to 3' orientation, a first restriction site $RA_m$, an annealable linker sequence $LA_m$, any DNA segment selected from the group $D_m$, a second restriction site $RB_m$, wherein m represents an integer one greater than the number of intermediate nucleic acid molecules;
   wherein each of restriction sites $RA_0$ through $RB_m$ is independently cleavable by one or more Type IIS restriction endonucleases, wherein each of restriction sites $RA_0$ through $RB_m$ is oriented so that cleavage of each of said restriction sites $RA_0$ through $RB_m$ separates their recognition and cleavage sites from the resulting respective nucleic acid molecule that comprises $D_0$ and $LB_0$; $LA_n$, $D_n$, and $LB_n$; or $LA_m$ and $D_m$;
   whereupon cleavage of restriction sites $RA_0$ through $RB_m$ and denaturation of the resulting linear nucleic acid molecules, each annealable linker sequence $LB_{(p-1)}$ is capable of hybridizing to the complement of annealable linker sequence $LA_p$, wherein n is an integer that varies from 1 to (m−1), wherein p represents an integer from 1 to m, and wherein each group $D_0, \ldots D_n, \ldots D_m$ independently consists of one or more DNA segments.

2. The composition of claim 1, wherein each of said one or more first nucleic acid molecules further comprises any primer binding segment selected from the group PA positioned 5' to the DNA segment selected from the group $D_0$, wherein each of said one or more last nucleic acid molecules further comprises any primer binding segment selected from the group PB positioned 3' to the DNA segment selected from the group $D_m$.

3. The composition of claim 1, wherein upon cleavage of restriction sites $RA_0$ through $RB_m$ and denaturation of the resulting linear nucleic acid molecules, each annealable linker sequence $LB_{(p-1)}$ is capable of selectively hybridizing to the complement of annealable linker sequence $LA_p$ compared to the other annealable linker sequences, or their complements, in the composition.

4. The composition of claim 1, wherein the restrictions sites $RA_0$ through $RB_m$ are cleavable by SapI or LguI restriction endonuclease.

5. The composition of claim 1, wherein two or more annealable linker sequences are at least 24 nucleotides in length and have a melting temperature of at least 60° C.

6. A composition comprising a plurality of linear nucleic acid molecules formed by digesting the composition of claim 1 with one or more Type IIS restriction endonucleases capable of cleaving the restriction sites $RA_0$ through $RB_m$.

7. A method of generating an assembled polynucleotide from a plurality of component polynucleotides comprising the steps of:
   (a) digesting an assembly composition with one or more Type IIS restriction endonucleases to generate a components composition, the assembly composition comprising:
       (i) one or more first nucleic acid molecules, wherein each first nucleic acid molecule is circular and comprises, in a 5' to 3' orientation, a first restriction site $RA_0$, any primer binding segment selected from the group PA, any DNA segment selected from the group $D_0$, an annealable linker sequence $LB_0$, and a second restriction site $RB_0$;
       (ii) one or more intermediate nucleic acid molecules, wherein each intermediate nucleic acid molecule n is circular and comprises, in a 5' to 3' orientation, a first restriction site $RA_n$, a first annealable linker sequence $LA_n$, any DNA segment selected from the group $D_n$, a second annealable linker sequence $LB_n$, and a second restriction site $RB_n$, and wherein n represents an integer from one to the number of intermediate nucleic acid molecules; and
       (iii) one or more last nucleic acid molecules, wherein each last nucleic acid molecule is circular and comprises, in a 5' to 3' orientation, a first restriction site $RA_m$, an annealable linker sequence $LA_m$, any DNA segment selected from the group Dm, any primer binding segment selected from the group PB, a second restriction site $RB_m$ wherein m represents an integer one greater than the number of intermediate nucleic acid molecules;
       wherein each of restriction sites $RA_0$ through $RB_m$ is independently cleavable by the one or more Type IIS restriction endonucleases, wherein each of restriction sites $RA_0$ through $RB_m$ is oriented so that cleavage of each of said restriction sites $RA_0$ through $RB_m$ separates their recognition and cleavage sites from the resulting respective nucleic acid molecule that comprises $D_0$ and $LB_0$; $LA_n$, $D_n$, and $LB_n$; or $LA_m$ and $D_m$;
       whereupon cleavage of restriction sites $RA_0$ through $RB_m$ and denaturation of the resulting linear nucleic acid molecules, each annealable linker sequence $LB_{(p-1)}$ is capable of hybridizing to the complement of annealable linker sequence $LA_p$, wherein n is an integer that varies from 1 to (m−1), wherein p represents an integer from 1 to m, and wherein each group $D_0, \ldots D_n, \ldots$ and $D_m$ consists of one or more DNA segments; and
   (b) contacting the components composition with DNA polymerase, deoxyribonucleoside triphosphates and one or more first primers and one or more second primers, under conditions suitable for denaturation of the nucleic acid molecules, annealing of annealable linker sequence $LB_{(p-1)}$ to annealable linker sequence $LA_p$, and extension therefrom; wherein each said first primer is capable of hybridizing to one of said primer binding segments selected from the group PA and each said second primer is capable of hybridizing to one of said primer binding segments selected from the group PB; and subjecting the components composition to polymerase chain reaction,
   wherein a polynucleotide is assembled which comprises, in a 5' to 3' orientation, one DNA segment selected from each of the groups $D_0, \ldots D_n \ldots$ and $D_m$.

8. The method of claim 7, wherein two or more annealable linker sequences are at least 24 nucleotides in length and have a melting temperature of at least 60° C.

9. The method of claim 7, wherein each annealable linker sequence $LB_{(p-1)}$ is identical in sequence to annealable linker sequence $LA_p$.

10. The method of claim 7, wherein the restriction sites $RA_0$ through $RB_m$ are cleavable by the same Type IIS restriction endonuclease.

11. The method of claim 7, wherein the restrictions sites $RA_0$ through $RB_m$ are cleavable by SapI or LguI restriction endonuclease, and the Type IIS restriction endonuclease of step (a) is SapI or LguI.

12. A method of generating a host cell comprising a polynucleotide, the method comprising the steps of:
    (a) transforming a host cell with a polynucleotide assembled according to claim 7; and
    (b) selecting a host cell comprising the assembled polynucleotide.

13. The method of claim 12, wherein the assembled polynucleotide comprises a selectable marker and step (b) comprises propagating the transformed host cell on selectable media.

14. The method of claim 12, further comprising transforming the host cell with a linearized plasmid comprising:
    (i) a first region of homology with primer binding segment PA; and
    (ii) a second region of homology with primer binding segment PB,
    wherein said first and second regions of homology are of sufficient length to initiate host cell mediated homologous recombination between said polynucleotide and said plasmid to form a circularized plasmid in the host cell.

15. A method of generating a host cell comprising a polynucleotide, the method comprising the steps of:
    (a) transforming a host cell with the composition of claim 6, wherein each annealable linker sequence $LB_{(p-1)}$ comprises a region of homology with annealable linker sequence $LA_p$ of sufficient length to initiate host cell mediated homologous recombination between $LB_{(p-1)}$ and $LA_p$ wherein p represents an integer from 1 to m, wherein said homologous recombination results in the assembly of a polynucleotide; and
    (b) selecting a host cell comprising an assembled polynucleotide, wherein the assembled polynucleotide comprises in a 5' to 3' orientation, one DNA segment selected from each of the groups $D_0, \ldots D_n, \ldots$ and $D_m$.

16. The method of claim 15, wherein
    (a) each of the one or more first linear nucleic acid molecules further comprises a first region of homology with a first integration site of the host cell genome; and
    (b) each of the one or more last linear nucleic acid molecules further comprises a second region of homology with a second integration site of the host cell genome,
    wherein said first and second regions of homology are of sufficient length to initiate host cell mediated homologous recombination with said first and second integration sites, respectively, wherein said homologous recombination results in integration of an assembled polynucleotide into the host cell genome.

17. The method of claim 15, wherein at least one homologous recombination of an annealable linker sequence $LB_{(p-1)}$ and $LA_p$ forms a nucleic acid sequence that encodes a selectable marker gene.

18. The method of claim 15, further comprising transforming the host cell with a linearized plasmid comprising:

(i) a first region of homology with the one or more first linear nucleic acid molecules; and
(ii) a second region of homology with the one or more last linear nucleic acid molecules, wherein said first and second regions of homology are of sufficient length to initiate host cell mediated homologous recombination between an assembled polynucleotide and said plasmid to form a circularized plasmid in the host cell.

* * * * *

```
                              SEQUENCE LISTING

<160> NUMBER OF SEQ ID NOS: 256

<210> SEQ ID NO 1
<211> LENGTH: 24
<212> TYPE: DNA
<213> ORGANISM: Artificial Sequence
<220> FEATURE:
<223> OTHER INFORMATION: Synthetic Linker Gold (Au)

<400> SEQUENCE: 1
gctcacacgc ggccaggggg agcc                                               24

<210> SEQ ID NO 2
<211> LENGTH: 24
<212> TYPE: DNA
<213> ORGANISM: Artificial Sequence
<220> FEATURE:
<223> OTHER INFORMATION: Synthetic Linker Lapis (La)

<400> SEQUENCE: 2
cgctcgtcca acgccggcgg acct                                               24

<210> SEQ ID NO 3
<211> LENGTH: 24
<212> TYPE: DNA
<213> ORGANISM: Artificial Sequence
<220> FEATURE:
<223> OTHER INFORMATION: Synthetic Linker Copper (Cu)

<400> SEQUENCE: 3
atccccgcgt gcttggccgg ccgt                                               24

<210> SEQ ID NO 4
<211> LENGTH: 24
<212> TYPE: DNA
<213> ORGANISM: Artificial Sequence
<220> FEATURE:
<223> OTHER INFORMATION: Synthetic Linker Quartz (Qz)

<400> SEQUENCE: 4
aacctgcagg ccgcgagcgc cgat                                               24

<210> SEQ ID NO 5
<211> LENGTH: 24
<212> TYPE: DNA
<213> ORGANISM: Artificial Sequence
<220> FEATURE:
<223> OTHER INFORMATION: Synthetic Linker Iron (Fe)

<400> SEQUENCE: 5
aacgcgatcg ccgacgccgc cgat                                               24

<210> SEQ ID NO 6
<211> LENGTH: 24
```

-continued

```
<212> TYPE: DNA
<213> ORGANISM: Artificial Sequence
<220> FEATURE:
<223> OTHER INFORMATION: Synthetic Linker Obsidian (Ob)

<400> SEQUENCE: 6
aaggcggccg ctggcgaggg agat                                              24

<210> SEQ ID NO 7
<211> LENGTH: 24
<212> TYPE: DNA
<213> ORGANISM: Artificial Sequence
<220> FEATURE:
<223> OTHER INFORMATION: Synthetic Linker Indigo (In)

<400> SEQUENCE: 7
aaggcgcgcc acggtcgtgc ggat                                              24

<210> SEQ ID NO 8
<211> LENGTH: 24
<212> TYPE: DNA
<213> ORGANISM: Artificial Sequence
<220> FEATURE:
<223> OTHER INFORMATION: Synthetic Linker Silver (Ag)

<400> SEQUENCE: 8
agcccctcag ccccccctagc gtcg                                             24

<210> SEQ ID NO 9
<211> LENGTH: 28
<212> TYPE: DNA
<213> ORGANISM: Artificial Sequence
<220> FEATURE:
<223> OTHER INFORMATION: Synthetic Linker Pme1-5prime

<400> SEQUENCE: 9
gacggcacgg ccacgcgttt aaaccgcc                                          28

<210> SEQ ID NO 10
<211> LENGTH: 28
<212> TYPE: DNA
<213> ORGANISM: Artificial Sequence
<220> FEATURE:
<223> OTHER INFORMATION: Synthetic Linker Pme1-3prime

<400> SEQUENCE: 10
cggtgtttaa accccagcgc ctggcggg                                          28

<210> SEQ ID NO 11
<211> LENGTH: 2737
<212> TYPE: DNA
<213> ORGANISM: Artificial Sequence
<220> FEATURE:
<223> OTHER INFORMATION: Synthetic pRYSE Entry vector 1

<400> SEQUENCE: 11
gtaaaacgac ggccagtatt aaccctcact aaagggaact cgaggctctt cagacggcac       60
ggccacgcgt ttaaaccgcc tggcagactc catatgctat gcggcatcag agcagattgt      120
actgagagtg caccatatgc ggtgtgaaat accgcacaga tgcgtaagga gaaaataccg      180
catcaggcgc cattcgccat tcaggctgcg caactgttgg gaagggcgat cggtgcgggc      240
ctcttcgcta ttacgccagc tggcgaaagg gggatgtgct gcaaggcgat taagttgggt      300
aacgccaggg ttttcccagt cacgacgttg taaaacgacg ccagtgaatt cgagctcgg      360 tacccgggga tcctctagcg tcgacctgca ggcatgcaag cttggcgtaa tcatggtcat      420
```

```
agctgtttcc tgtgtgaaat tgttatccgc tcacaattcc acacaacata cgagccggaa    480
gcataaagtg taaagcctgg ggtgcctaat gagtgagcta actcacatta attgcgttgc    540
gcgctagcga gtcatccagc tcacacgcgg ccagggggag cctgaagagc gagctcccgc    600
tgagcaataa ctagcgtcat agctgtttcc tgggtcgttc ggctgcggcg agcggtatca    660
gctcactcaa aggcggtaat acggttatcc acagaatcag gggataacgc aggaaagaac    720
atgtgagcaa aaggccagca aaaggccagg aaccgtaaaa aggccgcgtt gctggcgttt    780
ttccataggc tccgcccccc tgacgagcat cacaaaaatc gacgctcaag tcagaggtgg    840
cgaaacccga caggactata aagataccag gcgtttcccc ctggaagctc cctcgtgcgc    900
tctcctgttc cgaccctgcc gcttaccgga tacctgtccg cctttctccc ttcgggaagc    960
gtggcgcttt ctcatagctc acgctgtagg tatctcagtt cggtgtaggt cgttcgctcc   1020
aagctgggct gtgtgcacga accccccgtt cagcccgacc gctgcgcctt atccggtaac   1080
tatcgtcttg attccaaccc ggtaagacac gacttatcgc cactggcagc agccactggt   1140
aacaggatta gcagagcgag gtatgtaggc ggtgctacag agttcttgaa gtggtggcct   1200
aactacggct acactagaag aacagtattt ggtatctgcg ctctgctgaa gccagttacc   1260
ttcggaaaaa gagttggtag ctcttgatcc ggcaaacaaa ccaccgctgg tagcggtggt   1320
ttttttgttt gcaagcagca gattacgcgc agaaaaaaag gatctcaaga agatcctttg   1380
atcttttcta cggggtctga cgctcagtgg aacgaaaact cacgttaagg gattttggtc   1440
atgagattat caaaaaggat cttcacctag atccttttaa attaaaaatg aagttttaaa   1500
tcaatctaaa gtatatatga gtaacttggt ctgacagtta ccaatgctta atcagtgagg   1560
cacctatctc agcgatctgt ctatttcgtt catccatagt tgcctgactg cccgtcgtgt   1620
agataactac gatacgggag ggcttaccat ctggccccag tgctgcaatg ataccgcgag   1680
acccacgctc accggctcca gatttatcag caataaacca gccagccgga agggccgagc   1740
gcagaagtgg tcctgcaact ttatccgcct ccatccagtc tattaattgt tgccgggaag   1800
ctagagtaag tagttcgcca gttaatagtt tgcgcaacgt tgttgccatt gctacaggca   1860
tcgtggtgtc acgctcgtcg tttggtatgg cttcattcag ctccggttcc caacgatcaa   1920
ggcgagttac atgatccccc atgttgtgca aaaaagcggt tagctccttc ggtcctccga   1980
tcgttgtcag aagtaagttg gccgcagtgt tatcactcat ggttatggca gcactgcata   2040
attctcttac tgtcatgcca tccgtaagat gcttttctgt gactggtgag tactcaacca   2100
agtcattctg agaatagtgt atgcggcgac cgagttgctc ttgcccggcg tcaatacggg   2160
ataataccgc gccacatagc agaactttaa aagtgctcat cattggaaaa cgttcttcgg   2220
ggcgaaaact ctcaaggatc ttaccgctgt tgagatccag ttcgatgtaa cccactcgtg   2280
cacccaactg atcttcagca tcttttactt tcaccagcgt ttctgggtga gcaaaaacag   2340
gaaggcaaaa tgccgcaaaa aagggaataa gggcgacacg gaaatgttga atactcatca   2400
ttgccttttt caatattat tgaagcattt atcagggtta ttgtctcatg agcggttaca   2460
tatttgaatg tatttagaaa aataaacaaa taggggttcc gcgcacattt ccccgaaaag   2520
tgccacctga cgtctaagaa accattatta tcatgacatt aacctataaa aataggcgta   2580
tcacgaggcc ctttcatctc gcgcgtttcg gtgatgacgg tgaaaacctc tgacacatgc   2640
agctcccgga gacagtcaca gcttgtctgt aagcggatgc cgggagcaga caagcccgtc   2700
agggcgcgtc agcgggtgtt ggcgggtgtc ggggctg                             2737
```

<210> SEQ ID NO 12
<211> LENGTH: 7692
<212> TYPE: DNA
<213> ORGANISM: Artificial Sequence
<220> FEATURE:
<223> OTHER INFORMATION: Synthetic DNA fragment resulting from Stitch 7

<400> SEQUENCE: 12

```
gacggcacgg ccacgcgttt aaaccgccct ccaagctgac ataaatcgca ctttgtatct     60 acttttttt attcgaaaac aaggcacaac aatgaatcta tcgccctgtg agattttcaa    120
tctcaagttt gtgtaataga tagcgttata ttatagaact ataaaggtcc ttgaatatac    180
atagtgtttc attcctatta ctgtatatgt gactttacat tgttacttcc gcggctattt    240
gacgttttct gcttcaggtg cggcttggag ggcaaagtgt cagaaaatcg gccaggccgt    300
atgacacaaa agagtagaaa acgagatctc aaatatctcg aggcctgtcc tctatacaac    360
cgcccagctc tctgacaaag ctccagaacg gttgtctttt gtttcgaaaa gccaaggtcc    420
cttataattg ccctccattt tgtgtcacct atttaagcaa aaaattgaaa gtttactaac    480
ctttcattaa agaaaataa caatattata aaaagcgctt aaagctcaca cgcggccagg    540
gggagccgag ctcctcgaga agttaagatt atatgaataa ctaaatacta aatagaaatg    600
taaatacagt gagaacaaaa caaaaaaaaa cgaacagaga aactaaatcc acattaattg    660
agagttctat ctattagaaa atgcaaactc caactaaatg ggaaaacaga taacctcttt    720 tattttttt taatgtttga tattcgagtc tttttctttt gttaggttta tattcatcat    780
ttcaatgaat aaaagaagct tcttattttg gttgcaaaga atgaaaaaaa aggattttt    840 catacttcta aagcttcaat tataaccaaa aattttataa atgaagagaa aaaatctagt    900
agtatcaagt taaacctatt cctttgccct cggacgagtg ctggggcgtc ggtttccact    960
atcggcgagt acttctacac agccatcggt ccagacggcc gcgcttctgc gggcgatttg   1020
tgtacgcccg acagtcccgg ctccggatcg gacgattgcg tcgcatcgac cctgcgccca   1080
agctgcatca tcgaaattgc cgtcaaccaa gctctgatag agttggtcaa gaccaatgcg   1140
gagcatatac gcccggagcc gcggcgatcc tgcaagctcc ggatgcctcc gctcgaagta   1200
gcgcgtctgc tgctccatac aagccaacca cggcctccag aagaagatgt tggcgacctc   1260
gtattgggaa tccccgaaca tcgcctcgct ccagtcaatg accgctgtta tgcggccatt   1320
gtccgtcagg acattgttgg agccgaaatc cgcgtgcacg aggtgccgga cttcggggca   1380
gtcctcggcc caaagcatca gctcatcgag agcctgcgcg acggacgcac tgacggtgtc   1440
gtccatcaca gtttgccagt gatacacatg gggatcagca atcgcgcata tgaaatcacg   1500
ccatgtagtg tattgaccga ttccttgcgg tccgaatggg ccgaacccgc tcgtctggct   1560
aagatcggcc gcagcgatcg catccatggc ctccgcgacc ggctgcagaa cagcgggcag   1620
ttcggtttca ggcaggtctt gcaacgtgac accctgtgca cggcgggaga tgcaataggt   1680
caggctctcg ctgaattccc caatgtcaag cacttccgga atcgggagcg cggccgatgc   1740
aaagtgccga taaacataac gatctttgta gaaaccatcg cgcagctat ttacccgcag   1800 gacatatcca cgccctccta catcgaagct gaaagcacga gattcttcgc cctccgagag   1860
ctgcatcagg tcggagacgc tgtcgaactt ttcgatcaga aacttctcga cagacgtcgc   1920
ggtgagttca ggctttttca ttttaatgt tacttctctt gcagttaggg aactataatg   1980
taactcaaaa taagattaaa caaactaaaa taaaagaag ttatacagaa aaacccatat   2040
aaaccagtac taatccataa taataataca caaaaaaact atcaaataaa accagaaaac   2100
agattgaata gaaaaatttt ttcgatctcc ttttatattc aaaattcgat atatgaaaaa   2160
```

```
gggaactctc agaaaatcac caaatcaatt taattagatt tttctttttcc ttctagcgtt    2220 ggaaagaaaa attttttcttt ttttttttag aaatgaaaaa ttttttgccgt aggaatcacc   2280 gtataaaccc tgtataaacg ctactctgtt cacctgtgta ggctatgatt gacccagtgt    2340
tcattgttat tgcgagagag cgggagaaaa gaaccgatac aagagatcca tgctggtata   2400
gttgtctgtc caacactttg atgaacttgt aggacgatga tgtgtattac tagtgtcgac   2460
gctcgtccaa cgccggcgga cctcttttaa ttctgctgta acccgtacat gcccaaaata   2520
gggggcgggt tacacagaat atataacatc gtaggtgtct gggtgaacag tttattcctg   2580
gcatccacta aatataatgg agcccgcttt ttaagctggc atccagaaaa aaaaagaatc   2640
ccagcaccaa aatattgttt tcttcaccaa ccatcagttc ataggtccat tctcttagcg   2700
caactacaga gaacaggggc acaaacaggc aaaaaacggg cacaacctca atggagtgat   2760
gcaacctgcc tggagtaaat gatgacacaa ggcaattgac ccacgcatgt atctatctca   2820
ttttcttaca ccttctatta ccttctgctc tctctgattt ggaaaaagct gaaaaaaaag   2880 gttgaaaacca gttccctgaa attattcccc tacttgacta ataagtatat aaagacggta   2940
ggtattgatt gtaattctgt aaatctattt cttaaacttc ttaaattcta cttttatagt   3000
tagtcttttt tttagtttta aaacaccaag aacttagttt cgatccccgc gtgcttggcc   3060
ggccgtatga cagatgtagt aatagtatcc gccgcaagaa cagcagttgg aaagtttgga   3120
ggctctcttg caaagattcc agcccctgaa ttaggagctg ttgttataaa agccgcactt   3180
gaaagggcag gtgtgaagcc tgaacaagtc agtgaagtca taatgggtca agttttaact   3240
gccggctcag gtcaaaaccc agccagacag gctgctatta aagctggttt accggcaatg   3300
gttcccgcga tgactattaa caaagtttgt ggttccggcc ttaaagcagt gatgttagct   3360
gctaacgcaa taatggctgg ggatgctgaa atagtagtcg ccggaggaca agagaatatg   3420
agtgcagccc cacacgtttt accgggctcc agagatggat tccgtatggg tgacgctaag   3480
ttagttgata ctatgatagt agatggacta tgggatgtct ataaccaata tcacatgggt   3540
attacagccg aaaacgtggc gaaagaatat gggattacga gagaagcaca ggatgagttc   3600
gccgtgggta gtcaaaataa ggcggaggcg gctcaaaaag ccggtaaatt tgatgaggaa   3660
atagtacctg tccttatacc acagagaaaa ggagatccgg ttgcctttaa aaccgatgag   3720
tttgtcagac aaggcgccac attagacagc atgtctggtt tgaaacctgc ttttgataag   3780
gccgggaccg tgaccgctgc taatgcgtca ggactaaacg atggagctgc ggcggtggtt   3840
gttatgtctg ctgctaaagc aaaagaatta gggttaactc cattagccac tatcaaatct   3900
tatgctaacg cgggggtgga cccaaaagtg atgggaatgg gacctgttcc agccagtaag   3960
agggcgttat ctagggccga atggactcct caagacttgg atttaatgga aattaatgaa   4020
gcatttgccg cacaggcgtt agctgtccac caacagatgg gttgggatac aagtaaggtc   4080
aatgttaatg gaggtgcaat cgccattggt cacccaattg gtgcgtccgg atgtagaatt   4140
ttagttaccc tactgcatga gatgaagagg cgtgatgcaa agaaaggctt agcttcgttg   4200
tgtatcggtg gtggaatggg tgtggcatta gcagtcgagc gtaaataaaa cctgcaggcc   4260
gcgagcgccg attaagtgaa tttactttaa atcttgcatt taaataaatt ttcttttttat   4320 agctttatga cttagtttca atttatatac tattttaatg acattttcga ttcattgatt   4380
gaaagctttg tgttttttct tgatgcgcta ttgcattgtt cttgtctttt tcgccacatg   4440
taatatctgt agtagatacc tgatacattg tggatgctga gtgaaatttt agttaataat   4500
ggaggcgctc ttaataattt tggggatatt ggcttaacgc gatcgccgac gccgccgatt   4560
```

```
gacagcagga ttatcgtaat acgtaatagt tgaaaatctc aaaaatgtgt gggtcattac   4620
gtaaataatg ataggaatgg gattcttcta ttttccttt ttccattcta gcagccgtcg    4680
ggaaaacgtg gcatcctctc tttcgggctc aattggagtc acgctgccgt gagcatcctc   4740
tctttccata tctaacaact gagcacgtaa ccaatggaaa agcatgagct tagcgttgct   4800 ccaaaaagt  attggatggt taataccatt tgtctgttct cttctgactt tgactcctca    4860 aaaaaaaaa  atctacaatc aacagatcgc ttcaattacg ccctcacaaa aactttttc    4920 cttcttcttc gcccacgtta aattttatcc ctcatgttgt ctaacggatt tctgcacttg   4980
atttattata aaagacaaa  gacataatac ttctctatca atttcagtta ttgttcttcc    5040
ttgcgttatt cttctgttct ctttttcttt ttgtcatata taaccaaggc ggccgctggc   5100
gagggagata tgaaactctc aactaaactt tgttggtgtg gtattaaagg aagacttagg   5160
ccgcaaaagc aacaacaatt acacaataca aacttgcaaa tgactgaact aaaaaaacaa   5220
aagaccgctg aacaaaaaac cagacctcaa atgtcggta  ttaaaggtat ccaaatttac    5280
atcccaactc aatgtgtcaa ccaatctgag ctagagaaat ttgatggcgt ttctcaaggt   5340
aaatacacaa ttggtctggg ccaaaccaac atgtctttg  tcaatgacag agaagatatc    5400
tactcgatgt ccctaactgt tttgtctaag ttgatcaaga gttacaacat cgacaccaac   5460
aaaattggta gattagaagt cggtactgaa actctgattg acaagtccaa gtctgtcaag   5520
tctgtcttga tgcaattgtt tggtgaaaac actgacgtcg aaggtattga cacgcttaat   5580
gcctgttacg gtggtaccaa cgcgttgttc aactctttga actggattga atctaacgca   5640
tgggatggta gagacgccat tgtagtttgc ggtgatattg ccatctacga taagggtgcc   5700
gcaagaccaa ccggtggtgc cggtactgtt gctatgtgga tcggtcctga tgctccaatt   5760
gtatttgact ctgtaagagc ttcttacatg gaacacgcct acgattttta caagccagat   5820
ttcaccagcg aatatcctta cgtcgatggt cattttcat  taacttgtta cgtcaaggct    5880
cttgatcaag tttacaagag ttattccaag aaggctattt ctaaagggtt ggttagcgat   5940
cccgctggtt cggatgcttt gaacgttttg aaatatttcg actacaacgt tttccatgtt   6000
ccaacctgta aattggtcac aaaatcatac ggtagattac tatataacga tttcagagcc   6060
aatcctcaat tgttcccaga agttgacgcc gaattagcta ctcgcgatta tgacgaatct   6120
ttaaccgata agaacattga aaaacttttt gttaatgttg ctaagccatt ccacaaagag   6180
agagttgccc aatctttgat tgttccaaca aacacaggta acatgtacac cgcatctgtt   6240
tatgccgcct ttgcatctct attaaactat gttggatctg acgacttaca aggcaagcgt   6300
gttggtttat ttcttacgg  ttccggttta gctgcatctc tatattcttg caaaattgtt    6360
ggtgacgtcc aacatattat caaggaatta gatattacta acaaattagc caagagaatc   6420
accgaaactc caaggatta  cgaagctgcc atcgaattga gagaaaatgc ccatttgaag    6480
aagaacttca aacctcaagg ttccattgag catttgcaaa gtggtgttta ctacttgacc   6540
aacatcgatg acaaatttag aagatcttac gatgttaaaa aataatcttc ccccatcgat   6600
tgcatcttgc tgaacccct  tcataaatgc tttatttttt tggcagcctg cttttttttag   6660 ctctcattta atagagtagt tttttaatct atatactagg aaaactcttt atttaataac   6720
aatgatatat atatatattt tttttataaa gaattgtata tctatattta taacacaata   6780
aatctaatct caacttttt  ctttaaagtt aagcccaacc gattttttt  ctcataaggc     6840 gcgccacggt cgtgcggatt aaagcttttg attaagcctt ctagtccaaa aaacacgttt   6900
ttttgtcatt tatttcattt tcttagaata gtttagttta ttcattttat agtcacgaat   6960
```

```
gttttatgat tctatatagg gttgcaaaca agcattttc attttatgtt aaaacaattt    7020
caggtttacc ttttattctg cttgtggtga cgcgtgtatc cgcccgctct tttggtcacc    7080
catgtattta attgcataaa taattcttaa aagtggagct agtcagcccc tcagccccc     7140 tagcgtcgat aaactaatga ttttaaatcg ttaaaaaaat atgcgaattc tgtggatcga    7200
acacaggacc tccagataac ttgaccgaag ttttttcttc agtctggcgc tctcccaact    7260
gagctaaatc cgcttactat ttgttatcag ttcccttcat atctacatag aataggttaa    7320
gtattttatt agttgccaga agaactactg atagttggga atatttggtg aataatgaag    7380
attgggtgaa taatttgata attttgagat tcaattgtta atcaatgtta caatattatg    7440
tatacagagt atactagaag ttctcttcgg agatcttgaa gttcacaaaa gggaatcgat    7500
atttctacat aatattatca ttacttcttc cccatcttat atttgtcatt cattattgat    7560
tatgatcaat gcaataatga ttggtagttg ccaaacattt aatacgatcc tctgtaatat    7620
ttctatgaat aattatcaca gcaacgttca attatcttca attccggtgt ttaaacccca    7680
gcgcctggcg gg                                                        7692

<210> SEQ ID NO 13
<211> LENGTH: 3627
<212> TYPE: DNA
<213> ORGANISM: Artificial Sequence
<220> FEATURE:
<223> OTHER INFORMATION: Synthetic Vector pAM1466

<400> SEQUENCE: 13 gcactttcg gggaaatgtg cgcggaaccc ctatttgttt attttctaa atacattcaa       60 atatgtatcc gctcatgaga caataaccct gataaatgct tcaataatat tgaaaaagga    120
agagtatgag tattcaacat ttccgtgtcg cccttattcc cttttttgcg gcattttgcc    180
ttcctgtttt tgctcaccca gaaacgctgg tgaaagtaaa agatgctgaa gatcagttgg    240
gtgcacgagt gggttacatc gaactggatc tcaacagcgg taagatcctt gagagttttc    300
gccccgaaga acgttttcca atgatgagca cttttaaagt tctgctatgt ggcgcggtat    360
tatcccgtat tgacgccggg caagagcaac tcggtcgccg catacactat tctcagaatg    420
acttggttga gtactcacca gtcacagaaa agcatcttac ggatggcatg acagtaagag    480
aattatgcag tgctgccata accatgagtg ataacactgc ggccaactta cttctgacaa    540
cgatcggagg accgaaggag ctaaccgctt ttttgcacaa catgggggat catgtaactc    600
gccttgatcg ttgggaaccg gagctgaatg aagccatacc aaacgacgag cgtgacacca    660
cgatgcctgt agcaatggca acaacgttgc gcaaactatt aactggcgaa ctacttactc    720
tagcttcccg gcaacaatta atagactgga tggaggcgga taaagttgca ggaccacttc    780
tgcgctcggc ccttccggct ggctggttta ttgctgataa atctggagcc ggtgagcgtg    840
ggtctcgcgg tatcattgca gcactggggc cagatggtaa gccctcccgt atcgtagtta    900
tctacacgac ggggagtcag gcaactatgg atgaacgaaa tagacagatc gctgagatag    960
gtgcctcact gattaagcat tggtaactgt cagaccaagt ttactcatat atactttaga   1020
ttgatttaaa acttcatttt taatttaaaa ggatctaggt gaagatcctt tttgataatc   1080
tcatgaccaa aatcccttaa cgtgagtttt cgttccactg agcgtcagac cccgtagaaa   1140
agatcaaagg atcttcttga gatccttttt ttctgcgcgt aatctgctgc ttgcaaacaa   1200
aaaaaccacc gctaccagcg gtggtttgtt tgccggatca agagctacca actctttttc   1260
cgaaggtaac tggcttcagc agagcgcaga taccaaatac tgtccttcta gtgtagccgt   1320
```

```
agttaggcca ccacttcaag aactctgtag caccgcctac atacctcgct ctgctaatcc   1380
tgttaccagt ggctgctgcc agtggcgata agtcgtgtct taccgggttg gactcaagac   1440
gatagttacc ggataaggcg cagcggtcgg gctgaacggg gggttcgtgc acacagccca   1500
gcttggagcg aacgacctac accgaactga gatacctaca gcgtgagcta tgagaaagcg   1560
ccacgcttcc cgaagggaga aaggcggaca ggtatccggt aagcggcagg gtcggaacag   1620
gagagcgcac gagggagctt ccaggggaa acgcctggta tctttatagt cctgtcgggt    1680
ttcgccacct ctgacttgag cgtcgatttt tgtgatgctc gtcagggggg cggagcctat   1740
ggaaaaacgc cagcaacgcg gccttttttac ggttcctggc cttttgctgg cctttttgctc 1800
acatgttctt tcctgcgtta tcccctgatt ctgtggataa ccgtattacc gcctttgagt   1860
gagctgatac cgctcgccgc agccgaacga ccgagcggcc gccagcgagc tcagtgagcg   1920
aggaagcgga agagcgccca atacgcaaac cgcctctccc cgcgcgttgg ccgattcatt   1980
aatgcagctg gcacgacagg tttcccgact ggaaagcggg cagtgagcgc aacgcaatta   2040
atgtgagtta gctcactcat taggcacccc aggctttaca ctttatgctt ccggctcgta   2100
tgttgtgtgg aattgtgagc ggataacaat ttcacacagg aaacagctat gaccatgagt   2160
ttaaacatga gcaaaggcga agaactgttc acgggcgttg taccgatcct ggtggaactg   2220
gacggggatg tgaatgggca caagttttca gtgagcggcg aaggagaagg cgatgcgacc   2280
tacggcaaac tgaccctgaa attcatttgc accaccggta aacttcccgt gccgtggccc   2340
accctggtga ccacctttgg ctatggcgta cagtgcttcg cgcgttaccc ggatcacatg   2400
aaacgccacg acttctttaa gagcgctatg ccagagggct acgtccagga acgcaccata   2460
ttcttcaaag acgacggcaa ctacaagacg cgcgctgaag tcaagtttga gggacacg    2520
ctggtgaacc gtattgagct gaagggcatc gacttcaagg aggacgggaa catcctgggc   2580
cataagctgg agtacaatta caacagccac aacgtgtata tcatggcgga caagcagaag   2640
aacggcatca aggtcaactt caagatccgg cacaacatcg aggatggcag cgtgcagctg   2700
gcggatcatt atcaacagaa caccccgatt ggcgatggac cggtgctgct gcccgataat   2760
cattacctga gtacccagag cgccctgagc aaggacccga atgagaagcg tgatcacatg   2820
gtactgctgg aatttgtgac cgcggctggc atcacccacg gcatggatga actgtataaa   2880
taaggtaccg cggccgccgt ctccggggac agacgtctcg ccccttaggg tccatgcagt   2940
tggcttcgat ggtctctttt ttataggtcg agtaccaatt cgccctatag tgagtcgtat   3000
tacaattcac tggccgtcgt tttacaacgt cgtgactggg aaaaccctgg cgttacccaa   3060
cttaatcgcc ttgcagcaca tcccccttc gccagctggc gtaatagcga agaggcccgc    3120
accgatcgcc cttcccaaca gttgcgcagc ctgaatggcg aatgggacgc gccctgtagc   3180
ggcgcattaa gcgcggcggg tgtggtggtt acgcgcagcg tgaccgctac acttgccagc   3240
gccctagcgc ccgctccttt cgctttcttc ccttcctttc tcgccacgtt cgccggcttt   3300
ccccgtcaag ctctaaatcg ggggctccct ttagggttcc gatttagtgc tttacggcac   3360
ctcgacccca aaaaacttga ttagggtgat ggttcacgta gtgggccatc gccctgatag   3420
acggttttc gccctttgac gttggagtcc acgttcttta atagtggact cttgttccaa   3480
actggaacaa cactcaaccc tatctcggtc tattcttttg atttataagg gattttgccg   3540
atttcggcct attggttaaa aaatgagctg atttaacaaa aatttaacgc gaattttaac   3600
aaaatattaa cgcttacaat ttaggtg                                      3627
```

```
<210> SEQ ID NO 14
<211> LENGTH: 915
<212> TYPE: DNA
<213> ORGANISM: Artificial Sequence
<220> FEATURE:
<223> OTHER INFORMATION: Synthetic DNA fragment 1040

<400> SEQUENCE: 14
taagtagttg accatagcta tggaaggtct cacggaaatg ttgaatactc atcaattgcc      60
tttttcaata ttattgaagc atttatcagg gttattgtct catgagcggt tacatatttg     120
aatgtattta gaaaaataaa caaatagggg ttccgcgcac atttccccga aaagtgccac     180
ctgacgtcta agaaaccatt attatcatga cattaaccta taaaaatagg cgtatcacga     240
ggccctttca tctcgcgcgt ttcggtgatg acggtgaaaa cctctgacac atgcagctcc     300
cggagacagt cacagcttgt ctgtaagcgg atgccgggag cagacaagcc cgtcagggcg     360
cgtcagcggg tgttggcggg tgtcggggct ggtaaaacga cggccagtat taaccctcac     420
taaagggaac tcgaggctct tcacgctcgt ccaacgccgg cggaccttgg atgactcgct     480
agccgcccaa tacgcaaacc gcctctcccc gcgcgttggc cgattcatta atgcagctgg     540
cacgacaggt ttcccgactg gaaagcgggc agtgagcgca acgcaattaa tgtgagttag     600
ctcactcatt aggcacccca ggctttacac tttatgcttc cggctcgtat gttgtgtgga     660
attgtgagcg gataacaatt tcacacagga aacagctatg agcaaaggcg aagaactgtt     720
cacgggcgtt gtaccgatcc tggtggaact ggacggggat gtgaatgggc acaagttttc     780
agtgagcggc gaaggagaag gcgatgcgac ctacggcaaa ctgaccctga aattcatttg     840
caccaccggt aaacttcccg tgccgtggcc caccctggtg accacctttg gagacgccac     900
gtacatggct tattg                                                     915

<210> SEQ ID NO 15
<211> LENGTH: 882
<212> TYPE: DNA
<213> ORGANISM: Artificial Sequence
<220> FEATURE:
<223> OTHER INFORMATION: Synthetic DNA fragment 1041

<400> SEQUENCE: 15
taagtagttg accatagcta tggaaggtct ccctttggct atggcgtaca gtgcttcgcg      60
cgttacccgg atcacatgaa acgccacgac ttctttaaga gcgctatgcc agagggctac     120
gtccaggaac gcaccatatt cttcaaagac gacggcaact acaagacgcg cgctgaagtc     180
aagtttgaag gggacacgct ggtgaaccgt attgagctga agggcatcga cttcaaggag     240
gacgggaaca tcctgggcca taagctggag tacaattaca acagccacaa cgtgtatatc     300
atggcggaca agcagaagaa cggcatcaag gtcaacttca gatccggcaa caacatcgag     360
gatggcagcg tgcagctggc ggatcattat caacagaaca ccccgattgg cgatggaccg     420
gtgctgctgc ccgataatca ttacctgagt acccagagcg ccctgagcaa ggacccgaat     480
gagaagcgtg atcacatggt actgctggaa tttgtgaccg cggctggcat cacccacggc     540
atggatgaac tgtataaata acatatggag tctgccatcg gtgtttaaac cccagcgcct     600
ggcgggtgaa gagcgagctc ccgctgagca taactagcg tcatagctgt ttcctgggtc     660
gttcggctgc ggcgagcgt atcagctcac tcaaaggcgg taatacggtt atccacagaa     720
tcaggggata acgcaggaaa gaacatgtga gcaaaaggcc agcaaaaggc caggaaccgt     780
aaaaaggccg cgttgctggc gttttttccat aggctccgcc cccctgacga gcatcacaaa     840
aatcgacgct caagtcagag acgccacgta catggcttat tg                       882
```

-continued

<210> SEQ ID NO 16
<211> LENGTH: 787
<212> TYPE: DNA
<213> ORGANISM: Artificial Sequence
<220> FEATURE:
<223> OTHER INFORMATION: Synthetic DNA fragment 1042

<400> SEQUENCE: 16

| | | | | | |
|---|---|---|---|---|---|
| taagtagttg | accatagcta | tggaaggtct | caagtcagag | gtggcgaaac | ccgacaggac | 60 |
| tataaagata | ccaggcgttt | ccccctggaa | gctccctcgt | gcgctctcct | gttccgaccc | 120 |
| tgccgcttac | ccgatacctg | tccgcctttc | tcccttcggg | aagcgtggcg | ctttctcata | 180 |
| gctcacgctg | taggtatctc | agttcggtgt | aggtcgttcg | ctccaagctg | ggctgtgtgc | 240 |
| acgaaccccc | cgttcagccc | gaccgctgcg | ccttatccgg | taactatcgt | cttgtgtcca | 300 |
| acccggtaag | acacgactta | tcgccactgg | cagcagccac | tggtaacagg | attagcagag | 360 |
| cgaggtatgt | aggcggtgct | acagagttct | tgaagtggtg | gcctaactac | ggctacacta | 420 |
| gaagaacagt | atttggtatc | tgcgctctgc | tgaagccagt | taccttcgga | aaaagagttg | 480 |
| gtagctcttg | atccggcaaa | caaaccaccg | ctggtagcgg | tggttttttt | gtttgcaagc | 540 |
| agcagattac | gcgcagaaaa | aaaggatctc | aagaagatcc | tttgatcttt | tctacggggt | 600 |
| ctgacgctca | gtggaacgaa | aactcacgtt | aagggatttt | ggtcatgaga | ttatcaaaaa | 660 |
| ggatcttcac | ctagatcctt | ttaaattaaa | aatgaagttt | taaatcaatc | taaagtatat | 720 |
| atgagtaaac | ttggtcgcat | gcttaccaat | gcttaatcag | tggagacgcc | acgtacatgg | 780 |
| cttattg | | | | | | 787 |

<210> SEQ ID NO 17
<211> LENGTH: 36
<212> TYPE: DNA
<213> ORGANISM: Artificial Sequence
<220> FEATURE:
<223> OTHER INFORMATION: Synthetic Primer JCB158-17A

<400> SEQUENCE: 17
cgttcatcca tagttgcctg actgcccgtc gtgtag        36

<210> SEQ ID NO 18
<211> LENGTH: 36
<212> TYPE: DNA
<213> ORGANISM: Artificial Sequence
<220> FEATURE:
<223> OTHER INFORMATION: Synthetic Primer JCB158-17B

<400> SEQUENCE: 18
ctacacgacg ggcagtcagg caactatgga tgaacg        36

<210> SEQ ID NO 19
<211> LENGTH: 59
<212> TYPE: DNA
<213> ORGANISM: Artificial Sequence
<220> FEATURE:
<223> OTHER INFORMATION: Synthetic Primer JCB158-17C

<400> SEQUENCE: 19
atatgagtaa acttggtcgc atgcttacca atgcttaatc agtgaggcac ctatctcag        59

<210> SEQ ID NO 20
<211> LENGTH: 52
<212> TYPE: DNA
<213> ORGANISM: Artificial Sequence

```
<220> FEATURE:
<223> OTHER INFORMATION: Synthetic Primer JCB158-17D

<400> SEQUENCE: 20
ttgaaaaagg caattgatga gtattcaaca tttccgtgtc gcccttattc cc        52

<210> SEQ ID NO 21
<211> LENGTH: 39
<212> TYPE: DNA
<213> ORGANISM: Artificial Sequence
<220> FEATURE:
<223> OTHER INFORMATION: Synthetic Primer L012

<400> SEQUENCE: 21
ccggtaacta tcgtcttgat tccaacccgg taagacacg                       39

<210> SEQ ID NO 22
<211> LENGTH: 39
<212> TYPE: DNA
<213> ORGANISM: Artificial Sequence
<220> FEATURE:
<223> OTHER INFORMATION: Synthetic Primer L013

<400> SEQUENCE: 22
cgtgtcttac cgggttggaa tcaagacgat agttaccgg                       39

<210> SEQ ID NO 23
<211> LENGTH: 38
<212> TYPE: DNA
<213> ORGANISM: Artificial Sequence
<220> FEATURE:
<223> OTHER INFORMATION: Synthetic Primer L054

<400> SEQUENCE: 23
cgaaactaag ttcttggtgt tttaaaacta aaaaaag                         38

<210> SEQ ID NO 24
<211> LENGTH: 35
<212> TYPE: DNA
<213> ORGANISM: Artificial Sequence
<220> FEATURE:
<223> OTHER INFORMATION: Synthetic Primer L057

<400> SEQUENCE: 24
ggttatatat gacaaaagaa aaagaagaac agaag                           35

<210> SEQ ID NO 25
<211> LENGTH: 29
<212> TYPE: DNA
<213> ORGANISM: Artificial Sequence
<220> FEATURE:
<223> OTHER INFORMATION: Synthetic Primer L109

<400> SEQUENCE: 25
atgaaactct ctactaaact tgttggtg                                   29

<210> SEQ ID NO 26
<211> LENGTH: 28
<212> TYPE: DNA
<213> ORGANISM: Artificial Sequence
<220> FEATURE:
<223> OTHER INFORMATION: Synthetic Primer L110

<400> SEQUENCE: 26
atgagaaaaa aaatcggttg ggcttaac                                   28
```

```
<210> SEQ ID NO 27
<211> LENGTH: 31
<212> TYPE: DNA
<213> ORGANISM: Artificial Sequence
<220> FEATURE:
<223> OTHER INFORMATION: Synthetic Primer L176

<400> SEQUENCE: 27
gactagctcc acttttaaga attatttatg c                              31

<210> SEQ ID NO 28
<211> LENGTH: 38
<212> TYPE: DNA
<213> ORGANISM: Artificial Sequence
<220> FEATURE:
<223> OTHER INFORMATION: Synthetic Primer L185

<400> SEQUENCE: 28
gtgaatttac tttaaatctt gcatttaaat aaattttc                       38

<210> SEQ ID NO 29
<211> LENGTH: 30
<212> TYPE: DNA
<213> ORGANISM: Artificial Sequence
<220> FEATURE:
<223> OTHER INFORMATION: Synthetic Primer L186

<400> SEQUENCE: 29
aagccaatat ccccaaaatt attaagagcg                                30

<210> SEQ ID NO 30
<211> LENGTH: 54
<212> TYPE: DNA
<213> ORGANISM: Artificial Sequence
<220> FEATURE:
<223> OTHER INFORMATION: Synthetic Primer VH296-235-55-Leu2 12-1 F

<400> SEQUENCE: 30
gctcacacgc ggccaggggg agcccgttga gccattagta tcaatttgct tacc     54

<210> SEQ ID NO 31
<211> LENGTH: 57
<212> TYPE: DNA
<213> ORGANISM: Artificial Sequence
<220> FEATURE:
<223> OTHER INFORMATION: Synthetic Primer VH296-235-55-Leu2 12-1 R

<400> SEQUENCE: 31
aggtccgccg gcgttggacg agcgaggcgc ctgattcaag aaatatcttg accgcag  57

<210> SEQ ID NO 32
<211> LENGTH: 27
<212> TYPE: DNA
<213> ORGANISM: Artificial Sequence
<220> FEATURE:
<223> OTHER INFORMATION: Synthetic Primer L219

<400> SEQUENCE: 32
ctccaagctg acataaatcg cactttg                                   27

<210> SEQ ID NO 33
<211> LENGTH: 39
<212> TYPE: DNA
<213> ORGANISM: Artificial Sequence
<220> FEATURE:
<223> OTHER INFORMATION: Synthetic Primer L220

<400> SEQUENCE: 33
```

```
tttaagcgct ttttataata ttgttatttc tctttaatg                    39

<210> SEQ ID NO 34
<211> LENGTH: 37
<212> TYPE: DNA
<213> ORGANISM: Artificial Sequence
<220> FEATURE:
<223> OTHER INFORMATION: Synthetic Primer L221

<400> SEQUENCE: 34
ataaactaat gattttaaat cgttaaaaaa atatgcg                      37

<210> SEQ ID NO 35
<211> LENGTH: 28
<212> TYPE: DNA
<213> ORGANISM: Artificial Sequence
<220> FEATURE:
<223> OTHER INFORMATION: Synthetic Primer L222

<400> SEQUENCE: 35
gaattgaaga taattgaacg ttgctgtg                                28

<210> SEQ ID NO 36
<211> LENGTH: 28
<212> TYPE: DNA
<213> ORGANISM: Artificial Sequence
<220> FEATURE:
<223> OTHER INFORMATION: Synthetic Primer L224

<400> SEQUENCE: 36
cttttaattc tgctgtaacc cgtacatg                                28

<210> SEQ ID NO 37
<211> LENGTH: 24
<212> TYPE: DNA
<213> ORGANISM: Artificial Sequence
<220> FEATURE:
<223> OTHER INFORMATION: Synthetic Primer L225

<400> SEQUENCE: 37
tgacagcagg attatcgtaa tacg                                    24

<210> SEQ ID NO 38
<211> LENGTH: 27
<212> TYPE: DNA
<213> ORGANISM: Artificial Sequence
<220> FEATURE:
<223> OTHER INFORMATION: Synthetic Primer L226

<400> SEQUENCE: 38
atgacagatg tagtaatagt atccgcc                                 27

<210> SEQ ID NO 39
<211> LENGTH: 27
<212> TYPE: DNA
<213> ORGANISM: Artificial Sequence
<220> FEATURE:
<223> OTHER INFORMATION: Synthetic Primer L227

<400> SEQUENCE: 39
ttatttacgc tcgactgcta atgccac                                 27

<210> SEQ ID NO 40
<211> LENGTH: 26
<212> TYPE: DNA
<213> ORGANISM: Artificial Sequence
```

```
<220> FEATURE:
<223> OTHER INFORMATION: Synthetic Primer L229

<400> SEQUENCE: 40
atgaaaaatt gtgtcatcgt cagtgc                                              26

<210> SEQ ID NO 41
<211> LENGTH: 32
<212> TYPE: DNA
<213> ORGANISM: Artificial Sequence
<220> FEATURE:
<223> OTHER INFORMATION: Synthetic Primer L230

<400> SEQUENCE: 41
ttaattcaat ctttcaatca ccatcgcaat tc                                       32

<210> SEQ ID NO 42
<211> LENGTH: 26
<212> TYPE: DNA
<213> ORGANISM: Artificial Sequence
<220> FEATURE:
<223> OTHER INFORMATION: Synthetic Primer L235

<400> SEQUENCE: 42
atgaccatcg gtattgacaa gattag                                              26

<210> SEQ ID NO 43
<211> LENGTH: 38
<212> TYPE: DNA
<213> ORGANISM: Artificial Sequence
<220> FEATURE:
<223> OTHER INFORMATION: Synthetic Primer L236

<400> SEQUENCE: 43
ttaattacga taagatctta cagtattgtt aatcgcag                                 38

<210> SEQ ID NO 44
<211> LENGTH: 35
<212> TYPE: DNA
<213> ORGANISM: Artificial Sequence
<220> FEATURE:
<223> OTHER INFORMATION: Synthetic Primer L248

<400> SEQUENCE: 44
taaagctttt gattaagcct tctagtccaa aaaac                                    35

<210> SEQ ID NO 45
<211> LENGTH: 28
<212> TYPE: DNA
<213> ORGANISM: Artificial Sequence
<220> FEATURE:
<223> OTHER INFORMATION: Synthetic Primer S000

<400> SEQUENCE: 45
gacggcacgg ccacgcgttt aaaccgcc                                            28

<210> SEQ ID NO 46
<211> LENGTH: 28
<212> TYPE: DNA
<213> ORGANISM: Artificial Sequence
<220> FEATURE:
<223> OTHER INFORMATION: Synthetic Primer S001

<400> SEQUENCE: 46
ggcggtttaa acgcgtggcc gtgccgtc                                            28
```

<210> SEQ ID NO 47
<211> LENGTH: 24
<212> TYPE: DNA
<213> ORGANISM: Artificial Sequence
<220> FEATURE:
<223> OTHER INFORMATION: Synthetic Primer S002

<400> SEQUENCE: 47
gctcacacgc ggccaggggg agcc                                    24

<210> SEQ ID NO 48
<211> LENGTH: 24
<212> TYPE: DNA
<213> ORGANISM: Artificial Sequence
<220> FEATURE:
<223> OTHER INFORMATION: Synthetic Primer S003

<400> SEQUENCE: 48
ggctccccct ggccgcgtgt gagc                                    24

<210> SEQ ID NO 49
<211> LENGTH: 24
<212> TYPE: DNA
<213> ORGANISM: Artificial Sequence
<220> FEATURE:
<223> OTHER INFORMATION: Synthetic Primer S004

<400> SEQUENCE: 49
cgctcgtcca acgccggcgg acct                                    24

<210> SEQ ID NO 50
<211> LENGTH: 24
<212> TYPE: DNA
<213> ORGANISM: Artificial Sequence
<220> FEATURE:
<223> OTHER INFORMATION: Synthetic Primer S005

<400> SEQUENCE: 50
aggtccgccg gcgttggacg agcg                                    24

<210> SEQ ID NO 51
<211> LENGTH: 24
<212> TYPE: DNA
<213> ORGANISM: Artificial Sequence
<220> FEATURE:
<223> OTHER INFORMATION: Synthetic Primer S006

<400> SEQUENCE: 51
atccccgcgt gcttggccgg ccgt                                    24

<210> SEQ ID NO 52
<211> LENGTH: 24
<212> TYPE: DNA
<213> ORGANISM: Artificial Sequence
<220> FEATURE:
<223> OTHER INFORMATION: Synthetic Primer S007

<400> SEQUENCE: 52
acggccggcc aagcacgcgg ggat                                    24

<210> SEQ ID NO 53
<211> LENGTH: 24
<212> TYPE: DNA
<213> ORGANISM: Artificial Sequence
<220> FEATURE:
<223> OTHER INFORMATION: Synthetic Primer S008

<400> SEQUENCE: 53

-continued aacctgcagg ccgcgagcgc cgat                                              24

<210> SEQ ID NO 54
<211> LENGTH: 24
<212> TYPE: DNA
<213> ORGANISM: Artificial Sequence
<220> FEATURE:
<223> OTHER INFORMATION: Synthetic Primer S009

<400> SEQUENCE: 54
atcggcgctc gcggcctgca ggtt                                              24

<210> SEQ ID NO 55
<211> LENGTH: 24
<212> TYPE: DNA
<213> ORGANISM: Artificial Sequence
<220> FEATURE:
<223> OTHER INFORMATION: Synthetic Primer S010

<400> SEQUENCE: 55
aacgcgatcg ccgacgccgc cgat                                              24

<210> SEQ ID NO 56
<211> LENGTH: 24
<212> TYPE: DNA
<213> ORGANISM: Artificial Sequence
<220> FEATURE:
<223> OTHER INFORMATION: Synthetic Primer S011

<400> SEQUENCE: 56
atcggcggcg tcggcgatcg cgtt                                              24

<210> SEQ ID NO 57
<211> LENGTH: 24
<212> TYPE: DNA
<213> ORGANISM: Artificial Sequence
<220> FEATURE:
<223> OTHER INFORMATION: Synthetic Primer S012

<400> SEQUENCE: 57
aaggcggccg ctggcgaggg agat                                              24

<210> SEQ ID NO 58
<211> LENGTH: 24
<212> TYPE: DNA
<213> ORGANISM: Artificial Sequence
<220> FEATURE:
<223> OTHER INFORMATION: Synthetic Primer S013

<400> SEQUENCE: 58
atctccctcg ccagcggccg cctt                                              24

<210> SEQ ID NO 59
<211> LENGTH: 24
<212> TYPE: DNA
<213> ORGANISM: Artificial Sequence
<220> FEATURE:
<223> OTHER INFORMATION: Synthetic Primer S014

<400> SEQUENCE: 59
aaggcgcgcc acggtcgtgc ggat                                              24

<210> SEQ ID NO 60
<211> LENGTH: 24
<212> TYPE: DNA
<213> ORGANISM: Artificial Sequence

```
<220> FEATURE:
<223> OTHER INFORMATION: Synthetic Primer S015

<400> SEQUENCE: 60
atccgcacga ccgtggcgcg cctt                                              24

<210> SEQ ID NO 61
<211> LENGTH: 24
<212> TYPE: DNA
<213> ORGANISM: Artificial Sequence
<220> FEATURE:
<223> OTHER INFORMATION: Synthetic Primer S016

<400> SEQUENCE: 61
agcccctcag cccccctagc gtcg                                              24

<210> SEQ ID NO 62
<211> LENGTH: 24
<212> TYPE: DNA
<213> ORGANISM: Artificial Sequence
<220> FEATURE:
<223> OTHER INFORMATION: Synthetic Primer S017

<400> SEQUENCE: 62
cgacgctagg ggggctgagg ggct                                              24

<210> SEQ ID NO 63
<211> LENGTH: 28
<212> TYPE: DNA
<213> ORGANISM: Artificial Sequence
<220> FEATURE:
<223> OTHER INFORMATION: Synthetic Primer S018

<400> SEQUENCE: 63
cggtgtttaa accccagcgc ctggcggg                                          28

<210> SEQ ID NO 64
<211> LENGTH: 28
<212> TYPE: DNA
<213> ORGANISM: Artificial Sequence
<220> FEATURE:
<223> OTHER INFORMATION: Synthetic Primer S019

<400> SEQUENCE: 64
cccgccaggc gctggggttt aaacaccg                                          28

<210> SEQ ID NO 65
<211> LENGTH: 37
<212> TYPE: DNA
<213> ORGANISM: Artificial Sequence
<220> FEATURE:
<223> OTHER INFORMATION: Synthetic Primer S027

<400> SEQUENCE: 65
tggatgactc gctagcgcgc aacgcaatta atgtgag                                37

<210> SEQ ID NO 66
<211> LENGTH: 39
<212> TYPE: DNA
<213> ORGANISM: Artificial Sequence
<220> FEATURE:
<223> OTHER INFORMATION: Synthetic Primer S028

<400> SEQUENCE: 66
tggcagactc catatgctat gcggcatcag agcagattg                              39
```

<210> SEQ ID NO 67
<211> LENGTH: 42
<212> TYPE: DNA
<213> ORGANISM: Artificial Sequence
<220> FEATURE:
<223> OTHER INFORMATION: Synthetic Primer S036

<400> SEQUENCE: 67
tacccgggga tcctctagcg tcgacctgca ggcatgcaag ct            42

<210> SEQ ID NO 68
<211> LENGTH: 42
<212> TYPE: DNA
<213> ORGANISM: Artificial Sequence
<220> FEATURE:
<223> OTHER INFORMATION: Synthetic Primer S037

<400> SEQUENCE: 68
agcttgcatg cctgcaggtc gacgctagag gatccccggg ta            42

<210> SEQ ID NO 69
<211> LENGTH: 54
<212> TYPE: DNA
<213> ORGANISM: Artificial Sequence
<220> FEATURE:
<223> OTHER INFORMATION: Synthetic Primer J036

<400> SEQUENCE: 69
gccgcaaaaa agggaataag ggcgacacgg aaatgttgaa tactcatcaa ttgc      54

<210> SEQ ID NO 70
<211> LENGTH: 42
<212> TYPE: DNA
<213> ORGANISM: Artificial Sequence
<220> FEATURE:
<223> OTHER INFORMATION: Synthetic Primer J037

<400> SEQUENCE: 70
cgggtttcgc cacctctgac ttgagcgtcg attttttgtga tg            42

<210> SEQ ID NO 71
<211> LENGTH: 42
<212> TYPE: DNA
<213> ORGANISM: Artificial Sequence
<220> FEATURE:
<223> OTHER INFORMATION: Synthetic Primer J038

<400> SEQUENCE: 71
catcacaaaa atcgacgctc aagtcagagg tggcgaaacc cg            42

<210> SEQ ID NO 72
<211> LENGTH: 55
<212> TYPE: DNA
<213> ORGANISM: Artificial Sequence
<220> FEATURE:
<223> OTHER INFORMATION: Synthetic Primer J039

<400> SEQUENCE: 72
ctgagatagg tgcctcactg attaagcatt ggtaagcatg cgaccaagtt tactc     55

<210> SEQ ID NO 73
<211> LENGTH: 58
<212> TYPE: DNA
<213> ORGANISM: Artificial Sequence
<220> FEATURE:
<223> OTHER INFORMATION: Synthetic Primer J018

<400> SEQUENCE: 73

```
gacggcacgg ccacgcgttt aaaccgcctt ggatggatac gctagccgcc caatacgc        58

<210> SEQ ID NO 74
<211> LENGTH: 58
<212> TYPE: DNA
<213> ORGANISM: Artificial Sequence
<220> FEATURE:
<223> OTHER INFORMATION: Synthetic Primer J019

<400> SEQUENCE: 74
gctcacacgc ggccaggggg agccttggat ggatggatac gctagccgcc caatacgc        58

<210> SEQ ID NO 75
<211> LENGTH: 57
<212> TYPE: DNA
<213> ORGANISM: Artificial Sequence
<220> FEATURE:
<223> OTHER INFORMATION: Synthetic Primer J020

<400> SEQUENCE: 75
cgctcgtcca acgccggcgg accttggatg gatggatacg ctagccgccc aatacgc         57

<210> SEQ ID NO 76
<211> LENGTH: 57
<212> TYPE: DNA
<213> ORGANISM: Artificial Sequence
<220> FEATURE:
<223> OTHER INFORMATION: Synthetic Primer J021

<400> SEQUENCE: 76
atccccgcgt gcttggccgg ccgttggatg gatggatacg ctagccgccc aatacgc         57

<210> SEQ ID NO 77
<211> LENGTH: 57
<212> TYPE: DNA
<213> ORGANISM: Artificial Sequence
<220> FEATURE:
<223> OTHER INFORMATION: Synthetic Primer J022

<400> SEQUENCE: 77
aacctgcagg ccgcgagcgc cgattggatg gatggatacg ctagccgccc aatacgc         57

<210> SEQ ID NO 78
<211> LENGTH: 57
<212> TYPE: DNA
<213> ORGANISM: Artificial Sequence
<220> FEATURE:
<223> OTHER INFORMATION: Synthetic Primer J023

<400> SEQUENCE: 78
aacgcgatcg ccgacgccgc cgattggatg gatggatacg ctagccgccc aatacgc         57

<210> SEQ ID NO 79
<211> LENGTH: 57
<212> TYPE: DNA
<213> ORGANISM: Artificial Sequence
<220> FEATURE:
<223> OTHER INFORMATION: Synthetic Primer J024

<400> SEQUENCE: 79
aaggcggccg ctggcgaggg agattggatg gatggatacg ctagccgccc aatacgc         57

<210> SEQ ID NO 80
<211> LENGTH: 56
<212> TYPE: DNA
<213> ORGANISM: Artificial Sequence
```

```
<220> FEATURE:
<223> OTHER INFORMATION: Synthetic Primer J025

<400> SEQUENCE: 80
aaggcgcgcc acgtcgtgc ggatggatgg atggatacgc tagccgccca atacgc        56

<210> SEQ ID NO 81
<211> LENGTH: 58
<212> TYPE: DNA
<213> ORGANISM: Artificial Sequence
<220> FEATURE:
<223> OTHER INFORMATION: Synthetic Primer J026

<400> SEQUENCE: 81
agcccctcag ccccctagc gtcgttggat ggatggatac gctagccgcc caatacgc       58

<210> SEQ ID NO 82
<211> LENGTH: 56
<212> TYPE: DNA
<213> ORGANISM: Artificial Sequence
<220> FEATURE:
<223> OTHER INFORMATION: Synthetic Primer J029

<400> SEQUENCE: 82
acggccggcc aagcacgcgg ggattggcag gataccatat gttatttata cagttc        56

<210> SEQ ID NO 83
<211> LENGTH: 56
<212> TYPE: DNA
<213> ORGANISM: Artificial Sequence
<220> FEATURE:
<223> OTHER INFORMATION: Synthetic Primer J030

<400> SEQUENCE: 83
atcggcgctc gcggcctgca ggtttggcag gataccatat gttatttata cagttc        56

<210> SEQ ID NO 84
<211> LENGTH: 56
<212> TYPE: DNA
<213> ORGANISM: Artificial Sequence
<220> FEATURE:
<223> OTHER INFORMATION: Synthetic Primer J031

<400> SEQUENCE: 84
atcggcggcg tcggcgatcg cgtttggcag gataccatat gttatttata cagttc        56

<210> SEQ ID NO 85
<211> LENGTH: 56
<212> TYPE: DNA
<213> ORGANISM: Artificial Sequence
<220> FEATURE:
<223> OTHER INFORMATION: Synthetic Primer J032

<400> SEQUENCE: 85
atctccctcg ccagcggccg cctttggcag gataccatat gttatttata cagttc        56

<210> SEQ ID NO 86
<211> LENGTH: 56
<212> TYPE: DNA
<213> ORGANISM: Artificial Sequence
<220> FEATURE:
<223> OTHER INFORMATION: Synthetic Primer J033

<400> SEQUENCE: 86
atccgcacga ccgtggcgcg cctttggcag gataccatat gttatttata cagttc        56
```

```
<210> SEQ ID NO 87
<211> LENGTH: 56
<212> TYPE: DNA
<213> ORGANISM: Artificial Sequence
<220> FEATURE:
<223> OTHER INFORMATION: Synthetic Primer J034

<400> SEQUENCE: 87
cgacgctagg ggggctgagg ggcttggcag gataccatat gttatttata cagttc        56

<210> SEQ ID NO 88
<211> LENGTH: 50
<212> TYPE: DNA
<213> ORGANISM: Artificial Sequence
<220> FEATURE:
<223> OTHER INFORMATION: Synthetic Primer J055

<400> SEQUENCE: 88
aaagggaact cgaggctctt cagacggcac ggccacgcgt ttaaaccgcc               50

<210> SEQ ID NO 89
<211> LENGTH: 46
<212> TYPE: DNA
<213> ORGANISM: Artificial Sequence
<220> FEATURE:
<223> OTHER INFORMATION: Synthetic Primer J056

<400> SEQUENCE: 89
aaagggaact cgaggctctt cagctcacac gcggccaggg ggagcc                   46

<210> SEQ ID NO 90
<211> LENGTH: 46
<212> TYPE: DNA
<213> ORGANISM: Artificial Sequence
<220> FEATURE:
<223> OTHER INFORMATION: Synthetic Primer J057

<400> SEQUENCE: 90
aaagggaact cgaggctctt cacgctcgtc caacgccggc ggacct                   46

<210> SEQ ID NO 91
<211> LENGTH: 46
<212> TYPE: DNA
<213> ORGANISM: Artificial Sequence
<220> FEATURE:
<223> OTHER INFORMATION: Synthetic Primer J058

<400> SEQUENCE: 91
aaagggaact cgaggctctt caatccccgc gtgcttggcc ggccgt                   46

<210> SEQ ID NO 92
<211> LENGTH: 46
<212> TYPE: DNA
<213> ORGANISM: Artificial Sequence
<220> FEATURE:
<223> OTHER INFORMATION: Synthetic Primer J059

<400> SEQUENCE: 92
aaagggaact cgaggctctt caaacctgca ggccgcgagc gccgat                   46

<210> SEQ ID NO 93
<211> LENGTH: 46
<212> TYPE: DNA
<213> ORGANISM: Artificial Sequence
<220> FEATURE:
<223> OTHER INFORMATION: Synthetic Primer J060

<400> SEQUENCE: 93
```

```
aaagggaact cgaggctctt caaacgcgat cgccgacgcc gccgat          46
```

<210> SEQ ID NO 94
<211> LENGTH: 46
<212> TYPE: DNA
<213> ORGANISM: Artificial Sequence
<220> FEATURE:
<223> OTHER INFORMATION: Synthetic Primer J061

<400> SEQUENCE: 94

```
aaagggaact cgaggctctt caaaggcggc cgctggcgag ggagat          46
```

<210> SEQ ID NO 95
<211> LENGTH: 46
<212> TYPE: DNA
<213> ORGANISM: Artificial Sequence
<220> FEATURE:
<223> OTHER INFORMATION: Synthetic Primer J062

<400> SEQUENCE: 95

```
aaagggaact cgaggctctt caaaggcgcg ccacggtcgt gcggat          46
```

<210> SEQ ID NO 96
<211> LENGTH: 46
<212> TYPE: DNA
<213> ORGANISM: Artificial Sequence
<220> FEATURE:
<223> OTHER INFORMATION: Synthetic Primer J063

<400> SEQUENCE: 96

```
aaagggaact cgaggctctt caagcccctc agccccccta gcgtcg          46
```

<210> SEQ ID NO 97
<211> LENGTH: 46
<212> TYPE: DNA
<213> ORGANISM: Artificial Sequence
<220> FEATURE:
<223> OTHER INFORMATION: Synthetic Primer J064

<400> SEQUENCE: 97

```
ctcagcggga gctcgctctt caggctcccc ctggccgcgt gtgagc          46
```

<210> SEQ ID NO 98
<211> LENGTH: 46
<212> TYPE: DNA
<213> ORGANISM: Artificial Sequence
<220> FEATURE:
<223> OTHER INFORMATION: Synthetic Primer J065

<400> SEQUENCE: 98

```
ctcagcggga gctcgctctt caaggtccgc ggcgttgga cgagcg          46
```

<210> SEQ ID NO 99
<211> LENGTH: 46
<212> TYPE: DNA
<213> ORGANISM: Artificial Sequence
<220> FEATURE:
<223> OTHER INFORMATION: Synthetic Primer J066

<400> SEQUENCE: 99

```
ctcagcggga gctcgctctt caacggccgg ccaagcacgc ggggat          46
```

<210> SEQ ID NO 100
<211> LENGTH: 46
<212> TYPE: DNA
<213> ORGANISM: Artificial Sequence -continued

```
<220> FEATURE:
<223> OTHER INFORMATION: Synthetic Primer J067

<400> SEQUENCE: 100
ctcagcggga gctcgctctt caatcggcgc tcgcggcctg caggtt        46

<210> SEQ ID NO 101
<211> LENGTH: 46
<212> TYPE: DNA
<213> ORGANISM: Artificial Sequence
<220> FEATURE:
<223> OTHER INFORMATION: Synthetic Primer J068

<400> SEQUENCE: 101
ctcagcggga gctcgctctt caatcggcgg cgtcggcgat cgcgtt        46

<210> SEQ ID NO 102
<211> LENGTH: 46
<212> TYPE: DNA
<213> ORGANISM: Artificial Sequence
<220> FEATURE:
<223> OTHER INFORMATION: Synthetic Primer J069

<400> SEQUENCE: 102
ctcagcggga gctcgctctt caatctccct cgccagcggc cgcctt        46

<210> SEQ ID NO 103
<211> LENGTH: 46
<212> TYPE: DNA
<213> ORGANISM: Artificial Sequence
<220> FEATURE:
<223> OTHER INFORMATION: Synthetic Primer J070

<400> SEQUENCE: 103
ctcagcggga gctcgctctt caatccgcac gaccgtggcg cgcctt        46

<210> SEQ ID NO 104
<211> LENGTH: 46
<212> TYPE: DNA
<213> ORGANISM: Artificial Sequence
<220> FEATURE:
<223> OTHER INFORMATION: Synthetic Primer J071

<400> SEQUENCE: 104
ctcagcggga gctcgctctt cacgacgcta gggggctga ggggct         46

<210> SEQ ID NO 105
<211> LENGTH: 50
<212> TYPE: DNA
<213> ORGANISM: Artificial Sequence
<220> FEATURE:
<223> OTHER INFORMATION: Synthetic Primer J072

<400> SEQUENCE: 105
ctcagcggga gctcgctctt cacccgccag gcgctggggt ttaaacaccg    50

<210> SEQ ID NO 106
<211> LENGTH: 57
<212> TYPE: DNA
<213> ORGANISM: Artificial Sequence
<220> FEATURE:
<223> OTHER INFORMATION: Synthetic Primer J073

<400> SEQUENCE: 106
ggctccccct ggccgcgtgt gagcttggca ggataccata tgttatttat acagttc    57
```

```
<210> SEQ ID NO 107
<211> LENGTH: 57
<212> TYPE: DNA
<213> ORGANISM: Artificial Sequence
<220> FEATURE:
<223> OTHER INFORMATION: Synthetic Primer J074

<400> SEQUENCE: 107
aggtccgccg gcgttggacg agcgttggca ggataccata tgttatttat acagttc      57

<210> SEQ ID NO 108
<211> LENGTH: 58
<212> TYPE: DNA
<213> ORGANISM: Artificial Sequence
<220> FEATURE:
<223> OTHER INFORMATION: Synthetic Primer J075

<400> SEQUENCE: 108
cccgccaggc gctggggttt aaacaccgtt ggcaggatac catatgttat ttatacag     58

<210> SEQ ID NO 109
<211> LENGTH: 20
<212> TYPE: DNA
<213> ORGANISM: Artificial Sequence
<220> FEATURE:
<223> OTHER INFORMATION: Synthetic Primer K162

<400> SEQUENCE: 109
tgaagagcga gctcccgctg                                               20

<210> SEQ ID NO 110
<211> LENGTH: 24
<212> TYPE: DNA
<213> ORGANISM: Artificial Sequence
<220> FEATURE:
<223> OTHER INFORMATION: Synthetic Primer K163

<400> SEQUENCE: 110
tgaagagcct cgagttccct ttag                                          24

<210> SEQ ID NO 111
<211> LENGTH: 8139
<212> TYPE: DNA
<213> ORGANISM: Artificial Sequence
<220> FEATURE:
<223> OTHER INFORMATION: Synthetic Phase I-A stitch product

<400> SEQUENCE: 111
gacggcacgg ccacgcgttt aaaccgccca gatggaatcc cttccataga gagaaggagc    60
aagcaactga cccaatattg actgccactg gacctgaaga catgcaacaa agtgcaagca   120
tagtggggcc ttcttccaat gctaatccgg tcactgccac tgctgctacg gaaaaccaac   180
ctaaaggtat taacttcttc actataagaa aatcacacga gcgcccggac gatgtctctg   240
tttaaatggc gcaagttttc cgctttgtaa tatatattta taccccttc ttctctcccc    300 tgcaatataa tagtttaatt ctaatattaa taatatccta tattttcttc atttaccggc   360
gcactctcgc ccgaacgacc tcaaaatgtc tgctacattc ataataacca aaagctcata   420
actttttttt ttgaacctga atatatatac atcacatgtc actgctggtc cttgccgacc   480
agcgtataca atctcgatag ttggtttccc gttctttcca ctcccgtcgc tcacacgcgg   540
ccagggggag ccgagctcct cgagaagtta agattatatg aataactaaa tactaaatag   600
aaatgtaaat acagtgagaa caaaacaaaa aaaacgaac agagaaacta aatccacatt    660
aattgagagt tctatctatt agaaaatgca aactccaact aaatgggaaa acagataacc   720
```

```
tcttttattt ttttttaatg tttgatattc gagtcttttt cttttgttag gtttatattc    780
atcatttcaa tgaataaaag aagcttctta ttttggttgc aaagaatgaa aaaaaaggat    840
tttttcatac ttctaaagct tcaattataa ccaaaaattt tataaatgaa gagaaaaaat    900
ctagtagtat caagttaaac ctattccttt gccctcggac gagtgctggg gcgtcggttt    960
ccactatcgg cgagtacttc tacacagcca tcggtccaga cggccgcgct tctgcgggcg   1020
atttgtgtac gcccgacagt cccggctccg gatcggacga ttgcgtcgca tcgaccctgc   1080
gcccaagctg catcatcgaa attgccgtca accaagctct gatagagttg gtcaagacca   1140
atgcggagca tatacgcccg gagccgcggc gatcctgcaa gctccggatg cctccgctcg   1200
aagtagcgcg tctgctgctc catacaagcc aaccacggcc tccagaagaa gatgttggcg   1260
acctcgtatt gggaatcccc gaacatcgcc tcgctccagt caatgaccgc tgttatgcgg   1320
ccattgtccg tcaggacatt gttggagccg aaatccgcgt gcacgaggtg ccggacttcg   1380
gggcagtcct cggcccaaag catcagctca tcgagagcct gcgcgacgga cgcactgacg   1440
gtgtcgtcca tcacagtttg ccagtgatac acatggggat cagcaatcgc gcatatgaaa   1500
tcacgccatg tagtgtattg accgattcct tgcggtccga atgggccgaa cccgctcgtc   1560
tggctaagat cggccgcagc gatcgcatcc atggcctccg cgaccggctg cagaacagcg   1620
ggcagttcgg tttcaggcag gtcttgcaac gtgacaccct gtgcacggcg ggagatgcaa   1680
taggtcaggc tctcgctgaa ttccccaatg tcaagcactt ccggaatcgg gagcgcggcc   1740
gatgcaaagt gccgataaac ataacgatct ttgtagaaac catcggcgca gctatttacc   1800
cgcaggacat atccacgccc tcctacatcg aagctgaaag cacgagattc ttcgccctcc   1860
gagagctgca tcaggtcgga gacgctgtcg aacttttcga tcagaaactt ctcgacagac   1920
gtcgcggtga gttcaggctt tttcattttt aatgttactt ctcttgcagt tagggaacta   1980
taatgtaact caaaataaga ttaaacaaac taaaataaaa agaagttata cagaaaaacc   2040
catataaacc agtactaatc cataataata atacacaaaa aaactatcaa ataaaaccag   2100
aaaacagatt gaatagaaaa attttttcga tctccttttta tattcaaaat tcgatatatg   2160
aaaaagggaa ctctcagaaa atcaccaaat caatttaatt agattttttct tttccttcta   2220 gcgttggaaa gaaaaatttt tctttttttt tttagaaatg aaaaattttt gccgtaggaa   2280
tcaccgtata aaccctgtat aaacgctact ctgttcacct gtgtaggcta tgattgaccc   2340
agtgttcatt gttattgcga gagagcggga gaaaagaacc gatacaagag atccatgctg   2400
gtatagttgt ctgtccaaca ctttgatgaa cttgtaggac gatgatgtgt attactagtg   2460
tcgacgctcg tccaacgccg gcggacctag ttatgacaat tacaacaaca gaattctttc   2520
tatatatgca cgaacttgta atatggaaga aattatgacg tacaaactat aaagtaaata   2580
ttttacgtaa cacatggtgc tgttgtgctt cttttttcaag agaataccaa tgacgtatga   2640
ctaagtttag gatttaatgc aggtgacgga cccatctttc aaacgattta tatcagtggc   2700
gtccaaattg ttaggttttg ttggttcagc aggtttcctg ttgtgggtca tatgactttg   2760
aaccaaatgg ccggctgcta gggcagcaca taaggataat tcacctgcca agacggcaca   2820
ggcaactatt cttgctaatt gacgtgcgtt ggtaccagga gcggtagcat gtgggcctct   2880
tacacctaat aagtccaaca tggcaccttg tggttctaga acagtaccac caccgatggt   2940
acctacttcg atggatggca tggatacgga aattctcaaa tcaccgtcca cttctttcat   3000
caatgttata cagttggaac tttcgacatt ttgtgcagga tcttgtccta atgccaagaa   3060
aacagctgtc actaaattag ctgcatgtgc gttaaatcca ccaacagacc cagccattgc   3120
```

```
agatccaacc aaattcttag caatgttcaa ctcaaccaat gcggaaacat cacttttcaa   3180
cacttttctg acaacatcac caggaatagt agcttctgcg acgacactct taccacgacc   3240
ttcgatccag ttgatggcag ctggttttt gtcggtacag tagttaccag aaacggagac    3300
aacctccata tcttcccagc catactcttc taccatttgc tttaatgagt attcgacacc   3360
cttagaaatc atattcatac ccattgcgtc accagtagtt gttctaaatc tcatgaagag   3420
taaatctcct gctagacaag tttgaatatg ttgcagacgt gcaaatcttg atgtagagtt   3480
aaaagctttt ttaattgcgt tttgtccctc ttctgagtct aaccatatct tacaggcacc   3540
agatcttttc aaagttggga aacggactac tgggcctctt gtcataccat ccttagttaa   3600
aacagttgtt gcaccaccgc cagcattgat tgccttacag ccacgcatgg cagaagctac   3660
caaacaaccc tctgtagttg ccattggtat atgataagat gtaccatcga taaccaaggg   3720
gcctataaca ccaacgggca aaggcatgta acctataaca ttttcacaac aagcgccaaa   3780
tacgcggtcg tagtcataat ttttatatgg taaacgatca gatgctaata caggagcttc   3840
tgccaaaatt gaaagagcct tcctacgtac cgcaaccgct ctcgtagtat cacctaattt   3900
tttctccaaa gcgtacaaag gtaacttacc gtgaataacc aaggcagcga cctctttgtt   3960
cttcaattgt tttgtatttc cactacttaa taatgcttct aattcttcta aaggacgtat   4020
tttcttatcc aagctttcaa tatcgcggga atcatcttcc tcactagatg atgaaggtcc   4080
tgatgagctc gattgcgcag atgataaact tttgactttc gatccagaaa tgactgtttt   4140
attggttaaa actggtgtag aagccttttg tacaggagca gtaaaagact tcttggtgac   4200
ttcagtcttc accaattgat ctgcagccat atccccgcgt gcttggccgg ccgttacttt   4260 tttttttggat ggacgcaaag aagtttaata atcatattac atggcaatac caccatatac  4320
atatccatat ctaatcttac ttatatgttg tggaaatgta aagagcccca ttatcttagc   4380
ctaaaaaaac cttctctttg gaactttcag taatacgctt aactgctcat tgctatattg   4440
aagtacggat tagaagccgc cgagcgggcg acagccctcc gacggaagac tctcctccgt   4500
gcgtcctggt cttcaccggt cgcgttcctg aaacgcagat gtgcctcgcg ccgcactgct   4560
ccgaacaata aagattctac aatactagct tttatggtta tgaagaggaa aaattggcag   4620
taacctggcc ccacaaacct tcaaatcaac gaatcaaatt aacaaccata ggataataat   4680
gcgattagtt ttttagcctt atttctgggg taattaatca gcgaagcgat gattttttgat  4740 ctattaacag atatataaat gcaaaagctg cataaccact ttaactaata cttccaacat   4800
tttcggtttg tattacttct tattcaaatg tcataaaagt atcaacaaaa aattgttaat   4860
atacctctat acttaacctg caggccgcga gcgccgatat gtctcagaac gtttacattg   4920
tatcgactgc cagaacccca attggttcat tccagggttc tctatcctcc aagacagcag   4980
tggaattggg tgctgttgct ttaaaaggcg ccttggctaa ggttccagaa ttggatgcat   5040
ccaaggattt tgacgaaatt attttttggta acgttctttc tgccaatttg ggccaagctc   5100
cggccagaca agttgctttg gctgccggtt tgagtaatca tatcgttgca agcacagtta   5160
acaaggtctg tgcatccgct atgaaggcaa tcatttggg tgctcaatcc atcaaatgtg    5220
gtaatgctga tgttgtcgta gctggtggtt gtgaatctat gactaacgca ccatactaca   5280
tgccagcagc ccgtgcgggt gccaaatttg gccaaactgt tcttgttgat ggtgtcgaaa   5340
gagatgggtt gaacgatgcg tacgatggtc tagccatggg tgtacacgca gaaaagtgtg   5400
cccgtgattg ggatattact agagaacaac aagacaattt gcctatcgaa tcctaccaaa   5460
aatctcaaaa atctcaaaag gaaggtaaat tcgacaatga aattgtacct gttaccatta   5520
```

```
agggatttag aggtaagcct gatactcaag tcacgaagga cgaggaacct gctagattac    5580
acgttgaaaa attgagatct gcaaggactg ttttccaaaa agaaaacggt actgttactg    5640
ccgctaacgc ttctccaatc aacgatggtg ctgcagccgt catcttggtt tccgaaaaag    5700
ttttgaagga aaagaatttg aagcctttgg ctattatcaa aggttggggt gaggccgctc    5760
atcaaccagc tgattttaca tgggctccat ctcttgcagt tccaaaggct ttgaaacatg    5820
ctggcatcga agacatcaat tctgttgatt actttgaatt caatgaagcc ttttcggttg    5880
tcggtttggt gaacactaag attttgaagc tagacccatc taaggttaat gtatatggtg    5940
gtgctgttgc tctaggtcac ccattgggtt gttctggtgc tagagtggtt gttacactgc    6000
tatccatctt acagcaagaa ggaggtaaga tcggtgttgc cgccatttgt aatggtggtg    6060
gtggtgcttc ctctattgtc attgaaaaga tatgattacg ttctgcgatt ttctcatgat    6120
cttttttcata aaatacataa atatataaat ggctttatgt ataacaggca taatttaaag    6180
ttttatttgc gattcatcgt ttttcaggta ctcaaacgct gaggtgtgcc ttttgactta    6240
cttttccgcc ttggcaagct ggccgggtga tacttgcaca agttccacta attactgaca    6300
tttgtggtat taactcgttt gactgctcta caattgtagg atgttaatca atgtcttggc    6360
tgcctaacgc gatcgccgac gccgccgata tgagaaaaaa aatcggttgg cttaactttt    6420
aaagaaaaaa gttgagatta gatttattgt gttataaata tagatataca attctttata    6480
aaaaaaatat atatatatat cattgttatt aaataaagag ttttcctagt atatagatta    6540
aaaaactact ctattaaatg agagctaaaa aaagcaggct gccaaaaaaa taaagcattt    6600
atgaaggggg ttcagcaaga tgcaatcgat ggggaagat tatttttttaa catcgtaaga    6660
tcttctaaat ttgtcatcga tgttggtcaa gtagtaaaca ccactttgca aatgctcaat    6720
ggaaccttga ggtttgaagt tcttcttcaa atgggcattt tctctcaatt cgatggcagc    6780
ttcgtaatcc tttggagttt cggtgattct cttggctaat ttgttagtaa tatctaattc    6840
cttgataata tgttggacgt caccaacaat tttgcaagaa tatagagatg cagctaaacc    6900
ggaaccgtaa gaaaataaac caacacgctt gccttgtaag tcgtcagatc caacatagtt    6960
taatagagat gcaaaggcgg cataaacaga tgcggtgtac atgttacctg tgtttgttgg    7020
aacaatcaaa gattgggcaa ctctctcttt gtggaatggc ttagcaacat taacaaaagt    7080
tttttcaatg ttcttatcgg ttaaagattc gtcataatcg cgagtagcta attcggcgtc    7140
aacttctggg aacaattgag gattggctct gaaatcgtta tatagtaatc taccgtatga    7200
ttttgtgacc aatttacagg ttggaacatg gaaaacgttg tagtcgaaat atttcaaaac    7260
gttcaaagca tccgaaccag cgggatcgct aaccaaccct ttagaaatag ccttcttgga    7320
ataactcttg taaacttgat caagagcctt gacgtaacaa gttaatgaaa aatgaccatc    7380
gacgtaagga tattcgctgg tgaaatcggg cttgtaaaaa tcgtaggcgt gttccatgta    7440
agaagctctt acagagtcaa atacaattgg agcatcagga ccgatccaca tagcaacagt    7500
accggcacca ccggttggtc ttgcggcacc cttatcgtag atggcaatat caccgcaaac    7560
tacaatggcg tctctaccat cccatgcgtt agattcaatc cagttcaaag agttgaacaa    7620
cgcgttggta ccaccgtaac aggcattaag cgtgtcaata ccttcgacgt cagtgttttc    7680
accaaacaat tgcatcaaga cagacttgac agacttggac ttgtcaatca gagtttcagt    7740
accgacttct aatctaccaa ttttgttggt gtcgatgttg taactcttga tcaacttaga    7800
caaaacagtt agggacatcg agtagatatc ttctctgtca ttgacaaaag acatgttggt    7860
ttggcccaga ccaattgtgt atttaccttg agaaacgcca tcaaatttct ctagctcaga    7920
```

```
ttggttgaca cattgagttg ggatgtaaat ttggatacct ttaataccga cattttgagg    7980
tctggttttt tgttcagcgg tcttttgttt ttttagttca gtcatttgca agtttgtatt    8040
gtgtaattgt tgttgctttt gcggcctaag tcttccttta ataccacacc aacaaagttt    8100
agtagagagt ttcataaggc ggccgctggc gagggagat                            8139

<210> SEQ ID NO 112
<211> LENGTH: 2962
<212> TYPE: DNA
<213> ORGANISM: Artificial Sequence
<220> FEATURE:
<223> OTHER INFORMATION: Synthetic Phase I-B stitch product

<400> SEQUENCE: 112
aaggcggccg ctggcgaggg agataagtat agaggtatat taacaatttt ttgttgatac      60
ttttatgaca tttgaataag aagtaataca aaccgaaaat gttgaaagta ttagttaaag     120
tggttatgca gcttttgcat ttatatatct gttaatagat caaaaatcat cgcttcgctg     180
attaattacc ccagaaataa ggctaaaaaa ctaatcgcat tattatccta tggttgttaa     240
tttgattcgt tgatttgaag gtttgtgggg ccaggttact gccatttttt cctcttcata     300
accataaaag ctagtattgt agaatcttta ttgttcggag cagtgcggcg cgaggcacat     360
ctgcgtttca ggaacgcgac cggtgaagac caggacgcac ggaggagagt cttccgtcgg     420
agggctgtcg cccgctcggc ggcttctaat ccgtacttca atatagcaat gagcagttaa     480
gcgtattact gaaagttcca aagagaaggt tttttaggc taagataatg gggctcttta     540
catttccaca acatataagt aagattagat atggatatgt atatggtggt attgccatgt     600
aatatgatta ttaaacttct ttgcgtccat ccaaaaaaaa agtaaaggcg cgccacggtc     660
gtgcggatat ggctgcagat caattggtga agactgaagt caccaagaag tcttttactg     720
ctcctgtaca aaaggcttct acaccagttt taaccaataa aacagtcatt tctggatcga     780
aagtcaaaag tttatcatct gcgcaatcga gctcatcagg accttcatca tctagtgagg     840
aagatgattc ccgcgatatt gaaagcttgg ataagaaaat acgtccttta gaagaattag     900
aagcattatt aagtagtgga aatacaaaac aattgaagaa caaagaggtc gctgccttgg     960
ttattcacgg taagttacct ttgtacgctt tggagaaaaa attaggtgat actacgagag    1020
cggttgcggt acgtaggaag gctctttcaa ttttggcaga agctcctgta ttagcatctg    1080
atcgtttacc atataaaaat tatgactacg accgcgtatt tggcgcttgt tgtgaaaatg    1140
ttataggtta catgcctttg cccgttggtg ttataggccc cttggttatc gatggtacat    1200
cttatcatat accaatggca actacagagg gttgttggt agcttctgcc atgcgtggct    1260
gtaaggcaat caatgctggc ggtggtgcaa caactgtttt aactaaggat ggtatgacaa    1320
gaggcccagt agtccgtttc ccaactttga aaagatctgg tgcctgtaag atatggttag    1380
actcagaaga gggacaaaac gcaattaaaa aagcttttaa ctctacatca agatttgcac    1440
gtctgcaaca tattcaaact tgtctagcag gagatttact cttcatgaga tttagaacaa    1500
ctactggtga cgcaatgggt atgaatatga tttctaaggg tgtcgaatac tcattaaagc    1560
aaatggtaga agagtatggc tggaagata tggaggttgt ctccgtttct ggtaactact    1620
gtaccgacaa aaaccagct gccatcaact ggatcgaagg tcgtggtaag agtgtcgtcg    1680
cagaagctac tattcctggt gatgttgtca gaaaagtgtt aaaaagtgat gtttccgcat    1740
tggttgagtt gaacattgct aagaatttgg ttggatctgc aatggctggg tctgttggtg    1800
gatttaacgc acatgcagct aatttagtga cagctgtttt cttggcatta ggacaagatc    1860
```

```
ctgcacaaaa tgtcgaaagt tccaactgta taacattgat gaaagaagtg gacggtgatt     1920
tgagaatttc cgtatccatg ccatccatcg aagtaggtac catcggtggt ggtactgttc     1980
tagaaccaca aggtgccatg ttggacttat taggtgtaag aggcccacat gctaccgctc     2040
ctggtaccaa cgcacgtcaa ttagcaagaa tagttgcctg tgccgtcttg gcaggtgaat     2100
tatccttatg tgctgcccta gcagccggcc atttggttca aagtcatatg acccacaaca     2160
ggaaacctgc tgaaccaaca aaacctaaca atttggacgc cactgatata aatcgtttga     2220
aagatgggtc cgtcacctgc attaaatcct aaacttagtc atacgtcatt ggtattctct     2280 tgaaaagaa gcacaacagc accatgtgtt acgtaaaata tttactttat agtttgtacg       2340
tcataatttc ttccatatta caagttcgtg catatataga aagaattctg ttgttgtaat     2400
tgtcataact agcccctcag cccccctagc gtcgaagcat cttgccctgt gcttggcccc     2460
cagtgcagcg aacgttataa aaacgaatac tgagtatata tctatgtaaa acaaccatat    2520
catttcttgt tctgaacttt gtttacctaa ctagttttaa atttcccttt ttcgtgcatg     2580
cgggtgttct tatttattag catactacat ttgaaatatc aaatttcctt agtagaaaag     2640
tgagagaagg tgcactgaca caaaaaataa aatgctacgt ataactgtca aaactttgca    2700
gcagcgggca tccttccatc atagcttcaa acatattagc gttcctgatc ttcatacccg     2760
tgctcaaaat gatcaaacaa actgttattg ccaagaaata aacgcaaggc tgccttcaaa    2820
aactgatcca ttagatcctc atatcaagct tcctcataga acgcccaatt acaataagca    2880
tgttttgctg ttatcaccgg gtgataggtt tgctcaacca tggaaggtag catgcggtgt     2940 ttaaaccca gcgcctggcg gg                                                2962

<210> SEQ ID NO 113
<211> LENGTH: 9664
<212> TYPE: DNA
<213> ORGANISM: Artificial Sequence
<220> FEATURE:
<223> OTHER INFORMATION: Synthetic Phase II complete stitch product

<400> SEQUENCE: 113
gacggcacgg ccacgcgttt aaaccgccta ggataattat actctatttc tcaacaagta       60
attggttgtt tggccgagcg gtctaaggcg cctgattcaa gaaatatctt gaccgcagtt      120
aactgtggga atactcaggt atcgtaagat gcaagagttc gaatctctta gcaaccatta     180
ttttttccct caacataacg agaacacaca ggggcgctat cgcacagaat caaattcgat      240
gactggaaat ttttgttaa tttcagaggt cgcctgacgc atataccttt ttcaactgaa       300
aaattgggag aaaaaggaaa ggtgagagcg ccggaaccgg cttttcatat agaatagaga     360
agcgttcatg actaaatgct tgcatcacaa tacttgaagt tgacaatatt atttaaggac      420
ctattgtttt ttccaatagg tggttagcaa tcgtcttact ttctaacttt tcttaccttt      480
tacatttcag caatatatat atatatattt caaggatata ccattctagc tcacacgcgg     540 ccaggggag cctcgacact agtaatacac atcatcgtcc tacaagttca tcaaagtgtt      600
ggacagacaa ctataccagc atggatctct tgtatcggtt cttttctccc gctctctcgc       660
aataacaatg aacactgggt caatcatagc ctacacaggt gaacagagta gcgtttatac    720
agggtttata cggtgattcc tacggcaaaa atttttcatt tctaaaaaaa aaagaaaaa     780 tttttctttc caacgctaga aggaaaagaa aaatctaatt aaattgattt ggtgattttc       840
tgagagttcc cttttttcata tatcgaattt tgaatataaa aggagatcga aaaaatttt      900 ctattcaatc tgttttctgg ttttatttga tagttttttt gtgtattatt attatggatt     960
```

```
agtactggtt tatatgggtt tttctgtata acttcttttt attttagttt gtttaatctt    1020
attttgagtt acattatagt tccctaactg caagagaagt aacattaaaa atgaccactc    1080
ttgacgacac ggcttaccgg taccgcacca gtgtcccggg ggacgccgag gccatcgagg    1140
cactggatgg gtccttcacc accgacaccg tcttccgcgt caccgccacc ggggacggct    1200
tcaccctgcg ggaggtgccg gtggacccgc ccctgaccaa ggtgttcccc gacgacgaat    1260
cggacgacga atcggacgcc ggggaggacg gcgacccgga ctcccggacg ttcgtcgcgt    1320
acggggacga cggcgacctg gcgggcttcg tggtcgtctc gtactccggc tggaaccgcc    1380
ggctgaccgt cgaggacatc gaggtcgccc ggagcaccg ggggcacggg gtcgggcgcg    1440
cgttgatggg gctcgcgacg gagttcgccc gcgagcgggg cgccgggcac ctctggctgg    1500
aggtcaccaa cgtcaacgca ccggcgatcc acgcgtaccg gcggatgggg ttcaccctct    1560
gcggcctgga caccgccctg tacgacggca ccgcctcgga cggcgagcag gcgctctaca    1620
tgagcatgcc ctgcccctga gtttaacttg atactactag attttttctc ttcatttata    1680
aaatttttgg ttataattga agctttagaa gtatgaaaaa atccttttt ttcattcttt      1740 gcaaccaaaa taagaagctt cttttattca ttgaaatgat gaatataaac ctaacaaaag    1800
aaaaagactc gaatatcaaa cattaaaaaa aaataaaaga ggttatctgt tttcccattt    1860
agttggagtt tgcattttct aatagataga actctcaatt aatgtggatt tagtttctct    1920
gttcgttttt ttttgttttg ttctcactgt atttacattt ctatttagta tttagttatt    1980
catataatct taacttctcg aggagctccg ctcgtccaac gccggcggac ctattcgcgg    2040
gtggaaggac cttgtggagg aatatgaagt tgatagctca aagggattga atggctattt    2100
aactgattat gagtcaatgt atcaaggata ctatggtctg cttaaatttc attctgtctt    2160
cgaaagctga attgatacta cgaaaaattt ttttttgttt ctctttctat ctttattaca    2220
taaaacttca tacacagtta agattaaaaa caactaataa ataatgccta tcgcaaatta    2280
gcttatgaag tccatggtaa attcgtgttt cctggcaata atagatcgtc aatttgttgc    2340
tttgtggtag ttttatttc aaataattgg aatactaggg atttgatttt aagatcttta     2400 ttcaatttt ttgcgcttaa caaacagcag ccagtcccac ccaagtctgt ttcaaatgtc      2460
tcgtaactaa aatcatcttg caatttcttt ttgaaactgt caatttgctc ttgagtaatg    2520
tctcttcgta acaaagtcaa agagcaaccg ccgccaccag caccggtaag ttttgtggag    2580
ccaattctca aatcatcgct cagattttta ataagttcta atccaggatg agaaacaccg    2640
attgagacaa gcagtccatg atttattctt atcaattcca atagttgttc atacagttca    2700
ttattagttt ctacagcctc gtcatcggtg cctttacatt tacttaactt agtcatgatc    2760
tctaagcctt gtagggcaca ttcacccatg gcatctagaa ttggcttcat aacttcagga    2820
aatttctcgg tgaccaacac acgaacgcga gcaacaagat cttttgtaga ccttggaatt    2880
ctagtatagg ttaggatcat tggaatggct gggaaatcat ctaagaactt aaaattgttt    2940
gtgtttattg ttccattatg tgagtctttt tcaaatagca gggcattacc ataagtggcc    3000
acagcgttat ctattcctga aggggtaccg tgaatacact tttcacctat gaaggcccat    3060
tgattcacta tatgcttatc gttttctgac agcttttcca agtcattaga tcctattaac    3120
ccccccaagt aggccatagc taaggccagt gatacagaaa tagaggcgct tgagcccaac    3180
ccagcaccga tgggtaaagt agactttaaa gaaaacttaa tattcttggc atgggggcat    3240
aggcaaacaa acatatacag gaaacaaaac gctgcatggt agtggaagga ttcggatagt    3300
tgagctaaca acggatccaa aagactaacg agttcctgag acaagccatc ggtggcttgt    3360
```

```
tgagccttgg ccaattttg ggagtttact tgatcctcgg tgatggcatt gaaatcattg    3420
atggaccact tatgattaaa gctaatgtcc gggaagtcca attcaatagt atctggtgca    3480
gatgactcgc ttattagcag gtaggttctc aacgcagaca cactagcagc gacggcaggc    3540
ttgttgtaca cagcagagtg ttcaccaaaa ataataacct ttcccggtgc agaagttaag    3600
aacggtaatg acatatcccc gcgtgcttgg ccggccgtta cttttttttt ggatggacgc    3660
aaagaagttt aataatcata ttacatggca ataccaccat atacatatcc atatctaatc    3720
ttacttatat gttgtggaaa tgtaaagagc cccattatct tagcctaaaa aaaccttctc    3780
tttggaactt tcagtaatac gcttaactgc tcattgctat attgaagtac ggattagaag    3840
ccgccgagcg ggcgacagcc ctccgacgga agactctcct ccgtgcgtcc tggtcttcac    3900
cggtcgcgtt cctgaaacgc agatgtgcct cgcgccgcac tgctccgaac aataaagatt    3960
ctacaatact agcttttatg ttatgaaga ggaaaaattg gcagtaacct ggccccacaa    4020
accttcaaat caacgaatca aattaacaac cataggataa taatgcgatt agtttttag    4080 ccttatttct ggggtaatta atcagcgaag cgatgatttt tgatctatta acagatatat    4140
aaatgcaaaa gctgcataac cactttaact aatactttca acattttcgg tttgtattac    4200
ttcttattca aatgtcataa aagtatcaac aaaaaattgt taatataccct ctatacttaa    4260 cctgcaggcc gcgagcgccg atatgtcaga gttgagagcc ttcagtgccc cagggaaagc    4320
gttactagct ggtggatatt tagttttaga tccgaaatat gaagcatttg tagtcggatt    4380
atcggcaaga atgcatgctg tagcccatcc ttacggttca ttgcaagagt ctgataagtt    4440
tgaagtgcgt gtgaaaagta acaatttaa agatggggag tggctgtacc atataagtcc    4500
taaaactggc ttcattcctg tttcgatagg cggatctaag aacccttca ttgaaaaagt    4560 tatcgctaac gtatttagct actttaagcc taacatggac gactactgca atagaaactt    4620
gttcgttatt gatattttct ctgatgatgc ctaccattct caggaggaca gcgttaccga    4680
acatcgtggc aacagaagat tgagttttca ttcgcacaga attgaagaag ttcccaaaac    4740
agggctgggc tcctcggcag gtttagtcac agttttaact acagctttgg cctccttttt    4800
tgtatcggac ctggaaaata atgtagacaa atatagagaa gttattcata atttatcaca    4860
agttgctcat tgtcaagctc agggtaaaat tggaagcggg tttgatgtag cggcggcagc    4920
atatggatct atcagatata gaagattccc acccgcatta atctctaatt tgccagatat    4980
tggaagtgct acttacggca gtaaactggc gcatttggtt aatgaagaag actggaatat    5040
aacgattaaa agtaaccatt taccttcggg attaacttta tggatgggcg atattaagaa    5100
tggttcagaa acagtaaaac tggtccagaa ggtaaaaaat tggtatgatt cgcatatgcc    5160
ggaaagcttg aaaatatata cagaactcga tcatgcaaat tctagattta tggatggact    5220
atctaaacta gatcgcttac acgagactca tgacgattac agcgatcaga tatttgagtc    5280
tcttgagagg aatgactgta cctgtcaaaa gtatcctgag atcacagaag ttagagatgc    5340
agttgccaca attagacgtt cctttagaaa aataactaaa gaatctggtg ccgatatcga    5400
acctcccgta caaactagct tattggatga ttgccagacc ttaaaaggag ttcttacttg    5460
cttaatacct ggtgctggtg ttatgacgc cattgcagtg attgctaagc aagatgttga    5520
tcttagggct caaccgctg atgacaaaag atttttctaag gttcaatggc tggatgtaac    5580
tcaggctgac tggggtgtta ggaaagaaaa agatccggaa acttatcttg ataaataact    5640
taaggtagat aatagtggtc catgtgacat ctttataaat gtgaagtttg aagtgaccgc    5700
gcttaacatc taaccattca tcttccgata gtacttgaaa ttgttccttt cggcggcatg    5760
```

```
ataaaattcg tttaatgggt acaagctata catactagga tgaggatggt actgagaacg   5820
ataaataaac tttctagata tataaacttta tgtcatttaa atataaataa agtgcgtgtt   5880
agcttgaaag tgtgcactaa cgcgatcgcc gacgccgccg atgatgtgta ttactagtgt   5940
cgacgacagc attcgcccag tatttttttt attctacaaa ccttctataa tttcaaagta   6000
tttacataat tctgtatcag tttaatcacc ataatatcgt tttctttgtt tagtgcaatt   6060
aattttccct attgttactt cgggcctttt tctgttttat gagctatttt ttccgtcatc   6120
cttccggatc cagattttca gcttcatctc cagattgtgt ctacgtaatg cacgccatca   6180
ttttaagaga ggaaggcggc cgctggcgag ggagatatga agctactgtc ttctatcgaa   6240
caagcatgcg atatttgccg acttaaaaag ctcaagtgct ccaaagaaaa accgaagtgc   6300
gccaagtgtc tgaagaacaa ctgggagtgt cgctactctc ccaaaaccaa aaggtctccg   6360
ctgactaggg cacatctgac agaagtggaa tcaaggctag aaagactgga acagctattt   6420
ctactgattt ttcctcgaga agaccttgac atgatttga aaatggattc tttacaggat   6480
ataaaagcat tgttaacagg attatttgta caagataatg tgaataaaga tgccgtcaca   6540
gatagattgg cttcagtgga gactgatatg cctctaacat tgagacagca tagaataagt   6600
gcgacatcat catcggaaga gagtagtaac aaaggtcaaa gacagttgac tgtatcgatt   6660
gactcggcag ctcatcatga taactccaca attccgttgg attttatgcc cagggatgca   6720
cttcatggat ttgattggtc tgaagaggat gacatgtcgg atggcttgcc cttcctgaaa   6780 acggaccccca acaataatgg gttctttggc gacggttctc tcttatgtat tcttcgatct   6840
attggcttta aaccggaaaa ttacacgaac tctaacgtta acaggctccc gaccatgatt   6900
acggatagat acacgttggc ttctagatcc acaacatccc gtttacttca aagttatctc   6960
aataattttc accctactg ccctatcgtg cactcaccga cgctaatgat gttgtataat   7020
aaccagattg aaatcgcgtc gaaggatcaa tggcaaatcc ttttttaactg catattagcc   7080 attggagcct ggtgtataga gggggaatct actgatatag atgttttta ctatcaaaat   7140 gctaaatctc atttgacgag caaggtcttc gagtcaggtt ccataatttt ggtgacagcc   7200
ctacatcttc tgtcgcgata tacacagtgg aggcagaaaa caaatactag ctataatttt   7260
cacagctttt ccataagaat ggccatatca ttgggcttga atagggacct cccctcgtcc   7320
ttcagtgata gcagcattct ggaacaaaga cgccgaattt ggtggtctgt ctactcttgg   7380
gagatccaat tgtccctgct ttatggtcga tccatccagc tttctcagaa tacaatctcc   7440
ttcccttctt ctgtcgacga tgtgcagcgt accacaacag gtcccaccat atatcatggc   7500
atcattgaaa cagcaaggct cttacaagtt ttcacaaaaa tctatgaact agacaaaaca   7560
gtaactgcag aaaaaagtcc tatatgtgca aaaaaatgct tgatgatttg taatgagatt   7620
gaggaggttt cgagacaggc accaaagttt ttacaaatgg atatttccac caccgctcta   7680
accaatttgt tgaaggaaca cccttggcta tcctttacaa gattcgaact gaagtggaaa   7740
cagttgtctc ttatcatttta tgtattaaga gattttttca ctaattttac ccagaaaaag   7800
tcacaactag aacaggatca aaatgatcat caaagttatg aagttaaacg atgctccatc   7860
atgttaagcg atgcagcaca aagaactgtt atgtctgtaa gtagctatat ggacaatcat   7920
aatgtcaccc catattttgc ctggaattgt tcttattact tgttcaatgc agtcctagta   7980
cccataaaga ctctactctc aaactcaaaa tcgaatgctg agaataacga gaccgcacaa   8040
ttattacaac aaattaacac tgttctgatg ctattaaaaa aactggccac ttttaaaatc   8100
cagacttgtg aaaaatacat tcaagtactg gaagaggtat gtgcgccgtt tctgttatca   8160
```

| | |
|---|---:|
| cagtgtgcaa tcccattacc gcatatcagt tataacaata gtaatggtag cgccattaaa | 8220 |
| aatattgtcg gttctgcaac tatcgcccaa taccctactc ttccggagga aaatgtcaac | 8280 |
| aatatcagtg ttaaatatgt ttctcctggc tcagtagggc cttcacctgt gccattgaaa | 8340 |
| tcaggagcaa gtttcagtga tctagtcaag ctgttatcta accgtccacc ctctcgtaac | 8400 |
| tctccagtga caataccaag aagcacacct tcgcatcgct cagtcacgcc ttttctaggg | 8460 |
| caacagcaac agctgcaatc attagtgcca ctgaccccgt ctgctttgtt tggtggcgcc | 8520 |
| aattttaatc aaagtgggaa tattgctgat agctcattgt ccttcacttt cactaacagt | 8580 |
| agcaacggtc cgaacctcat aacaactcaa acaaattctc aagcgctttc acaaccaatt | 8640 |
| gcctcctcta acgttcatga taacttcatg aataatgaaa tcacggctag taaaattgat | 8700 |
| gatggtaata attcaaaacc actgtcacct ggttggacgg accaaactgc gtataacgcg | 8760 |
| tttggaatca ctacagggat gtttaatacc actacaatgg atgatgtata taactatcta | 8820 |
| ttcgatgatg aagataccc accaaaccca aaaaagagt aaaatgaatc gtagatactg | 8880 |
| aaaaaccccg caagttcact tcaactgtgc atcgtgcacc atctcaattt ctttcattta | 8940 |
| tacatcgttt tgccttcttt tatgtaacta tactcctcta agtttcaatc ttggccatgt | 9000 |
| aacctctgat ctatagaatt ttttaaatga ctagaattaa tgcccatctt ttttttggac | 9060 |
| ctaaattctt catgaaaata tattacgagg gcttattcag aagcttcgct caaggcgcg | 9120 |
| ccacggtcgt gcggataaag attctctttt tttatgatat ttgtacataa actttataaa | 9180 |
| tgaaattcat aatagaaacg acacgaaatt acaaatggaa atatgttcat agggtagacg | 9240 |
| aaactatata cgcaatctac atacatttat caagaaggag aaaaaggagg atgtaaagga | 9300 |
| atacaggtaa gcaaattgat actaatggct caacgtgata aggaaaaaga attgcactt | 9360 |
| aacattaata ttgacaagga ggagggcacc acacaaaaag ttaggtgtaa cagaaaatca | 9420 |
| tgaaactatg attcctaatt tatatattgg aggattttct ctaaaaaaaa aaaaatacaa | 9480 |
| caaataaaaa acactcaatg acctgaccat ttgatggagt ttaagtcaat accttcttga | 9540 |
| accatttccc ataatggtga aagttccctc aagaattta ctctgtcaga aacgccctta | 9600 |
| acgacgtagt cgacctcctc ttcagtacta aatctacggt gtttaaaccc cagcgcctgg | 9660 |
| cggg | 9664 |

<210> SEQ ID NO 114
<211> LENGTH: 4380
<212> TYPE: DNA
<213> ORGANISM: Artificial Sequence
<220> FEATURE:
<223> OTHER INFORMATION: Synthetic Phase III-A stitch product

<400> SEQUENCE: 114

| | |
|---|---:|
| gacggcacgg ccacgcgttt aaaccgccaa aagtgcagct cagagccccc agcaccagta | 60 |
| ttagaggtca taatgggctg cgaagcctgc taaaatgcag tggaggccgt gtaccctttg | 120 |
| ccaaattggc tattggaatc ggcagagaac ctgggtcccg ttctagagac cctgcgagcg | 180 |
| tgtcccggtg ggttctggga gctctaactc cgcaggaact acaaaccttg cttacacaga | 240 |
| gtgaacctgc tgcctggcgt gctctgactc agtacatttc atagcccatc ttcaacaaca | 300 |
| ataccgactt accatcctat ttgctttgcc cttttctttt tccactgcac tttgcatcgg | 360 |
| aaggcgttat cggttttggg tttagtgcct aaacgagcag cgagaacacg accacgggct | 420 |
| atataaatgg aaagttagga caggggcaaa gaataagagc acagaagaag agaaaagacg | 480 |
| aaaagcagaa gcggaaaacg tatacacgtc acatatcaca cacacacgct cacacgcggc | 540 |

```
caggggagc ctcgacacta gtaatacaca tcatcgtcct acaagttcat caaagtgttg    600
gacagacaac tataccagca tggatctctt gtatcggttc ttttctcccg ctctctcgca    660
ataacaatga acactgggtc aatcatagcc tacacaggtg aacagagtag cgtttataca    720
gggtttatac ggtgattcct acggcaaaaa ttttcattt ctaaaaaaaa aagaaaaat    780 ttttctttcc aacgctagaa ggaaaagaaa aatctaatta aattgatttg gtgattttct    840
gagagttccc tttttcatat atcgaatttt gaatataaaa ggagatcgaa aaaatttttc    900
tattcaatct gttttctggt tttatttgat agttttttg tgtattatta ttatggatta    960
gtactggttt atatgggttt tctgtataa cttctttta ttagtttg tttaatctta    1020 ttttgagtta cattatagtt ccctaactgc aagagaagta acattaaaaa tgggtaagga    1080
aaagactcac gtttcgaggc cgcgattaaa ttccaacatg gatgctgatt tatatgggta    1140
taaatgggct cgcgataatg tcgggcaatc aggtgcgaca atctatcgat tgtatgggaa    1200
gcccgatgcg ccagagttgt ttctgaaaca tggcaaaggt agcgttgcca atgatgttac    1260
agatgagatg gtcagactaa actggctgac ggaatttatg cctcttccga ccatcaagca    1320
ttttatccgt actcctgatg atgcatggtt actcaccact gcgatccccg gcaaaacagc    1380
attccaggta ttagaagaat atcctgattc aggtgaaaat attgttgatg cgctggcagt    1440
gttcctgcgc cggttgcatt cgattcctgt ttgtaattgt cctttaaca gcgatcgcgt    1500 atttcgtctc gctcaggcgc aatcacgaat gaataacggt ttggttgatg cgagtgattt    1560
tgatgacgag cgtaatggct ggcctgttga acaagtctgg aaagaaatgc ataagctttt    1620
gccattctca ccggattcag tcgtcactca tggtgatttc tcacttgata accttatttt    1680
tgacgagggg aaattaatag gttgtattga tgttggacga gtcggaatcg cagaccgata    1740
ccaggatctt gccatcctat ggaactgcct cggtgagttt tctcccttcat tacagaaacg    1800 gcttttcaa aaatatggta ttgataatcc tgatatgaat aaattgcagt tcatttgat    1860 gctcgatgag ttttctaag tttaacttga tactactaga ttttttctct tcatttataa    1920 aattttggt tataattgaa gcttagaag tatgaaaaaa tcctttttt tcattctttg    1980 caaccaaaat aagaagcttc ttttattcat tgaaatgatg aatataaacc taacaaaaga    2040 aaagactcg aatatcaaac attaaaaaaa aataaaagag gttatctgtt ttcccattta    2100
gttggagttt gcattttcta atagatagaa ctctcaatta atgtggattt agtttctctg    2160
ttcgtttttt tttgttttgt tctcactgta tttacatttc tatttagtat ttagttattc    2220
atataatctt aacttctcga ggagctccgc tcgtccaacg ccggcggacc tcttgtgcta    2280
agtggtgctg ttagacagct acgaataagg aaattccgaa gcatgtaggg aggtcatgat    2340 atgaaaagc aaaagagtag gcatcaaaaa gtttctcatt caagtggtaa ctgctgttaa    2400
aattaagata tttataaatt gaagcttggt cgttccgacc aataccgtag ggaaacgtaa    2460
attagctatt gtaaaaaag gaaagaaaa gaaagaaaa atgttacata tcgaattgat    2520
cttattcctt tggtagacca gtctttgcgt caatcaaaga ttcgtttgtt tcttgtgggc    2580
ctgaaccgac ttgagttaaa atcactctgg caacatcctt ttgcaactca agatccaatt    2640
cacgtgcagt aaagttagat gattcaaatt gatggttgaa agcctcaagc tgctcagtag    2700
taaatttctt gtcccatcca ggaacagagc caaacaattt atagataaat gcaagagttt    2760
tcgactcatt ttcagctaag tagtacaaca cagcatttgg acctgcatca aacgtgtatg    2820
caacgattgt ttctccgtaa aactgattaa tggtgtggca ccaactgatg atacgcttgg    2880
aagtgtcatt catgtagaat attggagga aagagtccaa acatgtggca tggaaagagt    2940
```

```
tggaatccat cattgtttcc tttgcaaagg tggcgaaatc tttttcaaca atggctttac    3000
gcatgacttc aaatctcttt ggtacgacat gttcaattct ttctttaaat agttcggagg    3060
ttgccacggt caattgcata ccctgagtgg aactcacatc cttttttaata tcgctgacaa   3120 ctaggacaca agctttcatc tgaggccagt cagagctgtc tgcgatttgt actgccatgg    3180
aatcatgacc atcttcagct tttcccattt cccaggccac gtatccgcca acaacgatc    3240 tacaagctga accagacccc tttcttgcta ttctagatat ttctgaagtt gactgtggta    3300
attggtataa cttagcaatt gcagagacca atgcagcaaa gccagcagcg gaggaagcta    3360
aaccagctgc tgtaggaaag ttattttcgg agacaatgtg gagtttccat tgagataatg    3420
tgggcaatga ggcgtccttc gattccattt cctttcttaa ttggcgtagg tcgcgcagac    3480
aattttgagt tctttcattg tcgatgctgt gtggttctcc atttaaccac aaagtgtcgc    3540
gttcaaactc aggtcagta gccgcagagg tcaacgttct gaggtcatct tgcgataaag    3600
tcactgatat ggacgaattg gtgggcagat tcaacttcgt gtcccttttc ccccaatact    3660
taagggttgc gatgttgacg ggtgcggtaa cggatgctgt gtaaacggtc atatccccgc    3720
gtgcttggcc ggccgttact tttttttttgg atggacgcaa agaagtttaa taatcatatt   3780
acatggcaat accaccatat acatatccat atctaatctt acttatatgt tgtggaaatg    3840
taaagagccc cattatctta gcctaaaaaa accttctctt tggaacttc agtaatacgc     3900 ttaactgctc attgctatat tgaagtacgg attagaagcc gccgagcggg cgacagccct    3960
ccgacggaag actctcctcc gtgcgtcctg gtcttcaccg gtcgcgttcc tgaaacgcag    4020
atgtgcctcg cgccgcactg ctccgaacaa taaagattct acaatactag cttttatggt    4080
tatgaagagg aaaaattggc agtaacctgg ccccacaaac cttcaaatca acgaatcaaa    4140
ttaacaacca taggataata atgcgattag ttttttagcc ttatttctgg ggtaattaat    4200
cagcgaagcg atgattttgg atctattaac agatatataa atgcaaaagc tgcataacca    4260 cttaactaa tactttcaac attttcggtt tgtattactt cttattcaaa tgtcataaaa      4320
gtatcaacaa aaaattgtta atatacctct atacttaacc tgcaggccgc gagcgccgat    4380
```

<210> SEQ ID NO 115
<211> LENGTH: 4284
<212> TYPE: DNA
<213> ORGANISM: Artificial Sequence
<220> FEATURE:
<223> OTHER INFORMATION: Synthetic Phase III-B stitch product

<400> SEQUENCE: 115

```
aacctgcagg ccgcgagcgc cgatatggct tcagaaaaag aaattaggag agagagattc      60
ttgaacgttt tccctaaatt agtagaggaa ttgaacgcat cgcttttggc ttacggtatg     120
cctaaggaag catgtgactg gtatgccac tcattgaact acaacactcc aggcggtaag     180
ttaaatagag gtttgtccgt tgtggacacg tatgctattc tctccaacaa gaccgttgaa    240 caattgggc aagaagaata cgaaaaggtt gctattctag gttggtgcat tgagttgttg      300
caggcttact tcttggtcgc cgatgatatg atggacaagt ccattaccag aagaggccaa    360
ccatgttggt acaaggttcc tgaagttggg gaaattgcca tcaatgacgc attcatgtta    420
gaggctgcta tctacaagct tttgaaatct cacttcagaa acgaaaaata ctacatagat    480
atcaccgaat tgttccatga agtcaccttc caaaccgaat gggccaatt gatggactta    540 atcactgcac ctgaagacaa agtcgacttg agtaagttct ccctaaagaa gcactccttc    600
atagttactt tcaagactgc ttactattct ttctacttgc ctgtcgcatt ggctatgtac    660
```

```
gttgccggta tcacagatga aaaggatttg aaacaagcca gagatgtctt gattccattg      720
ggtgaatatt tccaaattca agatgactac ttagactgct tcggtacccc agaacagatc      780
ggtaagatcg gtacagatat ccaagataac aaatgttctt gggtaatcaa caaggcatta      840
gaacttgctt ccgcagaaca agaaagact ttagacgaaa attacggtaa gaaggactca       900
gtcgcagaag ccaaatgcaa aaagattttc aatgacttga aaatcgacca gttataccac      960
gaatatgaag agtctgttgc caaggatttg aaggccaaga tctcccaagt cgacgagtct     1020
cgtggcttca agccgacgt cttaactgcg tttttgaaca aggttacaa gagaagtaaa       1080 taagactgga agcgttcaat cgataaaaat tggaatacag attagataag gaccatgtat     1140
aagaaatata tacttccact ataatatagt ataagcttac agataattat ctcttgattt     1200
accgttacac gtgactaaag gacgcttttt ctcagccaat gaaagtgaag aaaaacttga     1260
tcggaaatta cgggtagtac gtaaaaggaa cttgagccac cccccaaaaa tttacccata     1320
taataatagg aaaagcaacg acctcaaacg cgatcgccga cgccgccgat gacggtagca     1380
acaagaatat agcacgagcc gcgaagttca tttcgttact tttgatatcg ctcacaacta     1440
ttgcgaagcg cttcagtgaa aaaatcataa ggaaaagttg taaatattat ggtagtatt     1500 cgtttggtaa agtagagggg gtaattttc ccctttattt tgttcataca ttcttaaatt     1560
gctttgcctc tccttttgga aagctatact tcggagcact gttgagcgaa ggctcattag     1620
atatattttc tgtcattttc cttaacccaa aaataaggga aagggtccaa aaagcgctcg     1680
gacaactgtt gaccgtgatc cgaaggactg gctatacagt gttcacaaaa tagccaagct     1740
gaaaataatg tgtagctatg ttcagttagt ttggctagca aagatataaa agcaggtcgg     1800
aaatatttat gggcattatt atgcagagca tcaacatgat aaaaaaaagg cggccgctgg     1860
cgagggagat atgactgccg acaacaatag tatgccccat ggtgcagtat ctagttacgc     1920
caaattagtc aaaaccaaa cacctgaaga cattttggaa gagtttcctg aaattattcc     1980
attacaacaa agacctaata cccgatctag tgagacgtca aatgacgaaa gcggagaaac     2040 atgttttct ggtcatgatg aggagcaaat taagttaatg aatgaaaatt gtattgtttt      2100
ggattgggac gataatgcta ttggtgccgg taccaagaaa gtttgtcatt taatggaaaa     2160
tattgaaaag ggtttactac atcgtgcatt ctccgtcttt attttcaatg aacaaggtga     2220 attacttta caacaaagag ccactgaaaa aataactttc cctgatcttt ggactaacac      2280
atgctgctct catccactat gtattgatga cgaattaggt ttgaagggta agctagacga     2340
taagattaag ggcgctatta ctgcggcggt gagaaaacta gatcatgaat taggtattcc     2400
agaagatgaa actaagacaa ggggtaagtt tcactttta aacagaatcc attacatggc     2460
accaagcaat gaaccatggg gtgaacatga aattgattac atcctatttt ataagatcaa     2520
cgctaaagaa aacttgactg tcaacccaaa cgtcaatgaa gttagagact tcaaatgggt     2580
ttcaccaaat gatttgaaaa ctatgtttgc tgacccaagt tacaagttta cgccttggtt     2640
taagattatt tgcgagaatt acttattcaa ctggtgggag caattagatg acctttctga     2700
agtggaaaat gacaggcaaa ttcatagaat gctataacaa cgcgtcaata atataggcta     2760
cataaaaatc ataataactt tgttatcata gcaaatgtg atataaaacg tttcatttca     2820
cctgaaaaat agtaaaaata ggcgacaaaa atccttagta atatgtaaac tttattttct     2880
ttatttattt acagaactct gaatatacat tgattgttca cattttttt ttctcttctc      2940 aatttccctt gattatattc aaaaggttat tggcctcttg aatgtttccc actgatgaag     3000
gcgcgccacg gtcgtgcgga tgtattccaa tgagaatcgc tagaaatgct ttaccagaac     3060
```

```
tagactactt gtcgcagatc acttttgaac tgtatgagag tacgatgct tctggtcaaa    3120 aatcgcattc cattagactg aaaatgtctc ctgggtgtca tactcgagat ccgttagatg   3180
ttcaattaga tgacaggcat tatattagtt gtattccaaa gatttccctg acgaagcatt   3240
tggatatgga ctacgttcaa cagaaattga gaaacaaatt taccagggtc attatgcctc   3300
cgaaatttac accagtaaac attacgagcc ccaacttgag tttccagaaa cgcaaaacca   3360
gaagaaagtc ggtatctgtt gagaagttga agcttcctgc ctcgtccgga tcttcatcat   3420
ctacctccgt taacaagaca ttagattagt gatcacaccc aattttaat ttagcaaccc    3480 aaaataaata agtatttact caactttttt ttaataaaaa aaaacttaat tgaattttgc   3540
tcgcgatctt taggtccggg gttttcgttg aacccttaga cgagcaaatt agcgccataa   3600
ggatatacgt cagagcacat taattagtga catataccta tataaagagc aaccttctcc   3660
gatagacttg taatttatct tatttcattt cctaacactt tggtcgaaga gagggataa    3720 aaacagacga aagcccctca gcccccctag cgtcgatggg aaagctatta caattggcat   3780
tgcatccggt cgagatgaag gcagctttga agctgaagtt tgcagaaca ccgctattct    3840 ccatctatga tcagtccacg tctccatatc tcttgcactg tttcgaactg ttgaacttga   3900
cctccagatc gtttgctgct gtgatcagag agctgcatcc agaattgaga aactgtgtta   3960
ctctctttta tttgatttta agggctttgg ataccatcga agacgatatg tccatcgaac   4020
acgatttgaa aattgacttg ttgcgtcact tccacgagaa attgttgtta actaaatgga   4080
gtttcgacgg aaatgccccc gatgtgaagg acagagccgt tttgacagat ttcgaatcga   4140
ttcttattga attccacaaa ttgaaaccag aatatcaaga agtcatcaag gagatcaccg   4200
agaaaatggg taatggtatg gccgactaca tcttagatga aaattacaac ttgaatcggt   4260
gtttaaaccc cagcgcctgg cggg                                         4284
```

<210> SEQ ID NO 116
<211> LENGTH: 6344
<212> TYPE: DNA
<213> ORGANISM: Artificial Sequence
<220> FEATURE:
<223> OTHER INFORMATION: Synthetic Phase I marker recycling stitch
      product

<400> SEQUENCE: 116

```
gacggcacgg ccacgcgttt aaaccgccca gatggaatcc cttccataga gagaaggagc     60
aagcaactga cccaatattg actgccactg gacctgaaga catgcaacaa agtgcaagca    120
tagtggggcc ttcttccaat gctaatccgg tcactgccac tgctgctacg gaaaaccaac    180
ctaaaggtat taacttcttc actataagaa aatcacacga gcgcccggac gatgtctctg    240
tttaaatggc gcaagttttc cgctttgtaa tatatattta tacccctttc ttctctcccc    300
tgcaatataa tagtttaatt ctaatattaa taatatccta tattttcttc atttaccggc    360
gcactctcgc ccgaacgacc tcaaaatgtc tgctacattc ataataacca aaagctcata    420
actttttttt ttgaacctga atatatatac atcacatgtc actgctggtc cttgccgacc    480
agcgtataca atctcgatag ttggtttccc gttctttcca ctcccgtcgc tcacacgcgg    540
ccagggggag cctcactatt attccataag atgatcatta gcattacgtt caaaacgagt    600
acaaataact taagtaataa cacgagccat atgaccatta gcaagatgac aagcaagtta    660
agaccaatca gcttccatca tagcatcagc ttaacgttca ccattaataa gagtagaaat    720
ttcaccttca agacaataac gattttcgtg gtaataactg atataattaa attgaagctc    780
```

```
taatttgtga gtttagtata catgcattta cttataatac agttttttag ttttgctggc    840
cgcatcttct caaatatgct tcccagcctg cttttctgta acgttcaccc tctaccttag    900
catcccttcc ctttgcaaat agtcctcttc caacaataat aatgtcagat cctgtagaga    960
ccacatcatc cacggttcta tactgttgac ccaatgcgtc tcccttgtca tctaaaccca   1020
caccgggtgt cataatcaac caatcgtaac cttcatctct tccacccatg tctctttgag   1080
caataaagcc gataacaaaa tctttgtcac tcttcgcaat gtcaacagta cccttagtat   1140
attctccagt agctagggag cccttgcatg acaattctgc taacatcaaa aggcctctag   1200
gttcctttgt tacttcttcc gccgcctgct tcaaaccgct aacaatacct gggcccacca   1260
caccgtgtgc attcgtaatg tctgcccatt ctgctattct gtatacaccc gcagagtact   1320
gcaatttgac tgtattacca atgtcagcaa attttctgtc ttcgaagagt aaaaaattgt   1380
acttggcgga taatgccttt agcggcttaa ctgtgccctc catggaaaaa tcagtcaaga   1440
tatccacatg tgtttttagt aaacaaattt tgggacctaa tgcttcaact aactccagta   1500
attccttggt ggtacgaaca tccaatgaag cacacaagtt tgtttgcttt tcgtgcatga   1560
tattaaatag cttggcagca acaggactag gatgagtagc agcacgttcc ttatatgtag   1620
ctttcgacat gatttatctt cgtttcctgc aggttttgt tctgtgcagt tgggttaaga    1680
atactgggca atttcatgtt tcttcaacac cacatatgcg tatatatacc aatctaagtc   1740
tgtgctcctt ccttcgttct tccttctgct cggagattac cgaatcaaaa aaatttcaaa   1800
gaaaccggaa tcaaaaaaaa gaacaaaaaa aaaaagatg aattgaaaag ctttatggac    1860
cctgaaacca ctcactatta ttccataaga tgatcattag cattacgttc aaaacgagta   1920
caaataactt aagtaataac acgagccata tgaccattag caagatgaca agcaagttaa   1980
gaccaatcag cttccatcat agcatcagct taacgttcac cattaataag agtagaaatt   2040
tcaccttcaa gacaataacg attttcgtgc gctcgtccaa cgccggcgga cctgacggta   2100
gcaacaagaa tatagcacga gccgcggagt tcatttcgtt acttttgata tcactcacaa   2160
ctattgcgaa gcgcttcagt gaaaaaatca taaggaaaag ttgtaaatat tattggtagt   2220
attcgtttgg taaagtagag ggggtaattt ttcccctta ttttgttcat acattcttaa    2280
attgctttgc ctctcctttt ggaaagctat acttcggagc actgttgagc gaaggctcat   2340
tagatatatt ttctgtcatt ttccttaacc caaaaataag ggaaagggtc caaaaagcgc   2400
tcggacaact gttgaccgtg atccgaagga ctggctatac agtgttcaca aaatagccaa   2460
gctgaaaata atgtgtagct atgttcagtt agtttggcta gcaaagatat aaaagcaggt   2520
cggaaatatt tatgggcatt attatgcaga gcatcaacat gataaaaaaa aacagttgaa   2580
tattccctca aaaatccccg cgtgcttggc cggccgtaat taataatgtc aactttgcct   2640
atttcttctg tgtcattttc ctcttctaca tcaccattag tcgtggacga caaagtctca   2700
accaagcccg acgttatcag acatacaatg aatttcaatg cttctatttg gggagatcaa   2760
ttcttgacct atgatgagcc tgaagattta gttatgaaga acaattagt ggaggaatta    2820
aaagaggaag ttaagaagga attgataact atcaaaggtt caaatgagcc catgcagcat   2880
gtgaaattga ttgaattaat tgatgctgtt caacgtttag gtatagctta ccattttgaa   2940
gaagagatcg aggaagcttt gcaacatata catgttacct atggtgaaca gtgggtggat   3000
aaggaaaatt tacagagtat ttcattgtgg ttcaggttgt tgcgtcaaca gggctttaac   3060
gtctcctctg gcgttttcaa agactttatg gacgaaaaag gtaaattcaa agagtctta    3120
tgcaatgatg cacaaggaat attagcctta tatgaagctg catttatgag ggttgaagat   3180
```

```
gaaaccatct tagacaatgc tttggaattc acaaaagttc atttagatat catagcaaaa   3240
gacccatctt gcgattcttc attgcgtaca caaatccatc aagccttaaa acaacccttta  3300 agaaggagat tagcaaggat tgaagcatta cattacatgc caatctacca acaggaaaca   3360
tctcatgatg aagtattgtt gaaattagcc aagttggatt tcagtgtttt gcagtctatg   3420
cataaaaagg aattgtcaca tatctgtaag tggtggaaag atttagattt acaaaataag   3480
ttaccttatg tacgtgatcg tgttgtcgaa ggctacttct ggatattgtc catatactat   3540
gagccacaac acgctagaac aagaatgttt ttgatgaaaa catgcatgtg gttagtagtt   3600
ttggacgata cttttgataa ttatggaaca tacgaagaat tggagatttt tactcaagcc   3660
gtcgagagat ggtctatctc atgcttagat atgttgcccg aatatatgaa attaatctac   3720
caagaattag tcaatttgca tgtggaaatg aagaatctt tggaaaagga gggaaagacc   3780
tatcagattc attacgttaa ggagatggct aaagaattag ttcgtaatta cttagtagaa   3840
gcaagatggt tgaaggaagg ttatatgcct actttagaag aatacatgtc tgtttctatg   3900
gttactggta cttatggttt gatgattgca aggtcctatg ttggcagagg agacattgtt   3960
actgaagaca cattcaaatg ggtttctagt tacccaccta ttattaaagc ttcctgtgta   4020
atagtaagat taatggacga tattgtatct cacaaggaag aacaagaaag aggacatgtg   4080
gcttcatcta tagaatgtta ctctaaagaa tcaggtgctt ctgaagagga agcatgtgaa   4140
tatattagta ggaaagttga ggatgcctgg aaagtaatca atagagaatc tttgcgtcca   4200
acagccgttc ccttcccttt gttaatgcca gcaataaact tagctagaat gtgtgaggtc   4260
ttgtactctg ttaatgatgg ttttactcat gctgagggtg acatgaaatc ttatatgaag   4320
tccttcttcg ttcatcctat ggtcgtttga gctagctaag atccgctcta accgaaaagg   4380
aaggagttag acaacctgaa gtctaggtcc ctatttattt tttatagtt atgttagtat    4440 taagaacgtt atttatattt caaattttttc ttttttttct gtacagacgc gtgtacgcat   4500
gtaacattat actgaaaacc ttgcttgaga aggttttggg acgctcgaag aacctgcagg   4560
ccgcgagcgc cgatagttat gacaattaca acaacagaat tctttctata tatgcacgaa   4620
cttgtaatat ggaagaaatt atgacgtaca aactataaag taaatatttt acgtaacaca   4680
tggtgctgtt gtgcttcttt ttcaagagaa taccaatgac gtatgactaa gtttaggatt   4740
taatgcaggt gacggaccca tctttcaaac gattatatc agtggcgtcc aaattgttag   4800
gttttgttgg ttcagcaggt ttcctgttgt gggtcatatg actttgaacc aaatggccgg   4860
ctgctagggc agcacataag gataattcac ctgccaagac ggcacaggca actattcttg   4920
ctaattgacg tgcgttggta ccaggagcgg tagcatgtgg gcctcttaca cctaataagt   4980
ccaacatggc accttgtggt tctagaacag taccaccacc gatggtacct acttcgatgg   5040
atggcatgga tacggaaatt ctcaaatcac cgtccacttc tttcatcaat gttatacagt   5100
tggaactttc gacattttgt gcaggatctt gtcctaatgc caagaaaaca gctgtcacta   5160
aattagctgc atgtgcgtta aatccaccaa cagacccagc cattgcagat ccaaccaaat   5220
tcttagcaat gttcaactca accaatgcgg aaacatcact ttttaacact tttctgacaa   5280
catcaccagg aatagtagct tctgcgacga cactcttacc acgaccttcg atccagttga   5340
tggcagctgt tttttttgtcg gtacagtagt taccagaaac ggagacaacc tccatatctt   5400
cccagccata ctcttctacc atttgcttta atgagtattc gacacccttta gaaatcatat   5460 tcatacccat tgcgtcacca gtagttgttc taaatctcat gaagagtaaa tctcctgcta   5520
gacaagtttg aatatgttgc agacgtgcaa atcttgatgt agagttaaaa gctttttttaa  5580
```

-continued

| | |
|---|---|
| ttgcgttttg tccctcttct gagtctaacc atatcttaca ggcaccagat cttttcaaag | 5640 |
| ttgggaaacg gactactggg cctcttgtca taccatcctt agttaaaaca gttgttgcac | 5700 |
| caccgccagc attgattgcc ttacagccac gcatggcaga agctaccaaa caaccctctg | 5760 |
| tagttgccat tggtatatga taagatgtac catcgataac caaggggcct ataacaccaa | 5820 |
| cgggcaaagg catgtaacct ataacatttt cacaacaagc gccaaatacg cggtcgtagt | 5880 |
| cataattttt atatggtaaa cgatcagatg ctaatacagg agcttctgcc aaaattgaaa | 5940 |
| gagccttcct acgtaccgca accgctctcg tagtatcacc taattttttc tccaaagcgt | 6000 |
| acaaaggtaa cttaccgtga ataaccaagg cagcgacctc tttgttcttc aattgttttg | 6060 |
| tatttccact acttaataat gcttctaatt cttctaaagg acgtattttc ttatccaagc | 6120 |
| tttcaatatc gcgggaatca tcttcctcac tagatgatga aggtcctgat gagctcgatt | 6180 |
| gcgcagatga taaacttttg actttcgatc cagaaatgac tgttttattg gttaaaactg | 6240 |
| gtgtagaagc cttttgtaca ggagcagtaa aagacttctt ggtgacttca gtcttcacca | 6300 |
| attggtctgc agccatcggt gtttaaaccc cagcgcctgg cggg | 6344 |

<210> SEQ ID NO 117
<211> LENGTH: 6184
<212> TYPE: DNA
<213> ORGANISM: Artificial Sequence
<220> FEATURE:
<223> OTHER INFORMATION: Synthetic Phase II marker recycling stitch product

<400> SEQUENCE: 117

| | |
|---|---|
| gacggcacgg ccacgcgttt aaaccgccta ggataattat actctatttc tcaacaagta | 60 |
| attggttgtt tggccgagcg gtctaaggcg cctgattcaa gaaatatctt gaccgcagtt | 120 |
| aactgtggga atactcaggt atcgtaagat gcaagagttc gaatctctta gcaaccatta | 180 |
| tttttttcct caacataacg agaacacaca ggggcgctat cgcacagaat caaattcgat | 240 |
| gactggaaat tttttgttaa tttcagaggt cgcctgacgc atatacctt tcaactgaa | 300 |
| aaattgggag aaaaggaaa ggtgagagcg ccggaaccgg cttttcatat agaatagaga | 360 |
| agcgttcatg actaaatgct tgcatcacaa tacttgaagt tgacaatatt atttaaggac | 420 |
| ctattgtttt ttccaatagg tggttagcaa tcgtcttact ttctaacttt tcttaccttt | 480 |
| tacatttcag caatatatat atatatattt caaggatata ccattctagc tcacacgcgg | 540 |
| ccaggggggag cctcactatt attccataag atgatcatta gcattacgtt caaaacgagt | 600 |
| acaaataact taagtaataa cacgagccat atgaccatta gcaagatgac aagcaagtta | 660 |
| agaccaatca gcttccatca tagcatcagc ttaacgttca ccattaataa gagtagaaat | 720 |
| ttcaccttca agacaataac gattttcgtg gtaataactg atataattaa attgaagctc | 780 |
| taatttgtga gttagtata catgcattta cttataatac agttttttag ttttgctggc | 840 |
| cgcatcttct caaatatgct tcccagcctg ctttttctgta acgttcaccc tctaccttag | 900 |
| catcccttcc ctttgcaaat agtcctcttc caacaataat aatgtcagat cctgtagaga | 960 |
| ccacatcatc cacggttcta tactgttgac ccaatgcgtc tcccttgtca tctaaaccca | 1020 |
| caccgggtgt cataatcaac caatcgtaac cttcatctct tccacccatg tctctttgag | 1080 |
| caataaagcc gataacaaaa tctttgtcac tcttcgcaat gtcaacagta cccttagtat | 1140 |
| attctccagt agctagggag ccccttgcatg acaattctgc taacatcaaa aggcctctag | 1200 |
| gttcctttgt tacttcttcc gccgcctgct tcaaaccgct aacaatacct gggcccacca | 1260 |
| caccgtgtgc attcgtaatg tctgcccatt ctgctattct gtatacaccc gcagagtact | 1320 |

```
gcaatttgac tgtattacca atgtcagcaa attttctgtc ttcgaagagt aaaaaattgt   1380
acttggcgga taatgccttt agcggcttaa ctgtgccctc catggaaaaa tcagtcaaga   1440
tatccacatg tgttttagt aaacaaattt tgggacctaa tgcttcaact aactccagta   1500
attccttggt ggtacgaaca tccaatgaag cacacaagtt tgtttgcttt tcgtgcatga   1560
tattaaatag cttggcagca acaggactag gatgagtagc agcacgttcc ttatatgtag   1620
ctttcgacat gatttatctt cgtttcctgc aggttttgt tctgtgcagt tgggttaaga    1680
atactgggca atttcatgtt tcttcaacac cacatatgcg tatatatacc aatctaagtc   1740
tgtgctcctt ccttcgttct tccttctgct cggagattac cgaatcaaaa aaatttcaaa   1800
gaaaccggaa tcaaaaaaaa gaacaaaaaa aaaaagatg aattgaaaag ctttatggac    1860
cctgaaacca ctcactatta ttccataaga tgatcattag cattacgttc aaaacgagta   1920
caaataactt aagtaataac acgagccata tgaccattag caagatgaca agcaagttaa   1980
gaccaatcag cttccatcat agcatcagct taacgttcac cattaataag agtagaaatt   2040
tcaccttcaa gacaataacg attttcgtgc gctcgtccaa cgccggcgga cctgacggta   2100
gcaacaagaa tatagcacga gccgcggagt tcatttcgtt acttttgata tcactcacaa   2160
ctattgcgaa gcgcttcagt gaaaaaatca taggaaaag ttgtaaatat tattggtagt    2220
attcgtttgg taaagtagag ggggtaattt ttccccttta ttttgttcat acattcttaa   2280
attgctttgc ctctcctttt ggaaagctat acttcggagc actgttgagc gaaggctcat   2340
tagatatatt ttctgtcatt ttccttaacc caaaaataag ggaaagggtc caaaaagcgc   2400
tcggacaact gttgaccgtg atccgaagga ctggctatac agtgttcaca aaatagccaa   2460
gctgaaaata atgtgtagct atgttcagtt agtttggcta gcaaagatat aaaagcaggt   2520
cggaaatatt tatgggcatt attatgcaga gcatcaacat gataaaaaaa aacagttgaa   2580
tattccctca aaaatccccg cgtgcttggc cggccgtaat taataatgtc aactttgcct   2640
atttcttctg tgtcattttc ctcttctaca tcaccattag tcgtggacga caaagtctca   2700
accaagcccg acgttatcag acatacaatg aatttcaatg cttctatttg gggagatcaa   2760
ttcttgacct atgatgagcc tgaagattta gttatgaaga aacaattagt ggaggaatta   2820
aaagaggaag ttaagaagga attgataact atcaaaggtt caaatgagcc catgcagcat   2880
gtgaaattga ttgaattaat tgatgctgtt caacgtttag gtatagctta ccattttgaa   2940
gaagagatcg aggaagcttt gcaacatata catgttacct atggtgaaca gtgggtggat   3000
aaggaaaatt tacagagtat ttcattgtgg ttcaggttgt tgcgtcaaca gggctttaac   3060
gtctcctctg gcgttttcaa agactttatg gacgaaaaag gtaaattcaa agagtcttta   3120
tgcaatgatg cacaaggaat attagcctta tatgaagctg catttatgag ggttgaagat   3180
gaaaccatct tagacaatgc tttggaattc acaaaagttc atttagatat catagcaaaa   3240
gacccatctt gcgattcttc attgcgtaca caaatccatc aagccttaaa acaacccttta   3300 agaaggagat tagcaaggat tgaagcatta cattacatgc caatctacca acaggaaaca   3360
tctcatgatg aagtattgtt gaaattagcc aagttggatt tcagtgtttt gcagtctatg   3420
cataaaaagg aattgtcaca tatctgtaag tggtggaaag atttagattt acaaaataag   3480
ttaccttatg tacgtgatcg tgttgtcgaa ggctacttct ggatattgtc catatactat   3540
gagccacaac acgctagaac aagaatgttt ttgatgaaaa catgcatgtg ttagtagtt    3600 ttggacgata cttttgataa ttatggaaca tacgaagaat tggagatttt tactcaagcc   3660
gtcgagagat ggtctatctc atgcttagat atgttgcccg aatatatgaa attaatctac   3720
```

```
caagaattag tcaatttgca tgtggaaatg gaagaatctt tggaaaagga gggaaagacc   3780
tatcagattc attacgttaa ggagatggct aaagaattag ttcgtaatta cttagtagaa   3840
gcaagatggt tgaaggaagg ttatatgcct actttagaag aatacatgtc tgtttctatg   3900
gttactggta cttatggttt gatgattgca aggtcctatg ttggcagagg agacattgtt   3960
actgaagaca cattcaaatg ggtttctagt tacccaccta ttattaaagc ttcctgtgta   4020
atagtaagat taatggacga tattgtatct cacaaggaag aacaagaaag aggacatgtg   4080
gcttcatcta tagaatgtta ctctaaagaa tcaggtgctt ctgaagagga agcatgtgaa   4140
tatattagta ggaaagttga ggatgcctgg aaagtaatca atagagaatc tttgcgtcca   4200
acagccgttc ccttcccttt gttaatgcca gcaataaact tagctagaat gtgtgaggtc   4260
ttgtactctg ttaatgatgg ttttactcat gctgagggtg acatgaaatc ttatatgaag   4320
tccttcttcg ttcatcctat ggtcgtttga gctagctaag atccgctcta accgaaaagg   4380
aaggagttag acaacctgaa gtctaggtcc ctatttattt ttttatagtt atgttagtat   4440
taagaacgtt atttatattt caaattttc ttttttttct gtacagacgc gtgtacgcat   4500
gtaacattat actgaaaacc ttgcttgaga aggttttggg acgctcgaag aacctgcagg   4560
ccgcgagcgc cgtaattcgc gggtggaagg accttgtgga ggaatatgaa gttgatagct   4620
caaagggatt gaatggctat ttaactgatt atgagtcaat gtatcaagga tactatggtc   4680
tgcttaaatt tcattctgtc ttcgaaagct gaattgatac tacgaaaaat ttttttttgt   4740 ttctcttctct atctttatta cataaaactt catacacagt taagattaaa acaactaat   4800 aaataatgcc tatcgcaaat tagcttatga agtccatggt aaattcgtgt tcctggcaa   4860 taatagatcg tcaatttgtt gctttgtggt agttttattt tcaaataatt ggaatactag   4920
ggatttgatt ttaagatctt tattcaaatt ttttgcgctt aacaaacagc agccagtccc   4980
acccaagtct gtttcaaatg tctcgtaact aaaatcatct tgcaatttct ttttgaaact   5040
gtcaatttgc tcttgagtaa tgtctcttcg taacaaagtc aaagagcaac cgccgccacc   5100
agcaccggta agttttgtgg agccaattct caaatcatcg ctcagatttt taataagttc   5160
taatccagga tgagaaacac cgattgagac aagcagtcca tgatttattc ttatcaattc   5220
caatagttgt tcatacagtt cattattagt ttctacagcc tcgtcatcgg tgcctttaca   5280
tttacttaac ttagtcatga tctctaagcc ttgtagggca cattcaccca tggcatctag   5340
aattggcttc ataacttcag gaaatttctc ggtgaccaac acacgaacgc gagcaacaag   5400
atcttttgta gaccttggaa ttctagtata ggttaggatc attggaatgg ctgggaaatc   5460
atctaagaac ttaaaattgt ttgtgtttat tgttccatta tgtgagtctt tttcaaatag   5520
cagggcatta ccataagtgg ccacagcgtt atctattcct gaaggggtac cgtgaataca   5580
cttttcacct atgaaggccc attgattcac tatatgctta tcgttttctg acagcttttc   5640
caagtcatta gatcctatta accccccaa gtaggccata gctaaggcca gtgatacaga   5700
aatagaggcg cttgagccca acccagcacc gatgggtaaa gtagacttta agaaaactt   5760 aatattcttg gcatggggc ataggcaaac aaacatatac aggaaacaaa acgctgcatg   5820
gtagtggaag gattcggata gttgagctaa caacgatcc aaaagactaa cgagttcctg   5880
agacaagcca tcggtggctt gttgagcctt ggccaatttt tgggagttta cttgatcctc   5940
ggtgatggca ttgaaatcat tgatggacca cttatgatta aagctaatgt ccgggaagtc   6000
caattcaata gtatccggtg cagatgactc gcttattagc aggtaggttc tcaacgcaga   6060
cacactagca gcgacggcag gcttgttgta cacagcagag tgttcaccaa aataataac   6120
```

```
cttccccggt gcagaagtta agaacggtaa tgacatcggt gtttaaaccc cagcgcctgg    6180
cggg                                                                 6184

<210> SEQ ID NO 118
<211> LENGTH: 6042
<212> TYPE: DNA
<213> ORGANISM: Artificial Sequence
<220> FEATURE:
<223> OTHER INFORMATION: Synthetic Phase III marker recycling stitch
      product

<400> SEQUENCE: 118
gacggcacgg ccacgcgttt aaaccgccaa aagtgcagct cagagccccc agcaccagta      60
ttagaggtca taatgggctg cgaagcctgc taaaatgcag tggaggccgt gtaccctttg     120
ccaaattggc tattggaatc ggcagagaac ctgggtcccg ttctagagac cctgcgagcg     180
tgtcccggtg ggttctggga gctctaactc cgcaggaact acaaaccttg cttacacaga     240
gtgaacctgc tgcctggcgt gctctgactc agtacatttc atagcccatc ttcaacaaca     300
ataccgactt accatcctat ttgctttgcc cttttctttt tccactgcac tttgcatcgg     360
aaggcgttat cggttttggg tttagtgcct aaacgagcag cgagaacacg accacgggct     420
atataaatgg aaagttagga caggggcaaa gaataagagc acagaagaag agaaagacg      480 aaaagcagaa gcggaaaacg tatacacgtc acatatcaca cacacgct cacacgcggc       540 caggggggagc ctcactatta ttccataaga tgatcattag cattacgttc aaaacgagta    600
caaataactt aagtaataac acgagccata tgaccattag caagatgaca agcaagttaa    660
gaccaatcag cttccatcat agcatcagct taacgttcac cattaataag agtagaaatt    720
tcaccttcaa gacaataacg attttcgtgg taataactga taaattaaa ttgaagctct      780 aatttgtgag tttagtatac atgcatttac ttataataca gtttttttagt tttgctggcc    840 gcatcttctc aaatatgctt cccagcctgc ttttctgtaa cgttcaccct ctaccttagc     900
atcccttccc tttgcaaata gtcctcttcc aacaataata atgtcagatc ctgtagagac     960
cacatcatcc acgttctat actgttgacc caatgcgtct cccttgtcat ctaaacccac     1020
accgggtgtc ataatcaacc aatcgtaacc ttcatctctt ccacccatgt ctctttgagc    1080
aataaagccg ataacaaaat ctttgtcact cttcgcaatg tcaacagtac ccttagtata    1140
ttctccagta gctagggagc ccttgcatga caattctgct aacatcaaaa ggcctctagg    1200
ttcctttgtt acttcttccg ccgcctgctt caaaccgcta acaatacctg gcccaccac     1260 accgtgtgca ttcgtaatgt ctgcccattc tgctattctg tatacacccg cagagtactg    1320
caatttgact gtattaccaa tgtcagcaaa ttttctgtct tcgaagagta aaaaattgta    1380
cttggcggat aatgccttta gcggcttaac tgtgccctcc atggaaaaat cagtcaagat    1440
atccacatgt gttttagta aacaaatttt gggacctaat gcttcaacta actccagtaa     1500
ttccttggtg gtacgaacat ccaatgaagc acacaagttt gtttgctttt cgtgcatgat    1560
attaaatagc ttggcagcaa caggactagg atgagtagca gcacgttcct tatatgtagc    1620
tttcgacatg atttatcttc gtttcctgca ggttttttgtt ctgtgcagtt gggttaagaa    1680
tactgggcaa tttcatgttt cttcaacacc acatatgcgt atatatacca atctaagtct    1740
gtgctccttc cttcgttctt ccttctgctc ggagattacc gaatcaaaaa aatttcaaag    1800
aaaccggaat caaaaaaaag aacaaaaaaa aaaagatga attgaaaagc tttatggacc     1860
ctgaaaccac tcactattat tccataagat gatcattagc attacgttca aaacgagtac    1920
```

```
aataactta agtaataaca cgagccatat gaccattagc aagatgacaa gcaagttaag      1980
accaatcagc ttccatcata gcatcagctt aacgttcacc attaataaga gtagaaattt      2040
caccttcaag acaataacga ttttcgtgcg ctcgtccaac gccggcggac ctgacggtag      2100
caacaagaat atagcacgag ccgcggagtt catttcgtta cttttgatat cactcacaac      2160
tattgcgaag cgcttcagtg aaaaaatcat aaggaaaagt tgtaaatatt attggtagta      2220
ttcgtttggt aaagtagagg gggtaatttt tcccctttat tttgttcata cattcttaaa      2280
ttgctttgcc tctccttttg gaaagctata cttcggagca ctgttgagcg aaggctcatt      2340
agatatattt tctgtcattt tccttaaccc aaaaataagg gaagggtcc aaaaagcgct       2400 cggacaactg ttgaccgtga tccgaaggac tggctataca gtgttcacaa aatagccaag      2460
ctgaaaataa tgtgtagcta tgttcagtta gtttggctag caaagatata aaagcaggtc     2520
ggaaatattt atgggcatta ttatgcagag catcaacatg ataaaaaaaa acagttgaat     2580
attccctcaa aaatccccgc gtgcttggcc ggccgtaatt aataatgtca actttgccta    2640
tttcttctgt gtcattttcc tcttctacat caccattagt cgtggacgac aaagtctcaa   2700
ccaagcccga cgttatcaga catacaatga atttcaatgc ttctatttgg ggagatcaat    2760
tcttgaccta tgatgagcct gaagatttag ttatgaagaa acaattagtg gaggaattaa    2820
aagaggaagt taagaaggaa ttgataacta tcaaaggttc aaatgagccc atgcagcatg    2880
tgaaattgat tgaattaatt gatgctgttc aacgtttagg tatagcttac cattttgaag     2940
aagagatcga ggaagctttg caacatatac atgttaccta tggtgaacag tgggtggata    3000
aggaaaattt acagagtatt tcattgtggt tcaggttgtt gcgtcaacag ggctttaacg    3060
tctcctctgg cgttttcaaa gactttatgg acgaaaaagg taaattcaaa gagtctttat    3120
gcaatgatgc acaaggaata ttagccttat atgaagctgc atttatgagg gttgaagatg    3180
aaaccatctt agacaatgct ttggaattca caaaagttca tttagatatc atagcaaaag    3240
acccatcttg cgattcttca ttgcgtacac aaatccatca agccttaaaa caacctttaa    3300
gaaggagatt agcaaggatt gaagcattac attacatgcc aatctaccaa caggaaacat    3360
ctcatgatga agtattgttg aaattagcca agttggattt cagtgttttg cagtctatgc    3420
ataaaaagga attgtcacat atctgtaagt ggtggaaaga tttagattta caaaataagt    3480
taccttatgt acgtgatcgt gttgtcgaag gctacttctg gatattgtcc atatactatg    3540
agccacaaca cgctagaaca agaatgtttt tgatgaaaac atgcatgtgg ttagtagttt    3600
tggacgatac ttttgataat tatggaacat acgaagaatt ggagattttt actcaagccg    3660
tcgagagatg gtctatctca tgcttagata tgttgcccga atatatgaaa ttaatctacc    3720
aagaattagt caatttgcat gtggaaatgg aagaatcttt ggaaaaggag ggaaagacct    3780
atcagattca ttacgttaag gagatggcta agaattagt tcgtaattac ttagtagaag    3840
caagatggtt gaaggaaggt tatatgccta ctttagaaga atacatgtct gtttctatgg    3900
ttactggtac ttatggtttg atgattgcaa ggtcctatgt tggcagagga gacattgtta    3960
ctgaagacac attcaaatgg gtttctagtt acccacctat tattaaagct tcctgtgtaa    4020
tagtaagatt aatggacgat attgtatctc acaaggaaga acaagaaaga ggacatgtgg    4080
cttcatctat agaatgttac tctaaagaat caggtgcttc tgaagaggaa gcatgtgaat    4140
atattagtag gaaagttgag gatgcctgga agtaatcaa tagagaatct ttgcgtccaa     4200
cagccgttcc cttcccttg ttaatgccag caataaactt agctagaatg tgtgaggtct    4260
tgtactctgt taatgatggt tttactcatg ctgagggtga catgaaatct tatatgaagt    4320
```

```
ccttcttcgt tcatcctatg gtcgtttgag ctagctaaga tccgctctaa ccgaaaagga    4380
aggagttaga caacctgaag tctaggtccc tatttatttt tttatagtta tgttagtatt    4440
aagaacgtta tttatatttc aaattttct tttttttctg tacagacgcg tgtacgcatg    4500
taacattata ctgaaaacct tgcttgagaa ggttttggga cgctcgaaga acctgcaggc    4560
cgcgagcgcc gatcttgtgc taagtggtgc tgttagacag ctacgaataa ggaaattccg    4620
aagcatgtag ggaggtcatg atatgaaaaa gcaaagagt aggcatcaaa aagtttctca     4680
ttcaagtggt aactgctgtt aaaattaaga tatttataaa ttgaagcttg gtcgttccga    4740
ccaataccgt agggaaacgt aaattagcta ttgtaaaaaa aggaaaagaa aagaaaagaa    4800
aaatgttaca tatcgaattg atcttattcc tttggtagac cagtctttgc gtcaatcaaa    4860
gattcgtttg tttcttgtgg gcctgaaccg acttgagtta aaatcactct ggcaacatcc    4920
ttttgcaact caagatccaa ttcacgtgca gtaaagttag atgattcaaa ttgatggttg    4980
aaagcctcaa gctgctcagt agtaaatttc ttgtcccatc caggaacaga gccaaacaat    5040
ttatagataa atgcaaagag tttcgactca ttttcagcta agtagtacaa cacagcattt    5100
ggacctgcat caaacgtgta tgcaacgatt gtttctccgt aaaactgatt aatggtgtgg    5160
caccaactga tgatacgctt ggaagtgtca ttcatgtaga atattggagg gaaagagtcc    5220
aaacatgtgg catggaaaga gttggaatcc atcattgttt cctttgcaaa ggtggcgaaa    5280 tcttttcaa caatggcttt acgcatgact tcaaatctct ttggtacgac atgttcaatt     5340 ctttcttaa atagttcgga ggttgccacg gtcaattgca tacctgagt ggaactcaca      5400 tcctttta tatcgctgac aactaggaca caagcttca tctgaggcca gtcagagctg       5460
tctgcgattt gtactgccat ggaatcatga ccatcttcag ctttcccat ttcccaggcc     5520 acgtatccgc caaacaacga tctacaagct gaaccagacc cctttcttgc tattctagat    5580
atttctgaag ttgactgtgg taattggtat aacttagcaa ttgcagagac caatgcagca    5640
aagccagcag cggaggaagc taaaccagct gctgtaggaa agttatttc ggagacaatg     5700 tggagtttcc attgagataa tgtgggcaat gaggcgtcct tcgattccat ttcctttctt    5760
aattggcgta ggtcgcgcag acaattttga gttcttcat tgtcgatgct gtgtggttct     5820
ccatttaacc acaaagtgtc gcgttcaaac tcaggtgcag tagccgcaga ggtcaacgtt    5880
ctgaggtcat cttgcgataa agtcactgat atggacgaat tggtgggcag attcaacttc    5940
gtgtcccttt tcccccaata cttaagggtt gcgatgttga cgggtgcggt aacggatgct    6000
gtgtaaacgg tcatcggtgt ttaaacccca gcgcctggcg gg                       6042

<210> SEQ ID NO 119
<211> LENGTH: 5213
<212> TYPE: DNA
<213> ORGANISM: Artificial Sequence
<220> FEATURE:
<223> OTHER INFORMATION: Synthetic STE5 knockout stitch product

<400> SEQUENCE: 119
gacggcacgg ccacgcgttt aaaccgccac gaagtgactg acagaatact gacatcagct      60
gatttctcat agagctgttt ctctgataac acgttgtttg aacatcgaca agatgaaaat     120
ctagaagtat caagtttcct ttaaagggat atataacaga ttctaaaact gacagaaata    180
tttcgagtga agaagaagcg ttaaatattg gatctttccg cagttctact ctgatacatt    240
tttgaagtag gagagtcatt tagaaggcgt attgctcaat agtagaaagc aggcctgtgc    300
acatgaatta attaaaaaat ataaaggtag tgattagacg acacatgtcc ataggtaacc    360
```

```
tgtcataatt ttgaacaatt tcccttcttt tctttttttt ttttgggtgc ggcgatatgt    420
agcttgttaa tttacacatc atgtactttt ctgcatcaaa atatgaaagg cgatagtagc    480
taaagaaaat accgagaatt tcctcgaaaa gttgacgaca aaagaaaggc ataaaaaagt    540
aatttgaaaa tattttaaaa ctgttttaac ccatctagca tccgcgctaa aaaaggaaga    600
tacaggatac agcggaaaca acttttaagc tcacacgcgg ccaggggag ccatgcgtcc     660 atctttacag tcctgtctta ttgttcttga tttgtgcccc gtaaaatact gttacttggt    720
tctggcgagg tattggatag ttccttttta taaaggccat gaagcttttt ctttccaatt    780
tttttttttt cgtcattata gaaatcatta cgaccgagat tcccgggtaa taactgatat    840
aattaaattg aagctctaat ttgtgagttt agtatacatg catttactta taatacagtt    900
ttttagtttt gctggccgca tcttctcaaa tatgcttccc agcctgcttt tctgtaacgt    960
tcaccctcta ccttagcatc ccttcccttt gcaaatagtc ctcttccaac aataataatg   1020
tcagatcctg tagagaccac atcatccacg gttctatact gttgacccaa tgcgtctccc   1080
ttgtcatcta aacccacacc gggtgtcata atcaaccaat cgtaaccttc atctcttcca   1140
cccatgtctc tttgagcaat aaagccgata acaaaatctt tgtcgctctt cgcaatgtca   1200
acagtaccct tagtatattc tccagtagct agggagccct tgcatgacaa ttctgctaac   1260
atcaaaaggc ctctaggttc ctttgttact tcttccgccg cctgcttcaa accgctaaca   1320 ataccctgggc ccaccacacc gtgtgcattc gtaatgtctg cccattctgc tattctgtat   1380 acaccccgcag agtactgcaa tttgactgta ttaccaatgt cagcaaattt tctgtcttcg   1440
aagagtaaaa aattgtactt ggcggataat gcctttagcg gcttaactgt gccctccatg   1500
gaaaaatcag tcaagatatc cacatgtgtt tttagtaaac aaattttggg acctaatgct   1560
tcaactaact ccagtaattc cttggtggta cgaacatcca atgaagcaca caagtttgtt   1620
tgcttttcgt gcatgatatt aaatagcttg gcagcaacag gactaggatg agtagcagca   1680
cgttccttat atgtagcttt cgacatgatt tatcttcgtt tcctgcaggt ttttgttctg   1740
tgcagttggg ttaagaatac tgggcaattt catgttttctt caacaccaca tatgcgtata   1800
tataccaatc taagtctgtg ctccttcctt cgttcttcct tctgctcgga gattaccgaa   1860
tcaaaaaaat ttcaaagaaa ccggaatcaa aaaaagaac aaaaaaaaaa aagatgaatt   1920
gaaaagcttt atggaccctg aaaccacagc cacattaacc ttctttgatg gtcaaaactt   1980
atccttcacc ataaatatgc ctcgcaaaaa aggtaattaa catatataga attacattat   2040
ttatgaaata tcatcactat ctcttagcat ctttaatcct tttctacatc agataacttc   2100
ggtttgttat catcgtctgt attgtcatca attggcgcag tagcctcaat ttcaacgtcg   2160
tttgactctg gtgtttgttc atgtgcagat ccatgagatg atgaaccgct cgtccaacgc   2220
cggcggacct ctttttaattc tgctgtaacc cgtacatgcc caaaataggg ggcgggttac   2280
acagaatata taacatcgta ggtgtctggg tgaacagttt attcctggca tccactaaat   2340
ataatggagc ccgcttttta agctggcatc cagaaaaaaa aagaatccca gcaccaaaat   2400
attgttttct tcaccaacca tcagttcata ggtccattct cttagcgcaa ctacagagaa   2460
caggggcaca aacaggcaaa aaacgggcac aacctcaatg gagtgatgca acctgcctgg   2520
agtaaatgat gacacaaggc aattgaccca cgcatgtatc tatctcattt tcttacacct   2580
tctattacct tctgctctct ctgatttgga aaaagctgaa aaaaaaggtt gaaaccagtt   2640
ccctgaaatt attcccctac ttgactaata agtatataaa gacggtaggt attgattgta   2700
attctgtaaa tctatttctt aaacttctta aattctactt ttatagttag tctttttttt   2760
```

```
agttttaaaa caccaagaac ttagtttcga ataaacacac ataaacaaac aaattaataa    2820
tggctgcaga ccaattggtg aagactgaag tcaccaagaa gtcttttact gctcctgtac    2880
aaaaggcttc tacaccagtt ttaaccaata aaacagtcat ttctggatcg aaagtcaaaa    2940
gtttatcatc tgcgcaatcg agctcatcag gaccttcatc atctagtgag gaagatgatt    3000
cccgcgatat tgaaagcttg gataagaaaa tacgtccttt agaagaatta gaagcattat    3060
taagtagtgg aaatacaaaa caattgaaga acaaagaggt cgctgccttg gttattcacg    3120
gtaagttacc tttgtacgct ttggagaaaa aattaggtga tactacgaga gcggttgcgg    3180
tacgtaggaa ggctcttttca attttggcag aagctcctgt attagcatct gatcgtttac    3240
catataaaaa ttatgactac gaccgcgtat ttggcgcttg ttgtgaaaat gttataggtt    3300
acatgccttt gcccgttggt gttataggcc ccttggttat cgatggtaca tcttatcata    3360
taccaatggc aactacagag ggttgtttgg tagcttctgc catgcgtggc tgtaaggcaa    3420
tcaatgctgg cggtggtgca acaactgttt taactaagga tggtatgaca agaggcccag    3480
tagtccgttt cccaactttg aaaagatctg gtgcctgtaa gatatggtta gactcagaag    3540
agggacaaaa cgcaattaaa aaagctttta actctacatc aagatttgca cgtctgcaac    3600
atattcaaac ttgtctagca ggagatttac tcttcatgag atttagaaca actactggtg    3660
acgcaatggg tatgaatatg atttctaagg gtgtcgaata ctcattaaag caaatggtag    3720
aagagtatgg ctgggaagat atggaggttg tctccgtttc tggtaactac tgtaccgaca    3780 aaaaccagc tgccatcaac tggatcgaag gtcgtggtaa gagtgtcgtc gcagaagcta    3840
ctattcctgg tgatgttgtc agaaaagtgt taaaaagtga tgtttccgca ttggttgagt    3900
tgaacattgc taagaatttg gttggatctg caatggctgg gtctgttggt ggatttaacg    3960
cacatgcagc taatttagtg acagctgttt tcttggcatt aggacaagat cctgcacaaa    4020
atgtcgaaag ttccaactgt ataacattga tgaaagaagt ggacggtgat ttgagaattt    4080
ccgtatccat gccatccatc gaagtaggta ccatcggtgg tggtactgtt ctagaaccac    4140
aaggtgccat gttggactta ttaggtgtaa gaggcccaca tgctaccgct cctggtacca    4200
acgcacgtca attagcaaga atagttgcct gtgccgtctt ggcaggtgaa ttatccttat    4260
gtgctgccct agcagccggc catttggttc aaagtcatat gacccacaac aggaaacctg    4320
ctgaaccaac aaaaccgaac aatttggacg ccactgatat aaatcgtttg aaagatgggt    4380
ccgtcacctg cattaaatcc taaacttagt catacgtcat tggtattctc ttgaaaaaga    4440
agcacaacag caccatgtgt tacgtaaaat atttacttta tagtttgtac gtcataattt    4500
cttccatatt acaagttcgt gcatatatag aaagaattct gttgttgtaa ttgtcataac    4560
taacctgcag gccgcgagcg ccgatagtat acactaaatt ttatgcaata ataaaaagaa    4620
agcatcccgc caaacgtttc gtaactacat attgttacat agtttgattc cgtgaatttg    4680
aagtggacgc agttcttctt agtctttcaa gttcatagta aatagacatt acccaaagat    4740
ctctttcctg tcttgatctt gccatgaaaa ccattgactt gccgctcaca cctaactttt    4800
tagtgaaatg gatcttatct gtgttacttg gaacattaga gttattcaag tcagcttccg    4860
gagcagaagg tgggtcaata ttattatctt gtctaccata atcttgcgta tattgctttt    4920
cattcccttt cttctgtaag cgattgctag aaagggcacg ccttgttcca aaccaaagcg    4980
taaagcatcg cgaactctcg tcttctacag atcgccatcc gtccccataa actcgtggga    5040
gagcgtggga tccatagttt atttcgtcaa aagtacgatc tctctgcaga aggtctagtt    5100
ctgttgtggt cccagagtat aggtagcaat cgtcaatcgg aatggttaca taatgagcat    5160
```

```
actccaaaac ttccttagca aaacccggtg tttaaacccc agcgcctggc ggg         5213

<210> SEQ ID NO 120
<211> LENGTH: 5417
<212> TYPE: DNA
<213> ORGANISM: Artificial Sequence
<220> FEATURE:
<223> OTHER INFORMATION: Synthetic IME1 knockout stitch product

<400> SEQUENCE: 120
gacggcacgg ccacgcgttt aaaccgccat ccaattcctc tattatatgc atacattttt    60
ttgtttgatt atctatgctg tttataatat cgtatatagt taatgaataa ccctacaaca   120
cgaagggcag taatatattc tgattctcag ttgaaatttc aaattttca agctggtctt    180 actcggcagg taggaacttc ccagtgggtc tgagttttct ctccggaagg tatttatcat   240
tatgcacgac aagtgcgatt caatcgaaag attataaatt tcgcgatgaa caacatctga   300
taaaaaaaaa attaaaaaac aataatctaa atgatatgta tgggttaaaa aggatgtatg   360
gatggagggt tggcataaaa atgaaaggca gaagatgggc ggctaaaaag gtatagagat   420
cgtacgtcac cgtcacaaaa atcactcata gaatgcacta tcatccttac aataccatac   480
cagccgcaag aaaaaaagaa aaaaaaatca attcatatca tatattatct atatcatgct   540
gttctttccg ccacgctcac acgcggccag ggggagcccg ttgagccatt agtatcaatt   600
tgcttacctg tattccttta ctatcctcct tttttctcctt cttgataaat gtatgtagat   660
tgcgtatata gtttcgtcta ccctatgaac atattccatt ttgtaatttc gtgtcgtttc   720
tattatgaat ttcatttata aagtttatgt acaaatatca taaaaaaaga gaatcttttt   780
aagcaaggat tttcttaact tcttcggcga cagcatcacc gacttcggtg gtactgttgg   840
aaccacctaa atcaccagtt ctgatacctg catccaaaac cttttaact gcatcttcaa    900 tggccttacc ttcttcaggc aagttcaatg acaatttcaa catcattgca gcagacaaga   960
tagtggcgat agggtcaacc ttattctttg gcaaatctgg agcagaaccg tggcatggtt  1020
cgtacaaacc aaatgcggtg ttcttgtctg gcaaagaggc caaggacgca gatggcaaca  1080
aacccaagga acctgggata acggaggctt catcggagat gatatcacca aacatgttgc  1140
tggtgattat aataccattt aggtgggttg ggttcttaac taggatcatg gcggcagaat  1200
caatcaattg atgttgaacc ttcaatgtag ggaattcgtt cttgatggtt cctccacag    1260 ttttctccca taatcttgaa gaggccaaaa gattagcttt atccaaggac caaataggca   1320
atggtggctc atgttgtagg gccatgaaag cggccattct tgtgattctt tgcacttctg   1380
gaacggtgta ttgttcacta tcccaagcga caccatcacc atcgtcttcc tttctcttac  1440
caaagtaaat acctcccact aattctctga caacaacgaa gtcagtacct ttagcaaatt  1500
gtggcttgat tggagataag tctaaaagag agtcggatgc aaagttacat ggtcttaagt  1560
tggcgtacaa ttgaagttct ttacggattt ttagtaaacc ttgttcaggt ctaacactac   1620
cggtacccca tttaggacca gccacagcac ctaacaaaac ggcatcaacc ttcttggagg   1680
cttccagcgc ctcatctgga agtgggacac ctgtagcatc gatagcagca ccaccaatta   1740
aatgattttc gaaatcgaac ttgacattgg aacgaacatc agaaatagct ttaagaacct   1800
taatggcttc ggctgtgatt tcttgaccaa cgtggtcacc tggcaaaacg acgatcttct   1860
taggggcaga catagggggca gacattagaa tggtatatcc ttgaaatata tatatatatt   1920
gctgaaatgt aaaaggtaag aaaagttaga agtaagacg attgctaacc acctattgga   1980
aaaaacaata ggtccttaaa taatattgtc aacttcaagt attgtgatgc aagcatttag   2040
```

```
tcatgaacgc ttctctattc tatatgaaaa gccggttccg gcctctcacc tttccttttt    2100
ctcccaattt ttcagttgaa aaaggtatat gcgtcaggcg acctctgaaa ttaacaaaaa    2160
atttccagtc atcgaatttg attctgtgcg atagcgcccc tgtgtgttct cgttatgttg    2220
aggaaaaaaa taatggttgc taagagattc gaactcttgc atcttacgat acctgagtat    2280
tcccacagtt aactgcggtc aagatatttc ttgaatcagg cgcctcgctc gtccaacgcc    2340
ggcggacctc ttttaattct gctgtaaccc gtacatgccc aaaataggg gcgggttaca    2400 cagaatatat aacatcgtag gtgtctgggt gaacagttta ttcctggcat ccactaaata    2460
taatggagcc cgcttttta gctggcatcc agaaaaaaa agaatcccag caccaaaata    2520
ttgttttctt caccaaccat cagttcatag gtccattctc ttagcgcaac tacagagaac    2580
aggggcacaa acaggcaaaa aacgggcaca acctcaatgg agtgatgcaa cctgcctgga    2640
gtaaatgatg acacaaggca attgacccac gcatgtatct atctcatttt cttacacctt    2700
ctattacctt ctgctctctc tgatttggaa aaagctgaaa aaaaaggttg aaaccagttc    2760
cctgaaatta ttcccctact tgactaataa gtatataaag acggtaggta ttgattgtaa    2820
ttctgtaaat ctatttctta aacttcttaa attctacttt tatagttagt ctttttttta    2880
gttttaaaac accaagaact tagtttcgaa taaacacaca taaacaaaca aattaataat    2940
gtcaactttg cctatttctt ctgtgtcatt ttcctcttct acatcaccat tagtcgtgga    3000
cgacaaagtc tcaaccaagc ccgacgttat cagacataca atgaatttca atgcttctat    3060
ttggggagat caattcttga cctatgatga gcctgaagat ttagttatga agaaacaatt    3120
agtggaggaa ttaaaagagg aagttaagaa ggaattgata actatcaaag gttcaaatga    3180
gcccatgcag catgtgaaat tgattgaatt aattgatgct gttcaacgtt taggtatagc    3240
ttaccatttt gaagaagaga tcgaggaagc tttgcaacat atacatgtta cctatggtga    3300
acagtgggtg gataaggaaa atttacagag tatttcattg tggttcaggt tgttgcgtca    3360
acagggcttt aacgtctcct ctggcgtttt caaagacttt atggacgaaa aagtaaatt    3420 caaagagtct ttatgcaatg atgcacaagg aatattagcc ttatatgaag ctgcatttat    3480
gagggttgaa gatgaaacca tcttagacaa tgctttggaa ttcacaaaag ttcatttaga    3540
tatcatagca aaagacccat cttgcgattc ttcattgcgt acacaaatcc atcaagcctt    3600
aaaacaacct ttaagaagga gattagcaag gattgaagca ttacattaca tgccaatcta    3660
ccaacaggaa acatctcatg atgaagtatt gttgaaatta gccaagttgg atttcagtgt    3720
tttgcagtct atgcataaaa aggaattgtc acatatctgt aagtggtgga agatttaga    3780 tttacaaaat aagttacctt atgtacgtga tcgtgttgtc gaaggctact tctggatatt    3840
gtccatatac tatgagccac aacacgctag aacaagaatg ttttttgatga aaacatgcat    3900 gtggttagta gttttggacg atacttttga taattatgga acatacgaag aattggagat    3960
ttttactcaa gccgtcgaga gatggtctat ctcatgctta gatatgttgc ccgaatatat    4020
gaaattaatc taccaagaat tagtcaattt gcatgtggaa atggaagaat ctttggaaaa    4080
ggagggaaag acctatcaga ttcattacgt taaggagatg gctaagaat tagttcgtaa    4140 ttacttagta gaagcaagat ggttgaagga aggttatatg cctactttag aagaatacat    4200
gtctgtttct atggttactg gtacttatgg tttgatgatt gcaaggtcct atgttggcag    4260
aggagacatt gttactgaag acacattcaa atgggtttct agttacccac ctattattaa    4320
agcttcctgt gtaatagtaa gattaatgga cgatattgta tctcacaagg aagaacaaga    4380
aagaggacat gtggcttcat ctatagaatg ttactctaaa gaatcaggtg cttctgaaga    4440
```

| | |
|---|---|
| ggaagcatgt gaatatatta gtaggaaagt tgaggatgcc tggaaagtaa tcaatagaga | 4500 |
| atctttgcgt ccaacagccg ttcccttccc tttgttaatg ccagcaataa acttagctag | 4560 |
| aatgtgtgag gtcttgtact ctgttaatga tggttttact catgctgagg gtgacatgaa | 4620 |
| atcttatatg aagtccttct tcgttcatcc tatggtcgtt tgagctagct aagatccgct | 4680 |
| ctaaccgaaa aggaaggagt tagacaacct gaagtctagg tccctattta ttttttttata | 4740 |
| gttatgttag tattaagaac gttatttata tttcaaattt ttcttttttt tctgtacaga | 4800 |
| cgcgtgtacg catgtaacat tatactgaaa accttgcttg agaaggtttt gggacgctcg | 4860 |
| aagaacctgc aggccgcgag cgccgatctc gaaaagtact acaatcttcc cccttccctc | 4920 |
| aaaatatatc cattcacact catttcttta tttccattgt ctcactcaaa ttgctaagaa | 4980 |
| tttgtgtatt tgcatatata tatattatat ataggtatat atatgtattc aatgtctcaa | 5040 |
| gctccatgac ataataccgt agcgttatta gccttatcgt atgtcgcgat gggaaaggag | 5100 |
| attcgtttta atcttgaaaa accttcgtag cgaataatgc gacataaatc ttgagagagt | 5160 |
| acatcaccaa attcactttg ttaaaccgca ccatcgtgct ttgcattctt attccttttg | 5220 |
| cctacactaa aattattagc atttctctaa atgagctcca gtgaagacga agacgacaag | 5280 |
| ttcttgtatg gttccgactc cgaattagca ctaccttcat ctaaacgatc aagagatgat | 5340 |
| gaagcagacg caggtgcgtc cagtaatcct gatatagtta aaaggcaaac ggtgtttaaa | 5400 |
| ccccagcgcc tggcggg | 5417 |

<210> SEQ ID NO 121
<211> LENGTH: 1737
<212> TYPE: DNA
<213> ORGANISM: Artificial Sequence
<220> FEATURE:
<223> OTHER INFORMATION: Synthetic beta-farnesene synthase of Artemisia annua codon-optimized for expression in Saccharomyces cerevisiae

<400> SEQUENCE: 121

| | |
|---|---|
| ggatccatgt caactttgcc tatttcttct gtgtcatttt cctcttctac atcaccatta | 60 |
| gtcgtggacg acaaagtctc aaccaagccc gacgttatca gacatacaat gaatttcaat | 120 |
| gcttctatttt ggggagatca attcttgacc tatgatgagc ctgaagattt agttatgaag | 180 |
| aaacaattag tggaggaatt aaaagaggaa gttaagaagg aattgataac tatcaaaggt | 240 |
| tcaaatgagc ccatgcagca tgtgaaattg attgaattaa ttgatgctgt tcaacgttta | 300 |
| ggtatagctt accattttga agaagagatc gaggaagctt tgcaacatat acatgttacc | 360 |
| tatggtgaac agtgggtgga taaggaaaat ttacagtata tttcattgtg gttcaggttg | 420 |
| ttgcgtcaac agggctttaa cgtctcctct ggcgttttca aagactttat ggacgaaaaa | 480 |
| ggtaaattca aagagtcttt atgcaatgat gcacaaggaa tattagcctt atatgaagct | 540 |
| gcatttatga gggttgaaga tgaaaccatc ttagacaatg ctttggaatt cacaaaagtt | 600 |
| catttagata tcatagcaaa agaccccatct tgcgattctt cattgcgtac acaaatccat | 660 |
| caagccttaa acaacccttt aagaaggaga ttagcaagga ttgaagcatt acattacatg | 720 |
| ccaatctacc aacaggaaac atctcatgat gaagtattgt tgaaattagc caagttggat | 780 |
| ttcagtgttt tgcagtctat gcataaaaag gaattgtcac atatctgtaa gtggtggaaa | 840 |
| gatttagatt tacaaaataa gttacctat gtacgtgatc gtgttgtcga aggctacttc | 900 |
| tggatattgt ccatatacta tgagccacaa cacgctagaa caagaatgtt tttgatgaaa | 960 |
| acatgcatgg ggttagtagt tttggacgat acttttgata attatggaac atacgaagaa | 1020 |
| ttggagattt ttactcaagc cgtcgagaga tggtctatct catgcttaga tatgttgccc | 1080 |

```
gaatatatga aattaatcta ccaagaatta gtcaatttgc atgtggaaat ggaagaatct    1140
ttggaaaagg agggaaagac ctatcagatt cattacgtta aggagatggc taaagaatta    1200
gttcgtaatt acttagtaga agcaagatgg ttgaaggaag ttatatgcc tactttagaa     1260 gaatacatgt ctgtttctat ggttactggt acttatggtt tgatgattgc aaggtcctat    1320
gttggcagag gagacattgt tactgaagac acattcaaat gggtttctag ttacccacct    1380
attattaaag cttcctgtgt aatagtaaga ttaatggacg atattgtatc tcacaaggaa    1440
gaacaagaaa gaggacatgt ggcttcatct atagaatgtt actctaaaga atcaggtgct    1500
tctgaagagg aagcatgtga atatattagt aggaaagttg aggatgcctg gaaagtaatc    1560
aatagagaat ctttgcgtcc aacagccgtt cccttcccctt tgttaatgcc agcaataaac   1620
ttagctagaa tgtgtgaggt cttgtactct gttaatgatg gttttactca tgctgagggt    1680
gacatgaaat cttatatgaa gtccttcttc gttcatccta tggtcgtttg actcgag       1737

<210> SEQ ID NO 122
<211> LENGTH: 7348
<212> TYPE: DNA
<213> ORGANISM: Artificial Sequence
<220> FEATURE:
<223> OTHER INFORMATION: Synthetic Vector pAM178

<400> SEQUENCE: 122
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcgggctgg cttaactatg cggcatcaga gcagattgta ctgagagtgc     180
accatatcga ctacgtcgta aggccgtttc tgacagagta aaattcttga gggaactttc    240
accattatgg gaaatgcttc aagaaggtat tgacttaaac tccatcaaat ggtcaggtca    300
ttgagtgttt tttatttgtt gtatttttt tttttagag aaaatcctcc aatatcaaat      360
taggaatcgt agtttcatga ttttctgtta cacctaactt tttgtgtggt gccctcctcc    420
ttgtcaatat taatgttaaa gtgcaattct ttttccttat cacgttgagc cattagtatc    480
aatttgctta cctgtattcc tttactatcc tcctttttct ccttcttgat aaatgtatgt    540
agattgcgta tatagtttcg tctaccctat gaacatattc cattttgtaa tttcgtgtcg    600
tttctattat gaatttcatt tataaagttt atgtacaaat atcataaaaa aagagaatct    660
ttttaagcaa ggattttctt aacttcttcg gcgacagcat caccgacttc ggtggtactg    720
ttggaaccac ctaaatcacc agttctgata cctgcatcca aaaccttttt aactgcatct    780
tcaatggcct taccttcttc aggcaagttc aatgacaatt tcaacatcat tgcagcagac    840
aagatagtgg cgatagggtc aaccttattc tttggcaaat ctggagcaga accgtggcat    900
ggttcgtaca aaccaaatgc ggtgttcttg tctggcaaag aggccaagga cgcagatggc    960
aacaaaccca aggaacctgg gataacggag gcttcatcgg agatgatatc accaaacatg   1020
ttgctggtga ttataatacc atttaggtgg gttgggttct taactaggat catggcggca   1080
gaatcaatca attgatgttg aaccttcaat gtagggaatt cgttcttgat ggtttcctcc   1140 acagttttc tccataatct tgaagaggcc aaaagattag ctttatccaa ggaccaaata   1200
ggcaatggtg gctcatgttg tagggccatg aaagcggcca ttcttgtgat tctttgcact   1260
tctggaacgg tgtattgttc actatcccaa gcgacaccat caccatcgtc ttcctttctc   1320
ttaccaaagt aaataccctcc cactaattct ctgacaacaa cgaagtcagt acctttagca   1380
aattgtggct tgattggaga taagtctaaa agagagtcgg atgcaaagtt acatggtctt   1440
```

```
aagttggcgt acaattgaag ttctttacgg attttagta aaccttgttc aggtctaaca    1500
ctaccggtac cccatttagg accagccaca gcacctaaca aaacggcatc aaccttcttg    1560
gaggcttcca gcgcctcatc tggaagtgga acacctgtag catcgatagc agcaccacca    1620
attaaatgat tttcgaaatc gaacttgaca ttggaacgaa catcagaaat gctttaaga     1680 accttaatgg cttcggctgt gatttcttga ccaacgtggt cacctggcaa aacgacgatc    1740
ttcttagggg cagacattac aatggtatat ccttgaaata tatataaaaa aaggcgcctt    1800
agaccgctcg gccaaacaac caattacttg ttgagaaata gagtataatt atcctataaa    1860
tataacgttt ttgaacacac atgaacaagg aagtacagga caattgattt tgaagagaat    1920
gtggattttg atgtaattgt tgggattcca tttttaataa ggcaataata ttaggtatgt    1980
ggatatacta gaagttctcc tcgaccgtcg atatgcggtg tgaaataccg cacagatgcg    2040
taaggagaaa ataccgcatc aggaaattgt aaacgttaat attttgttaa aattcgcgtt    2100 aaattttgt taaatcagct cattttttaa ccaataggcc gaaatcggca aaatccctta    2160
taaatcaaaa gaatagaccg ataggggtt gagtgttgtt ccagtttgga acaagagtcc    2220
actattaaag aacgtggact ccaacgtcaa agggcgaaaa accgtctatc agggcgatgg    2280
cccactacgt gaaccatcac cctaatcaag ttttttgggg tcgaggtgcc gtaaagcact    2340
aaatcggaac cctaaaggga gcccccgatt tagagcttga cggggaaagc cggcgaacgt    2400
ggcgagaaag gaagggaaga aagcgaaagg agcgggcgct agggcgctgg caagtgtagc    2460
ggtcacgctg cgcgtaacca ccacacccgc cgcgcttaat gcgccgctac agggcgcgtc    2520
gcgccattcg ccattcaggc tgcgcaactg ttgggaaggg cgatcggtgc gggcctcttc    2580
gctattacgc cagctgaatt ggagcgacct catgctatac ctgagaaagc aacctgacct    2640
acaggaaaga gttactcaag aataagaatt ttcgttttaa aacctaagag tcactttaaa    2700
atttgtatac acttattttt tttataactt atttaataat aaaaatcata aatcataaga    2760
aattcgctta tttagaagtg tcaacaacgt atctaccaac gatttgaccc ttttccatct    2820
tttcgtaaat ttctggcaag gtagacaagc cgacaacctt gattggagac ttgaccaaac    2880
ctctggcgaa gaattgttaa ttaagagctc agatcttatc gtcgtcatcc ttgtaatcca    2940
tcgatactag tgcggccgcc ctttagtgag ggttgaattc gaattttcaa aaattcttac    3000
tttttttttg gatggacgca aagaagttta ataatcatat tacatggcat taccaccata    3060
tacatatcca tatacatatc catatctaat cttacttata tgttgtggaa atgtaaagag    3120
ccccattatc ttagcctaaa aaaaccttct ctttggaact ttcagtaata cgcttaactg    3180
ctcattgcta tattgaagta cggattagaa gccgccgagc gggtgacagc cctccgaagg    3240
aagactctcc tccgtgcgtc ctcgtcttca ccggtcgcgt tcctgaaacg cagatgtgcc    3300
tcgcgccgca ctgctccgaa caataaagat tctacaatac tagcttttat ggttatgaag    3360
aggaaaaatt ggcagtaacc tggccccaca aaccttcaaa tgaacgaatc aaattaacaa    3420
ccataggatg ataatgcgat tagttttta gccttatttc tggggtaatt aatcagcgaa    3480
gcgatgattt ttgatctatt aacagatata taaatgcaaa aactgcataa ccactttaac    3540
taatactttc aacattttcg gtttgtatta cttcttattc aaatgtaata aaagtatcaa    3600
caaaaaattg ttaatatacc tctatacttt aacgtcaagg agaaaaaacc ccggatccgt    3660
aatacgactc actataggc ccgggcgtcg acatggaaca gaagttgatt tccgaagaag    3720
acctcgagta agcttggtac cgcggctagc taagatccgc tctaaccgaa aaggaaggag    3780
ttagacaacc tgaagtctag gtccctattt attttttat agttatgtta gtattaagaa    3840
```

```
cgttatttat atttcaaatt tttcttttt ttctgtacag acgcgtgtac gcatgtaaca   3900
ttatactgaa aaccttgctt gagaaggttt tgggacgctc gaagatccag ctgcattaat   3960
gaatcggcca acgcgcgggg agaggcggtt tgcgtattgg gcgctcttcc gcttcctcgc   4020
tcactgactc gctgcgctcg gtcgttcggc tgcggcgagc ggtatcagct cactcaaagg   4080
cggtaatacg gttatccaca gaatcagggg ataacgcagg aaagaacatg tgagcaaaag   4140
gccagcaaaa ggccaggaac cgtaaaaagg ccgcgttgct ggcgtttttc cataggctcc   4200
gcccccctga cgagcatcac aaaaatcgac gctcaagtca gaggtggcga aacccgacag   4260
gactataaag ataccaggcg tttccccctg gaagctccct cgtgcgctct cctgttccga   4320
ccctgccgct taccggatac ctgtccgcct ttctcccttc gggaagcgtg gcgctttctc   4380
atagctcacg ctgtaggtat ctcagttcgg tgtaggtcgt tcgctccaag ctgggctgtg   4440
tgcacgaacc ccccgttcag cccgaccgct gcgccttatc cggtaactat cgtcttgagt   4500
ccaacccggt aagacacgac ttatcgccac tggcagcagc cactggtaac aggattagca   4560
gagcgaggta tgtaggcggt gctacagagt tcttgaagtg gtggcctaac tacggctaca   4620
ctagaaggac agtatttggt atctgcgctc tgctgaagcc agttaccttc ggaaaaagag   4680
ttggtagctc ttgatccggc aaacaaacca ccgctggtag cggtggtttt tttgtttgca   4740
agcagcagat tacgcgcaga aaaaaaggat ctcaagaaga tcctttgatc ttttctacgg   4800
ggtctgacgc tcagtggaac gaaaactcac gttaagggat tttggtcatg agattatcaa   4860
aaaggatctt cacctagatc cttttaaatt aaaaatgaag ttttaaatca atctaaagta   4920
tatatgagta aacttggtct gacagttacc aatgcttaat cagtgaggca cctatctcag   4980
cgatctgtct atttcgttca tccatagttg cctgactccc cgtcgtgtag ataactacga   5040
tacgggaggg cttaccatct ggccccagtg ctgcaatgat accgcgagac ccacgctcac   5100
cggctccaga tttatcagca ataaaccagc cagccggaag ggccgagcgc agaagtggtc   5160
ctgcaacttt atccgcctcc atccagtcta ttaattgttg ccgggaagct agagtaagta   5220
gttcgccagt taatagtttg cgcaacgttg ttgccattgc tacaggcatc gtggtgtcac   5280
gctcgtcgtt tggtatggct tcattcagct ccggttccca acgatcaagg cgagttacat   5340
gatcccccat gttgtgcaaa aaagcggtta gctccttcgg tcctccgatc gttgtcagaa   5400
gtaagttggc cgcagtgtta tcactcatgg ttatggcagc actgcataat tctcttactg   5460
tcatgccatc cgtaagatgc ttttctgtga ctggtgagta ctcaaccaag tcattctgag   5520
aatagtgtat gcggcgaccg agttgctctt gcccggcgtc aatacgggat aataccgcgc   5580
cacatagcag aactttaaaa gtgctcatca ttggaaaacg ttcttcgggg cgaaaactct   5640
caaggatctt accgctgttg agatccagtt cgatgtaacc cactcgtgca cccaactgat   5700
cttcagcatc ttttactttc accagcgttt ctgggtgagc aaaaacagga aggcaaaatg   5760
ccgcaaaaaa gggaataagg gcgacacgga aatgttgaat actcatactc ttcctttttc   5820
aatattattg aagcatttat cagggttatt gtctcatgag cggatacata tttgaatgta   5880
tttagaaaaa taaacaaata ggggttccgc gcacatttcc ccgaaaagtg ccacctgaac   5940
gaagcatctg tgcttcattt tgtagaacaa aaatgcaacg cgagagcgct aattttttcaa   6000
acaaagaatc tgagctgcat ttttacagaa cagaaatgca acgcgaaagc gctatttttac   6060
caacgaagaa tctgtgcttc attttttgtaa aacaaaaatg caacgcgaga gcgctaattt   6120
ttcaaacaaa gaatctgagc tgcatttttta cagaacagaa atgcaacgcg agagcgctat   6180
tttaccaaca aagaatctat acttcttttt tgttctacaa aaatgcatcc cgagagcgct   6240
```

```
attttttctaa caaagcatct tagattactt tttttctcct ttgtgcgctc tataatgcag    6300
tctcttgata acttttttgca ctgtaggtcc gttaaggtta gaagaaggct actttggtgt    6360
ctattttctc ttccataaaa aaagcctgac tccacttccc gcgtttactg attactagcg    6420
aagctgcggg tgcatttttt caagataaag gcatccccga ttatattcta taccgatgtg    6480
gattgcgcat actttgtgaa cagaaagtga tagcgttgat gattcttcat tggtcagaaa    6540
attatgaacg gtttcttcta ttttgtctct atatactacg tataggaaat gtttacattt    6600
tcgtattgtt ttcgattcac tctatgaata gttcttacta caatttttttt gtctaaagag    6660 taatactaga gataaacata aaaaatgtag aggtcgagtt tagatgcaag ttcaaggagc    6720
gaaaggtgga tgggtaggtt atataggat atagcacaga gatatatagc aaagagatac    6780
ttttgagcaa tgtttgtgga agcggtattc gcaatatttt agtagctcgt tacagtccgg    6840
tgcgtttttg gttttttgaa agtgcgtctt cagagcgctt ttggttttca aaagcgctct    6900
gaagttccta tactttctag agaataggaa cttcggaata ggaacttcaa agcgtttccg    6960
aaaacgagcg cttccgaaaa tgcaacgcga gctgcgcaca tacagctcac tgttcacgtc    7020
gcacctatat ctgcgtgttg cctgtatata tatatacatg agaagaacgg catagtgcgt    7080
gtttatgctt aaatgcgtac ttatatgcgt ctatttatgt aggatgaaag gtagtctagt    7140
acctcctgtg atattatccc attccatgcg gggtatcgta tgcttccttc agcactaccc    7200
tttagctgtt ctatatgctg ccactcctca attggattag tctcatcctt caatgctatc    7260
atttcctttg atattggatc atactaagaa accattatta tcatgacatt aacctataaa    7320
aataggcgta tcacgaggcc ctttcgtc                                       7348
```

<210> SEQ ID NO 123
<211> LENGTH: 746
<212> TYPE: DNA
<213> ORGANISM: Artificial Sequence
<220> FEATURE:
<223> OTHER INFORMATION: Synthetic URA3 knockout construct

<400> SEQUENCE: 123

```
tgcgaggcat atttatggtg aaggataagt tttgaccatc aaagaaggtt aatgtggctg      60
tggtttcagg gtccataaag cttttcaatt catctttttt tttttttgttc ttttttttga    120 ttccggtttc tttgaaattt ttttgattcg gtaatctccg agcagaagga agaacgaagg    180
aaggagcaca gacttagatt ggtatatata cgcatatgtg gtgttgaaga acatgaaat    240 tgcccagtat tcttaaccca actgcacaga acaaaaacct gcaggaaacg gctcacacgc    300
ggccaggggg agccctgtat tataagtaaa tgcatgtata ctaaactcac aaattagagc    360
ttcaatttaa ttatatcagt tattacccgg gaatctcggt cgtaatgatt tctataatga    420
cgaaaaaaaa aaaattggaa agaaaaagct tcatggcctt tataaaaagg aactatccaa    480
tacctcgcca gaaccaagta acagtatttt acggggcaca aatcaagaac aataagacag    540
gactgtaaag atggacgcat tgaactccaa agaacaacaa gagttccaaa agtagtgga    600 acaaaagcaa atgaaggatt tcatgcgttt gtactctaat ctggtagaaa gatgtttcac    660
agactgtgtc aatgacttca caacatcaaa gctaaccaat aaggaacaaa catgcatcat    720
gaagtgctca gaaaagttct tgaagc                                         746
```

<210> SEQ ID NO 124
<211> LENGTH: 27
<212> TYPE: DNA
<213> ORGANISM: Artificial Sequence

```
<220> FEATURE:
<223> OTHER INFORMATION: Synthetic Primer JU-106-168-110-ERG9 CDS-f

<400> SEQUENCE: 124
atgggaaagc tattacaatt ggcattg                                         27

<210> SEQ ID NO 125
<211> LENGTH: 34
<212> TYPE: DNA
<213> ORGANISM: Artificial Sequence
<220> FEATURE:
<223> OTHER INFORMATION: Synthetic Primer JU-107-168-110-ERG9 CDS-r

<400> SEQUENCE: 125
attcaagttg taattttcat ctaagatgta gtcg                                 34

<210> SEQ ID NO 126
<211> LENGTH: 20
<212> TYPE: DNA
<213> ORGANISM: Artificial Sequence
<220> FEATURE:
<223> OTHER INFORMATION: Synthetic Primer JU-108-168-110-ERG9 US-f

<400> SEQUENCE: 126
aaaagtgcag ctcagagccc                                                 20

<210> SEQ ID NO 127
<211> LENGTH: 37
<212> TYPE: DNA
<213> ORGANISM: Artificial Sequence
<220> FEATURE:
<223> OTHER INFORMATION: Synthetic Primer JU-162-168-110-LEU2 DS-f

<400> SEQUENCE: 127
aaagattctc ttttttatg atatttgtac ataaact                               37

<210> SEQ ID NO 128
<211> LENGTH: 28
<212> TYPE: DNA
<213> ORGANISM: Artificial Sequence
<220> FEATURE:
<223> OTHER INFORMATION: Synthetic Primer JU-163-168-110-LEU2 DS-r

<400> SEQUENCE: 128
tagatttagt actgaagagg aggtcgac                                        28

<210> SEQ ID NO 129
<211> LENGTH: 37
<212> TYPE: DNA
<213> ORGANISM: Artificial Sequence
<220> FEATURE:
<223> OTHER INFORMATION: Synthetic Primer JU-164-168-110-LEU2 US-f

<400> SEQUENCE: 129
taggataatt atactctatt tctcaacaag taattgg                              37

<210> SEQ ID NO 130
<211> LENGTH: 41
<212> TYPE: DNA
<213> ORGANISM: Artificial Sequence
<220> FEATURE:
<223> OTHER INFORMATION: Synthetic Primer JU-165-168-110-LEU2 US-r

<400> SEQUENCE: 130
tagaatggta tatccttgaa atatatatat atatattgct g                         41
```

```
<210> SEQ ID NO 131
<211> LENGTH: 25
<212> TYPE: DNA
<213> ORGANISM: Artificial Sequence
<220> FEATURE:
<223> OTHER INFORMATION: Synthetic Primer JU-169-168-110-URA3-f

<400> SEQUENCE: 131
gttcatcatc tcatggatct gcaca                                           25

<210> SEQ ID NO 132
<211> LENGTH: 23
<212> TYPE: DNA
<213> ORGANISM: Artificial Sequence
<220> FEATURE:
<223> OTHER INFORMATION: Synthetic Primer JU-170-168-110-URA3-r

<400> SEQUENCE: 132
atgcgtccat ctttacagtc ctg                                             23

<210> SEQ ID NO 133
<211> LENGTH: 60
<212> TYPE: DNA
<213> ORGANISM: Artificial Sequence
<220> FEATURE:
<223> OTHER INFORMATION: Synthetic Primer JU-172-168-110-ERG9 US-r1

<400> SEQUENCE: 133
gtgtgtgtgt gatatgtgac gtgtatacgt tttccgcttc tgcttttcgt cttttctctt     60

<210> SEQ ID NO 134
<211> LENGTH: 25
<212> TYPE: DNA
<213> ORGANISM: Artificial Sequence
<220> FEATURE:
<223> OTHER INFORMATION: Synthetic Primer JU-218-168-130-GAL80US-F

<400> SEQUENCE: 134
cagatggaat cccttccata gagag                                           25

<210> SEQ ID NO 135
<211> LENGTH: 20
<212> TYPE: DNA
<213> ORGANISM: Artificial Sequence
<220> FEATURE:
<223> OTHER INFORMATION: Synthetic Primer JU-219-168-130-GAL80US-R

<400> SEQUENCE: 135
gacgggagtg gaaagaacgg                                                 20

<210> SEQ ID NO 136
<211> LENGTH: 21
<212> TYPE: DNA
<213> ORGANISM: Artificial Sequence
<220> FEATURE:
<223> OTHER INFORMATION: Synthetic Primer JU-220-168-130-GAL80DS-F

<400> SEQUENCE: 136
aagcatcttg ccctgtgctt g                                               21

<210> SEQ ID NO 137
<211> LENGTH: 23
<212> TYPE: DNA
<213> ORGANISM: Artificial Sequence
<220> FEATURE:
<223> OTHER INFORMATION: Synthetic Primer JU-221-168-130-GAL80DS-R

<400> SEQUENCE: 137
```
catgctacct tccatggttg agc                                           23

<210> SEQ ID NO 138
<211> LENGTH: 44
<212> TYPE: DNA
<213> ORGANISM: Artificial Sequence
<220> FEATURE:
<223> OTHER INFORMATION: Synthetic Primer JU-284-275-31-GAL4-FIX-F2

<400> SEQUENCE: 138
ggattttatg cccagggatg cacttcatgg atttgattgg tctg                    44

<210> SEQ ID NO 139
<211> LENGTH: 44
<212> TYPE: DNA
<213> ORGANISM: Artificial Sequence
<220> FEATURE:
<223> OTHER INFORMATION: Synthetic Primer JU-285-275-31-GAL4-FIX-R2

<400> SEQUENCE: 139
cagaccaatc aaatccatga agtgcatccc tgggcataaa atcc                    44

<210> SEQ ID NO 140
<211> LENGTH: 29
<212> TYPE: DNA
<213> ORGANISM: Artificial Sequence
<220> FEATURE:
<223> OTHER INFORMATION: Synthetic Primer JU-286-275-31-GAL4-F

<400> SEQUENCE: 140
atgaagctac tgtcttctat cgaacaagc                                     29

<210> SEQ ID NO 141
<211> LENGTH: 24
<212> TYPE: DNA
<213> ORGANISM: Artificial Sequence
<220> FEATURE:
<223> OTHER INFORMATION: Synthetic Primer JU-287-275-31-GAL4-R

<400> SEQUENCE: 141
tgagcgaagc ttctgaataa gccc                                          24

<210> SEQ ID NO 142
<211> LENGTH: 50
<212> TYPE: DNA
<213> ORGANISM: Artificial Sequence
<220> FEATURE:
<223> OTHER INFORMATION: Synthetic Primer KB454-266-53

<400> SEQUENCE: 142
gacggcacgg ccacgcgttt aaaccgccat ccaattcctc tattatatgc              50

<210> SEQ ID NO 143
<211> LENGTH: 41
<212> TYPE: DNA
<213> ORGANISM: Artificial Sequence
<220> FEATURE:
<223> OTHER INFORMATION: Synthetic Primer KB455-266-53

<400> SEQUENCE: 143 ggctcccct ggccgcgtgt gagcgtggcg gaaagaacag c                        41

<210> SEQ ID NO 144
<211> LENGTH: 50
<212> TYPE: DNA
<213> ORGANISM: Artificial Sequence

```
<220> FEATURE:
<223> OTHER INFORMATION: Synthetic Primer KB457-266-53

<400> SEQUENCE: 144
cccgccaggc gctggggttt aaacaccgtt tgccttttaa ctatatcagg          50

<210> SEQ ID NO 145
<211> LENGTH: 54
<212> TYPE: DNA
<213> ORGANISM: Artificial Sequence
<220> FEATURE:
<223> OTHER INFORMATION: Synthetic Primer KMH14-276-4-linker9.ERG12.rev

<400> SEQUENCE: 145
cccgccaggc gctggggttt aaacaccgat gtcattaccg ttcttaactt ctgc     54

<210> SEQ ID NO 146
<211> LENGTH: 49
<212> TYPE: DNA
<213> ORGANISM: Artificial Sequence
<220> FEATURE:
<223> OTHER INFORMATION: Synthetic Primer KMH15-276-4-linker9.ERG19.rev

<400> SEQUENCE: 146
cccgccaggc gctggggttt aaacaccgat gaccgtttac acagcatcc           49

<210> SEQ ID NO 147
<211> LENGTH: 40
<212> TYPE: DNA
<213> ORGANISM: Artificial Sequence
<220> FEATURE:
<223> OTHER INFORMATION: Synthetic Primer KMH33-276-21-URA3 5 prime fwd

<400> SEQUENCE: 147
tgcgaggcat atttatggtg aaggataagt tttgaccatc                     40

<210> SEQ ID NO 148
<211> LENGTH: 64
<212> TYPE: DNA
<213> ORGANISM: Artificial Sequence
<220> FEATURE:
<223> OTHER INFORMATION: Synthetic Primer KMH34-276-21-URA3 5 prime rev

<400> SEQUENCE: 148
ggctccccct ggccgcgtgt gagccgtttc ctgcaggttt ttgttctgtg cagttgggtt  60
aaga                                                           64

<210> SEQ ID NO 149
<211> LENGTH: 73
<212> TYPE: DNA
<213> ORGANISM: Artificial Sequence
<220> FEATURE:
<223> OTHER INFORMATION: Synthetic Primer KMH35-276-21-URA3 3 prime fwd

<400> SEQUENCE: 149
gctcacacgc ggccaggggg agccctgtat tataagtaaa tgcatgtata ctaaactcac  60
aaattagagc ttc                                                 73

<210> SEQ ID NO 150
<211> LENGTH: 40
<212> TYPE: DNA
<213> ORGANISM: Artificial Sequence
<220> FEATURE:
<223> OTHER INFORMATION: Synthetic Primer KMH35-276-21-URA3 3 prime rev

<400> SEQUENCE: 150
```

```
gcttcaagaa cttttctgag cacttcatga tgcatgtttg                          40
```

<210> SEQ ID NO 151
<211> LENGTH: 44
<212> TYPE: DNA
<213> ORGANISM: Artificial Sequence
<220> FEATURE:
<223> OTHER INFORMATION: Synthetic Primer KMH46-276-43-ERG12linker4.fwd

<400> SEQUENCE: 151

```
aacctgcagg ccgcgagcgc cgatattcgc gggtggaagg acct                     44
```

<210> SEQ ID NO 152
<211> LENGTH: 49
<212> TYPE: DNA
<213> ORGANISM: Artificial Sequence
<220> FEATURE:
<223> OTHER INFORMATION: Synthetic Primer KMH47-276-43-ERG19linker4.fwd

<400> SEQUENCE: 152

```
aacctgcagg ccgcgagcgc cgatcttgtg ctaagtggtg ctgttagac                49
```

<210> SEQ ID NO 153
<211> LENGTH: 59
<212> TYPE: DNA
<213> ORGANISM: Artificial Sequence
<220> FEATURE:
<223> OTHER INFORMATION: Synthetic Primer
       KMH5-276-1-linker3.FS(Kozak).fwd

<400> SEQUENCE: 153

```
atccccgcgt gcttggccgg ccgtaattaa taatgtcaac tttgcctatt tcttctgtg     59
```

<210> SEQ ID NO 154
<211> LENGTH: 46
<212> TYPE: DNA
<213> ORGANISM: Artificial Sequence
<220> FEATURE:
<223> OTHER INFORMATION: Synthetic Primer KMH7-276-1-linker4.TCYC1.rev

<400> SEQUENCE: 154

```
tacggcgctc gcggcctgca ggttcttcga gcgtcccaaa accttc                   46
```

<210> SEQ ID NO 155
<211> LENGTH: 53
<212> TYPE: DNA
<213> ORGANISM: Artificial Sequence
<220> FEATURE:
<223> OTHER INFORMATION: Synthetic Primer KMH81-276-116-TDH3.rev.tHMG1

<400> SEQUENCE: 155

```
ggtctgcagc cattattaat ttgtttgttt atgtgtgttt attcgaaact aag           53
```

<210> SEQ ID NO 156
<211> LENGTH: 56
<212> TYPE: DNA
<213> ORGANISM: Artificial Sequence
<220> FEATURE:
<223> OTHER INFORMATION: Synthetic Primer KMH82-276-116-tHMG1.fwd.TDH3

<400> SEQUENCE: 156

```
cgaataaaca cacataaaca acaaattaa taatggctgc agaccaattg gtgaag         56
```

<210> SEQ ID NO 157
<211> LENGTH: 56
<212> TYPE: DNA

<213> ORGANISM: Artificial Sequence
<220> FEATURE:
<223> OTHER INFORMATION: Synthetic Primer KMH8-276-1-linker4.tHMG1.fwd

<400> SEQUENCE: 157
aacctgcagg ccgcgagcgc cgatagttat gacaattaca acaacagaat tctttc    56

<210> SEQ ID NO 158
<211> LENGTH: 56
<212> TYPE: DNA
<213> ORGANISM: Artificial Sequence
<220> FEATURE:
<223> OTHER INFORMATION: Synthetic Primer KMH91-276-116-TDH3.rev.FS

<400> SEQUENCE: 158
taggcaaagt tgacattatt aatttgtttg tttatgtgtg tttattcgaa actaag    56

<210> SEQ ID NO 159
<211> LENGTH: 54
<212> TYPE: DNA
<213> ORGANISM: Artificial Sequence
<220> FEATURE:
<223> OTHER INFORMATION: Synthetic Primer KMH92-276-116-FS.fwd.TDH3

<400> SEQUENCE: 159
aaacacacat aaacaaacaa attaataatg tcaactttgc ctatttcttc tgtg    54

<210> SEQ ID NO 160
<211> LENGTH: 48
<212> TYPE: DNA
<213> ORGANISM: Artificial Sequence
<220> FEATURE:
<223> OTHER INFORMATION: Synthetic Primer KMH9-276-1-linker9.tHMG1.rev

<400> SEQUENCE: 160
cccgccaggc gctggggttt aaacaccgat ggctgcagac caattggt    48

<210> SEQ ID NO 161
<211> LENGTH: 47
<212> TYPE: DNA
<213> ORGANISM: Artificial Sequence
<220> FEATURE:
<223> OTHER INFORMATION: Synthetic Primer KMH93-276-130-3 prime
      IME.linker4.fwd

<400> SEQUENCE: 161
aacctgcagg ccgcgagcgc cgatctcgaa aagtactaca atcttcc    47

<210> SEQ ID NO 162
<211> LENGTH: 44
<212> TYPE: DNA
<213> ORGANISM: Artificial Sequence
<220> FEATURE:
<223> OTHER INFORMATION: Synthetic Primer PW-91-093-CPK422-G

<400> SEQUENCE: 162
gatgtgtatt actagtgtcg acgacagcat tcgcccagta tttt    44

<210> SEQ ID NO 163
<211> LENGTH: 24
<212> TYPE: DNA
<213> ORGANISM: Artificial Sequence
<220> FEATURE:
<223> OTHER INFORMATION: Synthetic Primer TRIX_K_0142

<400> SEQUENCE: 163
gtattccaat gagaatcgct agaa    24

<210> SEQ ID NO 164
<211> LENGTH: 23
<212> TYPE: DNA
<213> ORGANISM: Artificial Sequence
<220> FEATURE:
<223> OTHER INFORMATION: Synthetic Primer TRIX_K_0143

<400> SEQUENCE: 164
ttcgtctgtt tttatccctc ttc                                      23

<210> SEQ ID NO 165
<211> LENGTH: 20
<212> TYPE: DNA
<213> ORGANISM: Artificial Sequence
<220> FEATURE:
<223> OTHER INFORMATION: Synthetic Primer TRIX_K_131

<400> SEQUENCE: 165
cctctcttaa aatgatggcg                                          20

<210> SEQ ID NO 166
<211> LENGTH: 30
<212> TYPE: DNA
<213> ORGANISM: Artificial Sequence
<220> FEATURE:
<223> OTHER INFORMATION: Synthetic Primer TRIX_L_034

<400> SEQUENCE: 166
gacggtagca acaagaatat agcacgagcc                               30

<210> SEQ ID NO 167
<211> LENGTH: 36
<212> TYPE: DNA
<213> ORGANISM: Artificial Sequence
<220> FEATURE:
<223> OTHER INFORMATION: Synthetic Primer TRIX_L_035

<400> SEQUENCE: 167
ttttgaggga atattcaact gttttttttt atcatg                        36

<210> SEQ ID NO 168
<211> LENGTH: 34
<212> TYPE: DNA
<213> ORGANISM: Artificial Sequence
<220> FEATURE:
<223> OTHER INFORMATION: Synthetic Primer TRIX_L_036

<400> SEQUENCE: 168 tttttttatca tgttgatgct ctgcataata atgc                         34

<210> SEQ ID NO 169
<211> LENGTH: 34
<212> TYPE: DNA
<213> ORGANISM: Artificial Sequence
<220> FEATURE:
<223> OTHER INFORMATION: Synthetic Primer TRIX_L_053

<400> SEQUENCE: 169
tttgtttgtt tatgtgtgtt tattcgaaac taag                          34

<210> SEQ ID NO 170
<211> LENGTH: 27
<212> TYPE: DNA
<213> ORGANISM: Artificial Sequence
<220> FEATURE:
<223> OTHER INFORMATION: Synthetic Primer TRIX_L_106

```
<400> SEQUENCE: 170
atgtctcaga acgtttacat tgtatcg                                          27

<210> SEQ ID NO 171
<211> LENGTH: 27
<212> TYPE: DNA
<213> ORGANISM: Artificial Sequence
<220> FEATURE:
<223> OTHER INFORMATION: Synthetic Primer TRIX_L_107

<400> SEQUENCE: 171
aggcagccaa gacattgatt aacatcc                                          27

<210> SEQ ID NO 172
<211> LENGTH: 29
<212> TYPE: DNA
<213> ORGANISM: Artificial Sequence
<220> FEATURE:
<223> OTHER INFORMATION: Synthetic Primer TRIX_L_109

<400> SEQUENCE: 172
atgaaactct ctactaaact ttgttggtg                                        29

<210> SEQ ID NO 173
<211> LENGTH: 28
<212> TYPE: DNA
<213> ORGANISM: Artificial Sequence
<220> FEATURE:
<223> OTHER INFORMATION: Synthetic Primer TRIX_L_110

<400> SEQUENCE: 173
atgagaaaaa aaatcggttg ggcttaac                                         28

<210> SEQ ID NO 174
<211> LENGTH: 26
<212> TYPE: DNA
<213> ORGANISM: Artificial Sequence
<220> FEATURE:
<223> OTHER INFORMATION: Synthetic Primer TRIX_L_112

<400> SEQUENCE: 174
atgtcattac cgttcttaac ttctgc                                           26

<210> SEQ ID NO 175
<211> LENGTH: 25
<212> TYPE: DNA
<213> ORGANISM: Artificial Sequence
<220> FEATURE:
<223> OTHER INFORMATION: Synthetic Primer TRIX_L_113

<400> SEQUENCE: 175
attcgcgggt ggaaggacct tgtgg                                            25

<210> SEQ ID NO 176
<211> LENGTH: 27
<212> TYPE: DNA
<213> ORGANISM: Artificial Sequence
<220> FEATURE:
<223> OTHER INFORMATION: Synthetic Primer TRIX_L_115

<400> SEQUENCE: 176
atgaccgttt acacagcatc cgttacc                                          27

<210> SEQ ID NO 177
<211> LENGTH: 25
```

<212> TYPE: DNA
<213> ORGANISM: Artificial Sequence
<220> FEATURE:
<223> OTHER INFORMATION: Synthetic Primer TRIX_L_116

<400> SEQUENCE: 177
cttgtgctaa gtggtgctgt tagac						25

<210> SEQ ID NO 178
<211> LENGTH: 25
<212> TYPE: DNA
<213> ORGANISM: Artificial Sequence
<220> FEATURE:
<223> OTHER INFORMATION: Synthetic Primer TRIX_L_118

<400> SEQUENCE: 178
atgtcagagt tgagagcctt cagtg						25

<210> SEQ ID NO 179
<211> LENGTH: 23
<212> TYPE: DNA
<213> ORGANISM: Artificial Sequence
<220> FEATURE:
<223> OTHER INFORMATION: Synthetic Primer TRIX_L_119

<400> SEQUENCE: 179
agtgcacact ttcaagctaa cac						23

<210> SEQ ID NO 180
<211> LENGTH: 27
<212> TYPE: DNA
<213> ORGANISM: Artificial Sequence
<220> FEATURE:
<223> OTHER INFORMATION: Synthetic Primer TRIX_L_121

<400> SEQUENCE: 180
atgactgccg acaacaatag tatgccc					27

<210> SEQ ID NO 181
<211> LENGTH: 26
<212> TYPE: DNA
<213> ORGANISM: Artificial Sequence
<220> FEATURE:
<223> OTHER INFORMATION: Synthetic Primer TRIX_L_122

<400> SEQUENCE: 181
catcagtggg aaacattcaa gaggcc					26

<210> SEQ ID NO 182
<211> LENGTH: 30
<212> TYPE: DNA
<213> ORGANISM: Artificial Sequence
<220> FEATURE:
<223> OTHER INFORMATION: Synthetic Primer TRIX_L_124

<400> SEQUENCE: 182
atggcttcag aaaagaaat taggagagag				30

<210> SEQ ID NO 183
<211> LENGTH: 30
<212> TYPE: DNA
<213> ORGANISM: Artificial Sequence
<220> FEATURE:
<223> OTHER INFORMATION: Synthetic Primer TRIX_L_125

<400> SEQUENCE: 183
tgaggtcgtt gcttttccta ttattatatg				30

<210> SEQ ID NO 184
<211> LENGTH: 28
<212> TYPE: DNA
<213> ORGANISM: Artificial Sequence
<220> FEATURE:
<223> OTHER INFORMATION: Synthetic Primer TRIX_L_193

<400> SEQUENCE: 184
tcgacactag taatacacat catcgtcc                                        28

<210> SEQ ID NO 185
<211> LENGTH: 28
<212> TYPE: DNA
<213> ORGANISM: Artificial Sequence
<220> FEATURE:
<223> OTHER INFORMATION: Synthetic Primer TRIX_L_194

<400> SEQUENCE: 185
gagctcctcg agaagttaag attatatg                                        28

<210> SEQ ID NO 186
<211> LENGTH: 26
<212> TYPE: DNA
<213> ORGANISM: Artificial Sequence
<220> FEATURE:
<223> OTHER INFORMATION: Synthetic Primer TRIX_L_194

<400> SEQUENCE: 186
atggctgcag atcaattggt gaagac                                          26

<210> SEQ ID NO 187
<211> LENGTH: 32
<212> TYPE: DNA
<213> ORGANISM: Artificial Sequence
<220> FEATURE:
<223> OTHER INFORMATION: Synthetic Primer TRIX_L_233

<400> SEQUENCE: 187
agttatgaca attacaacaa cagaattctt tc                                   32

<210> SEQ ID NO 188
<211> LENGTH: 32
<212> TYPE: DNA
<213> ORGANISM: Artificial Sequence
<220> FEATURE:
<223> OTHER INFORMATION: Synthetic Primer GW-52-84 pAM326 BamHI

<400> SEQUENCE: 188
taataaggat ccatgtcaac tttgcctatt tc                                   32

<210> SEQ ID NO 189
<211> LENGTH: 32
<212> TYPE: DNA
<213> ORGANISM: Artificial Sequence
<220> FEATURE:
<223> OTHER INFORMATION: Synthetic Primer GW-52-84 pAM326 NheI

<400> SEQUENCE: 189
ttatagctag ctcaaacgac cataggatga ac                                   32

<210> SEQ ID NO 190
<211> LENGTH: 26
<212> TYPE: DNA
<213> ORGANISM: Artificial Sequence
<220> FEATURE:
<223> OTHER INFORMATION: Synthetic Primer TRIX_L_266

-continued

```
<400> SEQUENCE: 190 tactttttt ttggatggac gcaaag                                               26

<210> SEQ ID NO 191
<211> LENGTH: 29
<212> TYPE: DNA
<213> ORGANISM: Artificial Sequence
<220> FEATURE:
<223> OTHER INFORMATION: Synthetic Primer TRIX_L_267

<400> SEQUENCE: 191
aagtatagag gtatattaac aattttttg                                           29

<210> SEQ ID NO 192
<211> LENGTH: 30
<212> TYPE: DNA
<213> ORGANISM: Artificial Sequence
<220> FEATURE:
<223> OTHER INFORMATION: Synthetic Primer TRIX_RN017

<400> SEQUENCE: 192
acgaagtgac tgacagaata ctgacatcag                                          30

<210> SEQ ID NO 193
<211> LENGTH: 30
<212> TYPE: DNA
<213> ORGANISM: Artificial Sequence
<220> FEATURE:
<223> OTHER INFORMATION: Synthetic Primer TRIX_RN018

<400> SEQUENCE: 193
ttaaaagttg tttccgctgt atcctgtatc                                          30

<210> SEQ ID NO 194
<211> LENGTH: 30
<212> TYPE: DNA
<213> ORGANISM: Artificial Sequence
<220> FEATURE:
<223> OTHER INFORMATION: Synthetic Primer TRIX_RN019

<400> SEQUENCE: 194
agtatacact aaattttatg caataataaa                                          30

<210> SEQ ID NO 195
<211> LENGTH: 30
<212> TYPE: DNA
<213> ORGANISM: Artificial Sequence
<220> FEATURE:
<223> OTHER INFORMATION: Synthetic Primer TRIX_RN020

<400> SEQUENCE: 195
ggttttgcta aggaagtttt ggagtatgct                                          30

<210> SEQ ID NO 196
<211> LENGTH: 26
<212> TYPE: DNA
<213> ORGANISM: Artificial Sequence
<220> FEATURE:
<223> OTHER INFORMATION: Synthetic Primer TRIX_Z025

<400> SEQUENCE: 196
cacgaaaatc gttattgtct tgaagg                                              26

<210> SEQ ID NO 197
<211> LENGTH: 52
```

```
<212> TYPE: DNA
<213> ORGANISM: Artificial Sequence
<220> FEATURE:
<223> OTHER INFORMATION: Synthetic Primer TRIX_Z026

<400> SEQUENCE: 197
gctttatgga ccctgaaacc actcactatt attccataag atgatcatta gc        52

<210> SEQ ID NO 198
<211> LENGTH: 54
<212> TYPE: DNA
<213> ORGANISM: Artificial Sequence
<220> FEATURE:
<223> OTHER INFORMATION: Synthetic Primer TRIX_Z027

<400> SEQUENCE: 198
gcttcaattt aattatatca gttattacca cgaaaatcgt tattgtcttg aagg       54

<210> SEQ ID NO 199
<211> LENGTH: 30
<212> TYPE: DNA
<213> ORGANISM: Artificial Sequence
<220> FEATURE:
<223> OTHER INFORMATION: Synthetic Primer TRIX_Z028

<400> SEQUENCE: 199
tcactattat tccataagat gatcattagc                                  30

<210> SEQ ID NO 200
<211> LENGTH: 22
<212> TYPE: DNA
<213> ORGANISM: Artificial Sequence
<220> FEATURE:
<223> OTHER INFORMATION: Synthetic Primer TRIX_Z033

<400> SEQUENCE: 200
gtggtttcag ggtccataaa gc                                          22

<210> SEQ ID NO 201
<211> LENGTH: 28
<212> TYPE: DNA
<213> ORGANISM: Artificial Sequence
<220> FEATURE:
<223> OTHER INFORMATION: Synthetic Primer TRIX_Z034

<400> SEQUENCE: 201
gtaataactg atataattaa attgaagc                                    28

<210> SEQ ID NO 202
<211> LENGTH: 39
<212> TYPE: DNA
<213> ORGANISM: Artificial Sequence
<220> FEATURE:
<223> OTHER INFORMATION: Synthetic Primer TRIX_Z035

<400> SEQUENCE: 202
ctgttgacat tgcgaagagt gacaaagatt ttgttatcg                        39

<210> SEQ ID NO 203
<211> LENGTH: 39
<212> TYPE: DNA
<213> ORGANISM: Artificial Sequence
<220> FEATURE:
<223> OTHER INFORMATION: Synthetic Primer TRIX_Z036

<400> SEQUENCE: 203
cgataacaaa atctttgtca ctcttcgcaa tgtcaacag                        39
```

```
<210> SEQ ID NO 204
<211> LENGTH: 45
<212> TYPE: DNA
<213> ORGANISM: Artificial Sequence
<220> FEATURE:
<223> OTHER INFORMATION: Synthetic Primer VH228-235-7-URA3LOF3RYSE12-1F

<400> SEQUENCE: 204
gctcacacgc ggccaggggg agcctcacta ttattccata agatg            45

<210> SEQ ID NO 205
<211> LENGTH: 46
<212> TYPE: DNA
<213> ORGANISM: Artificial Sequence
<220> FEATURE:
<223> OTHER INFORMATION: Synthetic Primer VH229-235-7-URA3LOF3RYSE12-1R

<400> SEQUENCE: 205
aggtccgccg gcgttggacg agcgcacgaa aatcgttatt gtcttg           46

<210> SEQ ID NO 206
<211> LENGTH: 198
<212> TYPE: DNA
<213> ORGANISM: Artificial Sequence
<220> FEATURE:
<223> OTHER INFORMATION: Synthetic DNA fragment

<400> SEQUENCE: 206
cacgaaaatc gttattgtct tgaaggtgaa atttctactc ttattaatgg tgaacgttaa     60
gctgatgcta tgatggaagc tgattggtct taacttgctt gtcatcttgc taatggtcat    120
atggctcgtg ttattactta agttatttgt actcgttttg aacgtaatgc taatgatcat    180
cttatggaat aatagtga                                                 198

<210> SEQ ID NO 207
<211> LENGTH: 2733
<212> TYPE: DNA
<213> ORGANISM: Artificial Sequence
<220> FEATURE:
<223> OTHER INFORMATION: Synthetic pRYSE Entry vector 2

<400> SEQUENCE: 207
gtaaaacgac ggccagtatt aaccctcact aaagggaact cgaggctctt cagctcacac     60
gcggccaggg ggagcctggc agactccata tgctatgcgg catcagagca gattgtactg    120
agagtgcacc atatgcggtg tgaaataccg cacagatgcg taaggagaaa ataccgcatc    180
aggcgccatt cgccattcag gctgcgcaac tgttgggaag ggcgatcggt gcgggcctct    240
tcgctattac gccagctggc gaaagggggga tgtgctgcaa ggcgattaag ttgggtaacg    300
ccagggtttt cccagtcacg acgttgtaaa acgacggcca gtgaattcga gctcggtacc    360
cggggatcct ctagcgtcga cctgcaggca tgcaagcttg gcgtaatcat ggtcatagct    420
gtttcctgtg tgaaattgtt atccgctcac aattccacac aacatacgag ccggaagcat    480
aaagtgtaaa gcctggggtg cctaatgagt gagctaactc acattaattg cgttgcgcgc    540
tagcgagtca tccacgctcg tccaacgccg gcggaccttg aagagcgagc tccgctgag    600 caataactag cgtcatagct gtttcctggg tcgttcggct gcggcgagcg gtatcagctc    660
actcaaaggc ggtaatacgg ttatccacag aatcagggga taacgcagga aagaacatgt    720
gagcaaaagg ccagcaaaag gccaggaacc gtaaaaaggc cgcgttgctg gcgttttttcc    780 ataggctccg cccccctgac gagcatcaca aaaatcgacg ctcaagtcag aggtggcgaa    840
```

```
acccgacagg actataaaga taccaggcgt ttccccctgg aagctccctc gtgcgctctc      900
ctgttccgac cctgccgctt acccgatacc tgtccgcctt tctcccttcg ggaagcgtgg      960
cgctttctca tagctcacgc tgtaggtatc tcagttcggt gtaggtcgtt cgctccaagc     1020
tgggctgtgt gcacgaaccc cccgttcagc ccgaccgctg cgccttatcc ggtaactatc     1080
gtcttgattc caacccggta agacacgact tatcgccact ggcagcagcc actggtaaca     1140
ggattagcag agcgaggtat gtaggcggtg ctacagagtt cttgaagtgg tggcctaact     1200
acggctacac tagaagaaca gtatttggta tctgcgctct gctgaagcca gttaccttcg     1260
gaaaaagagt tggtagctct tgatccggca aacaaaccac cgctggtagc ggtggttttt     1320
ttgtttgcaa gcagcagatt acgcgcagaa aaaaggatc tcaagaagat cctttgatct     1380
tttctacggg gtctgacgct cagtggaacg aaaactcacg ttaagggatt ttggtcatga     1440
gattatcaaa aaggatcttc acctagatcc ttttaaatta aaaatgaagt tttaaatcaa     1500
tctaaagtat atatgagtaa acttggtcgca tgcttaccaa tgcttaatca gtgaggcacc     1560
tatctcagcg atctgtctat ttcgttcatc catagttgcc tgactgcccg tcgtgtagat     1620
aactacgata cgggagggct taccatctgg ccccagtgct gcaatgatac cgcgagaccc     1680
acgctcaccg gctccagatt tatcagcaat aaaccagcca gccggaaggg ccgagcgcag     1740
aagtggtcct gcaactttat ccgcctccat ccagtctatt aattgttgcc gggaagctag     1800
agtaagtagt tcgccagtta atagtttgcg caacgttgtt gccattgcta caggcatcgt     1860
ggtgtcacgc tcgtcgtttg gtatggcttc attcagctcc ggttcccaac gatcaaggcg     1920
agttacatga tcccccatgt tgtgcaaaaa agcggttagc tccttcggtc ctccgatcgt     1980
tgtcagaagt aagttggccg cagtgttatc actcatggtt atggcagcac tgcataattc     2040
tcttactgtc atgccatccg taagatgctt ttctgtgact ggtgagtact caaccaagtc     2100
attctgagaa tagtgtatgc ggcgaccgag ttgctcttgc ccggcgtcaa tacgggataa     2160
taccgcgcca catagcagaa ctttaaaagt gctcatcatt ggaaaacgtt cttcggggcg     2220
aaaactctca aggatcttac cgctgttgag atccagttcg atgtaaccca ctcgtgcacc     2280
caactgatct tcagcatctt ttactttcac cagcgtttct gggtgagcaa aaacaggaag     2340
gcaaaatgcc gcaaaaaagg gaataagggc gacacggaaa tgttgaatac tcatcaattg     2400 ccttttttcaa tattattgaa gcatttatca gggttattgt ctcatgagcg gttacatatt     2460
tgaatgtatt tagaaaaata aacaaatagg ggttccgcgc acatttcccc gaaaagtgcc     2520
acctgacgtc taagaaacca ttattatcat gacattaacc tataaaaata ggcgtatcac     2580
gaggcccttt catctcgcgc gtttcggtga tgacggtgaa aacctctgac acatgcagct     2640
cccggagaca gtcacagctt gtctgtaagc ggatgccggg agcagacaag cccgtcaggg     2700
cgcgtcagcg ggtgttggcg ggtgtcgggg ctg                                  2733
```

<210> SEQ ID NO 208
<211> LENGTH: 2733
<212> TYPE: DNA
<213> ORGANISM: Artificial Sequence
<220> FEATURE:
<223> OTHER INFORMATION: Synthetic pRYSE Entry vector 3

<400> SEQUENCE: 208

```
gtaaaacgac ggccagtatt aaccctcact aaagggaact cgaggctctt cacgctcgtc       60
caacgccggc ggaccttggc agactccata tgctatgcgg catcagagca gattgtactg      120
agagtgcacc atatgcggtg tgaaataccg cacagatgcg taaggagaaa ataccgcatc      180
```

```
aggcgccatt cgccattcag gctgcgcaac tgttgggaag ggcgatcggt gcgggcctct    240
tcgctattac gccagctggc gaaaggggga tgtgctgcaa ggcgattaag ttgggtaacg    300
ccagggtttt cccagtcacg acgttgtaaa acgacggcca gtgaattcga gctcggtacc    360
cggggatcct ctagcgtcga cctgcaggca tgcaagcttg gcgtaatcat ggtcatagct    420
gtttcctgtg tgaaattgtt atccgctcac aattccacac aacatacgag ccggaagcat    480
aaagtgtaaa gcctggggtg cctaatgagt gagctaactc acattaattg cgttgcgcgc    540
tagcgagtca tccaatcccc gcgtgcttgg ccggccgttg aagagcgagc tcccgctgag    600
caataactag cgtcatagct gtttcctggg tcgttcggct gcggcgagcg gtatcagctc    660
actcaaaggc ggtaatacgg ttatccacag aatcagggga taacgcagga agaacatgt    720 gagcaaaagg ccagcaaaag gccaggaacc gtaaaaaggc cgcgttgctg gcgttttcc    780 ataggctccg ccccctgac gagcatcaca aaaatcgacg ctcaagtcag aggtggcgaa    840
acccgacagg actataaaga taccaggcgt ttcccctgg aagctccctc gtgcgctctc    900
ctgttccgac cctgccgctt acccgatacc tgtccgcctt ctcccttcg ggaagcgtgg    960 cgctttctca tagctcacgc tgtaggtatc tcagttcggt gtaggtcgtt cgctccaagc   1020
tgggctgtgt gcacgaaccc cccgttcagc ccgaccgctg cgccttatcc ggtaactatc   1080
gtcttgattc caacccggta agacacgact tatcgccact ggcagcagcc actggtaaca   1140
ggattagcag agcgaggtat gtaggcggtg ctacagagtt cttgaagtgg tggcctaact   1200
acggctacac tagaagaaca gtatttggta tctgcgctct gctgaagcca gttaccttcg   1260
gaaaaagagt tggtagctct tgatccggca acaaaccac cgctggtagc ggtggttttt   1320
ttgtttgcaa gcagcagatt acgcgcagaa aaaaggatc tcaagaagat cctttgatct   1380
tttctacggg gtctgacgct cagtggaacg aaaactcacg ttaagggatt ttggtcatga   1440
gattatcaaa aaggatcttc acctagatcc ttttaaatta aaaatgaagt tttaaatcaa   1500
tctaaagtat atatgagtaa cttggtcgca tgcttaccaa tgcttaatca gtgaggcacc   1560
tatctcagcg atctgtctat ttcgttcatc catagttgcc tgactgcccg tcgtgtagat   1620
aactacgata cgggagggct taccatctgg ccccagtgct gcaatgatac cgcgagaccc   1680
acgctcaccg gctccagatt tatcagcaat aaaccagcca gccggaaggg ccgagcgcag   1740
aagtggtcct gcaactttat ccgcctccat ccagtctatt aattgttgcc gggaagctag   1800
agtaagtagt tcgccagtta atagtttgcg caacgttgtt gccattgcta caggcatcgt   1860
ggtgtcacgc tcgtcgtttg gtatggcttc attcagctcc ggttcccaac gatcaaggcg   1920
agttacatga tcccccatgt tgtgcaaaaa agcggttagc tccttcggtc ctccgatcgt   1980
tgtcagaagt aagttggccg cagtgttatc actcatggtt atggcagcac tgcataattc   2040
tcttactgtc atgccatccg taagatgctt ttctgtgact ggtgagtact caaccaagtc   2100
attctgagaa tagtgtatgc ggcgaccgag ttgctcttgc ccggcgtcaa tacgggataa   2160
taccgcgcca catagcagaa ctttaaaagt gctcatcatt ggaaaacgtt cttcggggcg   2220
aaaactctca aggatcttac cgctgttgag atccagttcg atgtaaccca ctcgtgcacc   2280
caactgatct tcagcatctt ttactttcac cagcgtttct gggtgagcaa aaacaggaag   2340
gcaaaatgcc gcaaaaaagg gaataagggc gacacgaaaa tgttgaatac tcatcaattg   2400 ccttttttcaa tattattgaa gcatttatca gggttattgt ctcatgagcg gttacatatt   2460
tgaatgtatt tagaaaaata aacaaatagg ggttccgcgc acatttcccc gaaaagtgcc   2520
acctgacgtc taagaaacca ttattatcat gacattaacc tataaaaata ggcgtatcac   2580
```

```
gaggcccttt catctcgcgc gtttcggtga tgacggtgaa aacctctgac acatgcagct   2640
cccggagaca gtcacagctt gtctgtaagc ggatgccggg agcagacaag cccgtcaggg   2700
cgcgtcagcg ggtgttggcg ggtgtcgggg ctg                                2733
```

<210> SEQ ID NO 209
<211> LENGTH: 2733
<212> TYPE: DNA
<213> ORGANISM: Artificial Sequence
<220> FEATURE:
<223> OTHER INFORMATION: Synthetic pRYSE Entry vector 4

<400> SEQUENCE: 209

```
gtaaaacgac ggccagtatt aaccctcact aaagggaact cgaggctctt caatccccgc     60
gtgcttggcc ggccgttggc agactccata tgctatgcgg catcagagca gattgtactg    120
agagtgcacc atatgcggtg tgaaataccg cacagatgcg taaggagaaa ataccgcatc    180
aggcgccatt cgccattcag gctgcgcaac tgttgggaag ggcgatcggt gcgggcctct    240
tcgctattac gccagctggc gaaggggga tgtgctgcaa ggcgattaag ttgggtaacg    300
ccaggggttt cccagtcacg acgttgtaaa acgacggcca gtgaattcga gctcggtacc    360
cggggatcct ctagcgtcga cctgcaggca tgcaagcttg gcgtaatcat ggtcatagct    420
gtttcctgtg tgaaattgtt atccgctcac aattccacac aacatacgag ccggaagcat    480
aaagtgtaaa gcctggggtg cctaatgagt gagctaactc acattaattg cgttgcgcgc    540
tagcgagtca tccaaacctg caggccgcga gcgccgattg aagagcgagc tcccgctgag    600
caataactag cgtcatagct gtttcctggg tcgttcggct gcggcgagcg gtatcagctc    660
actcaaaggc ggtaatacgg ttatccacag aatcagggga taacgcagga agaacatgt    720 gagcaaaagg ccagcaaaag gccaggaacc gtaaaaaggc cgcgttgctg cgttttttcc    780
ataggctccg ccccctgac gagcatcaca aaaatcgacg ctcaagtcag aggtggcgaa    840
acccgacagg actataaaga taccaggcgt ttccccctgg aagctccctc gtgcgctctc    900
ctgttccgac cctgccgctt acccgatacc tgtccgcctt ctcccttcg ggaagcgtgg    960 cgctttctca tagctcacgc tgtaggtatc tcagttcggt gtaggtcgtt cgctccaagc   1020
tgggctgtgt gcacgaaccc cccgttcagc ccgaccgctg cgccttatcc ggtaactatc   1080
gtcttgattc caacccggta agacacgact tatcgccact ggcagcagcc actggtaaca   1140
ggattagcag agcgaggtat gtaggcggtg ctacagagtt cttgaagtgg tggcctaact   1200
acggctacac tagaagaaca gtatttggta tctgcgctct gctgaagcca gttaccttcg   1260
gaaaaagagt tggtagctct tgatccggca aacaaaccac cgctggtagc ggtggttttt   1320
ttgtttgcaa gcagcagatt acgcgcagaa aaaaggatc tcaagaagat cctttgatct   1380
tttctacggg gtctgacgct cagtggaacg aaaactcacg ttaagggatt ttggtcatga   1440
gattatcaaa aaggatcttc acctagatcc ttttaaatta aaaatgaagt tttaaatcaa   1500
tctaaagtat atatgagtaa cttggtcgca tgcttaccaa tgcttaatca gtgaggcacc   1560
tatctcagcg atctgtctat ttcgttcatc catagttgcc tgactgcccg tcgtgtagat   1620
aactacgata cgggagggct taccatctgg ccccagtgct gcaatgatac cgcgagaccc   1680
acgctcaccg gctccagatt tatcagcaat aaaccagcca gccggaaggg ccgagcgcag   1740
aagtggtcct gcaactttat ccgcctccat ccagtctatt aattgttgcc gggaagctag   1800
agtaagtagt tcgccagtta atagtttgcg caacgttgtt gccattgcta caggcatcgt   1860
ggtgtcacgc tcgtcgtttg gtatggcttc attcagctcc ggttcccaac gatcaaggcg   1920
```

```
agttacatga tcccccatgt tgtgcaaaaa agcggttagc tccttcggtc ctccgatcgt    1980
tgtcagaagt aagttggccg cagtgttatc actcatggtt atggcagcac tgcataattc    2040
tcttactgtc atgccatccg taagatgctt ttctgtgact ggtgagtact caaccaagtc    2100
attctgagaa tagtgtatgc ggcgaccgag ttgctcttgc ccggcgtcaa tacgggataa    2160
taccgcgcca catagcagaa ctttaaaagt gctcatcatt ggaaaacgtt cttcggggcg    2220
aaaactctca aggatcttac cgctgttgag atccagttcg atgtaaccca ctcgtgcacc    2280
caactgatct tcagcatctt ttactttcac cagcgtttct gggtgagcaa aacaggaag     2340 gcaaaatgcc gcaaaaaagg aataagggc gacacggaaa tgttgaatac tcatcaattg     2400 ccttttcaa tattattgaa gcatttatca gggttattgt ctcatgagcg ttacatatt      2460 tgaatgtatt tagaaaaata acaaatagg gttccgcgc acatttcccc gaaaagtgcc      2520
acctgacgtc taagaaacca ttattatcat gacattaacc tataaaaata ggcgtatcac    2580
gaggcccttt catctcgcgc gtttcggtga tgacggtgaa aacctctgac acatgcagct    2640
cccggagaca gtcacagctt gtctgtaagc ggatgccggg agcagacaag cccgtcaggg    2700
cgcgtcagcg ggtgttggcg ggtgtcgggg ctg                                2733

<210> SEQ ID NO 210
<211> LENGTH: 2733
<212> TYPE: DNA
<213> ORGANISM: Artificial Sequence
<220> FEATURE:
<223> OTHER INFORMATION: Synthetic pRYSE Entry vector 5

<400> SEQUENCE: 210
gtaaaacgac ggccagtatt aaccctcact aaagggaact cgaggctctt caaacctgca      60
ggccgcgagc gccgattggc agactccata tgctatgcgg catcagagca gattgtactg     120
agagtgcacc atatgcggtg tgaaatccg cacagatgcg taaggagaaa ataccgcatc      180
aggcgccatt cgccattcag gctgcgcaac tgttgggaag ggcgatcggt gcgggcctct     240
tcgctattac gccagctggc gaaagggggga tgtgctgcaa ggcgattaag ttgggtaacg    300
ccagggtttt cccagtcacg acgttgtaaa acgacggcca gtgaattcga gctcggtacc    360
cggggatcct ctagcgtcga cctgcaggca tgcaagcttg gcgtaatcat ggtcatagct    420
gtttcctgtg tgaaattgtt atccgctcac aattccacac aacatacgag ccggaagcat   480
aaagtgtaaa gcctggggtg cctaatgagt gagctaactc acattaattg cgttgcgcgc    540
tagcgagtca tccaaacgcg atcgccgacg ccgccgattg aagagcgagc tcccgctgag    600
caataactag cgtcatagct gtttcctggg tcgttcggct gcggcgagcg gtatcagctc    660
actcaaaggc ggtaatacgg ttatccacag aatcagggga taacgcagga agaacatgt     720 gagcaaaagg ccagcaaaag gccaggaacc gtaaaaaggc cgcgttgctg gcgtttttcc    780
ataggctccg cccccctgac gagcatcaca aaaatcgacg ctcaagtcag aggtggcgaa    840
acccgacagg actataaaga taccaggcgt ttccccctgg aagctccctc gtgcgctctc    900
ctgttccgac cctgccgctt acccgatacc tgtccgcctt tctcccttcg ggaagcgtgg    960
cgctttctca tagctcacgc tgtaggtatc tcagttcggt gtaggtcgtt cgctccaagc   1020
tgggctgtgt gcacgaaccc cccgttcagc ccgaccgctg cgccttatcc ggtaactatc   1080
gtcttgattc caaccggta agacacgact tatcgccact ggcagcagcc actggtaaca    1140
ggattagcag agcgaggtat gtaggcggtg ctacagagtt cttgaagtgg tggcctaact   1200
acggctacac tagaagaaca gtatttggta tctgcgctct gctgaagcca gttaccttcg   1260
```

```
gaaaaagagt tggtagctct tgatccggca aacaaaccac cgctggtagc ggtggttttt      1320
ttgtttgcaa gcagcagatt acgcgcagaa aaaaggatc tcaagaagat cctttgatct      1380
tttctacggg gtctgacgct cagtggaacg aaaactcacg ttaagggatt ttggtcatga      1440
gattatcaaa aaggatcttc acctagatcc ttttaaatta aaatgaagt tttaaatcaa      1500 tctaaagtat atatgagtaa cttggtcgca tgcttaccaa tgcttaatca gtgaggcacc      1560
tatctcagcg atctgtctat ttcgttcatc catagttgcc tgactgcccg tcgtgtagat      1620
aactacgata cgggagggct taccatctgg ccccagtgct gcaatgatac cgcgagaccc      1680
acgctcaccg gctccagatt tatcagcaat aaaccagcca gccggaaggg ccgagcgcag      1740
aagtggtcct gcaactttat ccgcctccat ccagtctatt aattgttgcc gggaagctag      1800
agtaagtagt tcgccagtta atagtttgcg caacgttgtt gccattgcta caggcatcgt      1860
ggtgtcacgc tcgtcgtttg gtatggcttc attcagctcc ggttcccaac gatcaaggcg      1920
agttacatga tcccccatgt tgtgcaaaaa agcggttagc tccttcggtc ctccgatcgt      1980
tgtcagaagt aagttggccg cagtgttatc actcatggtt atggcagcac tgcataattc      2040
tcttactgtc atgccatccg taagatgctt ttctgtgact ggtgagtact caaccaagtc      2100
attctgagaa tagtgtatgc ggcgaccgag ttgctcttgc ccggcgtcaa tacgggataa      2160
taccgcgcca catagcagaa ctttaaaagt gctcatcatt ggaaaacgtt cttcggggcg      2220
aaaactctca aggatcttac cgctgttgag atccagttcg atgtaaccca ctcgtgcacc      2280
caactgatct tcagcatctt ttactttcac cagcgtttct gggtgagcaa aaacaggaag      2340
gcaaaatgcc gcaaaaaagg aataagggc gacacggaaa tgttgaatac tcatcaattg      2400 ccttttcaa tattattgaa gcatttatca gggttattgt ctcatgagcg gttacatatt      2460
tgaatgtatt tagaaaaata aacaaatagg ggttccgcgc acatttcccc gaaaagtgcc      2520
acctgacgtc taagaaacca ttattatcat gacattaacc tataaaaata ggcgtatcac      2580
gaggcccttt catctcgcgc gtttcggtga tgacggtgaa aacctctgac acatgcagct      2640
cccggagaca gtcacagctt gtctgtaagc ggatgccggg agcagacaag cccgtcaggg      2700
cgcgtcagcg ggtgttggcg ggtgtcgggg ctg                                  2733

<210> SEQ ID NO 211
<211> LENGTH: 2733
<212> TYPE: DNA
<213> ORGANISM: Artificial Sequence
<220> FEATURE:
<223> OTHER INFORMATION: Synthetic pRYSE Entry vector 6

<400> SEQUENCE: 211
gtaaaacgac ggccagtatt aaccctcact aaagggaact cgaggctctt caaacgcgat       60
cgccgacgcc gccgattggc agactccata tgctatgcgg catcagagca gattgtactg      120
agagtgcacc atatgcggtg tgaaataccg cacagatgcg taaggagaaa ataccgcatc      180
aggcgccatt cgccattcag gctgcgcaac tgttgggaag ggcgatcggt gcgggcctct      240
tcgctattac gccagctggc gaaaggggga tgtgctgcaa ggcgattaag ttgggtaacg      300
ccagggtttt cccagtcacg acgttgtaaa acgacggcca gtgaattcga gctcggtacc      360
cggggatcct ctagcgtcga cctgcaggca tgcaagcttg gcgtaatcat ggtcatagct      420
gtttcctgtg tgaaattgtt atccgctcac aattccacac aacatacgag ccggaagcat      480
aaagtgtaaa gcctggggtg cctaatgagt gagctaactc acattaattg cgttgcgcgc      540
tagcgagtca tccaaaggcg gccgctggcg agggagattg aagagcgagc tcccgctgag      600
```

```
caataactag cgtcatagct gtttcctggg tcgttcggct gcggcgagcg gtatcagctc      660
actcaaaggc ggtaatacgg ttatccacag aatcagggga taacgcagga agaacatgt      720 gagcaaaagg ccagcaaaag gccaggaacc gtaaaaaggc cgcgttgctg gcgttttttcc    780 ataggctccg cccccctgac gagcatcaca aaaatcgacg ctcaagtcag aggtggcgaa     840
acccgacagg actataaaga taccaggcgt ttccccctgg aagctccctc gtgcgctctc     900
ctgttccgac cctgccgctt acccgatacc tgtccgcctt tctcccttcg ggaagcgtgg     960
cgctttctca tagctcacgc tgtaggtatc tcagttcggt gtaggtcgtt cgctccaagc    1020
tgggctgtgt gcacgaaccc cccgttcagc ccgaccgctg cgccttatcc ggtaactatc    1080
gtcttgattc aacccggta agacacgact tatcgccact ggcagcagcc actggtaaca    1140
ggattagcag agcgaggtat gtaggcggtg ctacagagtt cttgaagtgg tggcctaact    1200
acggctacac tagaagaaca gtatttggta tctgcgctct gctgaagcca gttaccttcg    1260
gaaaaagagt tggtagctct tgatccggca acaaaccac cgctggtagc ggtggttttt     1320
ttgtttgcaa gcagcagatt acgcgcagaa aaaaggatc tcaagaagat cctttgatct    1380
tttctacggg gtctgacgct cagtggaacg aaaactcacg ttaagggatt ttggtcatga    1440
gattatcaaa aaggatcttc acctagatcc ttttaaatta aaaatgaagt tttaaatcaa    1500
tctaaagtat atatgagtaa cttggtcgca tgcttaccaa tgcttaatca gtgaggcacc    1560
tatctcagcg atctgtctat ttcgttcatc catagttgcc tgactgcccg tcgtgtagat    1620
aactacgata cgggagggct taccatctgg ccccagtgct gcaatgatac cgcgagaccc    1680
acgctcaccg gctccagatt tatcagcaat aaaccagcca gccggaaggg ccgagcgcag    1740
aagtggtcct gcaactttat ccgcctccat ccagtctatt aattgttgcc gggaagctag    1800
agtaagtagt tcgccagtta atagtttgcg caacgttgtt gccattgcta caggcatcgt    1860
ggtgtcacgc tcgtcgtttg gtatggcttc attcagctcc ggttcccaac gatcaaggcg    1920
agttacatga tcccccatgt tgtgcaaaaa agcggttagc tccttcggtc ctccgatcgt    1980
tgtcagaagt aagttggccg cagtgttatc actcatggtt atggcagcac tgcataattc    2040
tcttactgtc atgccatccg taagatgctt ttctgtgact ggtgagtact caaccaagtc    2100
attctgagaa tagtgtatgc ggcgaccgag ttgctcttgc ccggcgtcaa tacgggataa    2160
taccgcgcca catagcagaa ctttaaaagt gctcatcatt ggaaaacgtt cttcggggcg    2220
aaaactctca aggatcttac cgctgttgag atccagttcg atgtaaccca ctcgtgcacc    2280
caactgatct tcagcatctt ttactttcac cagcgtttct gggtgagcaa aaacaggaag    2340
gcaaaatgcc gcaaaaaagg gaataagggc gacacggaaa tgttgaatac tcatcaattg    2400
cctttttcaa tattattgaa gcatttatca gggttattgt ctcatgagcg gttacatatt    2460
tgaatgtatt tagaaaaata acaaataggg gttccgcgc acatttcccc gaaaagtgcc    2520
acctgacgtc taagaaacca ttattatcat gacattaacc tataaaaata ggcgtatcac    2580
gaggcccttt catctcgcgc gtttcggtga tgacggtgaa aacctctgac acatgcagct    2640
cccggagaca gtcacagctt gtctgtaagc ggatgccggg agcagacaag cccgtcaggg    2700
cgcgtcagcg ggtgttggcg ggtgtcgggg ctg                                  2733
```

<210> SEQ ID NO 212
<211> LENGTH: 2733
<212> TYPE: DNA
<213> ORGANISM: Artificial Sequence
<220> FEATURE:
<223> OTHER INFORMATION: Synthetic pRYSE Entry vector 7

<400> SEQUENCE: 212

```
gtaaaacgac ggccagtatt aaccctcact aaagggaact cgaggctctt caaaggcggc      60
cgctggcgag ggagattggc agactccata tgctatgcgg catcagagca gattgtactg     120
agagtgcacc atatgcggtg tgaaataccg cacagatgcg taaggagaaa ataccgcatc     180
aggcgccatt cgccattcag gctgcgcaac tgttgggaag ggcgatcggt gcgggcctct     240
tcgctattac gccagctggc gaaaggggga tgtgctgcaa ggcgattaag ttgggtaacg     300
ccagggtttt cccagtcacg acgttgtaaa acgacggcca gtgaattcga gctcggtacc     360
cggggatcct ctagcgtcga cctgcaggca tgcaagcttg gcgtaatcat ggtcatagct     420
gtttcctgtg tgaaattgtt atccgctcac aattccacac aacatacgag ccggaagcat     480
aaagtgtaaa gcctggggtg cctaatgagt gagctaactc acattaattg cgttgcgcgc     540
tagcgagtca tccaaaggcg cgccacggtc gtgcggattg aagagcgagc tcccgctgag     600
caataactag cgtcatagct gtttcctggg tcgttcggct gcggcgagcg gtatcagctc     660
actcaaaggc ggtaatacgg ttatccacag aatcagggga taacgcagga agaacatgt     720
gagcaaaagg ccagcaaaag gccaggaacc gtaaaaaggc cgcgttgctg gcgttttcc     780
ataggctccg ccccccctgac gagcatcaca aaaatcgacg ctcaagtcag aggtggcgaa     840
acccgacagg actataaaga taccaggcgt ttccccctgg aagctccctc gtgcgctctc     900
ctgttccgac cctgccgctt acccgatacc tgtccgcctt tctcccttcg ggaagcgtgg     960
cgctttctca tagctcacgc tgtaggtatc tcagttcggt gtaggtcgtt cgctccaagc    1020
tgggctgtgt gcacgaaccc cccgttcagc ccgaccgctg cgccttatcc ggtaactatc    1080
gtcttgattc aacccggta agacacgact tatcgccact ggcagcagcc actggtaaca    1140
ggattagcag agcgaggtat gtaggcggtg ctacagagtt cttgaagtgg tggcctaact    1200
acggctacac tagaagaaca gtatttggta tctgcgctct gctgaagcca gttaccttcg    1260
gaaaaagagt tggtagctct tgatccggca aacaaaccac cgctggtagc ggtggttttt    1320
ttgtttgcaa gcagcagatt acgcgcagaa aaaaaggatc tcaagaagat cctttgatct    1380
tttctacggg gtctgacgct cagtggaacg aaaactcacg ttaagggatt ttggtcatga    1440
gattatcaaa aaggatcttc acctagatcc ttttaaatta aaaatgaagt tttaaatcaa    1500
tctaaagtat atatgagtaa cttggtcgca tgcttaccaa tgcttaatca gtgaggcacc    1560
tatctcagcg atctgtctat ttcgttcatc catagttgcc tgactgcccg tcgtgtagat    1620
aactacgata cgggagggct taccatctgg ccccagtgct gcaatgatac cgcgagaccc    1680
acgctcaccg gctccagatt tatcagcaat aaaccagcca gccggaaggg ccgagcgcag    1740
aagtggtcct gcaactttat ccgcctccat ccagtctatt aattgttgcc gggaagctag    1800
agtaagtagt tcgccagtta atagtttgcg caacgttgtt gccattgcta caggcatcgt    1860
ggtgtcacgc tcgtcgtttg gtatggcttc attcagctcc ggttcccaac gatcaaggcg    1920
agttacatga tcccccatgt tgtgcaaaaa agcggttagc tccttcggtc ctccgatcgt    1980
tgtcagaagt aagttggccg cagtgttatc actcatggtt atggcagcac tgcataattc    2040
tcttactgtc atgccatccg taagatgctt ttctgtgact ggtgagtact caaccaagtc    2100
attctgagaa tagtgtatgc ggcgaccgag ttgctcttgc ccggcgtcaa tacgggataa    2160
taccgcgcca catagcagaa ctttaaaagt gctcatcatt ggaaaacgtt cttcggggcg    2220
aaaactctca aggatcttac cgctgttgag atccagttcg atgtaaccca ctcgtgcacc    2280
caactgatct tcagcatctt ttactttcac cagcgtttct gggtgagcaa aaacaggaag    2340
```

| | |
|---|---:|
| gcaaaatgcc gcaaaaaagg gaataagggc gacacggaaa tgttgaatac tcatcaattg | 2400 |
| ccttttttcaa tattattgaa gcatttatca gggttattgt ctcatgagcg gttacatatt | 2460 |
| tgaatgtatt tagaaaaata aacaaatagg gttccgcgc acatttcccc gaaaagtgcc | 2520 |
| acctgacgtc taagaaacca ttattatcat gacattaacc tataaaaata ggcgtatcac | 2580 |
| gaggcccttt catctcgcgc gtttcggtga tgacggtgaa aacctctgac acatgcagct | 2640 |
| cccggagaca gtcacagctt gtctgtaagc ggatgccggg agcagacaag cccgtcaggg | 2700 |
| cgcgtcagcg ggtgttggcg ggtgtcgggg ctg | 2733 |

<210> SEQ ID NO 213
<211> LENGTH: 2733
<212> TYPE: DNA
<213> ORGANISM: Artificial Sequence
<220> FEATURE:
<223> OTHER INFORMATION: Synthetic pRYSE Entry vector 8

<400> SEQUENCE: 213

| | |
|---|---:|
| gtaaaacgac ggccagtatt aaccctcact aaagggaact cgaggctctt caaaggcgcg | 60 |
| ccacggtcgt gcggattggc agactccata tgctatgcgg catcagagca gattgtactg | 120 |
| agagtgcacc atatgcggtg tgaaataccg cacagatgcg taaggagaaa ataccgcatc | 180 |
| aggcgccatt cgccattcag gctgcgcaac tgttgggaag ggcgatcggt gcgggcctct | 240 |
| tcgctattac gccagctggc gaaaggggga tgtgctgcaa ggcgattaag ttgggtaacg | 300 |
| ccagggtttt cccagtcacg acgttgtaaa acgacggcca gtgaattcga gctcggtacc | 360 |
| cggggatcct ctagcgtcga cctgcaggca tgcaagcttg cgtaatcat ggtcatagct | 420 |
| gtttcctgtg tgaaattgtt atccgctcac aattccacac aacatacgag ccggaagcat | 480 |
| aaagtgtaaa gcctggggtg cctaatgagt gagctaactc acattaattg cgttgcgcgc | 540 |
| tagcgagtca tccaagcccc tcagcccccc tagcgtcgtg aagagcgagc tcccgctgag | 600 |
| caataactag cgtcatagct gtttcctggg tcgttcggct gcggcgagcg gtatcagctc | 660 |
| actcaaaggc ggtaatacgg ttatccacag aatcagggga taacgcagga agaacatgt | 720 |
| gagcaaaagg ccagcaaaag gccaggaacc gtaaaaaggc cgcgttgctg gcgttttttcc | 780 |
| ataggctccg ccccctgac gagcatcaca aaaatcgacg ctcaagtcag aggtggcgaa | 840 |
| acccgacagg actataaaga taccaggcgt ttccccctgg aagctccctc gtgcgctctc | 900 |
| ctgttccgac cctgccgctt acccgatacc tgtccgcctt ctccttcg ggaagcgtgg | 960 |
| cgctttctca tagctcacgc tgtaggtatc tcagttcggt gtaggtcgtt cgctccaagc | 1020 |
| tgggctgtgt gcacgaaccc cccgttcagc ccgaccgctg cgccttatcc ggtaactatc | 1080 |
| gtcttgattc caacccggta agacacgact tatcgccact ggcagcagcc actggtaaca | 1140 |
| ggattagcag agcgaggtat gtaggcggtg ctacagagtt cttgaagtgg tggcctaact | 1200 |
| acggctacac tagaagaaca gtatttggta tctgcgctct gctgaagcca gttaccttcg | 1260 |
| gaaaaagagt tggtagctct tgatccggca aacaaaccac cgctggtagc ggtggttttt | 1320 |
| ttgtttgcaa gcagcagatt acgcgcagaa aaaaaggatc tcaagaagat cctttgatct | 1380 |
| tttctacggg gtctgacgct cagtggaacg aaaactcacg ttaagggatt ttggtcatga | 1440 |
| gattatcaaa aaggatcttc acctagatcc ttttaaatta aaaatgaagt tttaaatcaa | 1500 |
| tctaaagtat atatgagtaa cttggtcgca tgcttaccaa tgcttaatca gtgaggcacc | 1560 |
| tatctcagcg atctgtctat ttcgttcatc catagttgcc tgactgcccg tcgtgtagat | 1620 |
| aactacgata cgggagggct taccatctgg ccccagtgct gcaatgatac cgcgagaccc | 1680 |

```
acgctcaccg gctccagatt tatcagcaat aaaccagcca gccggaaggg ccgagcgcag    1740
aagtggtcct gcaactttat ccgcctccat ccagtctatt aattgttgcc gggaagctag    1800
agtaagtagt tcgccagtta atagtttgcg caacgttgtt gccattgcta caggcatcgt    1860
ggtgtcacgc tcgtcgtttg gtatggcttc attcagctcc ggttcccaac gatcaaggcg    1920
agttacatga tcccccatgt tgtgcaaaaa agcggttagc tccttcggtc ctccgatcgt    1980
tgtcagaagt aagttggccg cagtgttatc actcatggtt atggcagcac tgcataattc    2040
tcttactgtc atgccatccg taagatgctt ttctgtgact ggtgagtact caaccaagtc    2100
attctgagaa tagtgtatgc ggcgaccgag ttgctcttgc ccggcgtcaa tacgggataa    2160
taccgcgcca catagcagaa ctttaaaagt gctcatcatt ggaaaacgtt cttcggggcg    2220
aaaactctca aggatcttac cgctgttgag atccagttcg atgtaaccca ctcgtgcacc    2280
caactgatct tcagcatctt ttactttcac cagcgtttct gggtgagcaa aaacaggaag    2340
gcaaaatgcc gcaaaaaagg gaataagggc gacacggaaa tgttgaatac tcatcaattg    2400 ccttttcaa tattattgaa gcatttatca gggttattgt ctcatgagcg gttacatatt    2460
tgaatgtatt tagaaaaata aacaaatagg ggttccgcgc acatttcccc gaaaagtgcc    2520
acctgacgtc taagaaacca ttattatcat gacattaacc tataaaaata ggcgtatcac    2580
gaggcccttt catctcgcgc gtttcggtga tgacggtgaa aacctctgac acatgcagct    2640
cccggagaca gtcacagctt gtctgtaagc ggatgccggg agcagacaag cccgtcaggg    2700
cgcgtcagcg ggtgttggcg ggtgtcgggg ctg                                 2733

<210> SEQ ID NO 214
<211> LENGTH: 2737
<212> TYPE: DNA
<213> ORGANISM: Artificial Sequence
<220> FEATURE:
<223> OTHER INFORMATION: Synthetic pRYSE Entry vector 9

<400> SEQUENCE: 214
gtaaaacgac ggccagtatt aaccctcact aaagggaact cgaggctctt cacgctcgtc      60
caacgccggc ggaccttggc agactccata tgctatgcgg catcagagca gattgtactg     120
agagtgcacc atatgcggtg tgaaataccg cacagatgcg taaggagaaa ataccgcatc     180
aggcgccatt cgccattcag gctgcgcaac tgttgggaag ggcgatcggt gcgggcctct     240
tcgctattac gccagctggc gaaagggggga tgtgctgcaa ggcgattaag ttgggtaacg     300
ccagggtttt cccagtcacg acgttgtaaa acgacggcca gtgaattcga gctcggtacc     360
cggggatcct ctagcgtcga cctgcaggca tgcaagcttg gcgtaatcat ggtcatagct     420
gtttcctgtg tgaaattgtt atccgctcac aattccacac aacatacgag ccggaagcat     480
aaagtgtaaa gcctggggtg cctaatgagt gagctaactc acattaattg cgttgcgcgc     540
tagcgagtca tccacggtgt ttaaacccca gcgcctggcg ggtgaagagc gagctcccgc     600
tgagcaataa ctagcgtcat agctgttttcc tgggtcgttc ggctgcggcg agcggtatca     660
gctcactcaa aggcggtaat acggttatcc acagaatcag gggataacgc aggaaagaac     720
atgtgagcaa aaggccagca aaaggccagg aaccgtaaaa aggccgcgtt gctggcgttt     780
ttccataggc tccgcccccc tgacgagcat cacaaaaatc gacgctcaag tcagaggtgg     840
cgaaacccga caggactata aagataccag gcgtttcccc ctggaagctc cctcgtgcgc     900
tctcctgttc cgaccctgcc gcttaccgga tacctgtccg cctttctccc ttcgggaagc     960
gtggcgcttt ctcatagctc acgctgtagg tatctcagtt cggtgtaggt cgttcgctcc    1020
```

```
aagctgggct gtgtgcacga accccccgtt cagcccgacc gctgcgcctt atccggtaac   1080
tatcgtcttg attccaaccc ggtaagacac gacttatcgc cactggcagc agccactggt   1140
aacaggatta gcagagcgag gtatgtaggc ggtgctacag agttcttgaa gtggtggcct   1200
aactacggct acactagaag aacagtattt ggtatctgcg ctctgctgaa gccagttacc   1260
ttcggaaaaa gagttggtag ctcttgatcc ggcaaacaaa ccaccgctgg tagcggtggt   1320
ttttttgttt gcaagcagca gattacgcgc agaaaaaaag gatctcaaga agatcctttg   1380
atcttttcta cggggtctga cgctcagtgg aacgaaaact cacgttaagg gattttggtc   1440
atgagattat caaaaaggat cttcacctag atccttttaa attaaaaatg aagttttaaa   1500
tcaatctaaa gtatatatga gtaacttggt cgcatgctta ccaatgctta atcagtgagg   1560
cacctatctc agcgatctgt ctatttcgtt catccatagt tgcctgactg cccgtcgtgt   1620
agataactac gatacgggag ggcttaccat ctggccccag tgctgcaatg ataccgcgag   1680
acccacgctc accggctcca gatttatcag caataaacca gccagccgga agggccgagc   1740
gcagaagtgg tcctgcaact ttatccgcct ccatccagtc tattaattgt tgccgggaag   1800
ctagagtaag tagttcgcca gttaatagtt tgcgcaacgt tgttgccatt gctacaggca   1860
tcgtggtgtc acgctcgtcg tttggtatgg cttcattcag ctccggttcc caacgatcaa   1920
ggcgagttac atgatccccc atgttgtgca aaaaagcggt tagctccttc ggtcctccga   1980
tcgttgtcag aagtaagttg gccgcagtgt tatcactcat ggttatggca gcactgcata   2040
attctcttac tgtcatgcca tccgtaagat gcttttctgt gactggtgag tactcaacca   2100
agtcattctg agaatagtgt atgcggcgac cgagttgctc ttgcccggcg tcaatacggg   2160
ataataccgc gccacatagc agaactttaa aagtgctcat cattggaaaa cgttcttcgg   2220
ggcgaaaact ctcaaggatc ttaccgctgt tgagatccag ttcgatgtaa cccactcgtg   2280
cacccaactg atcttcagca tcttttactt tcaccagcgt ttctgggtga gcaaaaacag   2340
gaaggcaaaa tgccgcaaaa aagggaataa gggcgacacg gaaatgttga atactcatca   2400
attgcctttt tcaatattat tgaagcattt atcagggtta ttgtctcatg agcggttaca   2460
tatttgaatg tatttagaaa aataaacaaa taggggttcc gcgcacattt ccccgaaaag   2520
tgccacctga cgtctaagaa accattatta tcatgacatt aacctataaa aataggcgta   2580
tcacgaggcc ctttcatctc gcgcgtttcg gtgatgacgg tgaaaacctc tgacacatgc   2640
agctcccgga gacagtcaca gcttgtctgt aagcggatgc cgggagcaga caagcccgtc   2700
agggcgcgtc agcgggtgtt ggcgggtgtc ggggctg                             2737
```

<210> SEQ ID NO 215
<211> LENGTH: 2737
<212> TYPE: DNA
<213> ORGANISM: Artificial Sequence
<220> FEATURE:
<223> OTHER INFORMATION: Synthetic pRYSE Entry vector 10

<400> SEQUENCE: 215

```
gtaaaacgac ggccagtatt aaccctcact aaagggaact cgaggctctt caatccccgc     60
gtgcttggcc ggccgttggc agactccata tgctatgcgg catcagagca gattgtactg    120
agagtgcacc atatgcggtg tgaaataccg cacagatgcg taaggagaaa ataccgcatc    180
aggcgccatt cgccattcag gctgcgcaac tgttgggaag ggcgatcggt gcgggcctct    240
tcgctattac gccagctggc gaaagggggga tgtgctgcaa ggcgattaag ttgggtaacg    300
ccagggtttt cccagtcacg acgttgtaaa acgacggcca gtgaattcga gctcggtacc    360
```

```
cggggatcct ctagcgtcga cctgcaggca tgcaagcttg gcgtaatcat ggtcatagct    420
gtttcctgtg tgaaattgtt atccgctcac aattccacac aacatacgag ccggaagcat    480
aaagtgtaaa gcctggggtg cctaatgagt gagctaactc acattaattg cgttgcgcgc    540
tagcgagtca tccacggtgt ttaaacccca gcgcctggcg ggtgaagagc gagctcccgc    600
tgagcaataa ctagcgtcat agctgttccc tgggtcgttc ggctgcggcg agcggtatca    660
gctcactcaa aggcggtaat acggttatcc acagaatcag gggataacgc aggaaagaac    720
atgtgagcaa aaggccagca aaaggccagg aaccgtaaaa aggccgcgtt gctggcgttt    780
ttccataggc tccgcccccc tgacgagcat cacaaaaatc gacgctcaag tcagaggtgg    840
cgaaacccga caggactata agataccagg cgtttccccc tggaagctc cctcgtgcgc     900 tctcctgttc cgaccctgcc gcttaccga tacctgtccg cctttctccc ttcgggaagc     960
gtggcgcttt ctcatagctc acgctgtagg tatctcagtt cggtgtaggt cgttcgctcc    1020
aagctgggct gtgtgcacga accccccgtt cagcccgacc gctgcgcctt atccggtaac    1080
tatcgtcttg attccaaccc ggtaagacac gacttatcgc cactggcagc agccactggt    1140
aacaggatta gcagagcgag gtatgtaggc ggtgctacag agttcttgaa gtggtggcct    1200
aactacggct acactagaag aacagtattt ggtatctgcg ctctgctgaa gccagttacc    1260
ttcggaaaaa gagttggtag ctcttgatcc ggcaaacaaa ccaccgctgg tagcggtggt    1320 tttttttgttt gcaagcagca gattacgcgc agaaaaaaag gatctcaaga agatcctttg    1380
atcttttcta cggggtctga cgctcagtgg aacgaaaact cacgttaagg gattttggtc    1440
atgagattat caaaaaggat cttcacctag atccttttaa attaaaaatg aagttttaaa    1500
tcaatctaaa gtatatatga gtaacttggt cgcatgctta ccaatgctta atcagtgagg    1560
cacctatctc agcgatctgt ctatttcgtt catccatagt tgcctgactg cccgtcgtgt    1620
agataactac gatacgggag gcttaccat ctggccccag tgctgcaatg ataccgcgag    1680
acccacgctc accggctcca gatttatcag caataaacca gccagccgga agggccgagc    1740
gcagaagtgg tcctgcaact ttatccgcct ccatccagtc tattaattgt tgccgggaag    1800
ctagagtaag tagttcgcca gttaatagtt tgcgcaacgt tgttgccatt gctacaggca    1860
tcgtggtgtc acgctcgtcg tttggtatgg cttcattcag ctccggttcc caacgatcaa    1920
ggcgagttac atgatccccc atgttgtgca aaaaagcggt tagctccttc ggtcctccga    1980
tcgttgtcag aagtaagttg gccgcagtgt tatcactcat ggttatggca gcactgcata    2040
attctcttac tgtcatgcca tccgtaagat gcttttctgt gactggtgag tactcaacca    2100
agtcattctg agaatagtgt atgcggcgac cgagttgctc ttgcccggcg tcaatacggg    2160
ataataccgc gccacatagc agaactttaa aagtgctcat cattggaaaa cgttcttcgg    2220
ggcgaaaact ctcaaggatc ttaccgctgt tgagatccag ttcgatgtaa cccactcgtg    2280
cacccaactg atcttcagca tcttttactt tcaccagcgt ttctgggtga gcaaaaacag    2340
gaaggcaaaa tgccgcaaaa aagggaataa gggcgacacg gaaatgttga atactcatca    2400
attgcctttt tcaatattat tgaagcattt atcagggtta ttgtctcatg agcggttaca    2460
tatttgaatg tatttagaaa aataaacaaa taggggttcc gcgcacattt ccccgaaaag    2520
tgccacctga cgtctaagaa accattatta tcatgacatt aacctataaa aataggcgta    2580
tcacgaggcc ctttcatctc gcgcgtttcg gtgatgacgg tgaaaacctc tgacacatgc    2640
agctcccgga gacagtcaca gcttgtctgt aagcggatgc cgggagcaga caagcccgtc    2700
agggcgcgtc agcgggtgtt ggcgggtgtc ggggctg                             2737
```

<210> SEQ ID NO 216
<211> LENGTH: 2737
<212> TYPE: DNA
<213> ORGANISM: Artificial Sequence
<220> FEATURE:
<223> OTHER INFORMATION: Synthetic pRYSE Entry vector 11

<400> SEQUENCE: 216

| | | | | | |
|---|---|---|---|---|---|
| gtaaaacgac | ggccagtatt | aaccctcact | aaagggaact | cgaggctctt | caaacctgca | 60 |
| ggccgcgagc | gccgattggc | agactccata | tgctatgcgg | catcagagca | gattgtactg | 120 |
| agagtgcacc | atatgcggtg | tgaaataccg | cacagatgcg | taaggagaaa | ataccgcatc | 180 |
| aggcgccatt | cgccattcag | gctgcgcaac | tgttgggaag | ggcgatcggt | gcgggcctct | 240 |
| tcgctattac | gccagctggc | gaaagggga | tgtgctgcaa | ggcgattaag | ttgggtaacg | 300 |
| ccagggtttt | cccagtcacg | acgttgtaaa | acgacggcca | gtgaattcga | gctcggtacc | 360 |
| cggggatcct | ctagcgtcga | cctgcaggca | tgcaagcttg | gcgtaatcat | ggtcatagct | 420 |
| gtttcctgtg | tgaaattgtt | atccgctcac | aattccacac | aacatacgag | ccggaagcat | 480 |
| aaagtgtaaa | gcctggggtg | cctaatgagt | gagctaactc | acattaattg | cgttgcgcgc | 540 |
| tagcgagtca | tccacggtgt | ttaaaccccca | gcgcctggcg | ggtgaagagc | gagctcccgc | 600 |
| tgagcaataa | ctagcgtcat | agctgtttcc | tgggtcgttc | ggctgcggcg | agcggtatca | 660 |
| gctcactcaa | aggcggtaat | acggttatcc | acagaatcag | gggataacgc | aggaaagaac | 720 |
| atgtgagcaa | aaggccagca | aaaggccagg | aaccgtaaaa | aggccgcgtt | gctggcgttt | 780 |
| ttccataggc | tccgcccccc | tgacgagcat | cacaaaaatc | gacgctcaag | tcagaggtgg | 840 |
| cgaaacccga | caggactata | aagataccag | gcgtttcccc | ctggaagctc | cctcgtgcgc | 900 |
| tctcctgttc | cgaccctgcc | gcttacccga | tacctgtccg | cctttctccc | ttcgggaagc | 960 |
| gtggcgcttt | ctcatagctc | acgctgtagg | tatctcagtt | cggtgtaggt | cgttcgctcc | 1020 |
| aagctgggct | gtgtgcacga | accccccgtt | cagcccgacc | gctgcgcctt | atccggtaac | 1080 |
| tatcgtcttg | attccaaccc | ggtaagacac | gacttatcgc | cactggcagc | agccactggt | 1140 |
| aacaggatta | gcagagcgag | gtatgtaggc | ggtgctacag | agttcttgaa | gtggtggcct | 1200 |
| aactacggct | acactagaag | aacagtattt | ggtatctgcg | ctctgctgaa | gccagttacc | 1260 |
| ttcggaaaaa | gagttggtag | ctcttgatcc | ggcaaacaaa | ccaccgctgg | tagcggtggt | 1320 |
| ttttttgttt | gcaagcagca | gattacgcgc | agaaaaaaag | gatctcaaga | agatcctttg | 1380 |
| atcttttcta | cggggtctga | cgctcagtgg | aacgaaaact | cacgttaagg | gattttggtc | 1440 |
| atgagattat | caaaaaggat | cttcacctag | atccttttaa | attaaaaatg | aagttttaaa | 1500 |
| tcaatctaaa | gtatatatga | gtaacttggt | cgcatgctta | ccaatgctta | atcagtgagg | 1560 |
| cacctatctc | agcgatctgt | ctatttcgtt | catccatagt | tgcctgactg | cccgtcgtgt | 1620 |
| agataactac | gatacgggag | ggcttaccat | ctggccccag | tgctgcaatg | ataccgcgag | 1680 |
| acccacgctc | accggctcca | gatttatcag | caataaacca | gccagccgga | agggccgagc | 1740 |
| gcagaagtgg | tcctgcaact | ttatccgcct | ccatccagtc | tattaattgt | tgccgggaag | 1800 |
| ctagagtaag | tagttcgcca | gttaatagtt | tgcgcaacgt | tgttgccatt | gctacaggca | 1860 |
| tcgtggtgtc | acgctcgtcg | tttggtatgg | cttcattcag | ctccggttcc | caacgatcaa | 1920 |
| ggcgagttac | atgatccccc | atgttgtgca | aaaaagcggt | tagctccttc | ggtcctccga | 1980 |
| tcgttgtcag | aagtaagttg | gccgcagtgt | tatcactcat | ggttatggca | gcactgcata | 2040 |
| attctcttac | tgtcatgcca | tccgtaagat | gcttttctgt | gactggtgag | tactcaacca | 2100 |

```
agtcattctg agaatagtgt atgcggcgac cgagttgctc ttgcccggcg tcaatacggg   2160
ataataccgc gccacatagc agaactttaa aagtgctcat cattggaaaa cgttcttcgg   2220
ggcgaaaact ctcaaggatc ttaccgctgt tgagatccag ttcgatgtaa cccactcgtg   2280
cacccaactg atcttcagca tcttttactt tcaccagcgt ttctgggtga gcaaaaacag   2340
gaaggcaaaa tgccgcaaaa aagggaataa gggcgacacg gaaatgttga atactcatca   2400
attgcctttt tcaatattat tgaagcattt atcagggtta ttgtctcatg agcggttaca   2460
tatttgaatg tatttagaaa aataaacaaa taggggttcc gcgcacattt ccccgaaaag   2520
tgccacctga cgtctaagaa accattatta tcatgacatt aacctataaa aataggcgta   2580
tcacgaggcc ctttcatctc gcgcgtttcg gtgatgacgg tgaaaacctc tgacacatgc   2640
agctcccgga gacagtcaca gcttgtctgt aagcggatgc cgggagcaga caagcccgtc   2700
agggcgcgtc agcgggtgtt ggcgggtgtc ggggctg                            2737

<210> SEQ ID NO 217
<211> LENGTH: 2737
<212> TYPE: DNA
<213> ORGANISM: Artificial Sequence
<220> FEATURE:
<223> OTHER INFORMATION: Synthetic pRYSE Entry vector 12

<400> SEQUENCE: 217
gtaaaacgac ggccagtatt aaccctcact aaagggaact cgaggctctt caaacgcgat     60
cgccgacgcc gccgattggc agactccata tgctatgcgg catcagagca gattgtactg    120
agagtgcacc atatgcggtg tgaaataccg cacagatgcg taaggagaaa ataccgcatc    180
aggcgccatt cgccattcag gctgcgcaac tgttgggaag ggcgatcggt gcgggcctct    240
tcgctattac gccagctggc gaaaggggga tgtgctgcaa ggcgattaag ttgggtaacg    300
ccagggtttt cccagtcacg acgttgtaaa acgacggcca gtgaattcga gctcggtacc    360
cggggatcct ctagcgtcga cctgcaggca tgcaagcttg gcgtaatcat ggtcatagct    420
gtttcctgtg tgaaattgtt atccgctcac aattccacac aacatacgag ccggaagcat    480
aaagtgtaaa gcctggggtg cctaatgagt gagctaactc acattaattg cgttgcgcgc    540
tagcgagtca tccacggtgt ttaaacccca gcgcctggcg ggtgaagagc gagctcccgc    600
tgagcaataa ctagcgtcat agctgtttcc tgggtcgttc ggctgcggcg agcggtatca    660
gctcactcaa aggcggtaat acggttatcc acagaatcag gggataacgc aggaaagaac    720
atgtgagcaa aaggccagca aaaggccagg aaccgtaaaa aggccgcgtt gctggcgttt    780
ttccataggc tccgcccccc tgacgagcat cacaaaaatc gacgctcaag tcagaggtgg    840
cgaaacccga caggactata agataccagg cgtttccccc tggaagctcc ctcgtgcgc    900 tctcctgttc cgaccctgcc gcttaccgga tacctgtccg cctttctccc ttcgggaagc    960
gtggcgcttt ctcatagctc acgctgtagg tatctcagtt cggtgtaggt cgttcgctcc   1020
aagctgggct gtgtgcacga accccccgtt cagcccgacc gctgcgcctt atccggtaac   1080
tatcgtcttg attccaaccc ggtaagacac gacttatcgc cactggcagc agccactggt   1140
aacaggatta gcagagcgag gtatgtaggc ggtgctacag agttcttgaa gtggtggcct   1200
aactacggct acactagaag aacagtattt ggtatctgcg ctctgctgaa gccagttacc   1260
ttcggaaaaa gagttggtag ctcttgatcc ggcaaacaaa ccaccgctgg tagcggtggt   1320
ttttttgttt gcaagcagca gattacgcgc agaaaaaaag gatctcaaga agatcctttg   1380
atcttttcta cggggtctga cgctcagtgg aacgaaaact cacgttaagg gattttggtc   1440
```

```
atgagattat caaaaaggat cttcacctag atccttttaa attaaaaatg aagttttaaa    1500
tcaatctaaa gtatatatga gtaacttggt cgcatgctta ccaatgctta atcagtgagg    1560
cacctatctc agcgatctgt ctatttcgtt catccatagt tgcctgactg cccgtcgtgt    1620
agataactac gatacgggag ggcttaccat ctggccccag tgctgcaatg ataccgcgag    1680
acccacgctc accggctcca gatttatcag caataaacca gccagccgga agggccgagc    1740
gcagaagtgg tcctgcaact ttatccgcct ccatccagtc tattaattgt tgccgggaag    1800
ctagagtaag tagttcgcca gttaatagtt tgcgcaacgt tgttgccatt gctacaggca    1860
tcgtggtgtc acgctcgtcg tttggtatgg cttcattcag ctccggttcc caacgatcaa    1920
ggcgagttac atgatccccc atgttgtgca aaaaagcggt tagctccttc ggtcctccga    1980
tcgttgtcag aagtaagttg gccgcagtgt tatcactcat ggttatggca gcactgcata    2040
attctcttac tgtcatgcca tccgtaagat gcttttctgt gactggtgag tactcaacca    2100
agtcattctg agaatagtgt atgcggcgac cgagttgctc ttgcccggcg tcaatacggg    2160
ataataccgc gccacatagc agaactttaa aagtgctcat cattggaaaa cgttcttcgg    2220
ggcgaaaact ctcaaggatc ttaccgctgt tgagatccag ttcgatgtaa cccactcgtg    2280
cacccaactg atcttcagca tcttttactt tcaccagcgt ttctgggtga gcaaaaacag    2340
gaaggcaaaa tgccgcaaaa aagggaataa gggcgacacg gaaatgttga atactcatca    2400
attgcctttt tcaatattat tgaagcattt atcagggtta ttgtctcatg agcggttaca    2460
tatttgaatg tatttagaaa aataaacaaa taggggttcc gcgcacattt ccccgaaaag    2520
tgccacctga cgtctaagaa accattatta tcatgacatt aacctataaa aataggcgta    2580
tcacgaggcc ctttcatctc gcgcgtttcg gtgatgacgg tgaaaacctc tgacacatgc    2640
agctcccgga gacagtcaca gcttgtctgt aagcggatgc cgggagcaga caagcccgtc    2700
agggcgcgtc agcgggtgtt ggcgggtgtc ggggctg                             2737
```

<210> SEQ ID NO 218
<211> LENGTH: 2737
<212> TYPE: DNA
<213> ORGANISM: Artificial Sequence
<220> FEATURE:
<223> OTHER INFORMATION: Synthetic pRYSE Entry vector 13

<400> SEQUENCE: 218

```
gtaaaacgac ggccagtatt aaccctcact aaagggaact cgaggctctt caaaggcggc     60
cgctggcgag ggagattggc agactccata tgctatgcgg catcagagca gattgtactg    120
agagtgcacc atatgcggtg tgaaataccg cacagatgcg taaggagaaa ataccgcatc    180
aggcgccatt cgccattcag gctgcgcaac tgttgggaag ggcgatcggt gcgggcctct    240
tcgctattac gccagctggc gaagggggga tgtgctgcaa ggcgattaag ttgggtaacg    300
ccagggtttt cccagtcacg acgttgtaaa acgacggcca gtgaattcga gctcggtacc    360
cggggatcct ctagcgtcga cctgcaggca tgcaagcttg gcgtaatcat ggtcatagct    420
gtttcctgtg tgaaattgtt atccgctcac aattccacac aacatacgag ccggaagcat    480
aaagtgtaaa gcctggggtg cctaatgagt gagctaactc acattaattg cgttgcgcgc    540
tagcgagtca tccacggtgt ttaaacccca gcgcctggcg ggtgaagagc gagctcccgc    600
tgagcaataa ctagcgtcat agctgttttcc tgggtcgttc ggctgcgcg agcggtatca    660 gctcactcaa aggcggtaat acggttatcc acagaatcag gggataacgc aggaaagaac    720
atgtgagcaa aaggccagca aaaggccagg aaccgtaaaa aggccgcgtt gctggcgttt    780
```

```
ttccataggc tccgcccccc tgacgagcat cacaaaaatc gacgctcaag tcagaggtgg      840
cgaaacccga caggactata aagataccag gcgtttcccc ctggaagctc cctcgtgcgc      900
tctcctgttc cgaccctgcc gcttaccgga tacctgtccg cctttctccc ttcgggaagc      960
gtggcgcttt ctcatagctc acgctgtagg tatctcagtt cggtgtaggt cgttcgctcc     1020
aagctgggct gtgtgcacga accccccgtt cagcccgacc gctgcgcctt atccggtaac     1080
tatcgtcttg attccaaccc ggtaagacac gacttatcgc cactggcagc agccactggt     1140
aacaggatta gcagagcgag gtatgtaggc ggtgctacag agttcttgaa gtggtggcct     1200
aactacggct acactagaag aacagtattt ggtatctgcg ctctgctgaa gccagttacc     1260
ttcggaaaaa gagttggtag ctcttgatcc ggcaaacaaa ccaccgctgg tagcggtggt     1320
ttttttgttt gcaagcagca gattacgcgc agaaaaaaag gatctcaaga agatcctttg     1380
atcttttcta cggggtctga cgctcagtgg aacgaaaact cacgttaagg gattttggtc     1440
atgagattat caaaaaggat cttcacctag atccttttaa attaaaaatg aagttttaaa     1500
tcaatctaaa gtatatatga gtaacttggt ctgacagtta ccaatgctta atcagtgagg     1560
cacctatctc agcgatctgt ctatttcgtt catccatagt tgcctgactg cccgtcgtgt     1620
agataactac gatacgggag ggcttaccat ctggccccag tgctgcaatg ataccgcgag     1680
acccacgctc accggctcca gatttatcag caataaacca gccagccgga agggccgagc     1740
gcagaagtgg tcctgcaact ttatccgcct ccatccagtc tattaattgt tgccgggaag     1800
ctagagtaag tagttcgcca gttaatagtt tgcgcaacgt tgttgccatt gctacaggca     1860
tcgtggtgtc acgctcgtcg tttggtatgg cttcattcag ctccggttcc caacgatcaa     1920
ggcgagttac atgatccccc atgttgtgca aaaaagcggt tagctccttc ggtcctccga     1980
tcgttgtcag aagtaagttg gccgcagtgt tatcactcat ggttatggca gcactgcata     2040
attctcttac tgtcatgcca tccgtaagat gcttttctgt gactggtgag tactcaacca     2100
agtcattctg agaatagtgt atgcggcgac cgagttgctc ttgcccggcg tcaatacggg     2160
ataataccgc gccacatagc agaactttaa aagtgctcat cattggaaaa cgttcttcgg     2220
ggcgaaaact ctcaaggatc ttaccgctgt tgagatccag ttcgatgtaa cccactcgtg     2280
cacccaactg atcttcagca tcttttactt tcaccagcgt ttctgggtga gcaaaaacag     2340
gaaggcaaaa tgccgcaaaa aagggaataa gggcgacacg gaaatgttga atactcatca     2400
attgcctttt tcaatattat tgaagcattt atcagggtta ttgtctcatg agcggttaca     2460
tatttgaatg tatttagaaa aataaacaaa taggggttcc gcgcacattt ccccgaaaag     2520
tgccacctga cgtctaagaa accattatta tcatgacatt aacctataaa aataggcgta     2580
tcacgaggcc ctttcatctc gcgcgtttcg gtgatgacgg tgaaaacctc tgacacatgc     2640
agctcccgga gacagtcaca gcttgtctgt aagcggatgc cgggagcaga caagcccgtc     2700
agggcgcgtc agcgggtgtt ggcgggtgtc gggctg                               2737
```

<210> SEQ ID NO 219
<211> LENGTH: 2737
<212> TYPE: DNA
<213> ORGANISM: Artificial Sequence
<220> FEATURE:
<223> OTHER INFORMATION: Synthetic pRYSE Entry vector 14

<400> SEQUENCE: 219

```
gtaaaacgac ggccagtatt aaccctcact aaagggaact cgaggctctt caaaggcgcg       60
ccacggtcgt gcggattggc agactccata tgctatgcgg catcagagca gattgtactg      120
```

```
agagtgcacc atatgcggtg tgaaataccg cacagatgcg taaggagaaa ataccgcatc      180
aggcgccatt cgccattcag gctgcgcaac tgttgggaag ggcgatcggt gcgggcctct      240
tcgctattac gccagctggc gaaaggggga tgtgctgcaa ggcgattaag ttgggtaacg      300
ccagggtttt cccagtcacg acgttgtaaa acgacggcca gtgaattcga gctcggtacc      360
cggggatcct ctagcgtcga cctgcaggca tgcaagcttg gcgtaatcat ggtcatagct      420
gtttcctgtg tgaaattgtt atccgctcac aattccacac aacatacgag ccggaagcat      480
aaagtgtaaa gcctggggtg cctaatgagt gagctaactc acattaattg cgttgcgcgc      540
tagcgagtca tccacggtgt ttaaacccca gcgcctggcg ggtgaagagc gagctcccgc      600
tgagcaataa ctagcgtcat agctgttttcc tgggtcgttc ggctgcggcg agcggtatca      660
gctcactcaa aggcggtaat acggttatcc acagaatcag gggataacgc aggaaagaac      720
atgtgagcaa aaggccagca aaaggccagg aaccgtaaaa aggccgcgtt gctggcgttt      780
ttccataggc tccgcccccc tgacgagcat cacaaaaatc gacgctcaag tcagaggtgg      840
cgaaacccga caggactata agataccagg cgtttccccc ctggaagctc cctcgtgcgc      900
tctcctgttc cgaccctgcc gcttaccgga tacctgtccg cctttctccc ttcgggaagc      960
gtggcgcttt ctcatagctc acgctgtagg tatctcagtt cggtgtaggt cgttcgctcc     1020
aagctgggct gtgtgcacga accccccgtt cagcccgacc gctgcgcctt atccggtaac     1080
tatcgtcttg attccaaccc ggtaagacac gacttatcgc cactggcagc agccactggt     1140
aacaggatta gcagagcgag gtatgtaggc ggtgctacag agttcttgaa gtggtggcct     1200
aactacggct acactagaag aacagtattt ggtatctgcg ctctgctgaa gccagttacc     1260
ttcggaaaaa gagttggtag ctcttgatcc ggcaaacaaa ccaccgctgg tagcggtggt     1320
ttttttgttt gcaagcagca gattacgcgc agaaaaaaag gatctcaaga agatcctttg     1380
atcttttcta cggggtctga cgctcagtgg aacgaaaact cacgttaagg attttggtc      1440 atgagattat caaaaaggat cttcacctag atccttttaa attaaaaatg aagttttaaa     1500
tcaatctaaa gtatatatga gtaacttggt ctgcatgctta ccaatgctta atcagtgagg    1560
cacctatctc agcgatctgt ctatttcgtt catccatagt tgcctgactg cccgtcgtgt     1620
agataactac gatacgggag ggcttaccat ctggccccag tgctgcaatg ataccgcgag    1680
acccacgctc accggctcca gatttatcag caataaacca gccagccgga agggccgagc    1740
gcagaagtgg tcctgcaact ttatccgcct ccatccagtc tattaattgt tgccgggaag    1800
ctagagtaag tagttcgcca gttaatagtt tgcgcaacgt tgttgccatt gctacaggca    1860
tcgtggtgtc acgctcgtcg tttggtatgg cttcattcag ctccggttcc caacgatcaa    1920
ggcgagttac atgatccccc atgttgtgca aaaaagcggt tagctccttc ggtcctccga    1980
tcgttgtcag aagtaagttg gccgcagtgt tatcactcat ggttatggca gcactgcata    2040
attctcttac tgtcatgcca tccgtaagat gcttttctgt gactggtgag tactcaacca    2100
agtcattctg agaatagtgt atgcggcgac cgagttgctc ttgcccggcg tcaatacggg    2160
ataataccgc gccacatagc agaactttaa aagtgctcat cattggaaaa cgttcttcgg    2220
ggcgaaaact ctcaaggatc ttaccgctgt tgagatccag ttcgatgtaa cccactcgtg    2280
cacccaactg atcttcagca tcttttactt tcaccagcgt ttctgggtga gcaaaaacag    2340
gaaggcaaaa tgccgcaaaa aagggaataa gggcgacacg gaaatgttga atactcatca    2400 attgccttt tcaatattat tgaagcattt atcagggtta ttgtctcatg agcggttaca    2460
tatttgaatg tatttagaaa aataaacaaa tagggggttcc gcgcacattt ccccgaaaag    2520
```

```
tgccacctga cgtctaagaa accattatta tcatgacatt aacctataaa aataggcgta    2580
tcacgaggcc ctttcatctc gcgcgtttcg gtgatgacgg tgaaaacctc tgacacatgc    2640
agctcccgga gacagtcaca gcttgtctgt aagcggatgc cgggagcaga caagcccgtc    2700
agggcgcgtc agcgggtgtt ggcgggtgtc ggggctg                             2737

<210> SEQ ID NO 220
<211> LENGTH: 2737
<212> TYPE: DNA
<213> ORGANISM: Artificial Sequence
<220> FEATURE:
<223> OTHER INFORMATION: Synthetic pRYSE Entry vector 15

<400> SEQUENCE: 220
gtaaaacgac ggccagtatt aaccctcact aaagggaact cgaggctctt caagcccctc      60
agccccccta gcgtcgtggc agactccata tgctatgcgg catcagagca gattgtactg     120
agagtgcacc atatgcggtg tgaaataccg cacagatgcg taaggagaaa ataccgcatc     180
aggcgccatt cgccattcag gctgcgcaac tgttgggaag ggcgatcggt gcgggcctct     240
tcgctattac gccagctggc gaaagggggga tgtgctgcaa ggcgattaag ttgggtaacg     300
ccagggtttt cccagtcacg acgttgtaaa acgacggcca gtgaattcga gctcggtacc     360
cggggatcct ctagcgtcga cctgcaggca tgcaagcttg gcgtaatcat ggtcatagct     420
gtttcctgtg tgaaattgtt atccgctcac aattccacac aacatacgag ccggaagcat     480
aaagtgtaaa gcctggggtg cctaatgagt gagctaactc acattaattg cgttgcgcgc     540
tagcgagtca tccacggtgt ttaaacccca gcgcctggcg ggtgaagagc gagctcccgc     600
tgagcaataa ctagcgtcat agctgtttcc tgggtcgttc ggctgcggcg agcggtatca     660
gctcactcaa aggcggtaat acggttatcc acagaatcag gggataacgc aggaaagaac     720
atgtgagcaa aaggccagca aaaggccagg aaccgtaaaa aggccgcgtt gctggcgttt     780
ttccataggc tccgcccccc tgacgagcat cacaaaaatc gacgctcaag tcagaggtgg     840
cgaaacccga caggactata agataccagg cgtttccccc tggaagctcc ctcgtgcgc     900 tctcctgttc cgaccctgcc gcttaccgga tacctgtccg cctttctccc ttcgggaagc     960
gtggcgcttt ctcatagctc acgctgtagg tatctcagtt cggtgtaggt cgttcgctcc    1020
aagctgggct gtgtgcacga accccccgtt cagcccgacc gctgcgcctt atccggtaac    1080
tatcgtcttg attccaaccc ggtaagacac gacttatcgc cactggcagc agccactggt    1140
aacaggatta gcagagcgag gtatgtaggc ggtgctacag agttcttgaa gtggtggcct    1200
aactacggct acactagaag aacagtattt ggtatctgcg ctctgctgaa gccagttacc    1260
ttcggaaaaa gagttggtag ctcttgatcc ggcaaacaaa ccaccgctgg tagcggtggt    1320 tttttttgttt gcaagcagca gattacgcgc agaaaaaaag gatctcaaga agatcctttg    1380
atcttttcta cggggtctga cgctcagtgg aacgaaaact cacgttaagg gattttggtc    1440
atgagattat caaaaaggat cttcacctag atccttttaa attaaaaatg aagttttaaa    1500
tcaatctaaa gtatatatga gtaacttggt cgcatgctta ccaatgctta atcagtgagg    1560
cacctatctc agcgatctgt ctatttcgtt catccatagt tgcctgactg cccgtcgtgt    1620
agataactac gatacgggag ggcttaccat ctggccccag tgctgcaatg ataccgcgag    1680
acccacgctc accggctcca gatttatcag caataaacca gccagccgga agggccgagc    1740
gcagaagtgg tcctgcaact ttatccgcct ccatccagtc tattaattgt tgccgggaag    1800
ctagagtaag tagttcgcca gttaatagtt tgcgcaacgt tgttgccatt gctacaggca    1860
```

```
tcgtggtgtc acgctcgtcg tttggtatgg cttcattcag ctccggttcc caacgatcaa    1920
ggcgagttac atgatccccc atgttgtgca aaaaagcggt tagctccttc ggtcctccga    1980
tcgttgtcag aagtaagttg gccgcagtgt tatcactcat ggttatggca gcactgcata    2040
attctcttac tgtcatgcca tccgtaagat gcttttctgt gactggtgag tactcaacca    2100
agtcattctg agaatagtgt atgcggcgac cgagttgctc ttgcccggcg tcaatacggg    2160
ataataccgc gccacatagc agaactttaa aagtgctcat cattggaaaa cgttcttcgg    2220
ggcgaaaact ctcaaggatc ttaccgctgt tgagatccag ttcgatgtaa cccactcgtg    2280
cacccaactg atcttcagca tctttttactt tcaccagcgt ttctgggtga gcaaaaacag    2340
gaaggcaaaa tgccgcaaaa aagggaataa gggcgacacg gaaatgttga atactcatca    2400
attgcctttt tcaatattat tgaagcattt atcagggtta ttgtctcatg agcggttaca    2460
tatttgaatg tatttagaaa aataaacaaa taggggttcc gcgcacattt ccccgaaaag    2520
tgccacctga cgtctaagaa accattatta tcatgacatt aacctataaa aataggcgta    2580
tcacgaggcc ctttcatctc gcgcgtttcg gtgatgacgg tgaaaacctc tgacacatgc    2640
agctcccgga gacagtcaca gcttgtctgt aagcggatgc cgggagcaga caagcccgtc    2700
agggcgcgtc agcgggtgtt ggcgggtgtc ggggctg                             2737
```

<210> SEQ ID NO 221
<400> SEQUENCE: 221

000

<210> SEQ ID NO 222
<400> SEQUENCE: 222

000

<210> SEQ ID NO 223
<400> SEQUENCE: 223

000

<210> SEQ ID NO 224
<400> SEQUENCE: 224

000

<210> SEQ ID NO 225
<400> SEQUENCE: 225

000

<210> SEQ ID NO 226
<400> SEQUENCE: 226

000

<210> SEQ ID NO 227
<400> SEQUENCE: 227

000

<210> SEQ ID NO 228
<400> SEQUENCE: 228
000

<210> SEQ ID NO 229
<400> SEQUENCE: 229
000

<210> SEQ ID NO 230
<400> SEQUENCE: 230
000

<210> SEQ ID NO 231
<400> SEQUENCE: 231
000

<210> SEQ ID NO 232
<400> SEQUENCE: 232
000

<210> SEQ ID NO 233
<400> SEQUENCE: 233
000

<210> SEQ ID NO 234
<400> SEQUENCE: 234
000

<210> SEQ ID NO 235
<400> SEQUENCE: 235
000

<210> SEQ ID NO 236
<400> SEQUENCE: 236
000

<210> SEQ ID NO 237
<400> SEQUENCE: 237
000

<210> SEQ ID NO 238
<400> SEQUENCE: 238
000

<210> SEQ ID NO 239

<400> SEQUENCE: 239

000

<210> SEQ ID NO 240

<400> SEQUENCE: 240

000

<210> SEQ ID NO 241

<400> SEQUENCE: 241

000

<210> SEQ ID NO 242

<400> SEQUENCE: 242

000

<210> SEQ ID NO 243

<400> SEQUENCE: 243

000

<210> SEQ ID NO 244

<400> SEQUENCE: 244

000

<210> SEQ ID NO 245

<400> SEQUENCE: 245

000

<210> SEQ ID NO 246

<400> SEQUENCE: 246

000

<210> SEQ ID NO 247

<400> SEQUENCE: 247

000

<210> SEQ ID NO 248
<211> LENGTH: 26
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (2)..(9)
<223> OTHER INFORMATION: n is a, c, g, or t
<220> FEATURE:
<221> NAME/KEY: misc_feature
<222> LOCATION: (11)..(13)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t
<220> FEATURE:

```
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t

<400> SEQUENCE: 248
annnnnnnna nnnaantann ttnana                                         26

<210> SEQ ID NO 249
<211> LENGTH: 8
<212> TYPE: PRT
<213> ORGANISM: Artificial Sequence
<220> FEATURE:
<223> OTHER INFORMATION: Synthetic Annealable Linker Sequence

<400> SEQUENCE: 249

Thr Ala Gly Gln Ala Arg Gly Asp
1               5

<210> SEQ ID NO 250
<211> LENGTH: 8
<212> TYPE: PRT
<213> ORGANISM: Artificial Sequence
<220> FEATURE:
<223> OTHER INFORMATION: Synthetic Annealable Linker Sequence

<400> SEQUENCE: 250

Asn Leu Gln Ala Ala Ser Ala Asp
1               5

<210> SEQ ID NO 251
<211> LENGTH: 8
<212> TYPE: PRT
<213> ORGANISM: Artificial Sequence
<220> FEATURE:
<223> OTHER INFORMATION: Synthetic Annealable Linker Sequence

<400> SEQUENCE: 251

Ile Gly Ala Arg Gly Leu Gln Val
1               5

<210> SEQ ID NO 252
<211> LENGTH: 8
<212> TYPE: PRT
<213> ORGANISM: Artificial Sequence
<220> FEATURE:
<223> OTHER INFORMATION: Synthetic Annealable Linker Sequence

<400> SEQUENCE: 252

Asn Ala Ile Ala Asp Ala Ala Asp
1               5

<210> SEQ ID NO 253
<211> LENGTH: 8
<212> TYPE: PRT
<213> ORGANISM: Artificial Sequence
<220> FEATURE:
<223> OTHER INFORMATION: Synthetic Annealable Linker Sequence

<400> SEQUENCE: 253

Ile Gly Gly Val Gly Asp Arg Val
1               5
```

```
<210> SEQ ID NO 254
<211> LENGTH: 8
<212> TYPE: PRT
<213> ORGANISM: Artificial Sequence
<220> FEATURE:
<223> OTHER INFORMATION: Synthetic Annealable Linker Sequence

<400> SEQUENCE: 254

Lys Ala Ala Ala Gly Glu Gly Asp
1               5

<210> SEQ ID NO 255
<211> LENGTH: 8
<212> TYPE: PRT
<213> ORGANISM: Artificial Sequence
<220> FEATURE:
<223> OTHER INFORMATION: Synthetic Annealable Linker Sequence

<400> SEQUENCE: 255

Ile Ser Leu Ala Ser Gly Arg Leu
1               5

<210> SEQ ID NO 256
<211> LENGTH: 8
<212> TYPE: PRT
<213> ORGANISM: Artificial Sequence
<220> FEATURE:
<223> OTHER INFORMATION: Synthetic Annealable Linker Sequence

<400> SEQUENCE: 256

Lys Ala Arg His Gly Arg Arg Asp
1               5
```